United States Patent
Van Ness et al.

(10) Patent No.: US 6,312,893 B1
(45) Date of Patent: *Nov. 6, 2001

(54) METHODS AND COMPOSITIONS FOR DETERMINING THE SEQUENCE OF NUCLEIC ACID MOLECULES

(75) Inventors: Jeffrey Van Ness, Seattle; John C. Tabone, Bothell; J. Jeffry Howbert, Bellevue; John T. Mulligan, Seattle, all of WA (US)

(73) Assignee: Qiagen Genomics, Inc., Bothell, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/898,180

(22) Filed: Jul. 22, 1997

Related U.S. Application Data

(63) Continuation-in-part of application No. 08/786,835, filed on Jan. 22, 1997, now abandoned.
(60) Provisional application No. 60/010,462, filed on Jan. 23, 1996.

(51) Int. Cl.[7] .................................................. C12Q 1/68
(52) U.S. Cl. ............................. 435/6; 436/536; 436/518
(58) Field of Search ............................. 435/6; 436/536, 436/518

(56) References Cited

U.S. PATENT DOCUMENTS

| | | | |
|---|---|---|---|
| 4,650,750 | 3/1987 | Giese | 435/7 |
| 4,709,016 | 11/1987 | Giese | 530/389 |
| 4,762,779 | 8/1988 | Snitman | 435/6 |
| 4,775,619 | 10/1988 | Urdea | 435/6 |
| 4,942,124 | 7/1990 | Church | 435/6 |
| 4,962,020 | 10/1990 | Tabor et al. | 435/6 |
| 4,965,349 | 10/1990 | Woo et al. | 536/27 |
| 4,994,372 | 2/1991 | Tabor et al. | 435/6 |
| 4,997,928 | 3/1991 | Hobbs, Jr. | 536/27 |
| 5,118,605 | 6/1992 | Urdea | 435/6 |
| 5,135,870 | 8/1992 | Williams et al. | 436/173 |
| 5,149,625 | 9/1992 | Church et al. | 435/6 |
| 5,262,536 | 11/1993 | Hobbs, Jr. | 546/25 |
| 5,266,466 | 11/1993 | Tabor et al. | 435/91.5 |
| 5,288,644 | 2/1994 | Beavis et al. | 436/94 |
| 5,290,925 | 3/1994 | Fino | 536/25.32 |
| 5,292,873 | 3/1994 | Rokita et al. | 536/24.3 |
| 5,302,509 | 4/1994 | Cheeseman | 435/6 |
| 5,324,631 | 6/1994 | Helentjaris et al. | 435/6 |
| 5,346,670 | 9/1994 | Renzoni et al. | 422/52 |
| 5,360,819 | 11/1994 | Giese | 514/538 |
| 5,403,708 | 4/1995 | Brennan et al. | 435/6 |
| 5,409,811 | 4/1995 | Tabor et al. | 435/6 |
| 5,451,463 | 9/1995 | Nelson et al. | 428/402 |
| 5,516,931 | 5/1996 | Giese et al. | 560/59 |
| 5,547,835 | 8/1996 | Köster | 435/6 |
| 5,602,273 | 2/1997 | Giese et al. | 560/60 |
| 5,604,097 | 2/1997 | Brenner | 435/6 |
| 5,604,104 | 2/1997 | Giese et al. | 435/7.1 |
| 5,610,020 | 3/1997 | Giese et al. | 435/7.1 |
| 5,622,824 | 4/1997 | Köster | 435/6 |
| 5,635,400 | 6/1997 | Brenner | 435/320.1 |
| 5,650,270 | 7/1997 | Giese et al. | 435/6 |
| 5,654,413 | 8/1997 | Brenner | 536/22.1 |
| 5,674,716 | 10/1997 | Tabor et al. | 435/91.1 |
| 5,691,141 | 11/1997 | Köster | 435/6 |
| 5,695,934 | 12/1997 | Brenner | 435/6 |
| 5,700,921 | 12/1997 | Westling et al. | 536/22.1 |
| 5,728,526 | 3/1998 | George, Jr. et al. | 435/6 |
| 5,763,175 | 6/1998 | Brenner | 435/6 |
| 5,821,058 | 10/1998 | Smith et al. | 435/6 |
| 5,851,765 | 12/1998 | Köster | 435/6 |
| 5,856,097 | 1/1999 | Pinkel et al. | 435/6 |
| 5,863,722 | 1/1999 | Brenner | 435/6 |
| 5,872,003 | 2/1999 | Köster | 435/283.1 |
| 5,908,745 | 6/1999 | Mirzabekov et al. | 435/6 |
| 5,952,654 | 9/1999 | Giese | 250/288 |
| 5,962,223 | 10/1999 | Whiteley et al. | 435/6 |
| 6,013,431 | 1/2000 | Söderlund et al. | 435/5 |
| 6,033,909 | 3/2000 | Uhlmann et al. | 435/375 |
| 6,087,095 | 7/2000 | Rosenthal et al. | 435/6 |
| 6,087,186 | 7/2000 | Cargill et al. | 436/518 |

FOREIGN PATENT DOCUMENTS

| | | |
|---|---|---|
| 2062454 A1 | 9/1992 | (CA) . |
| 127 154 A2 | 12/1984 | (EP) . |

(List continued on next page.)

OTHER PUBLICATIONS

Aebersold et al., "Design, synthesis, characterization of a protein sequencing reagent yielding amino acid derivatives with enhanced detectability by mass spectrometry," *Protein Science* 1:494–503, 1992.

(List continued on next page.)

*Primary Examiner*—Scott W. Houtteman
(74) *Attorney, Agent, or Firm*—Seed Intellectual Property Law Group PLLC

(57) ABSTRACT

Methods and compounds, including compositions therefrom, are provided for determining the sequence of nucleic acid molecules. The methods permit the determination of multiple nucleic acid sequences simultaneously. The compounds are used as tags to generate tagged nucleic acid fragments which are complementary to a selected target nucleic acid molecule. Each tag is correlative with a particular nucleotide and, in a preferred embodiment, is detectable by mass spectrometry. Following separation of the tagged fragments by sequential length, the tags are cleaved from the tagged fragments. In a preferred embodiment, the tags are detected by mass spectrometry and the sequence of the nucleic acid molecule is determined therefrom. The individual steps of the methods can be used in automated format, e.g., by the incorporation into systems.

58 Claims, 42 Drawing Sheets

FOREIGN PATENT DOCUMENTS

| | | |
|---|---|---|
| 251 786 A2 | 1/1988 | (EP). |
| 300 730 A1 | 1/1989 | (EP). |
| 360 940 A2 | 4/1990 | (EP). |
| 401 821 A1 | 12/1990 | (EP). |
| 502 595 A2 | 9/1992 | (EP). |
| 514 927 A1 | 11/1992 | (EP). |
| 539 343 A1 | 4/1993 | (EP). |
| 639 647 A2 | 2/1995 | (EP). |
| 711 362 B1 | 5/1996 | (EP). |
| 6-289018 | 10/1994 | (JP). |
| WO 89/12694 | 12/1989 | (WO). |
| WO 90/13666 | 11/1990 | (WO). |
| WO 92/02528 | 2/1992 | (WO). |
| WO 92/02638 | 2/1992 | (WO). |
| WO 92/10587 | 6/1992 | (WO). |
| WO 93/20233 | 10/1993 | (WO). |
| WO 93/20236 | 10/1993 | (WO). |
| WO 93/21340 | 10/1993 | (WO). |
| WO 94/08051 | 4/1994 | (WO). |
| WO 94/16101 | 7/1994 | (WO). |
| WO 94/21822 | 9/1994 | (WO). |
| WO 94/28418 | 12/1994 | (WO). |
| WO 95/04160 | 2/1995 | (WO). |
| WO 95/06752 | 3/1995 | (WO). |
| WO 95/11961 | 5/1995 | (WO). |
| WO 95/14108 | 5/1995 | (WO). |
| WO 95/25737 | 9/1995 | (WO). |
| WO 95/28640 | 10/1995 | (WO). |
| WO 96/00378 | 1/1996 | (WO). |
| WO 96/22966 | 8/1996 | (WO). |

OTHER PUBLICATIONS

Amankwa and Kuhr, "Trypsin–Modified fused Silica Capillary Microreactor for Peptide Mapping by Capillary Zone Electrophoresis," *Anal. Chem.* 64:1610–1613, 1992.

Baldwin et al., "Synthesis of a Small Molecule Combinatorial Library Encoded with Molecular Tags," *J. Am. Chem. Soc.* 117:5588–5589, 1995 (+Supplementary Material 21 pages).

Borchardt and Still, "Synthetic Receptor Binding Elucidated with an Encoded Combinatorial Library," *J. Am. Chem. Soc.* 116:373–374, 1994.

Brown et al., "A single–bead decode strategy using electrospray ionization mass spectrometry and a new photolabile linker: 3–Amino–3–(2–nitrophenyl)propionic acid," *Molecular Diversity* 1:4–12, 1995.

Ching et al., "Polymers as Surface–Based Tethers with Photolytic Triggers Enabling Laser–Induced Release/Desorption of Covalently Bound Molecules," *Bioconjugate Chemistry* 7(5):525–528, 1996.

Ching et al., "Surface Chemistries Enabling Photoinduced Uncoupling/Desorption of Covalently Tethered Biomolecules," *J. Org. Chem.* 61:3582–3583, 1996.

Church et al., "New Technologies For Genome Sequencing And Analysis," *DOE Human Genome Program Contractor–Grantee Workshop V*, Sante Fe, New Mexico, Jan. 28–Feb. 1, 1966, available NTIS, CONF–960143, 1996, p. 51.

Church and Keiffer–Higgins, "Multiplex DNA Sequencing," *Science* 240:185–188, 1988.

Cobb and Novotny, "High–Sensitivity Peptide Mapping by Capillary Zone Electrophoresis and Microcolumn Liquid Chromatography, Using Immobilized Trypsin for Protein Digestion," *Anal. Chem.* 61:2226–2231, 1989.

Covey et al., "The Determination of Protein, Oligonucleotide and Peptide Molecular Weights by Ion–spray Mass Spectrometry," *Rapid Communications In Mass Spectrometry* 2(11):249–256, 1988.

Colombo, Roberto, "Liquid–Phase Synthesis of Naturally Occurring Peptides, II. Syntheses of Three Mast Cell Degranulating Tetradecapeptide Amides from Wasp Venoms," *Hoppe–Seyler's Z. Physiol. Chem.* 362:1393–1403, 1981.

Geysen et al., "Isotope or mass encoding of combinatorial libraries," *Chemistry & Biology* 3(8):679–688, 1996.

Giese et al., "Electrophore Mass Labels For TOF–MS DNA Sequencing," in *Proceedings of the 44$^{th}$ ASMS Conference on Mass Spectrometry and Allied Topics*, Portland, Oregon, May 12–16, 1996, p. 673.

Roger W. Giese, "Electrophoric release tags:ultrasensitive molecular labels providing multiplicity," *Trends in Analytical Chemistry* 2(7):166–168, 1983.

Greenberg and Gilmore, "Cleavage of Oligonucleotides From Solid–Phase Supports Using o–Nitrobenzyl Photochemistry," *J. Org. Chem.* 59:746–753, 1994.

Marc M. Greenberg,"Photochemical Cleavage of Oligonucleotides From Solid–Phase Supports," *Tetrahedron Letters* 34(2):251–254, 1993.

Holmes and Jones, "Reagents for Combinatorial Organic Synthesis: Development of a New o–Nitrobenzyl Photolabile Linker for Solid Phase Synthesis," *J. Org. Chem.* 60:2318–2319, 1995. (+Supplementary Material 7 Pages).

Jacobson et al., "Applications of Mass Spectrometry to DNA Sequencing," *Genetic Analysis Techniques and Applications* 8(8):223–229, 1991.

Jane et al., "High–Performance Liquid Chromatographic Analysis Of Basic Drugs on Silica Columns Using Non––Aqueous Ionic Eluents," *Journal of Chromatography* 323:191–225, 1985.

Kremsky et al., "Immobilization of DNA via oligonucleotides containing an aldehyde or carboxylic acid group at the 5'terminus," *Nucleic Acids Research* 15(7):2891–2909, 1987.

Little et al., "Rapid Sequencing of Oligonucleotides by High–Resolution Mass Spectrometry," *J. Am. Chem. Soc.* 116:4893–4897, 1994.

Lloyd–Williams et al., "Convergent Solid–Phase Peptide Synthesis," *Tetrahedron* 49(48):11065–11133, 1993.

Musch et al., "Expert System For Pharmaceutical Analysis. I. Selection Of The Detection System In High–Performance Liquid Chromatographic Analysis: UV Versus Amperometric Detection," *Journal of Chromatography* 348:97–110, 1985.

Nashabeh and El Rassi, "Enzymophoresis of nucleic acids by tandem capillary enzyme reactor–capillary zone electrophoresis," *Journal of Chromatography* 596:251–264, 1992.

Nestler et al., "A General Method for Molecular Tagging of Encoded Combinatorial Chemistry Libraries," *J. Org. Chem.* 59:4723–4724, 1994.

Ordoukhanian and Taylor, "Design and Synthesis of a Versatile Photocleavable DNA Building Block. Application to Phototriggered Hybridization," *J. Am. Chem. Soc.* 117:9570–9571, 1995.

V. N. Rajasekharan Pillai, "Photoremovable Protecting Groups in Organic Synthesis," *Synthesis* 1:1–26, 1980.

Rich and Gurwara, "Preparation of a New o–Nitrobenzyl Resin for Solid–Phase Synthesis of tert–Butyloxycarbonyl––Protected Peptide Acids," *J. Am. Chem. Soc.* 97:1575–1579, 1975.

Rock and Chan, "Synthesis and Photolysis Properties of a Photolabile Linker Based on 3'–Methoxybenzoin," *J. Org. Chem.* 61:1526–1529, 1996.

Sanger et al., "DNA sequencing with chain–terminating inhibitors," *Proc. Natl. Acad. Sci.* USA 74(12):5463–5467, 1977.

Senter et al., "Novel Photocleavable Protein Crosslinking Reagents And Their Use In The Preparation Of Antibody––Toxin Conjugates," *Photochemistry and Photobiology* 42(3):231–237, 1985.

Sumer et al., "Factors Determining Relative Sensitivity of Analytes in Positive Mode Atmospheric Pressure Ionization Mass Spectrometry," *Anal. Chem.* 60:1300–1307, 1988.

Simon J. Teague, "Facile Synthesis of a o–Nitrobenzyl Photolabile Linker for Combinatorial Chemistry," *Tetrahedron Letters* 37(32):5751–5754, 1996.

Thiele and Fahrenholz, "Photocleavable Biotinylated Ligands for Affinity Chromatography," *Analytical Biochemistry* 218:330–337, 1994.

Valaskovic et al., "Attomole–Sensitivity Electrospray Source for Large–Molecule Mass Spectrometry," *Anal. Chem.* 67:3802–3805, 1995.

Voivodov et al., "Surface Arrays of Energy Absorbing Polymers Enabling Covalent Attachment of Biomolecules for Subsequent Laser–Induced Uncoupling/Desorption," *Tetrahedron Letters* 37(32):5669–5672, 1996.

Charles Hignite, "Nucleic Acids And Derivatives," in *Biochemical Applications Of mass Spectrometry, First Supplementary Volume*, Waller et al. (eds.), John Wiley & Sons, New York, 1981, pp. 527–566.

Yoo and Greenberg, "Synthesis of Oligonucleotides Containing 3'–Alkyl Carboxylic Acids Using Universal, Photolabile Solid Phase Synthesis Supports," *J. Org. Chem.* 60:3358–3364, 1995.

Zablocki et al., "Potent in Vitro and in Vivo Inhibitors of Platelet Aggregation Based Upon the Arg–Gly–Asp Sequence of Fibrinogen. (Aminobenzamidino)succinyl (ABAS) Series Orally Active Fibrinogen Receptor Antagonists," *J. Med. Chem.* 38:2378–2394, 1995.

X₁₋₃₆
FROM
EXAMPLE A

5'-Aminohexyl-tailed oligonculeotides
XI₁₋₃₆

STEP A 100 mM
Sodium Borate
pH 8.3

5'-CMST-Oligonucleotide Conjugate
XII₁₋₃₆

METHODS AND COMPOSITIONS FOR DETERMINING THE SEQUENCE OF NUCLEIC ACID MOLECULES

CROSS-REFERENCE TO RELATED APPLICATIONS

This application is a continuation-in-part of U.S. patent application Ser. No. 08/786,835, filed Jan. 22, 1997 now abandoned, which application claims the benefit of provisional application No. 60/010,462, filed Jan. 23, 1996, both of which are incorporated by reference herein in their entirety.

TECHNICAL FIELD

The present invention relates generally to methods and compositions for determining the sequence of nucleic acid molecules, and more specifically, to methods and compositions which allow the determination of multiple nucleic acid sequences simultaneously.

BACKGROUND OF THE INVENTION

Deoxyribonucleic acid (DNA) sequencing is one of the basic techniques of biology. It is at the heart of molecular biology and plays a rapidly expanding role in the rest of biology. The Human Genome Project is a multi-national effort to read the entire human genetic code. It is the largest project ever undertaken in biology, and has already begun to have a major impact on medicine. The development of cheaper and faster sequencing technology will ensure the success of this project. Indeed, a substantial effort has been funded by the NIH and DOE branches of the Human Genome Project to improve sequencing technology, however, without a substantial impact on current practices (Sulston and Waterston, *Nature* 376:175, 1995).

In the past two decades, determination and analysis of nucleic acid sequence has formed one of the building blocks of biological research. This, along with new investigational tools and methodologies, has allowed scientists to study genes and gene products in order to better understand the function of these genes, as well as to develop new therapeutics and diagnostics.

Two different DNA sequencing methodologies that were developed in 1977, are still in wide use today. Briefly, the enzymatic method described by Sanger (*Proc. Natl. Acad. Sci.* (*USA*) 74:5463, 1977) which utilizes dideoxy-terminators, involves the synthesis of a DNA strand from a single-stranded template by a DNA polymerase. The Sanger method of sequencing depends on the fact that that dideoxy-nucleotides (ddNTPs) are incorporated into the growing strand in the same way as normal deoxynucleotides (albeit at a lower efficiency). However, ddNTPs differ from normal deoxynucleotides (dNTPs) in that they lack the 3'-OH group necessary for chain elongation. When a ddNTP is incorporated into the DNA chain, the absence of the 3'-hydroxy group prevents the formation of a new phosphodiester bond and the DNA fragment is terminated with the ddNTP complementary to the base in the template DNA. The Maxam and Gilbert method (Maxam and Gilbert, *Proc. Natl. Acad. Sci.* (*USA*) 74:560, 1977) employs a chemical degradation method of the original DNA (in both cases the DNA must be clonal). Both methods produce populations of fragments that begin from a particular point and terminate in every base that is found in the DNA fragment that is to be sequenced. The termination of each fragment is dependent on the location of a particular base within the original DNA fragment. The DNA fragments are separated by polyacrylamide gel electrophoresis and the order of the DNA bases (adenine, cytosine, thymine, guanine; also known as A,C,T, G, respectively) is read from a autoradiograph of the gel.

A cumbersome DNA pooling sequencing strategy (Church and Kieffer-Higgins, *Science* 24:185, 1988) is one of the more recent approaches to DNA sequencing. A pooling sequencing strategy consists of pooling a number of DNA templates (samples) and processing the samples as pools. In order to separate the sequence information at the end of the processing, the DNA molecules of interest are ligated to a set of oligonucleotide "tags" at the beginning. The tagged DNA molecules are pooled, amplified and chemically fragmented in 96-well plates. After electrophoresis of the pooled samples, the DNA is transferred to a solid support and then hybridized with a sequential series of specific labeled oligonucleotides. These membranes are then probed as many times as there are tags in the original pool, producing, in each set of probing, autoradiographs similar to those from standard DNA sequencing methods. Thus each reaction and gel yields a quantity of data equivalent to that obtained from conventional reactions and gels multiplied by the number of probes used. If alkaline phosphatase is used as the reporter enzyme, 1,2-dioxetane substrate can be used which is detected in a chemiluminescent assay format. However, this pooling strategy's major disadvantage is that the sequences can only be read by Southern blotting the sequencing gel and hybridizing this membrane once for each clone in the pool.

In addition to advances in sequencing methodologies, advances in speed have occurred due to the advent of automated DNA sequencing. Briefly, these methods use fluorescent-labeled primers which replace methods which employed radiolabeled components. Fluorescent dyes are attached either to the sequencing primers or the ddNTP-terminators. Robotic components now utilize polymerase chain reaction (PCR) technology which has lead to the development of linear amplification strategies. Current commercial sequencing allows all 4 dideoxy-terminator reactions to be run on a single lane. Each dideoxy-terminator reaction is represented by a unique fluorescent primer (one fluorophore for each base type: A,T,C,G). Only one template DNA (i.e., DNA sample) is represented per lane. Current gels permit the simultaneous electrophoresis of up to 64 samples in 64 different lanes. Different ddNTP-terminated fragments are detected by the irradiation of the gel lane by light followed by detection of emitted light from the fluorophore. Each electrophoresis step is about 4–6 hours long. Each electrophoresis separation resolves about 400–600 nucleotides (nt), therefore, about 6000 nt can be sequenced per hour per sequencer.

The use of mass spectrometry for the study of monomeric constituents of nucleic acids has also been described (Hignite, In *Biochemical Applications of Mass Spectrometry*, Waller and Dermer (eds.), Wiley-Interscience, Chapter 16, p. 527, 1972). Briefly, for larger oligomers, significant early success was obtained by plasma desorption for protected synthetic oligonucleotides up to 14 bases long, and for unprotected oligos up to 4 bases in length. As with proteins, the applicability of ESI-MS to oligonucleotides has been demonstrated (Covey et al., *Rapid Comm. in Mass Spec.* 2:249–256, 1988). These species are ionized in solution, with the charge residing at the acidic bridging phosphodiester and/ or terminal phosphate moieties, and yield in the gas phase multiple charged molecular anions, in addition to sodium adducts.

Sequencing DNA with <100 bases by the common enzymatic ddNTP technique is more complicated than it is for larger DNA templates, so that chemical degradation is sometimes employed. However, the chemical decomposition method requires about 50 pmol of radioactive $^{32}P$ end-labeled material, 6 chemical steps, electrophoretic separation, and film exposure. For small oligonucleotides (<14 nts) the combination of electrospray ionization (ESI) and Fourier transform (FT) mass spectrometry (MS) is far faster and more sensitive. Dissociation products of multiply-charged ions measured at high ($10^5$) resolving power represent consecutive backbone cleavages providing the full sequence in less than one minute on sub-picomole quantity of sample (Little et al., *J. Am. Chem. Soc.* 116:4893, 1994). For molecular weight measurements, ESI/MS has been extended to larger fragments (Potier et al., *Nuc. Acids Res.* 22:3895, 1994). ESI/FTMS appears to be a valuable complement to classical methods for sequencing and pinpoint mutations in nucleotides as large as 100-mers. Spectral data have recently been obtained loading $3\times10^{-13}$ mol of a 50-mer using a more sensitive ESI source (Valaskovic, *Anal. Chem.* 68:259, 1995).

The other approach to DNA sequencing by mass spectrometry is one in which DNA is labeled with individual isotopes of an element and the mass spectral analysis simply has to distinguish the isotopes after a mixtures of sizes of DNA have been separated by electrophoresis. (The other approach described above utilizes the resolving power of the mass spectrometer to both separate and detect the DNA oligonucleotides of different lengths, a difficult proposition at best.) All of the procedures described below employ the Sanger procedure to convert a sequencing primer to a series of DNA fragments that vary in length by one nucleotide. The enzymatically synthesized DNA molecules each contain the original primer, a replicated sequence of part of the DNA of interest, and the dideoxy terminator. That is, a set of DNA molecules is produced that contain the primer and differ in length by from each other by one nucleotide residue.

Brennen et al. (*Biol. Mass Spec.*, New York, Elsevier, p. 219, 1990) has described methods to use the four stable isotopes of sulfur as DNA labels that enable one to detect DNA fragments that have been separated by capillary electrophoresis. Using the α-thio analogues of the ddNTPs, a single sulfur isotope is incorporated into each of the DNA fragments. Therefore each of the four types of DNA fragments (ddTTP, ddATP, ddGTP, ddCTP-terminated) can be uniquely labeled according to the terminal nucleotide; for example, $^{32}S$ for fragments ending in A, $^{33}S$ for G, $^{34}S$ for C, and $^{36}S$ for T, and mixed together for electrophoresis column, fractions of a few picoliters are obtained by a modified ink-jet printer head, and then subjected to complete combustion in a firnace. This process oxidizes the thiophosphates of the labeled DNA to $SO_2$, which is subjected to analysis in a quadrupole or magnetic sector mass spectrometer. The $SO_2$ mass unit representation is 64 for fragments ending in A, 65 for G, 66 for C, and 68 for T. Maintenance of the resolution of the DNA fragments as they emerge from the column depends on taking sufficiently small fractions. Because the mass spectrometer is coupled directly to the capillary gel column, the rate of analysis is determined by the rate of electrophoresis. This process is unfortunately expensive, liberates radioactive gas and has not been commercialized. Two other basic constraints also operate on this approach: (a) No other components with mass of 64, 65, 66, or 68 (isobaric contaminants) can be tolerated and (b) the % natural abundances of the sulfur isotopes ($^{32}S$ is 95.0, $^{33}S$ is 0.75, $^{34}S$ is 4.2, and $^{36}S$ is 0.11) govern the sensitivity and cost. Since $^{32}S$ is 95% naturally abundant, the other isotopes must be enriched to >99% to eliminate contaminating $^{32}S$. Isotopes that are <1% abundant are quite expensive to obtain at 99% enrichment; even when $^{36}S$ is purified 100-fold it contains as much or more $^{34}S$ as it does $^{36}S$.

Gilbert has described an automated DNA sequencer (EPA, 92108678.2) that consists of an oligomer synthesizer, an array on a membrane, a detector which detects hybridization and a central computer. The synthesizer synthesizes and labels multiple oligomers of arbitrary predicted sequence. The oligomers are used to probe immobilized DNA on membranes. The detector identifies hybridization patterns and then sends those patterns to a central computer which constructs a sequence and then predicts the sequence of the next round of synthesis of oligomers. Through an iterative process, a DNA sequence can be obtained in an automated fashion.

Brennen has described a method for sequencing nucleic acids based on ligation of oligomers (U.S. Pat. No. 5,403,708). Methods and compositions are described for forming ligation product hybridized to a nucleic acid template. A primer is hybridized to a DNA template and then a pool of random extension oligonucleotides is also hybridized to the primed template in the presence ligase(s). The ligase enzyme covalently ligates the hybridized oligomers to the primer. Modifications permit the determination of the nucleotide sequence of one or more members of a first set of target nucleotide residues in the nucleic acid template that are spaced at intervals of N nucleotides. In this method, the labeled ligated product is formed wherein the position and type of label incorporated into the ligation product provides information concerning the nucleotide residue in the nucleic acid template with which the labeled nucleotide residue is base paired.

Koster has described an method for sequencing DNA by mass spectrometry after degradation of DNA by an exonuclease (PCT/US94/02938). The method described is simple in that DNA sequence is directly determined (the Sanger reaction is not used). DNA is cloned into standard vectors, the 5' end is immobilized and the strands are then sequentially degraded at the 3' end via an exonuclease and the enzymatic product (nucleotides) are detected by mass spectrometry.

Weiss et al. have described an automated hybridization/imaging device for fluorescent multiplex DNA sequencing (PCT/US94/11918). The method is based on the concept of hybridizing enzyme-linked probes to a membrane containing size separated DNA fragments arising from a typical Sanger reaction.

The demand for sequencing information is larger than can be supplied by the currently existing sequencing machines, such as the ABI377 and the Pharmacia ALF. One of the principal limitations of the current technology is the small number of tags which can be resolved using the current tagging system. The Church pooling system discussed above uses more tags, but the use and detection of these tags is laborious.

The present invention discloses novel compositions and methods which may be utilized to sequence nucleic acid molecules with greatly increased speed and sensitivity than the methods described above, and further provides other related advantages.

SUMMARY OF THE INVENTION

Briefly stated, the present invention provides methods, compounds, compositions, kits and systems for determining the sequence of nucleic acid molecules. Within one aspect of the invention, methods are provided for determining the sequence of a nucleic acid molecule. The methods includes the steps: (a) generating tagged nucleic acid fragments which are complementary to a selected target nucleic acid molecule, wherein a tag is correlative with a particular nucleotide and detectable by non-fluorescent spectrometry or potentiometry; (b) separating the tagged fragments by sequential length; (c) cleaving the tags from the tagged fragments; and (d) detecting the tags by non-fluorescent spectrometry or potentiometry, and therefrom determining the sequence of the nucleic acid molecule. In preferred embodiments, the tags are detected by mass spectrometry, infrared spectrometry, ultraviolet spectrometry or potentiostatic amperometry.

In another aspect, the invention provides a compound of the formula:

$$T^{ms}-L-X$$

wherein $T^{ms}$ is an organic group detectable by mass spectrometry, comprising carbon, at least one of hydrogen and fluoride, and optional atoms selected from oxygen, nitrogen, sulfur, phosphorus and iodine; L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid; X is a fuinctional group selected from hydroxyl, amino, thiol, carboxylic acid, haloalkyl, and derivatives thereof which either activate or inhibit the activity of the group toward coupling with other moieties, or is a nucleic acid fragment attached to L at other than the 3' end of the nucleic acid fragment; with the provisos that the compound is not bonded to a solid support through X nor has a mass of less than 250 daltons.

In another aspect, the invention provides a composition comprising a plurality of compounds of the formula $T^{ms}-L-MOI$, wherein, $T^{ms}$ is an organic group detectable by mass spectrometry, comprising carbon, at least one of hydrogen and fluoride, and optional atoms selected from oxygen, nitrogen, sulfur, phosphorus and iodine; L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid; MOI is a nucleic acid fragment wherein L is conjugated to the MOI at a location other than the 3' end of the MOI; and wherein no two compounds have either the same $T^{ms}$ or the same MOI.

In another aspect, the invention provides a composition comprising water and a compound of the formula $T^{ms}-L-MOI$, wherein, $T^{ms}$ is an organic group detectable by mass spectrometry, comprising carbon, at least one of hydrogen and fluoride, and optional atoms selected from oxygen, nitrogen, sulfur, phosphorus and iodine; L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid; and MOI is a nucleic acid fragment wherein L is conjugated to the MOI at a location other than the 3' end of the MOI.

In another aspect, the invention provides for a composition comprising a plurality of sets of compounds, each set of compounds having the formula $T^{ms}-L-MOI$, wherein, $T^{ms}$ is an organic group detectable by mass spectrometry, comprising carbon, at least one of hydrogen and fluoride, and optional atoms selected from oxygen, nitrogen, sulfur, phosphorus and iodine; L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid; MOI is a nucleic acid fragment wherein L is conjugated to the MOI at a location other than the 3' end of the MOI; wherein within a set, all members have the same $T^{ms}$ group, and the MOI fragments have variable lengths that terminate with the same dideoxynucleotide selected from ddAMP, ddGMP, ddCMP and ddTMP; and wherein between sets, the $T^{ms}$ groups differ by at least 2 amu.

In another aspect, the invention provides for a composition comprising a first plurality of sets of compounds as described in the preceding paragraph, in combination with a second plurality of sets of compounds having the formula $T^{ms}-L-MOI$, wherein, $T^{ms}$ is an organic group detectable by mass spectrometry, comprising carbon, at least one of hydrogen and fluoride, and optional atoms selected from oxygen, nitrogen, sulfur, phosphorus and iodine; L is an organic group which allows a $T^{ms}$-containing moiety to be cleaved from the remainder of the compound, wherein the $T^{ms}$-containing moiety comprises a fumctional group which supports a single ionized charge state when the compound is subjected to mass spectrometry and is selected from tertiary amine, quaternary amine and organic acid; MOI is a nucleic acid fragment wherein L is conjugated to the MOI at a location other than the 3' end of the MOI; and wherein all members within the second plurality have an MOI sequence which terminates with the same dideoxynucleotide selected from ddAMP, ddGMP, ddCMP and ddTMP; with the proviso that the dideoxynucleotide present in the compounds of the first plurality is not the same dideoxynucleotide present in the compounds of the second plurality.

In another aspect, the invention provides for a kit for DNA sequencing analysis. The kit comprises a plurality of container sets, each container set comprising at least five containers, wherein a first container contains a vector, a second, third, fourth and fifth containers contain compounds of the formula $T^{ms}-L-MOI$ wherein, $T^{ms}$ is an organic group detectable by mass spectrometry, comprising carbon, at least one of hydrogen and fluoride, and optional atoms selected from oxygen, nitrogen, sulfur, phosphorus and iodine; L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid; and MOI is a nucleic acid fragment wherein L is conjugated to the MOI at a location other than the 3' end of the MOI; such that the MOI for the second, third, fourth and fifth containers is identical and complementary to a portion of the vector within the set of containers, and the $T^{ms}$ group within each container is different from the other $T^{ms}$ groups in the kit.

In another aspect, the invention provides for systems for determining the sequence of a nucleic acid molecule in a sample. In one embodiment, a system comprises a system for determining the sequence of a nucleic acid molecule in a sample, the sample including tagged nucleic acid fragments having nucleic acid fragments and tags attached to the nucleic acid fragments, comprising a separation apparatus that separates tagged nucleic acid fragments, a cleavage apparatus that receives separated tagged cleaves nucleic acid fragments and the tags from the nucleic acid fragments, each tag being correlative with a particular nucleotide of the nucleic acid fragment and detectable by electrochemical detection, and an apparatus for electrochemical detection that receives and detects electrochemical signatures of the tags. In a preferred embodiment, the system further includes a data processor that correlates the electrochemical signature of a tag to a particular nucleotide and to a specific sample. In another embodiment, a system comprises a system for determining the sequence of a nucleic acid molecule in a sample, the sample including tagged nucleic acid fragments having nucleic acid fragments and tags attached to the nucleic acid fragments, comprising a separation apparatus that separates tagged nucleic acid fragments, a cleavage apparatus that receives separated tagged nucleic acid fragments and cleaves from the nucleic acid fragments, each tag being correlative with a particular nucleotide of the nucleic acid fragment and detectable by mass spectrometry, a mass spectrometer that receives the tags and detects a mass of a tag, and a data processor that correlates the mass of a tag to a particular nucleotide and to a specific sample.

Within other embodiments of the invention, 4, 5, 10, 15, 20, 25, 30, 35, 40, 50, 60, 70, 80, 90, 100, 200, 250, 300, 350, 400, 450 or greater than 500 different and unique tagged molecules may be utilized within a given reaction simultaneously, wherein each tag is unique for a selected nucleic acid fragment, probe, or first or second member, and may be separately identified.

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety.

DETAILED DESCRIPTION OF THE INVENTION

Figure 1A:
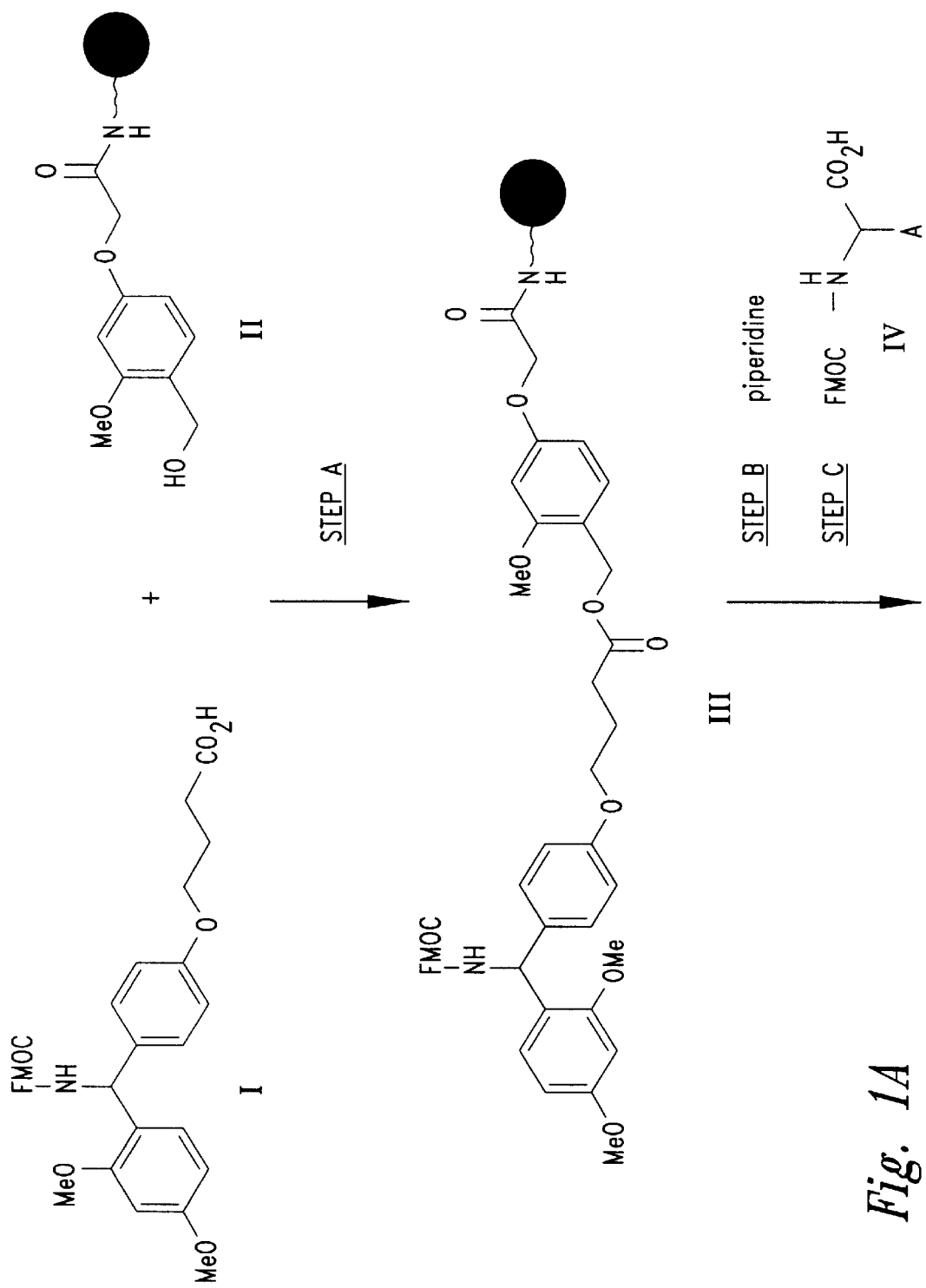
FIG. 1 depicts the flowchart for the synthesis of pentafluorophenyl esters of chemically cleavable mass spectroscopy tags, to liberate tags with carboxyl amide termini.

Briefly stated, in one aspect the present invention provides compounds wherein a molecule of interest, or precursor thereto, is linked via a labile bond (or labile bonds) to a tag. Thus, compounds of the invention may be viewed as having the general formula:

T—L—X 

wherein T is the tag component, L is the linker component that either is, or contains, a labile bond, and X is either the molecule of interest (MOI) component or a fumctional group component ($L_h$) through which the MOI may be joined to T—L. Compounds of the invention may therefore be represented by the more specific general formulas:

T—L—MOI 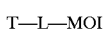

and

T—L—$L_h$ 

For reasons described in detail below, sets of T—L—MOI compounds may be purposely subjected to conditions that cause the labile bond(s) to break, thus releasing a tag moiety from the remainder of the compound. The tag moiety is then characterized by one or more analytical techniques, to thereby provide direct information about the structure of the tag moiety, and (most importantly) indirect information about the identity of the corresponding MOI.

As a simple illustrative example of a representative compound of the invention wherein L is a direct bond, reference is made to the following structure (i):

Structure (i)

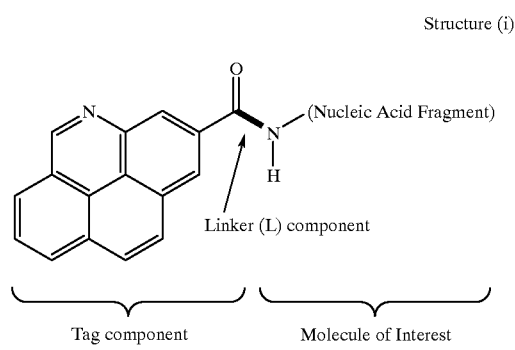

In structure (i), T is a nitrogen-containing polycyclic aromatic moiety bonded to a carbonyl group, X is a MOI (and specifically a nucleic acid fragment terminating in an amine group), and L is the bond which forms an amide group. The amide bond is labile relative to the bonds in T because, as recognized in the art, an amide bond may be chemically cleaved (broken) by acid or base conditions which leave the bonds within the tag component unchanged. Thus, a tag moiety (i.e., the cleavage product that contains T) may be released as shown below:

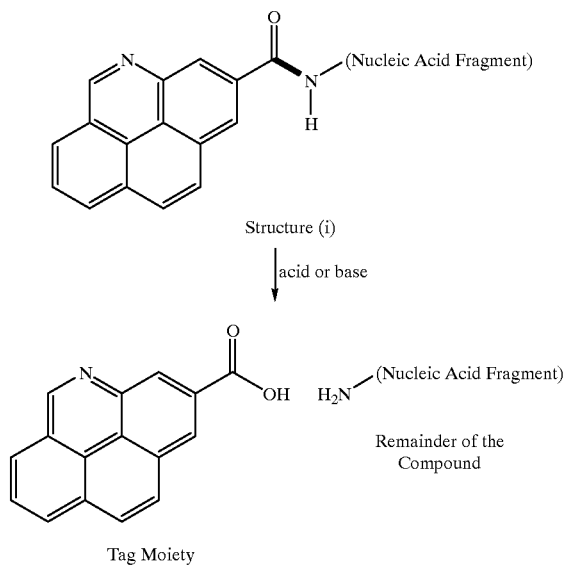

However, the linker L may be more than merely a direct bond, as shown in the following illustrative example, where reference is made to another representative compound of the invention having the structure (ii) shown below:

Structure (ii)

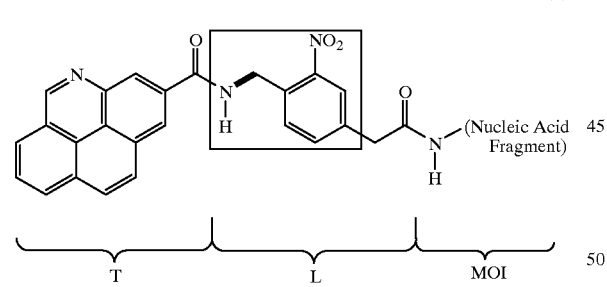

It is well-known that compounds having an ortho-nitrobenzylamine moiety (see boxed atoms within structure (ii)) are photolytically unstable, in that exposure of such compounds to actinic radiation of a specified wavelength will cause selective cleavage of the benzylamine bond (see bond denoted with heavy line in structure (ii)). Thus, structure (ii) has the same T and MOI groups as structure (i), however the linker group contains multiple atoms and bonds within which there is a particularly labile bond. Photolysis of structure (ii) thus releases a tag moiety (T-containing moiety) from the remainder of the compound, as shown below.

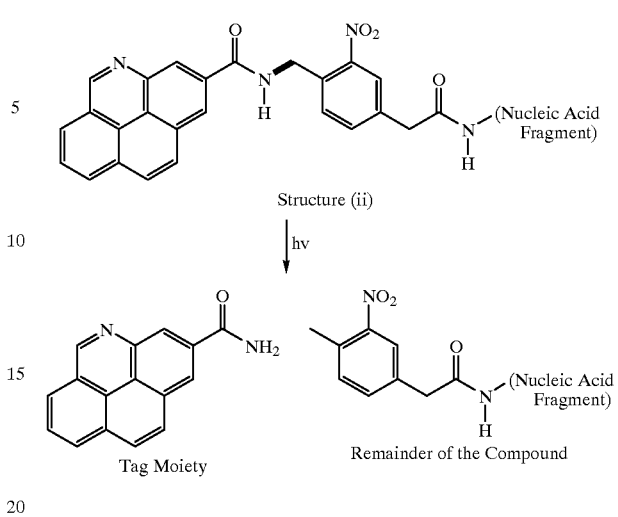

The invention thus provides compounds which, upon exposure to appropriate cleavage conditions, undergo a cleavage reaction so as to release a tag moiety from the remainder of the compound. Compounds of the invention may be described in terms of the tag moiety, the MOI (or precursor thereto, $L_h$), and the labile bond(s) which join the two groups together. Alternatively, the compounds of the invention may be described in terms of the components from which they are formed. Thus, the compounds may be described as the reaction product of a tag reactant, a linker reactant and a MOI reactant, as follows.

The tag reactant consists of a chemical handle ($T_h$) and a variable component ($T_{vc}$), so that the tag reactant is seen to have the general structure:

$T_{vc}$—$T_h$

To illustrate this nomenclature, reference may be made to structure (iii), which shows a tag reactant that may be used to prepare the compound of structure (ii). The tag reactant having structure (iii) contains a tag variable component and a tag handle, as shown below:

Structure (iii)

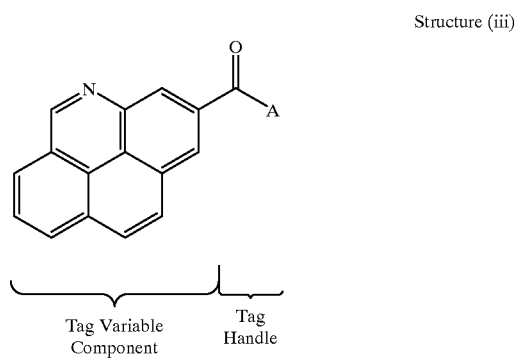

In structure (iii), the tag handle (—C(=O)—A) simply provides an avenue for reacting the tag reactant with the linker reactant to form a T—L moiety. The group "A" in structure (iii) indicates that the carboxyl group is in a chemically active state, so it is ready for coupling with other handles. "A" may be, for example, a hydroxyl group or pentafluorophenoxy, among many other possibilities. The invention provides for a large number of possible tag handles which may be bonded to a tag variable component, as discussed in detail below. The tag variable component is thus a part of "T" in the formula T—L—X, and will also be part of the tag moiety that forms from the reaction that cleaves L.

As also discussed in detail below, the tag variable component is so-named because, in preparing sets of compounds according to the invention, it is desired that members of a set have unique variable components, so that the individual members may be distinguished from one another by an analytical technique. As one example, the tag variable component of structure (iii) may be one member of the following set, where members of the set may be distinguished by their UV or mass spectra:

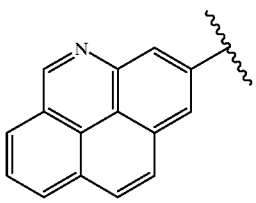

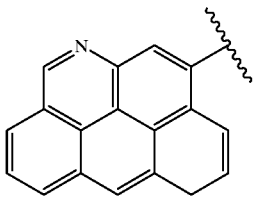

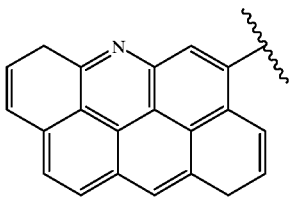

Likewise, the linker reactant may be described in terms of its chemical handles (there are necessarily at least two, each of which may be designated as $L_h$) which flank a linker labile component, where the linker labile component consists of the required labile moiety ($L^2$) and optional labile moieties ($L^1$ and $L^3$), where the optional labile moieties effectively serve to separate $L^2$ from the handles $L_h$, and the required labile moiety serves to provide a labile bond within the linker labile component. Thus, the linker reactant may be seen to have the general formula:

$$L_h—L^1—L^2—L^3—L_h$$

The nomenclature used to describe the linker reactant may be illustrated in view of structure (iv), which again draws from the compound of structure (ii):

Structure (iv)

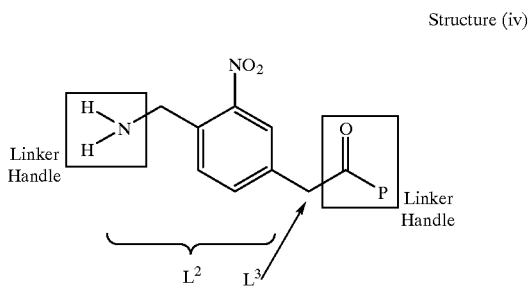

As structure (iv) illustrates, atoms may serve in more than one functional role. Thus, in structure (iv), the benzyl nitrogen functions as a chemical handle in allowing the linker reactant to join to the tag reactant via an amide-forming reaction, and subsequently also serves as a necessary part of the structure of the labile moiety $L^2$ in that the benzylic carbon-nitrogen bond is particularly susceptible to photolytic cleavage. Structure (iv) also illustrates that a linker reactant may have an $L^3$ group (in this case, a methylene group), although not have an $L^1$ group. Likewise, linker reactants may have an $L^1$ group but not an $L^3$ group, or may have $L^1$ and $L^3$ groups, or may have neither of $L^1$ nor $L^3$ groups. In structure (iv), the presence of the group "P" next to the carbonyl group indicates that the carbonyl group is protected from reaction. Given this configuration, the activated carboxyl group of the tag reactant (iii) may cleanly react with the amine group of the linker reactant (iv) to form an amide bond and give a compound of the formula T—L—$L_h$.

The MOI reactant is a suitably reactive form of a molecule of interest. Where the molecule of interest is a nucleic acid fragment, a suitable MOI reactant is a nucleic acid fragment bonded through its 5' hydroxyl group to a phosphodiester group and then to an alkylene chain that terminates in an amino group. This amino group may then react with the carbonyl group of structure (iv), (after, of course, deprotecting the carbonyl group, and preferably after subsequently activating the carbonyl group toward reaction with the amine group) to thereby join the MOI to the linker.

When viewed in a chronological order, the invention is seen to take a tag reactant (having a chemical tag handle and a tag variable component), a linker reactant (having two chemical linker handles, a required labile moiety and 0–2 optional labile moieties) and a MOI reactant (having a molecule of interest component and a chemical molecule of interest handle) to form T—L—MOI. Thus, to form T—L—MOI, either the tag reactant and the linker reactant are first reacted together to provide T—L—$L_h$, and then the MOI reactant is reacted with T—L—$L_h$ so as to provide T—L—MOI, or else (less preferably) the linker reactant and the MOI reactant are reacted together first to provide $L_h$—L—MOI, and then $L_h$—L—MOI is reacted with the tag reactant to provide T—L—MOI. For purposes of convenience, compounds having the formula T—L—MOI will be described in terms of the tag reactant, the linker reactant and the MOI reactant which may be used to form such compounds. Of course, the same compounds of formula T—L—MOI could be prepared by other (typically, more laborious) methods, and still fall within the scope of the inventive T—L—MOI compounds.

In any event, the invention provides that a T—L—MOI compound be subjected to cleavage conditions, such that a tag moiety is released from the remainder of the compound. The tag moiety will comprise at least the tag variable component, and will typically additionally comprise some or all of the atoms from the tag handle, some or all of the atoms from the linker handle that was used to join the tag reactant to the linker reactant, the optional labile moiety $L^1$ if this group was present in T—L—MOI, and will perhaps contain some part of the required labile moiety $L^2$ depending on the precise structure of $L^2$ and the nature of the cleavage chemistry. For convenience, the tag moiety may be referred to as the T-containing moiety because T will typically constitute the major portion (in terms of mass) of the tag moiety.

Given this introduction to one aspect of the present invention, the various components T, L and X will be described in detail. This description begins with the following definitions of certain terms, which will be used hereinafter in describing T, L and X.

As used herein, the term "nucleic acid fragment" means a molecule which is complementary to a selected target nucleic acid molecule (i.e., complementary to all or a portion thereof), and may be derived from nature or synthetically or recombinantly produced, including non-naturally occurring molecules, and may be in double or single stranded form where appropriate; and includes an oligonucleotide (e.g., DNA or RNA), a primer, a probe, a nucleic acid analog (e.g., PNA), an oligonucleotide which is extended in a 5' to 3' direction by a polymerase, a nucleic acid which is cleaved chemically or enzymatically, a nucleic acid that is terminated with a dideoxy terminator or capped at the 3' or 5' end with a compound that prevents polymerization at the 5' or 3' end, and combinations thereof. The complementarity of a nucleic acid fragment to a selected target nucleic acid molecule generally means the exhibition of at least about 70% specific base pairing throughout the length of the fragment. Preferably the nucleic acid fragment exhibits at least about 80% specific base pairing; and most preferably at least about 90%. Assays for determining the percent mismatch (and thus the percent specific base pairing) are well known in the art and are based upon the percent mismatch as a function of the Tm when referenced to the fully base paired control.

As used herein, the term "alkyl," alone or in combination, refers to a saturated, straight-chain or branched-chain hydrocarbon radical containing from 1 to 10, preferably from 1 to 6 and more preferably from 1 to 4, carbon atoms. Examples of such radicals include, but are not limited to, methyl, ethyl, n-propyl, iso-propyl, n-butyl, iso-butyl, sec-butyl, tert-butyl, pentyl, iso-amyl, hexyl, decyl and the like. The term "alkylene" refers to a saturated, straight-chain or branched chain hydrocarbon diradical containing from 1 to 10, preferably from 1 to 6 and more preferably from 1 to 4, carbon atoms. Examples of such diradicals include, but are not limited to, methylene, ethylene (—CH$_2$—CH$_2$—), propylene, and the like.

The term "alkenyl," alone or in combination, refers to a straight-chain or branched-chain hydrocarbon radical having at least one carbon-carbon double bond in a total of from 2 to 10, preferably from 2 to 6 and more preferably from 2 to 4, carbon atoms. Examples of such radicals include, but are not limited to, ethenyl, E- and Z-propenyl, isopropenyl, E- and Z-butenyl, E- and Z-isobutenyl, E- and Z-pentenyl, decenyl and the like. The term "alkenylene" refers to a straight-chain or branched-chain hydrocarbon diradical having at least one carbon-carbon double bond in a total of from 2 to 10, preferably from 2 to 6 and more preferably from 2 to 4, carbon atoms. Examples of such diradicals include, but are not limited to, methylidene (=CH$_2$), ethylidene (—CH=CH—), propylidene (—CH$_2$—CH=CH—) and the like.

The term "alkynyl," alone or in combination, refers to a straight-chain or branched-chain hydrocarbon radical having at least one carbon-carbon triple bond in a total of from 2 to 10, preferably from 2 to 6 and more preferably from 2 to 4, carbon atoms. Examples of such radicals include, but are not limited to, ethynyl (acetylenyl), propynyl (propargyl), butynyl, hexynyl, decynyl and the like. The term "alkynylene", alone or in combination, refers to a straight-chain or branched-chain hydrocarbon diradical having at least one carbon-carbon triple bond in a total of from 2 to 10, preferably from 2 to 6 and more preferably from 2 to 4, carbon atoms. Examples of such radicals include, but are not limited, ethynylene (—C≡C—), propynylene (—CH$_2$—C≡C—) and the like.

The term "cycloalkyl," alone or in combination, refers to a saturated, cyclic arrangement of carbon atoms which number from 3 to 8 and preferably from 3 to 6, carbon atoms. Examples of such cycloalkyl radicals include, but are not limited to, cyclopropyl, cyclobutyl, cyclopentyl, cyclohexyl and the like. The term "cycloalkylene" refers to a diradical form of a cycloalkyl.

The term "cycloalkenyl," alone or in combination, refers to a cyclic carbocycle containing from 4 to 8, preferably 5 or 6, carbon atoms and one or more double bonds. Examples of such cycloalkenyl radicals include, but are not limited to, cyclopentenyl, cyclohexenyl, cyclopentadienyl and the like. The term "cycloalkenylene" refers to a diradical form of a cycloalkenyl.

The term "aryl" refers to a carbocyclic (consisting entirely of carbon and hydrogen) aromatic group selected from the group consisting of phenyl, naphthyl, indenyl, indanyl, azulenyl, fluorenyl, and anthracenyl; or a heterocyclic aromatic group selected from the group consisting of furyl, thienyl, pyridyl, pyrrolyl, oxazolyly, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl.

"Aryl" groups, as defined in this application may independently contain one to four substituents which are independently selected from the group consisting of hydrogen, halogen, hydroxyl, amino, nitro, trifluoromethyl, trifluoromethoxy, alkyl, alkenyl, alkynyl, cyano, carboxy, carboalkoxy, 1,2-dioxyethylene, alkoxy, alkenoxy or alkynoxy, alkylamino, alkenylamino, alkynylamino, aliphatic or aromatic acyl, alkoxy-carbonylamino, alkylsulfonylamino, morpholinocarbonylamino, thiomorpholinocarbonylamino, N-alkyl guanidino, aralkylaminosulfonyl; aralkoxyalkyl; N-aralkoxyurea; N-hydroxylurea; N-alkenylurea; N,N-(alkyl, hydroxyl)urea; heterocyclyl; thioaryloxy-substituted aryl; N,N-(aryl, alkyl) hydrazino; Ar'-substituted sulfonylheterocyclyl; aralkyl-substituted heterocyclyl; cycloalkyl and cycloakenyl-substituted heterocyclyl; cycloalkyl-fused aryl; aryloxy-substituted alkyl; heterocyclylamino; aliphatic or aromatic acylaminocarbonyl; aliphatic or aromatic acyl-substituted alkenyl; Ar'-substituted aminocarbonyloxy; Ar', Ar'- disubstituted aryl; aliphatic or aromatic acyl-substituted acyl; cycloalkylcarbonylalkyl; cycloalkyl-substituted amino; aryloxycarbonylalkyl; phosphorodiamidyl acid or ester;

"Ar" is a carbocyclic or heterocyclic aryl group as defined above having one to three substituents selected from the group consisting of hydrogen, halogen, hydroxyl, amnino, nitro, trifluoromethyl, trifluoromethoxy, alkyl, alkenyl, alkynyl, 1,2-dioxymethylene, 1,2-dioxyethylene, alkoxy, alkenoxy, alkynoxy, alkylamino, alkenylamino or alkynylamino, alkylcarbonyloxy, aliphatic or aromatic acyl, alkylcarbonylamino, alkoxycarbonylamino, alkylsulfonylamino, N-alkyl or N,N-dialkyl urea.

The term "alkoxy," alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "alkenoxy," alone or in combination, refers to a radical of formula alkenyl-O—, wherein the term "alkenyl" is as defined above provided that the radical is not an enol ether. Examples of suitable alkenoxy radicals include, but are not limited to, allyloxy, E- and Z-3-methyl-2-propenoxy and the like.

The term "alkynyloxy," alone or in combination, refers to a radical of formula alkynyl-O—, wherein the term "alkynyl" is as defined above provided that the radical is not an ynol ether. Examples of suitable alkynoxy radicals include, but are not limited to, propargyloxy, 2-butynyloxy and the like.

The term "thioalkoxy" refers to a thioether radical of formula alkyl-S—, wherein alkyl is as defined above.

The term "alkylamino," alone or in combination, refers to a mono- or di-alkyl-substituted amino radical (i.e., a radical of formula alkyl-NH— or (alkyl)$_2$—N—), wherein the term "alkyl" is as defined above. Examples of suitable alkylamino radicals include, but are not limited to, methylamino, ethylamino, propylamino, isopropylamino, t-butylamino, N,N-diethylamino and the like.

The term "alkenylamino," alone or in combination, refers to a radical of formula alkenyl-NH— or (alkenyl)$_2$N—, wherein the term "alkenyl" is as defined above, provided that the radical is not an enamine. An example of such alkenylamino radicals is the allylamino radical.

The term "alkynylamino," alone or in combination, refers to a radical of formula alkynyl-NH— or (alkynyl)$_2$N—, wherein the term "alkynyl" is as defined above, provided that the radical is not an ynamine. An example of such alkynylamino radicals is the propargyl amino radical.

The term "amide" refers to either —N(R$^1$)—C(=O)— or —C(=O)—N(R$^1$)— where R$^1$ is defined herein to include hydrogen as well as other groups. The term "substituted amide" refers to the situation where R$^1$ is not hydrogen, while the term "unsubstituted amide" refers to the situation where R$^1$ is hydrogen.

The term "aryloxy," alone or in combination, refers to a radical of formula aryl-O—, wherein aryl is as defined above. Examples of aryloxy radicals include, but are not limited to, phenoxy, naphthoxy, pyridyloxy and the like.

The term "arylamino," alone or in combination, refers to a radical of formula aryl-NH—, wherein aryl is as defined above. Examples of arylamino radicals include, but are not limited to, phenylamino (anilido), naphthylamino, 2-, 3- and 4-pyridylamino and the like.

The term "aryl-fused cycloalkyl," alone or in combination, refers to a cycloalkyl radical which shares two adjacent atoms with an aryl radical, wherein the terms "cycloalkyl" and "aryl" are as defined above. An example of an aryl-fused cycloalkyl radical is the benzofused cyclobutyl radical.

The term "alkylcarbonylamino," alone or in combination, refers to a radical of formula alkyl-CONH, wherein the term "alkyl" is as defined above.

The term "alkoxycarbonylamino," alone or in combination, refers to a radical of formula alkyl-OCONH—, wherein -the term "alkyl" is as defined above.

The term "alkylsulfonylamino," alone or in combination, refers to a radical of formula alkyl-SO$_2$NH—, wherein the term "alkyl" is as defined above.

The term "arylsulfonylamino," alone or in combination, refers to a radical of formula aryl-SO$_2$NH—, wherein the term "aryl" is as defined above.

The term "N-alkylurea," alone or in combination, refers to a radical of formula alkyl-NH—CO—NH—, wherein the term "alkyl" is as defined above.

The termr "N-arylurea," alone or in combination, refers to a radical of formula aryl-NH—CO—NH—, wherein the term "aryl" is as defined above.

The term "halogen" means fluorine, chlorine, bromine and iodine.

The term "hydrocarbon radical" refers to an arrangement of carbon and hydrogen atoms which need only a single hydrogen atom to be an independent stable molecule. Thus, a hydrocarbon radical has one open valence site on a carbon atom, through which the hydrocarbon radical may be bonded to other atom(s). Alkyl, alkenyl, cycloalkyl, etc. are examples of hydrocarbon radicals.

The term "hydrocarbon diradical" refers to an arrangement of carbon and hydrogen atoms which need two hydrogen atoms in order to be an independent stable molecule. Thus, a hydrocarbon radical has two open valence sites on one or two carbon atoms, through which the hydrocarbon radical may be bonded to other atom(s). Alkylene, alkenylene, alkynylene, cycloalkylene, etc. are examples of hydrocarbon diradicals.

The term "hydrocarbyl" refers to any stable arrangement consisting entirely of carbon and hydrogen having a single valence site to which it is bonded to another moiety, and thus includes radicals known as alkyl, alkenyl, alkynyl, cycloalkyl, cycloalkenyl, aryl (without heteroatom incorporation into the aryl ring), arylalkyl, alkylaryl and the like. Hydrocarbon radical is another name for hydrocarbyl.

The term "hydrocarbylene" refers to any stable arrangement consisting entirely of carbon and hydrogen having two valence sites to which it is bonded to other moieties, and thus includes alkylene, alkenylene, alkynylene, cycloalkylene, cycloalkenylene, arylene (without heteroatom incorporation into the arylene ring), arylalkylene, alkylarylene and the like. Hydrocarbon diradical is another name for hydrocarbylene.

The term "hydrocarbyl-O-hydrocarbylene" refers to a hydrocarbyl group bonded to an oxygen atom, where the oxygen atom is likewise bonded to a hydrocarbylene group at one of the two valence sites at which the hydrocarbylene group is bonded to other moieties. The terms "hydrocarbyl-S-hydrocarbylene", "hydrocarbyl-NH-hydrocarbylene" and "hydrocarbyl-amide-hydrocarbylene" have equivalent meanings, where oxygen has been replaced with sulfur, —NH— or an amide group, respectively.

The term N-(hydrocarbyl)hydrocarbylene refers to a hydrocarbylene group wherein one of the two valence sites is bonded to a nitrogen atom, and that nitrogen atom is simultaneously bonded to a hydrogen and a hydrocarbyl group. The term N,N-di(hydrocarbyl)hydrocarbylene refers to a hydrocarbylene group wherein one of the two valence sites is bonded to a nitrogen atom, and that nitrogen atom is simultaneously bonded to two hydrocarbyl groups.

The term "hydrocarbylacyl-hydrocarbylene" refers to a hydrocarbyl group bonded through an acyl (—C(=O)—) group to one of the two valence sites of a hydrocarbylene group.

The terms "heterocyclylhydrocarbyl" and "heterocylyl" refer to a stable, cyclic arrangement of atoms which include carbon atoms and up to four atoms (referred to as heteroatoms) selected from oxygen, nitrogen, phosphorus and sulfur. The cyclic arrangement may be in the form of a monocyclic ring of 3–7 atoms, or a bicyclic ring of 8–11 atoms. The rings may be saturated or unsaturated (including aromatic rings), and may optionally be benzofused. Nitrogen and sulfur atoms in the ring may be in any oxidized form, including the quaternized form of nitrogen. A heterocyclylhydrocarbyl may be attached at any endocyclic carbon or heteroatom which results in the creation of a stable structure. Preferred heterocyclylhydrocarbyls include 5–7 membered monocyclic heterocycles containing one or two nitrogen heteroatoms.

A substituted heterocyclylhydrocarbyl refers to a heterocyclylhydrocarbyl as defined above, wherein at least one ring atom thereof is bonded to an indicated substituent which extends off of the ring.

In referring to hydrocarbyl and hydrocarbylene groups, the term "derivatives of any of the foregoing wherein one or more hydrogens is replaced with an equal number of fluorides" refers to molecules that contain carbon, hydrogen and fluoride atoms, but no other atoms.

The term "activated ester" is an ester that contains a "leaving group" which is readily displaceable by a nucleophile, such as an amine, an alcohol or a thiol nucleophile. Such leaving groups are well known and include, without limitation, N-hydroxysuccinimide, N-hydroxybenzotriazole, halogen (halides), alkoxy including tetrafluorophenolates, thioalkoxy and the like. The term "protected ester" refers to an ester group that is masked or otherwise unreactive. See, e.g., Greene, "Protecting Groups In Organic Synthesis."

In view of the above definitions, other chemical terms used throughout this application can be easily understood by those of skill in the art. Terms may be used alone or in any combination thereof. The preferred and more preferred chain lengths of the radicals apply to all such combinations.

A. Generation of Tagged Nucleic Acid Fragments

As noted above, one aspect of the present invention provides a general scheme for DNA sequencing which allows the use of more than 16 tags in each lane; with continuous detection, the tags can be detected and the sequence read as the size separation is occurring, just as with conventional fluorescence-based sequencing. This scheme is applicable to any of the DNA sequencing techniques based on size separation of tagged molecules. Suitable tags and linkers for use within the present invention, as well as methods for sequencing nucleic acids, are discussed in more detail below.

1. Tags

"Tag", as used herein, generally refers to a chemical moiety which is used to uniquely identify a "molecule of interest", and more specifically refers to the tag variable component as well as whatever may be bonded most closely to it in any of the tag reactant, tag component and tag moiety.

A tag which is useful in the present invention possesses several attributes:

1) It is capable of being distinguished from all other tags. This discrimination from other chemical moieties can be based on the chromatographic behavior of the tag (particularly after the cleavage reaction), its spectroscopic or potentiometric properties, or some combination thereof. Spectroscopic methods by which tags are usefully distinguished include mass spectroscopy (MS), infrared (IR), ultraviolet (UV), and fluorescence, where MS, IR and UV are preferred, and MS most preferred spectroscopic methods. Potentiometric amperometry is a preferred potentiometric method.

2) The tag is capable of being detected when present at $10^{-22}$ to $10^{-6}$ mole.

3) The tag possesses a chemical handle through which it can be attached to the MOI which the tag is intended to uniquely identify. The attachment may be made directly to the MOI, or indirectly through a "linker" group.

4) The tag is chemically stable toward all manipulations to which it is subjected, including attachment and cleavage from the MOI, and any manipulations of the MOI while the tag is attached to it.

5) The tag does not significantly interfere with the manipulations performed on the MOI while the tag is attached to it. For instance, if the tag is attached to an oligonucleotide, the tag must not significantly interfere with any hybridization or enzymatic reactions (e.g., PCR sequencing reactions) performed on the oligonucleotide. Similarly, if the tag is attached to an antibody, it must not significantly interfere with antigen recognition by the antibody.

A tag moiety which is intended to be detected by a certain spectroscopic or potentiometric method should possess properties which enhance the sensitivity and specificity of detection by that method. Typically, the tag moiety will have those properties because they have been designed into the tag variable component, which will typically constitute the major portion of the tag moiety. In the following discussion, the use of the word "tag" typically refers to the tag moiety (i.e., the cleavage product that contains the tag variable component), however can also be considered to refer to the tag variable component itself because that is the portion of the tag moiety which is typically responsible for providing the uniquely detectable properties. In compounds of the formula T—L—X, the "T" portion will contain the tag variable component. Where the tag variable component has been designed to be characterized by, e.g., mass spectrometry, the "T" portion of T—L—X may be referred to as $T^{ms}$. Likewise, the cleavage product from T—L—X that contains T may be referred to as the $T^{ms}$-containing moiety. The following spectroscopic and potentiometric methods may be used to characterize $T^{ms}$-containing moieties. *a. Characteristics of MS Tags*

Where a tag is analyzable by mass spectrometry (i.e., is a MS-readable tag, also referred to herein as a MS tag or "$T^{ms}$-containing moiety"), the essential feature of the tag is that it is able to be ionized. It is thus a preferred element in the design of MS-readable tags to incorporate therein a chemical functionality which can carry a positive or negative charge under conditions of ionization in the MS. This feature confers improved efficiency of ion formation and greater overall sensitivity of detection, particularly in electrospray ionization. The chemical functionality that supports an ionized charge may derive from $T^{ms}$ or L or both. Factors that can increase the relative sensitivity of an analyte being detected by mass spectrometry are discussed in, e.g., Sunner, J., et al., *Anal. Chem.* 60:1300–1307 (1988).

A preferred functionality to facilitate the carrying of a negative charge is an organic acid, such as phenolic hydroxyl, carboxylic acid, phosphonate, phosphate, tetrazole, sulfonyl urea, perfluoro alcohol and sulfonic acid.

Preferred functionality to facilitate the carrying of a positive charge under ionization conditions are aliphatic or aromatic amines. Examples of amine functional groups which give enhanced detectability of MS tags include quaternary amines (i.e., amines that have four bonds, each to carbon atoms, see Aebersold, U.S. Pat. No. 5,240,859) and tertiary amines (i.e., amines that have three bonds, each to carbon atoms, which includes C=N—C groups such as are present in pyridine, see Hess et al., *Anal. Biochem.* 224:373, 1995; Bures et al., *Anal. Biochem.* 224:364, 1995). Hindered tertiary amines are particularly preferred. Tertiary and quaternary amines may be alkyl or aryl. A $T^{ms}$-containing moiety must bear at least one ionizable species, but may possess more than one ionizable species. The preferred charge state is a single ionized species per tag. Accordingly, it is preferred that each $T^{ms}$-containing moiety (and each tag variable component) contain only a single hindered amine or organic acid group.

Suitable amine-containing radicals that may form part of the $T^{ms}$-containing moiety include the following:

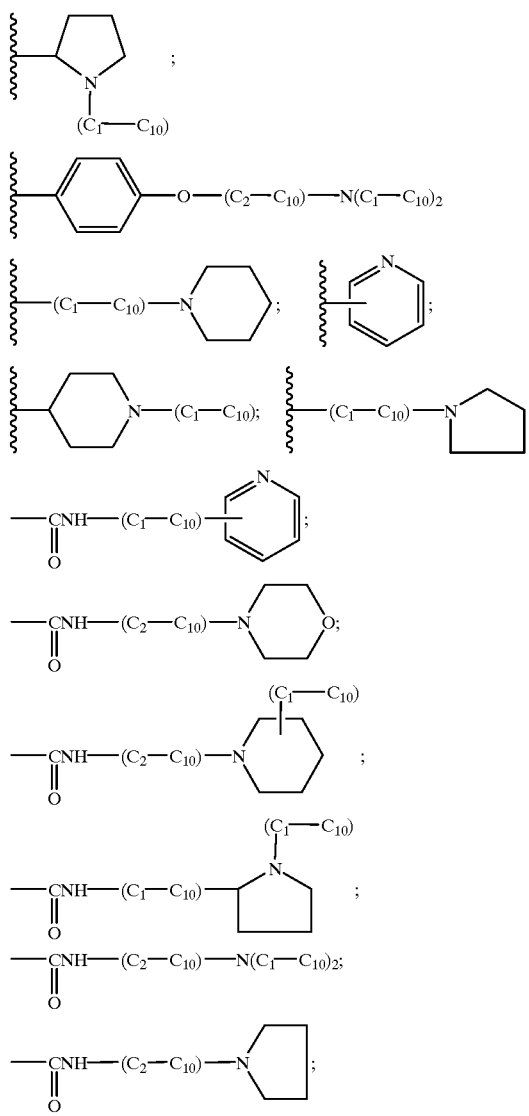

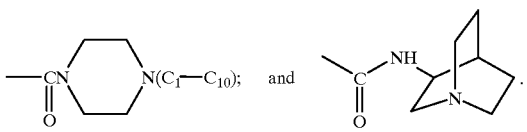

The identification of a tag by mass spectrometry is preferably based upon its molecular mass to charge ratio (m/z). The preferred molecular mass range of MS tags is from about 100 to 2,000 daltons, and preferably the $T^{ms}$-containing moiety has a mass of at least about 250 daltons, more preferably at least about 300 daltons, and still more preferably at least about 350 daltons. It is generally difficult for mass spectrometers to distinguish among moieties having parent ions below about 200–250 daltons (depending on the precise instrument), and thus preferred $T^{ms}$-containing moieties of the invention have masses above that range.

As explained above, the $T^{ms}$-containing moiety may contain atoms other than those present in the tag variable component, and indeed other than present in $T^{ms}$ itself. Accordingly, the mass of $T^{ms}$ itself may be less than about 250 daltons, so long as the $T^{ms}$-containing moiety has a mass of at least about 250 daltons. Thus, the mass of $T^{ms}$ may range from 15 (i.e., a methyl radical) to about 10,000 daltons, and preferably ranges from 100 to about 5,000 daltons, and more preferably ranges from about 200 to about 1,000 daltons.

It is relatively difficult to distinguish tags by mass spectrometry when those tags incorporate atoms that have more than one isotope in significant abundance. Accordingly, preferred T groups which are intended for mass spectroscopic identification ($T^{ms}$ groups), contain carbon, at least one of hydrogen and fluoride, and optional atoms selected from oxygen, nitrogen, sulfur, phosphorus and iodine. While other atoms may be present in the $T^{ms}$, their presence can render analysis of the mass spectral data somewhat more difficult. Preferably, the $T^{ms}$ groups have only carbon, nitrogen and oxygen atoms, in addition to hydrogen and/or fluoride.

Fluoride is an optional yet preferred atom to have in a $T^{ms}$ group. In comparison to hydrogen, fluoride is, of course, much heavier. Thus, the presence of fluoride atoms rather than hydrogen atoms leads to $T^{ms}$ groups of higher mass, thereby allowing the $T^{ms}$ group to reach and exceed a mass of greater than 250 daltons, which is desirable as explained above. In addition, the replacement of hydrogen with fluoride confers greater volatility on the $T^{ms}$-containing moiety, and greater volatility of the analyte enhances sensitivity when mass spectrometry is being used as the detection method.

The molecular formula of $T^{ms}$ falls within the scope of $C_{1-500}N_{0-100}O_{0-100}S_{0-10}P_{0-10}H_\alpha F_\beta P_\delta$ wherein the sum of $\alpha$, $\beta$ and $\delta$ is sufficient to satisfy the otherwise unsatisfied valencies of the C, N, O, S and P atoms. The designation $C_{1-500}N_{0-100}O_{0-100}S_{0-10}P_{0-10}H_\alpha F_\beta I_\delta$ means that $T^{ms}$ contains at least one, and may contain any number from 1 to 500 carbon atoms, in addition to optionally containing as many as 100 nitrogen atoms ("$N_0$" means that $T^{ms}$ need not contain any nitrogen atoms), and as many as 100 oxygen atoms, and as many as 10 sulfur atoms and as many as 10 phosphorus atoms. The symbols $\alpha$, $\beta$ and $\delta$ represent the number of hydrogen, fluoride and iodide atoms in $T^{ms}$, where any two of these numbers may be zero, and where the sum of these numbers equals the total of the otherwise unsatisfied valencies of the C, N, O, S and P atoms. Preferably, $T^{ms}$ has a molecular formula that falls within the scope of $C_{1-50}N_{0-10}O_{0-10}H_\alpha F_\beta$ where the sum of α and β equals the number of hydrogen and fluoride atoms, respectively, present in the moiety.

b. Characteristics of IR Tags

There are two primary forms of IR detection of organic chemical groups:

Raman scattering IR and absorption IR Raman scattering IR spectra and absorption IR spectra are complementary spectroscopic methods. In general, Raman excitation depends on bond polarizability changes whereas IR absorption depends on bond dipole moment changes. Weak IR absorption lines become strong Raman lines and vice versa. Wavenumber is the characteristic unit for IR spectra. There are 3 spectral regions for IR tags which have separate applications: near IR at 12500 to 4000 $cm^{-1}$, mid IR at 4000 to 600 $cm^{-1}$, far IR at 600 to 30 $cm^{-1}$. For the uses described herein where a compound is to serve as a tag to identify an MOI, probe or primer, the mid spectral regions would be preferred. For example, the carbonyl stretch (1850 to 1750 $cm^{-1}$) would be measured for carboxylic acids, carboxylic esters and amides, and alkyl and aryl carbonates, carbamates and ketones. N—H bending (1750 to 160 $cm^{-1}$) would be used to identify amines, ammonium ions, and amides. At 1400 to 1250 $cm^{-1}$, R—OH bending is detected as well as the C—N stretch in amides. Aromatic substitution patterns are detected at 900 to 690 $cm^{-1}$ (C—H bending, N—H bending for $ArNH_2$). Saturated C—H, olefins, aromatic rings, double and triple bonds, esters, acetals, ketals, ammonium salts, N—O compounds such as oximes, nitro, N-oxides, and nitrates, azo, hydrazones, quinones, carboxylic acids, amides, and lactams all possess vibrational infrared correlation data (see Pretsch et al., *Spectral Data for Structure Determination of Organic Compounds*, Springer-Verlag, New York, 1989). Preferred compounds would include an aromatic nitrile which exhibits a very strong nitrile stretching vibration at 2230 to 2210 $cm^{-1}$. Other useful types of compounds are aromatic alkynes which have a strong stretching vibration that gives rise to a sharp absorption band between 2140 and 2100 $cm^{-1}$. A third compound type is the aromatic azides which exhibit an intense absorption band in the 2160 to 2120 $cm^{-1}$ region. Thiocyanates are representative of compounds that have a strong absorption at 2275 to 2263 $cm^{-1}$.

c. Characteristics of UV Tags

A compilation of organic chromophore types and their respective UV-visible properties is given in Scott (*Interpretation of the UV Spectra of Natural Products*, Permagon Press, New York, 1962). A chromophore is an atom or group of atoms or electrons that are responsible for the particular light absorption. Empirical rules exist for the π to π* maxima in conjugated systems (see Pretsch et al., *Spectral Data for Structure Determination of Organic Compounds*, p. B65 and B70, Springer-Verlag, New York, 1989). Preferred compounds (with conjugated systems) would possess n to π* and π to π* transitions. Such compounds are exemplified by Acid Violet 7, Acridine Orange, Acridine Yellow G, Brilliant Blue G, Congo Red, Crystal Violet, Malachite Green oxalate, Metanil Yellow, Methylene Blue, Methyl Orange, Methyl Violet B, Naphtol Green B, Oil Blue N, Oil Red O, 4-phenylazophenol, Safranie O, Solvent Green 3, and Sudan Orange G, all of which are commercially available (Aldrich, Milwaukee, Wis.). Other suitable compounds are listed in, e.g., Jane, I., et al., *J. Chrom*. 323:191–225 (1985).

d. Characteristic of a Fluorescent Tag

Fluorescent probes are identified and quantitated most directly by their absorption and fluorescence emission wavelengths and intensities. Emission spectra (fluorescence and phosphorescence) are much more sensitive and permit more specific measurements than absorption spectra. Other photophysical characteristics such as excited-state lifetime and fluorescence anisotropy are less widely used. The most generally useful intensity parameters are the molar extinction coefficient (ε) for absorption and the quantum yield (QY) for fluorescence. The value of ε is specified at a single wavelength (usually the absorption maximum of the probe), whereas QY is a measure of the total photon emission over the entire fluorescence spectral profile. A narrow optical bandwidth (<20 nm) is usually used for fluorescence excitation (via absorption), whereas the fluorescence detection bandwidth is much more variable, ranging from full spectrum for maximal sensitivity to narrow band (~20 nm) for maximal resolution. Fluorescence intensity per probe molecule is proportional to the product of ε and QY. The range of these parameters among fluorophores of current practical importance is approximately 10,000 to 100,000 $cm^{-1}M^{-1}$ for ε and 0.1 to 1.0 for QY. Compounds that can serve as fluorescent tags are as follows: fluorescein, rhodamine, lambda blue 470, lambda green, lambda red 664, lambda red 665, acridine orange, and propidium iodide, which are commercially available from Lambda Fluorescence Co. (Pleasant Gap, Pa.). Fluorescent compounds such as nile red, Texas Red, lissamine™, BODIPY™ s are available from Molecular Probes (Eugene, Oreg.).

e. Characteristics of Potentiometric Tags

The principle of electrochemical detection (ECD) is based on oxidation or reduction of compounds which at certain applied voltages, electrons are either donated or accepted thus producing a current which can be measured. When certain compounds are subjected to a potential difference, the molecules undergo a molecular rearrangement at the working electrodes' surface with the loss (oxidation) or gain (reduction) of electrons, such compounds are said to be electronic and undergo electrochemical reactions. EC detectors apply a voltage at an electrode surface over which the HPLC eluent flows. Electroactive compounds eluting from the column either donate electrons (oxidize) or acquire electrons (reduce) generating a current peak in real time. Importantly the amount of current generated depends on both the concentration of the analyte and the voltage applied, with each compound having a specific voltage at which it begins to oxidize or reduce. The currently most popular electrochemical detector is the amperometric detector in which the potential is kept constant and the current produced from the electrochemical reaction is then measured. This type of spectrometry is currently called "potentiostatic amperometry". Commercial amperometers are available from ESA, Inc., Chelmford, Mass.

When the efficiency of detection is 100%, the specialized detectors are termed "coulometric". Coulometric detectors are sensitive which have a number of practical advantages with regard to selectivity and sensitivity which make these types of detectors useful in an array. In coulometric detectors, for a given concentration of analyte, the signal current is plotted as a function of the applied potential (voltage) to the working electrode. The resultant sigmoidal graph is called the current-voltage curve or hydrodynamic voltammagram (HDV). The HDV allows the best choice of applied potential to the working electrode that permits one to maximize the observed signal. A major advantage of ECD is its inherent sensitivity with current levels of detection in the subfemtomole range.

Numerous chemicals and compounds are electrochemically active including many biochemicals, pharmaceuticals and pesticides. Chromatographically coeluting compounds can be effectively resolved even if their half-wave potentials (the potential at half signal maximum) differ by only 30–60 mV.

Recently developed coulometric sensors provide selectivity, identification and resolution of co-eluting compounds when used as detectors in liquid chromatography based separations. Therefore, these arrayed detectors add another set of separations accomplished in the detector itself. Current instruments possess 16 channels which are in principle limited only by the rate at which data can be acquired. The number of compounds which can be resolved on the EC array is chromatographically limited (i.e., plate count limited). However, if two or more compounds that chromatographically co-elute have a difference in half wave potentials of 30–60 mV, the array is able to distinguish the compounds. The ability of a compound to be electrochemically active relies on the possession of an EC active group (i.e., —OH, —O, —N, —S).

Compounds which have been successfully detected using coulometric detectors include 5-hydroxytryptamine, 3-methoxy-4-hydroxyphenyl-glycol, homogentisic acid, dopamine, metanephrine, 3-hydroxykynureninr, acetominophen, 3-hydroxytryptophol, 5-hydroxyindoleacetic acid, octanesulfonic acid, phenol, o-cresol, pyrogallol, 2-nitrophenol, 4-nitrophenol, 2,4-dinitrophenol, 4,6-dinitrocresol, 3-methyl-2-nitrophenol, 2,4-dichlorophenol, 2,6-dichlorophenol, 2,4,5-trichlorophenol, 4-chloro-3-methylphenol, 5-methylphenol, 4-methyl-2-nitrophenol, 2-hydroxyaniline, 4-hydroxyaniline, 1,2-phenylenediamine, benzocatechin, buturon, chlortholuron, diuron, isoproturon, linuron, methobromuron, metoxuron, monolinuron, monuron, methionine, tryptophan, tyrosine, 4-aminobenzoic acid, 4-hydroxybenzoic acid, 4-hydroxycoumaric acid, 7-methoxycoumarin, apigenin baicalein, caffeic acid, catechin, centaurein, chlorogenic acid, daidzein, datiscetin, diosmetin, epicatechin gallate, epigallo catechin, epigallo catechin gallate, eugenol, eupatorin, ferulic acid, fisetin, galangin, gallic acid, gardenin, genistein, gentisic acid, hesperidin, irigenin, kaemferol, leucoyanidin, luteolin, mangostin, morin, myricetin, naringin, narirutin, pelargondin, peonidin, phloretin, pratensein, protocatechuic acid, rhamnetin, quercetin, sakuranetin, scutellarein, scopoletin, syringaldehyde, syringic acid, tangeritin, troxerutin, umbelliferone, vanillic acid, 1,3-dimethyl tetrahydroisoquinoline, 6-hydroxydopamine, r-salsolinol, N-methyl-r-salsolinol, tetrahydroisoquinoline, amitriptyline, apomorphine, capsaicin, chlordiazepoxide, chlorpromazine, daunorubicin, desipramine, doxepin, fluoxetine, flurazepam, imipramine, isoproterenol, methoxamine, morphine, morphine-3-glucuronide, nortriptyline, oxazepam, phenylephrine, trimipramine, ascorbic acid, N-acetyl serotonin, 3,4-dihydroxybenzylamine, 3,4-dihydroxymandelic acid (DOMA), 3,4-dihydroxyphenylacetic acid (DOPAC), 3,4-dihydroxyphenylalanine (L-DOPA), 3,4-dihydroxyphenylglycol (DHPG), 3-hydroxyanthranilic acid, 2-hydroxyphenylacetic acid (2HPAC), 4-hydroxybenzoic acid (4HBAC), 5-hydroxyindole-3-acetic acid (5HIAA), 3-hydroxykynurenine, 3-hydroxymandelic acid, 3-hydroxy-4-methoxyphenylethylamine, 4-hydroxyphenylacetic acid (4HPAC), 4-hydroxyphenyllactic acid (4HPLA), 5-hydroxytryptophan (5HTP), 5-hydroxytryptophol (5HTOL), 5-hydroxytryptamine (5HT), 5-hydroxytryptamine sulfate, 3-methoxy-4-hydroxyphenylglycol (MHPG), 5-methoxytryptamine, 5-methoxytryptophan, 5-methoxytryptophol, 3-methoxytyramine (3MT), 3-methoxytyrosine (3-OM-DOPA), 5-methylcysteine, 3-methylguanine, bufotenin, dopamine dopamine-3-glucuronide, dopamine-3-sulfate, dopamine-4-sulfate, epinephrine, epinine, folic acid, glutathione (reduced), guanine, guanosine, homogentisic acid (HGA), homovanillic acid (HVA), homovanillyl alcohol (HVOL), homoveratic acid, hva sulfate, hypoxanthine, indole, indole-3-acetic acid, indole-3-lactic acid, kynurenine, melatonin, metanephrine, N-methyltryptamine, N-methyltyramine, N,N-dimethyltryptamine, N,N-dimethyltyramine, norepinephrine, normetanephrine, octopamine, pyridoxal, pyridoxal phosphate, pyridoxamine, synephrine, tryptophol, tryptamine, tyramine, uric acid, vanillylmandelic acid (vma), xanthine and xanthosine. Other suitable compounds are set forth in, e.g., Jane, I., et al. *J. Chrom.* 323:191–225 (1985) and Musch, G., et al., *J. Chrom.* 348:97–110 (1985). These compounds can be incorporated into compounds of formula T—L—X by methods known in the art. For example, compounds having a carboxylic acid group may be reacted with amine, hydroxyl, etc. to form amide, ester and other linkages between T and L.

In addition to the above properties, and regardless of the intended detection method, it is preferred that the tag have a modular chemical structure. This aids in the construction of large numbers of structurally related tags using the techniques of combinatorial chemistry. For example, the $T^{ms}$ group desirably has several properties. It desirably contains a functional group which supports a single ionized charge state when the $T^{ms}$-containing moiety is subjected to mass spectrometry (more simply referred to as a "mass spec sensitivity enhancer" group, or MSSE). Also, it desirably can serve as one member in a family of $T^{ms}$-containing moieties, where members of the family each have a different mass/charge ratio, however have approximately the same sensitivity in the mass spectrometer. Thus, the members of the family desirably have the same MSSE. In order to allow the creation of families of compounds, it has been found convenient to generate tag reactants via a modular synthesis scheme, so that the tag components themselves may be viewed as comprising modules.

In a preferred modular approach to the structure of the $T^{ms}$ group, $T^{ms}$ has the formula

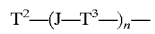

$$T^2-(J-T^3-)_n-$$

wherein $T^2$ is an organic moiety formed from carbon and one or more of hydrogen, fluoride, iodide, oxygen, nitrogen, sulfur and phosphorus, having a mass range of 15 to 500 daltons; $T^3$ is an organic moiety formed from carbon and one or more of hydrogen, fluoride, iodide, oxygen, nitrogen, sulfur and phosphorus, having a mass range of 50 to 1000 daltons; J is a direct bond or a functional group such as amide, ester, amine, sulfide, ether, thioester, disulfide, thioether, urea, thiourea, carbamate, thiocarbamate, Schiff base, reduced Schiff base, imine, oxime, hydrazone, phosphate, phosphonate, phosphoramide, phosphonamide, sulfonate, sulfonamide or carbon-carbon bond; and n is an integer ranging from 1 to 50, such that when n is greater than 1, each $T^3$ and J is independently selected.

The modular structure $T^2-(J-T^3)_n-$ provides a convenient entry to families of T—L—X compounds, where each member of the family has a different T group. For instance, when T is $T^{ms}$, and each family member desirably has the same MSSE, one of the $T^3$ groups can provide that MSSE structure. In order to provide variability between members of a family in terms of the mass of $T^{ms}$, the $T^2$ group may be varied among family members. For instance, one family member may have $T^2$=methyl, while another has $T^2$=ethyl, and another has $T^2$=propyl, etc.

Figure 13:
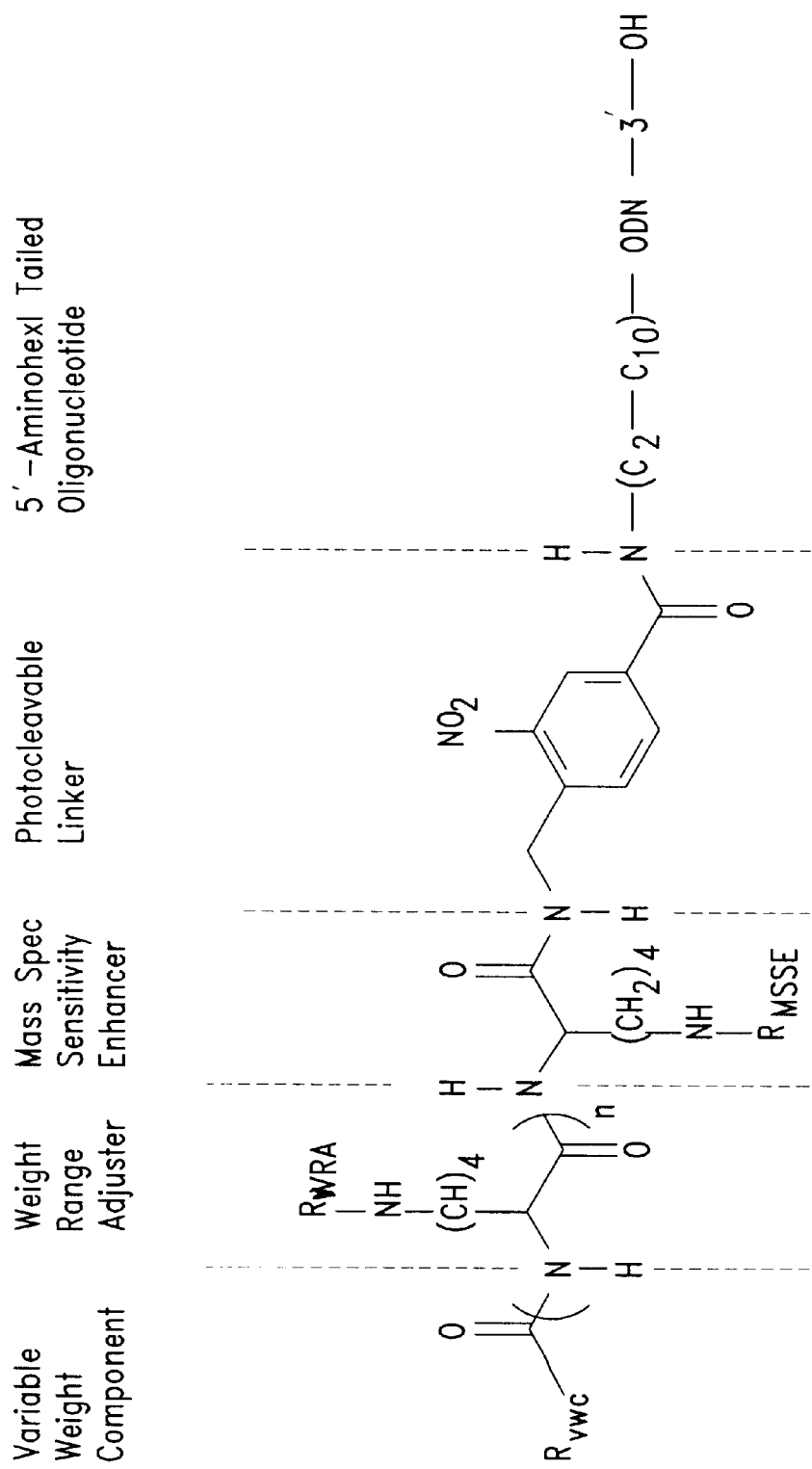
FIG. 13 depicts a modularly-constructed tagged nucleic acid fragment.
Figure 14A:
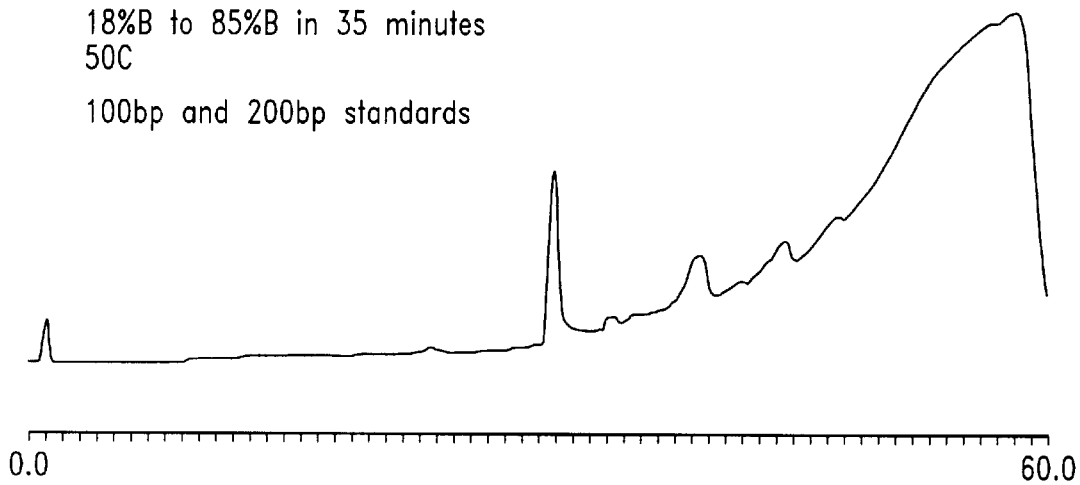
FIGS. 14A–14I show the separation of DNA fragments by HPLC using a variety of different buffer solutions.
Figure 14B:
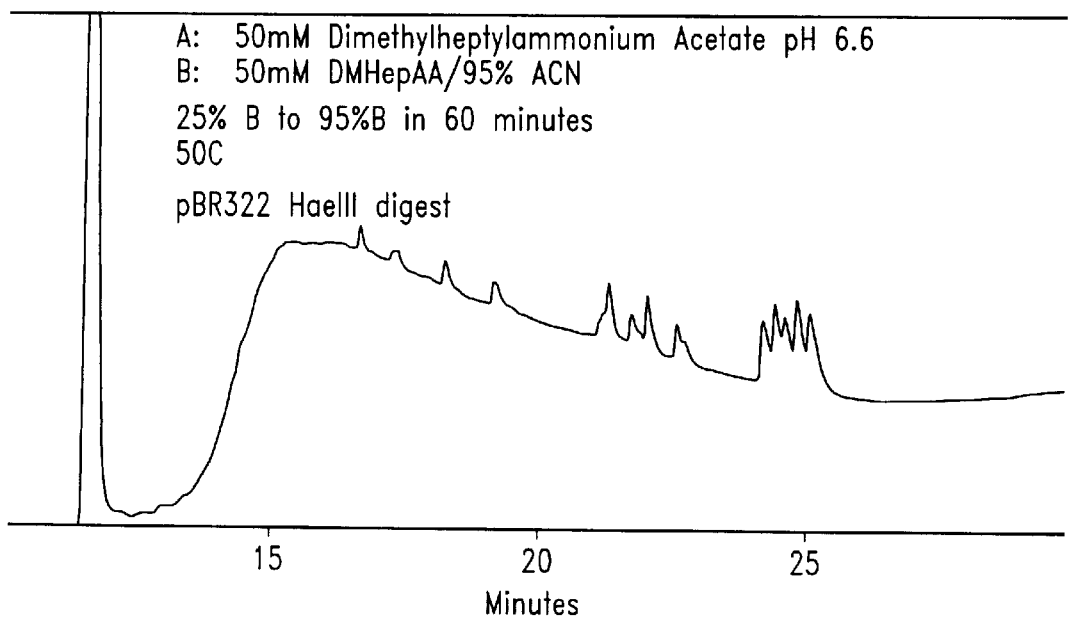
Figure 14C:
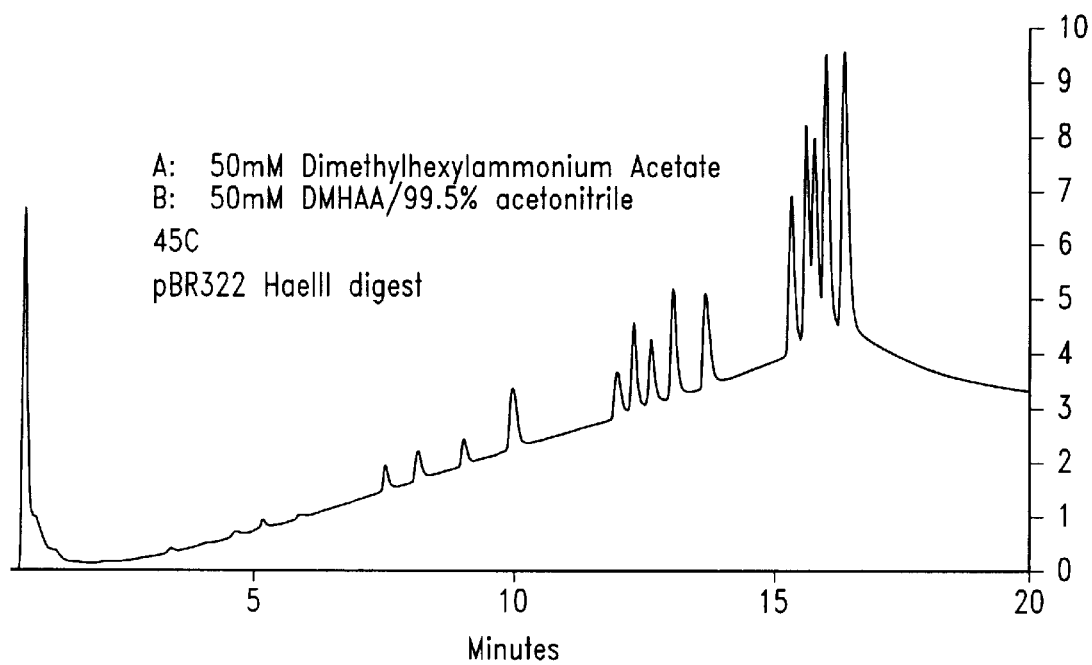
Figure 14D:
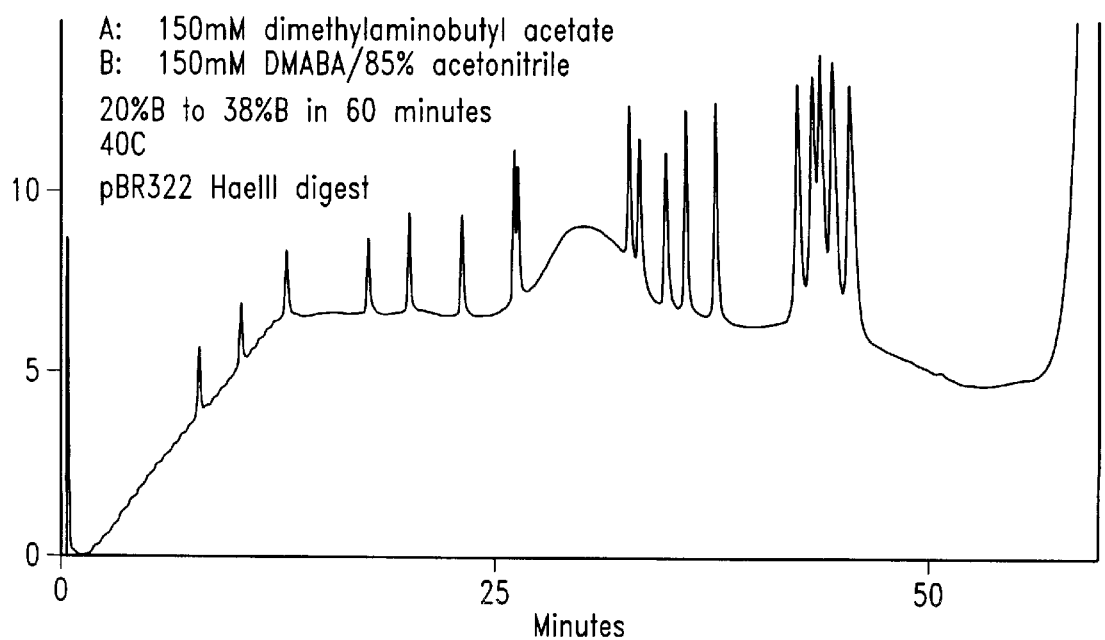
Figure 14E:
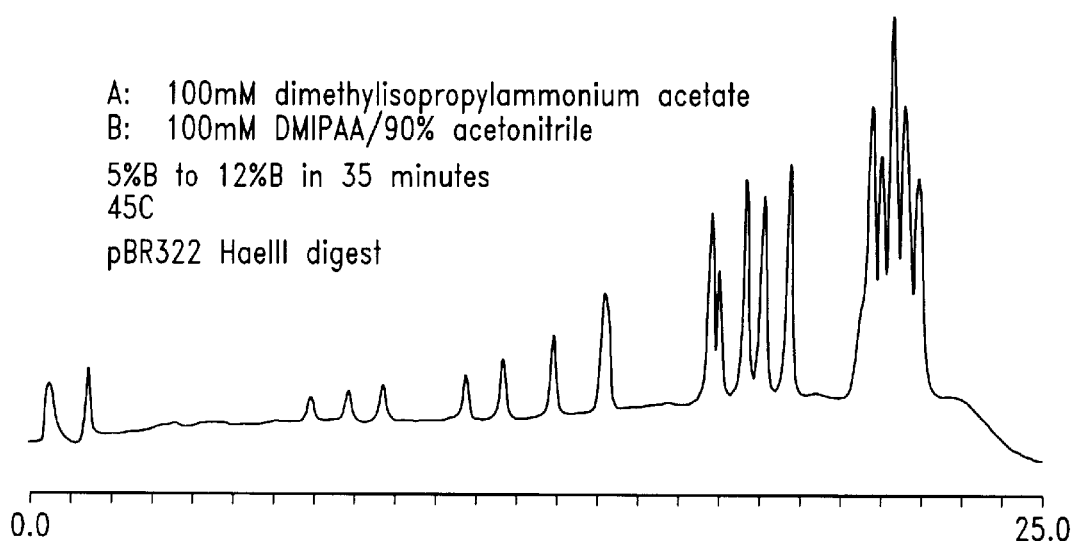
Figure 14F:
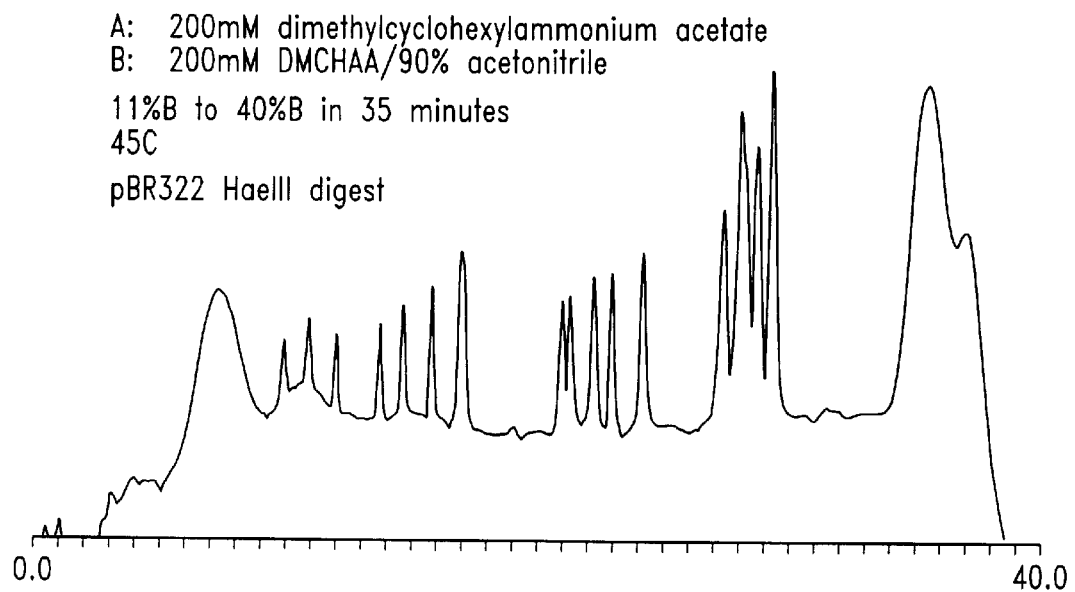
Figure 14G:
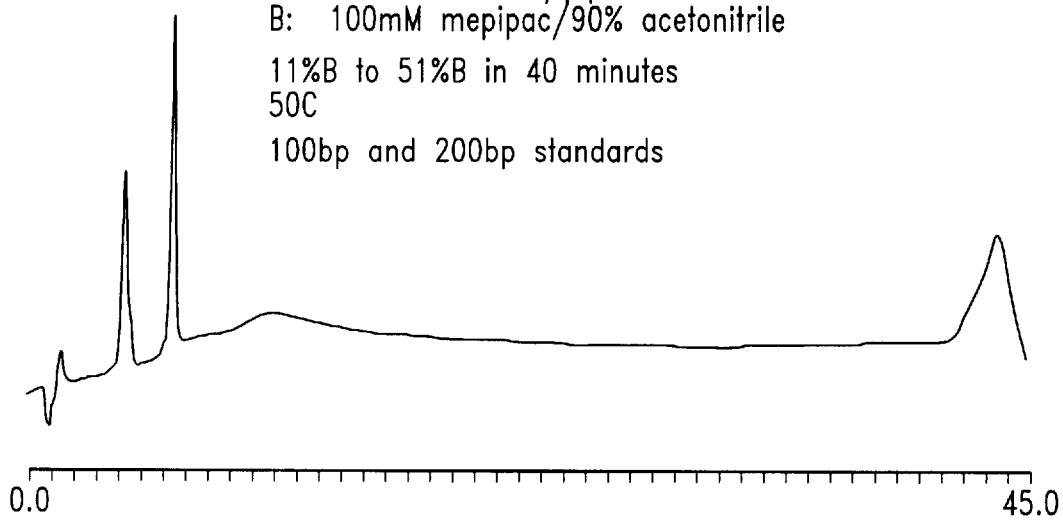
Figure 14H:
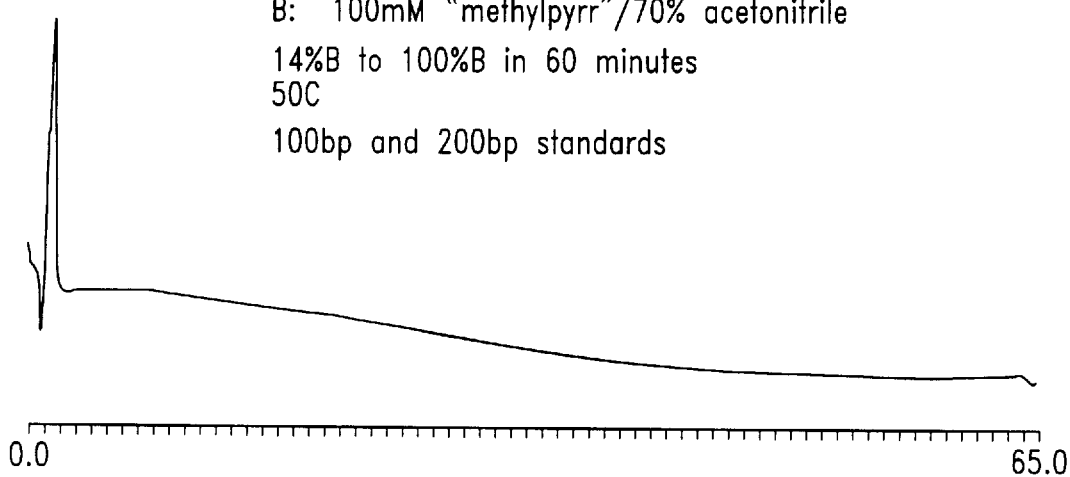
Figure 14I:
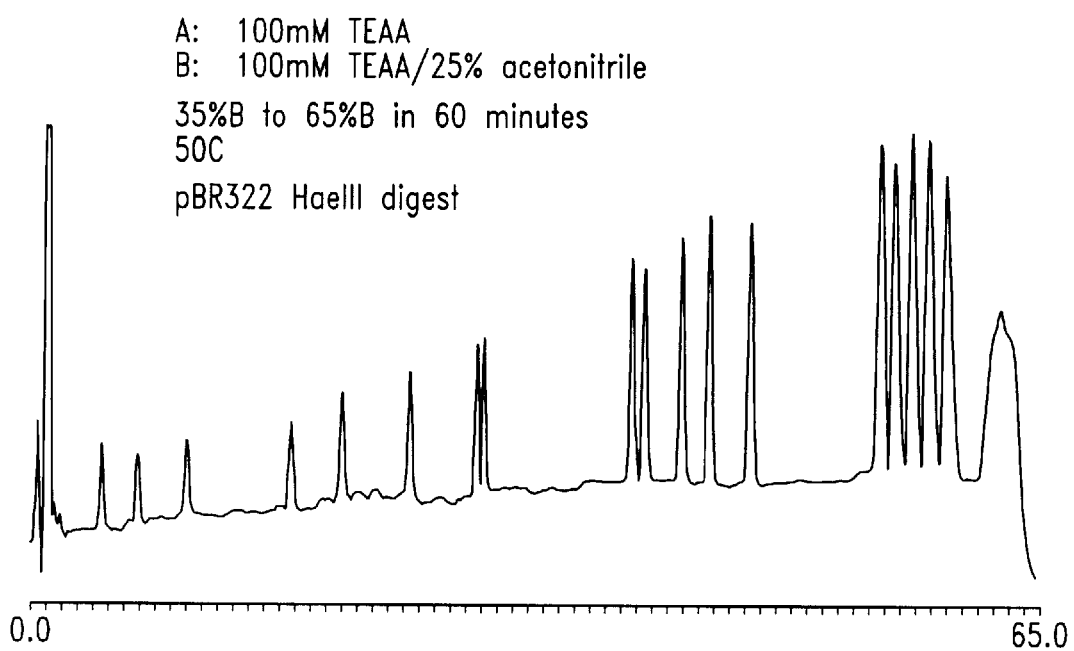

In order to provide "gross" or large jumps in mass, a $T^3$ group may be designed which adds significant (e.g, one or several hundreds) of mass units to T—L—X. Such a $T^3$ group may be referred to as a molecular weight range adjuster group ("WRA"). A WRA is quite useful if one is working with a single set of $T^2$ groups, which will have masses extending over a limited range. A single set of $T^2$ groups may be used to create $T^{ms}$ groups having a wide range of mass simply by incorporating one or more WRA $T^3$ groups into the $T^{ms}$. Thus, using a simple example, if a set of $T^2$ groups affords a mass range of 250–340 daltons for the $T^{ms}$, the addition of a single WRA, having, as an exemplary number 100 dalton, as a $T^3$ group provides access to the mass range of 350–440 daltons while using the same set of $T^2$ groups. Similarly, the addition of two 100 dalton MWA groups (each as a $T^3$ group) provides access to the mass range of 450–540 daltons, where this incremental addition of WRA groups can be continued to provide access to a very large mass range for the $T^{ms}$ group. Preferred compounds of the formula $T^2$—$(J$—$T^3$—$)_n$—L—X have the formula $R_{VWC}$—$(R_{WRA})_W$—$R_{MSSE}$—L—X where VWC is a "$T^2$" group, and each of the WRA and MSSE groups are "$T^3$" groups. This structure is illustrated in FIG. 13, and represents one modular approach to the preparation of $T^{ms}$.

In the formula $T^2$—$(J$—$T^3$—$)_n$—, $T^2$ and $T^3$ are preferably selected from hydrocarbyl, hydrocarbyl-O-hydrocarbylene, hydrocarbyl-S-hydrocarbylene, hydrocarbyl-NH-hydrocarbylene, hydrocarbyl-amide-hydrocarbylene, N-(hydrocarbyl)hydrocarbylene, N,N-di(hydrocarbyl)hydrocarbylene, hydrocarbylacyl-hydrocarbylene, heterocyclylhydrocarbyl wherein the heteroatom(s) are selected from oxygen, nitrogen, sulfur and phosphorus, substituted heterocyclylhydrocarbyl wherein the heteroatom(s) are selected from oxygen, nitrogen, sulfur and phosphorus and the substituents are selected from hydrocarbyl, hydrocarbyl-O-hydrocarbylene, hydrocarbyl-NH-hydrocarbylene, hydrocarbyl-S-hydrocarbylene, N-(hydrocarbyl)hydrocarbylene, N,N-di(hydrocarbyl) hydrocarbylene and hydrocarbylacyl-hydrocarbylene. In addition, $T^2$ and/or $T^3$ may be a derivative of any of the previously listed potential $T^2/T^3$ groups, such that one or more hydrogens are replaced fluorides.

Also regarding the formula $T^2$—$(J$—$T^3$—$)_n$—, a preferred $T^3$ has the formula —$G(R^2)$—, wherein G is $C_{1-6}$ alkylene chain having a single $R^2$ substituent. Thus, if G is ethylene (—$CH_2$—$CH_2$—) either one of the two ethylene carbons may have a $R^2$ substituent, and $R^2$ is selected from alkyl, alkenyl, alkynyl, cycloalkyl, aryl-fused cycloalkyl, cycloalkenyl, aryl, aralkyl, aryl-substituted alkenyl or alkynyl, cycloalkyl-substituted alkyl, cycloalkenyl-substituted cycloalkyl, biaryl, alkoxy, alkenoxy, alkynoxy, aralkoxy, aryl-substituted alkenoxy or alkynoxy, alkylamino, alkenylamino or alkynylamino, aryl-substituted alkylamino, aryl-substituted alkenylamino or alkynylamino, aryloxy, arylarnino, N-alkylurea-substituted alkyl, N-arylurea-substituted alkyl, alkylcarbonylamino-substituted alkyl, aminocarbonyl-substituted alkyl, heterocyclyl, heterocyclyl-substituted alkyl, heterocyclyl-substituted amino, carboxyalkyl substituted aralkyl, oxocarbocyclyl-fused aryl and heterocyclylalkyl; cycloalkenyl, aryl-substituted alkyl and, aralkyl, hydroxy-substituted alkyl, alkoxy-substituted alkyl, aralkoxy-substituted alkyl, alkoxy-substituted alkyl, aralkoxy-substituted alkyl, amino-substituted alkyl, (aryl-substituted alkyloxycarbonylamino)-substituted alkyl, thiol-substituted alkyl, alkylsulfonyl-substituted alkyl, (hydroxy-substituted alkylthio)-substituted alkyl, thioalkoxy-substituted alkyl, hydrocarbylacylamino-substituted alkyl, heterocyclylacylamino-substituted alkyl, hydrocarbyl-substituted-heterocyclylacylamino-substituted alkyl, alkylsulfonylamino-substituted alkyl, arylsulfonylamino-substituted alkyl, morpholino-alkyl, thiomorpholino-alkyl, morpholino carbonyl-substituted alkyl, thiomorpholinocarbonyl-substituted alkyl, [N-(alkyl, alkenyl or alkynyl)- or N,N-[dialkyl, dialkenyl, dialkynyl or (alkyl, alkenyl)-amino]carbonyl-substituted alkyl, heterocyclylaminocarbonyl, heterocylylalkyleneaminocarbonyl, heterocyclylaminocarbonyl-substituted alkyl, heterocylylalkyleneaminocarbonyl-substituted alkyl, N,N-[dialkyl]alkyleneaminocarbonyl, N,N-[dialkyl]alkyleneaminocarbonyl-substituted alkyl, alkyl-substituted heterocyclylcarbonyl, alkyl-substituted heterocyclylcarbonyl-alkyl, carboxyl-substituted alkyl, dialkylamino-substituted acylaminoalkyl and amino acid side chains selected from arginine, asparagine, glutamine, S-methyl cysteine, methionine and corresponding sulfoxide and sulfone derivatives thereof, glycine, leucine, isoleucine, allo-isoleucine, tert-leucine, norleucine, phenylalanine, tyrosine, tryptophan, proline, alanine, ornithine, histidine, glutamine, valine, threonine, serine, aspartic acid, beta-cyanoalanine, and allothreonine; alynyl and heterocyclylcarbonyl, aminocarbonyl, amido, mono- or dialkylaminocarbonyl, mono- or diarylaminocarbonyl, alkylarylaminocarbonyl, diarylaminocarbonyl, mono- or diacylaminocarbonyl, aromatic or aliphatic acyl, alkyl optionally substituted by substituents selected from amino, carboxy, hydroxy, mercapto, mono- or dialkylamino, mono- or diarylamino, alkylarylamino, diarylamino, mono- or diacylamino, alkoxy, alkenoxy, aryloxy, thioalkoxy, thioalkenoxy, thioalkynoxy, thioaryloxy and heterocyclyl.

A preferred compound of the formula $T^2$—$(J$—$T^3$—$)_n$—L—X has the structure:

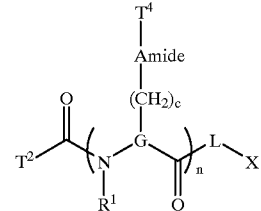

wherein G is $(CH_2)_{1-6}$ such that a hydrogen on one and only one of the $CH_2$ groups represented by a single "G" is replaced with —$(CH_2)_c$-Amide-$T^4$; $T^2$ and $T^4$ are organic moieties of the formula $C_{1-25}N_{0-9}O_{0-9}H_\alpha F_\beta$ such that the sum of $\alpha$ and $\beta$ is sufficient to satisfy the otherwise unsatisfied valencies of the C, N, and O atoms; amide is

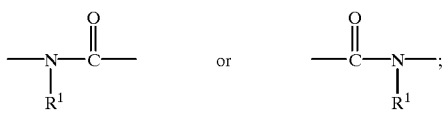

$R^1$ is hydrogen or $C_{1-10}$ alkyl; c is an integer ranging from 0 to 4; and n is an integer ranging from 1 to 50 such that when n is greater than 1, G, c, Amide, $R^1$ and $T^4$ are independently selected.

In a further preferred embodiment, a compound of the formula $T^2$—$(J$—$T^3$—$)_n$—L—X has the structure:

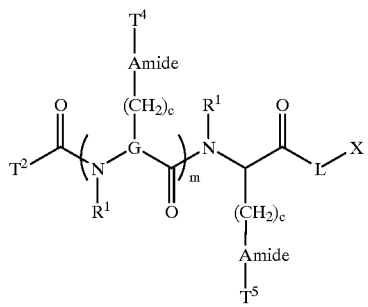

wherein $T^5$ is an organic moiety of the formula $C_{1-25}N_{0-N0-9}O_{0-9}H_\alpha F_\beta$ such that the sum of α and β is sufficient to satisfy the otherwise unsatisfied valencies of the C, N, and O atoms; and $T^5$ includes a tertiary or quaternary amine or an organic acid; m is an integer ranging from 0–49, and $T^2$, $T^4$, $R^1$, L and X have been previously defined.

Another preferred compound having the formula $T^2$—$(J-T^3-)_n$—L—X has the particular structure:

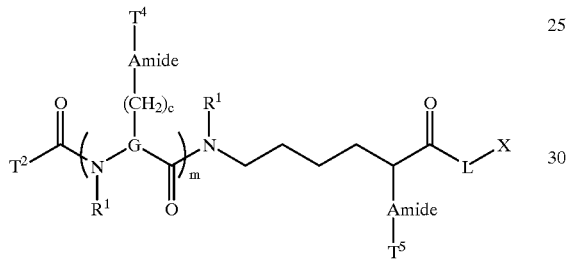

wherein $T^5$ is an organic moiety of the formula $C_{1-25}N_{0-9}O_{0-9}H_\alpha F_\beta$ such that the sum of α and β is sufficient to satisfy the otherwise unsatisfied valencies of the C, N, and O atoms; and $T^5$ includes a tertiary or quaternary amine or an organic acid; m is an integer ranging from 0–49, and $T^2$, $T^4$, c, $R^1$, "Amide", L and X have been previously defined.

In the above structures that have a $T^5$ group, -Amide-$T^5$ is preferably one of the following, which are conveniently made by reacting organic acids with free amino groups extending from "G":

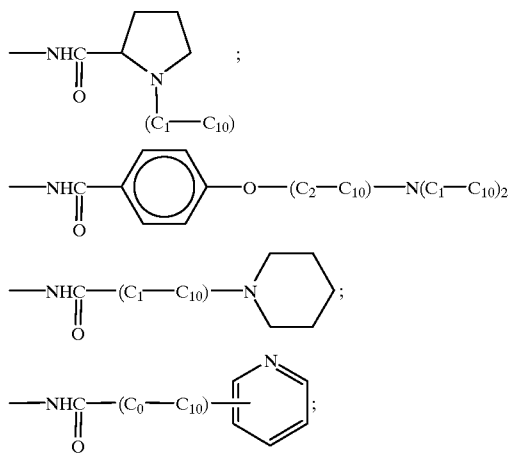

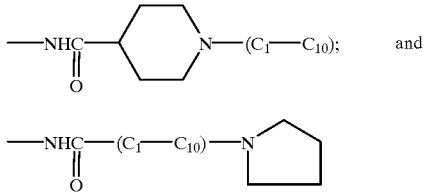

Where the above compounds have a $T^5$ group, and the "G" group has a free carboxyl group (or reactive equivalent thereof), then the following are preferred -Amide-$T^5$ group, which may conveniently be prepared by reacting the appropriate organic amine with a free carboxyl group extending from a "G" group:

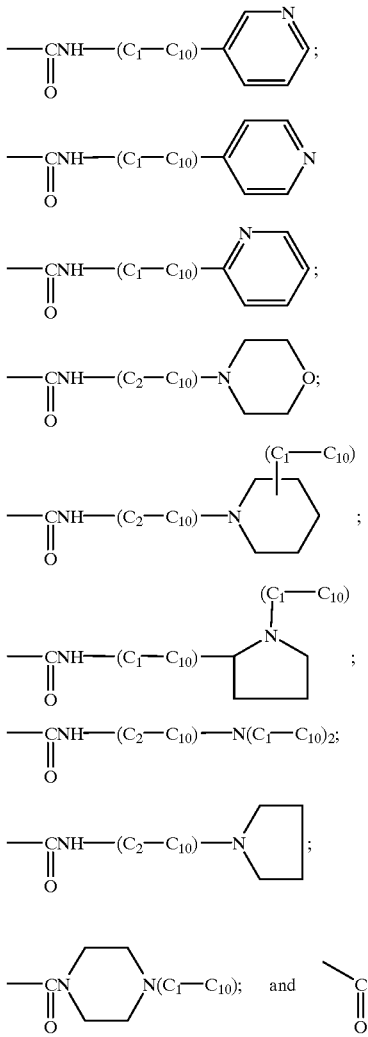

In three preferred embodiments of the invention, T—L—MOI has the structure:

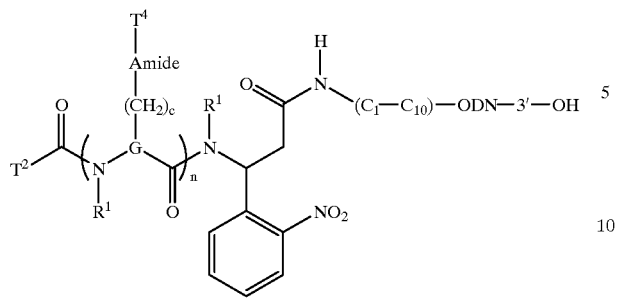

or the structure:

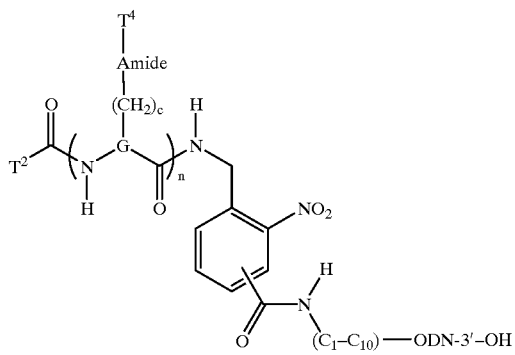

or the structure:

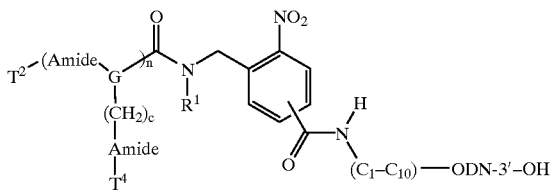

wherein $T^2$ and $T^4$ are organic moieties of the formula $C_{1-25}N_{0-9}O_{0-9}S_{0-3}P_{0-3}H_\alpha F_\beta I_\delta$ such that the sum of $\alpha$, $\beta$ and $\delta$ is sufficient to satisfy the otherwise unsatisfied valencies of the C, N, O, S and P atoms; G is $(CH_2)_{1-6}$ wherein one and only one hydrogen on the $CH_2$ groups represented by each G is replaced with —$(CH_2)_c$-Amide-$T^4$; Amide is

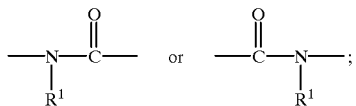

$R^1$ is hydrogen or $C_{1-10}$ alkyl; c is an integer ranging from 0 to 4; "$C_2$–$C_{10}$" represents a hydrocarbylene group having from 2 to 10 carbon atoms, "ODN-3'-OH" represents a nucleic acid fragment having a terminal 3' hydroxyl group (i.e., a nucleic acid fragment joined to $(C_1-C_{10})$ at other than the 3' end of the nucleic acid fragment); and n is an integer ranging from 1 to 50 such that when n is greater than 1, then G, c, Amide, $R^1$ and $T^4$ are independently selected. Preferably there are not three heteroatoms bonded to a single carbon atom.

wherein $T^2$ and $T^4$ are organic moieties of the formula $C_{1-25}N_{0-9}O_{0-9}H_\alpha F_\beta$ such that the sum of $\alpha$ and $\beta$ is sufficient to satisfy the otherwise unsatisfied valencies of the C, N, and O atoms; G is $(CH_2)_{1-6}$ wherein one and only one hydrogen on the $CH_2$ groups represented by each G is replaced with —$(CH_2)_c$-Amide-$T^4$; Amide is

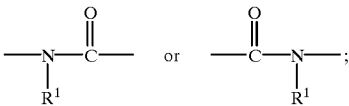

$R^1$ is hydrogen or $C_{1-10}$ alkyl; c is an integer ranging from 0 to 4; "ODN-3'-OH" represents a nucleic acid fragment having a terminal 3' hydroxyl group; and n is an integer ranging from 1 to 50 such that when n is greater than 1, G, c, Amide, $R^1$ and $T^4$ are independently selected.

In structures as set forth above that contain a $T^2$—C(=O)—N($R^1$)— group, this group may be formed by reacting an amine of the formula $HN(R^1)$— with an organic acid selected from the following, which are exemplary only and do not constitute an exhaustive list of potential organic acids: Formic acid, Acetic acid, Propiolic acid, Propionic acid, Fluoroacetic acid, 2-Butynoic acid, Cyclopropanecarboxylic acid, Butyric acid, Methoxyacetic acid, Difluoroacetic acid, 4-Pentynoic acid, Cyclobutanecarboxylic acid, 3,3-Dimethylacrylic acid, Valeric acid, N,N-Dimethylglycine, N-Formyl-Gly-OH, Ethoxyacetic acid, (Methylthio)acetic acid, Pyrrole-2-carboxylic acid, 3-Furoic acid, Isoxazole-5-carboxylic acid, trans-3-Hexenoic acid, Trifluoroacetic acid, Hexanoic acid, Ac-Gly-OH, 2-Hydroxy-2-methylbutyric acid, Benzoic acid, Nicotinic acid, 2-Pyrazinecarboxylic acid, 1-Methyl-2-pyrrolecarboxylic acid, 2-Cyclopentene-1-acetic acid, Cyclopentylacetic acid, (S)-(−)-2-Pyrrolidone-5-carboxylic acid, N-Methyl-L-proline, Heptanoic acid, Ac-b-Ala-OH, 2-Ethyl-2-hydroxybutyric acid, 2-(2-Methoxyethoxy)acetic acid, p-Toluic acid, 6-Methylnicotinic acid, 5-Methyl-2-pyrazinecarboxylic acid, 2,5-Dimethylpyrrole-3-carboxylic acid, 4-Fluorobenzoic acid, 3,5-Dimethylisoxazole-4-carboxylic acid, 3-Cyclopentylpropionic acid, Octanoic acid, N,N-Dimethylsuccinamic acid, Phenylpropiolic acid, Cinnamic acid, 4-Ethylbenzoic acid, p-Anisic acid, 1,2,5-Trimethylpyrrole-3-carboxylic acid, 3-Fluoro-4-methylbenzoic acid, Ac-DL-Propargylglycine, 3-(Trifluoromethyl)butyric acid, 1-Piperidinepropionic acid, N-Acetylproline, 3,5-Difluorobenzoic acid, Ac-L-Val-OH, Indole-2-carboxylic acid, 2-Benzofurancarboxylic acid, Benzotriazole-5-carboxylic acid, 4-n-Propylbenzoic acid, 3-Dimethylaminobenzoic acid, 4-Ethoxybenzoic acid, 4-(Methylthio)benzoic acid, N-(2-Furoyl)glycine, 2-(Methylthio)nicotinic acid, 3-Fluoro-4-methoxybenzoic acid, Tfa-Gly-OH, 2-Napthoic acid, Quinaldic acid, Ac-L-Ile-OH, 3-Methylindene-2-carboxylic acid, 2-Quinoxalinecarboxylic acid, 1-Methylindole-2-carboxylic acid, 2,3,6-Trifluorobenzoic acid, N-Formyl-L-Met-OH, 2-[2-(2-Methoxyethoxy)ethoxy]acetic acid, 4-n-Butylbenzoic acid, N-Benzoylglycine, 5-Fluoroindole-2-carboxylic acid, 4-n-Propoxybenzoic acid, 4-Acetyl-3,5-dimethyl-2-pyrrolecarboxylic acid, 3,5-Dimethoxybenzoic acid, 2,6-Dimethoxynicotinic acid, Cyclohexanepentanoic acid, 2-Naphthylacetic acid, 4-(1H-Pyrrol-1-yl)benzoic acid, Indole-3-propionic acid, m-Trifluoromethylbenzoic acid, 5-Methoxyindole-2-carboxylic acid, 4-Pentylbenzoic acid, Bz-b-Ala-OH, 4-Diethylaminobenzoic acid, 4-n-Butoxybenzoic acid, 3-Methyl-5-CF3-isoxazole-4-carboxylic acid, (3,4-Dimethoxyphenyl)acetic acid, 4-Biphenylcarboxylic acid, Pivaloyl-Pro-OH, Octanoyl-Gly-OH, (2-Naphthoxy)acetic acid, Indole-3-butyric acid, 4-(Trifluoromethyl)phenylacetic acid, 5-Methoxyindole-3- acetic acid, 4-(Trifluoromethoxy)benzoic acid, Ac-L-Phe-OH, 4-Pentyloxybenzoic acid, Z-Gly-OH, 4-Carboxy-N-(fur-2-ylmethyl)pyrrolidin-2-one, 3,4-Diethoxybenzoic acid, 2,4-Dimethyl-5-CO₂Et-pyrrole-3-carboxylic acid, N-(2-Fluorophenyl)succinamic acid, 3,4,5-Trimethoxybenzoic acid, N-Phenylanthranilic acid, 3-Phenoxybenzoic acid, Nonanoyl-Gly-OH, 2-Phenoxypyridine-3-carboxylic acid, 2,5-Dimethyl-1-phenylpyrrole-3-carboxylic acid, trans-4-(Trifluoromethyl) cinnamic acid, (5-Methyl-2-phenyloxazol-4-yl)acetic acid, 4-(2-Cyclohexenyloxy)benzoic acid, 5-Methoxy-2-methylindole-3-acetic acid, trans-4-Cotininecarboxylic acid, Bz-5-Aminovaleric acid, 4-Hexyloxybenzoic acid, N-(3-Methoxyphenyl)succinamic acid, Z-Sar-OH, 4-(3,4-Dimethoxyphenyl)butyric acid, Ac-o-Fluoro-DL-Phe-OH, N-(4-Fluorophenyl)glutaramic acid, 4'-Ethyl-4-biphenylcarboxylic acid, 1,2,3,4-Tetrahydroacridinecarboxylic acid, 3-Phenoxyphenylacetic acid, N-(2,4-Difluorophenyl)succinamic acid, N-Decanoyl-Gly-OH, (+)-6-Methoxy-a-methyl-2-naphthaleneacetic acid, 3-(Trifluoromethoxy)cinnamic acid, N-Formyl-DL-Trp-OH, (R)-(+)-a-Methoxy-a-(trifluoromethyl) phenylacetic acid, Bz-DL-Leu-OH, 4-(Trifluoromethoxy) phenoxyacetic acid, 4-Heptyloxybenzoic acid, 2,3,4-Trimethoxycinnamic acid, 2,6-Dimethoxybenzoyl-Gly-OH, 3-(3,4,5-Trimethoxyphenyl)propionic acid, 2,3,4,5,6-Pentafluorophenoxyacetic acid, N-(2,4-Difluorophenyl) glutaramic acid, N-Undecanoyl-Gly-OH, 2-(4-Fluorobenzoyl)benzoic acid, 5-Trifluoromethoxyindole-2-carboxylic acid, N-(2,4-Difluorophenyl)diglycolamic acid, Ac-L-Trp-OH, Tfa-L-Phenylglycine-OH, 3-Iodobenzoic acid, 3-(4-n-Pentylbenzoyl)propionic acid, 2-Phenyl-4-quinolinecarboxylic acid, 4-Octyloxybenzoic acid, Bz-L-Met-OH, 3,4,5-Triethoxybenzoic acid, N-Lauroyl-Gly-OH, 3,5-Bis(trifluoromethyl)benzoic acid, Ac-5-Methyl-DL-Trp-OH, 2-Iodophenylacetic acid, 3-Iodo-4-methylbenzoic acid, 3-(4-n-Hexylbenzoyl)propionic acid, N-Hexanoyl-L-Phe-OH, 4-Nonyloxybenzoic acid, 4'-(Trifluoromethyl)-2-biphenylcarboxylic acid, Bz-L-Phe-OH, N-Tridecanoyl-Gly-OH, 3,5-Bis(trifluoromethyl)phenylacetic acid, 3-(4-n-Heptylbenzoyl)propionic acid, N-Hepytanoyl-L-Phe-OH, 4-Decyloxybenzoic acid, N-(α,α,α-trifluoro-m-tolyl) anthranilic acid, Niflumic acid, 4-(2-Hydroxyhexafluoroisopropyl)benzoic acid, N-Myristoyl-Gly-OH, 3-(4-n-Octylbenzoyl)propionic acid, N-Octanoyl-L-Phe-OH, 4-Undecyloxybenzoic acid, 3-(3,4,5-Trimethoxyphenyl)propionyl-Gly-OH, 8-Iodonaphthoic acid, N-Pentadecanoyl-Gly-OH, 4-Dodecyloxybenzoic acid, N-Palmitoyl-Gly-OH, and N-Stearoyl-Gly-OH. These organic acids are available from one or more of Advanced ChemTech, Louisville, Ky.; Bachem Bioscience Inc., Torrance, Calif.; Calbiochem-Novabiochem Corp., San Diego, Calif.; Farchan Laboratories Inc., Gainesville Fla.; Lancaster Synthesis, Windham N.H.; and MayBridge Chemical Company (c/o Ryan Scientific), Columbia, S.C. The catalogs from these companies use the abbreviations which are used above to identify the acids.

f. Combinatorial Chemistry as a Means for Preparing Tags

Combinatorial chemistry is a type of synthetic strategy which leads to the production of large chemical libraries (see, for example, PCT Application Publication No. WO 94/08051). These combinatorial libraries can be used as tags for the identification of molecules of interest (MOIs). Combinatorial chemistry may be defined as the systematic and repetitive, covalent connection of a set of different "building blocks" of varying structures to each other to yield a large array of diverse molecular entities. Building blocks can take many forms, both naturally occurring and synthetic, such as nucleophiles, electrophiles, dienes, alkylating or acylating agents, diamines, nucleotides, amino acids, sugars, lipids, organic monomers, synthons, and combinations of the above. Chemical reactions used to connect the building blocks may involve alkylation, acylation, oxidation, reduction, hydrolysis, substitution, elimination, addition, cyclization, condensation, and the like. This process can produce libraries of compounds which are oligomeric, non-oligomeric, or combinations thereof. If oligomeric, the compounds can be branched, unbranched, or cyclic. Examples of oligomeric structures which can be prepared by combinatorial methods include oligopeptides, oligonucleotides, oligosaccharides, polylipids, polyesters, polyamides, polyurethanes, polyureas, polyethers, poly(phosphorus derivatives), e.g., phosphates, phosphonates, phosphoramides, phosphonamides, phosphites, phosphinamides, etc., and poly(sulfuir derivatives), e.g., sulfones, sulfonates, sulfites, sulfonamides, sulfenamides, etc.

One common type of oligomeric combinatorial library is the peptide combinatorial library. Recent innovations in peptide chemistry and molecular biology have enabled libraries consisting of tens to hundreds of millions of different peptide sequences to be prepared and used. Such libraries can be divided into three broad categories. One category of libraries involves the chemical synthesis of soluble non-support-bound peptide libraries (e.g., Houghten et al., *Nature* 354:84, 1991). A second category involves the chemical synthesis of support-bound peptide libraries, presented on solid supports such as plastic pins, resin beads, or cotton (Geysen et al., *Mol. Immunol.* 23:709, 1986; Lam et al., *Nature* 354:82, 1991; Eichler and Houghten, *Biochemistry* 32:11035, 1993). In these first two categories, the building blocks are typically L-amino acids, D-amino acids, unnatural amino acids, or some mixture or combination thereof. A third category uses molecular biology approaches to prepare peptides or proteins on the surface of filamentous phage particles or plasmids (Scott and Craig, *Curr. Opinion Biotech.* 5:40, 1994). Soluble, nonsupport-bound peptide libraries appear to be suitable for a number of applications, including use as tags. The available repertoire of chemical diversities in peptide libraries can be expanded by steps such as permethylation (Ostresh et al., *Proc. Natl. Acad. Sci., USA* 91:11138, 1994).

Numerous variants of peptide combinatorial libraries are possible in which the peptide backbone is modified, and/or the amide bonds have been replaced by mimetic groups. Amide mimetic groups which may be used include ureas, urethanes, and carbonylmethylene groups. Restructuring the backbone such that sidechains emanate from the amide nitrogens of each amino acid, rather than the alpha-carbons, gives libraries of compounds known as peptoids (Simon et al., *Proc. Natl. Acad. Sci., USA* 89:9367, 1992).

Another common type of oligomeric combinatorial library is the oligonucleotide combinatorial library, where the building blocks are some form of naturally occurring or unnatural nucleotide or polysaccharide derivatives, including where various organic and inorganic groups may substitute for the phosphate linkage, and nitrogen or sulfur may substitute for oxygen in an ether linkage (Schneider et al., *Biochem.* 34:9599, 1995; Freier et al., *J. Med. Chem.* 38:344, 1995; Frank, *J. Biotechnology* 41:259, 1995; Schneider et al., Published PCT WO 942052; Ecker et al., *Nucleic Acids Res.* 21:1853, 1993).

More recently, the combinatorial production of collections of non-oligomeric, small molecule compounds has been described (DeWitt et al., *Proc. Natl. Acad. Sci., USA* 90:690, 1993; Bunin et al., *Proc. Natl. Acad. Sci., USA* 91:4708, 1994). Structures suitable for elaboration into small-molecule libraries encompass a wide variety of organic molecules, for example heterocyclics, aromatics, alicyclics, aliphatics, steroids, antibiotics, enzyme inhibitors, ligands, hormones, drugs, alkaloids, opioids, terpenes, porphyrins, toxins, catalysts, as well as combinations thereof.

g. Specific Methods for Combinatorial Synthesis of Tags

Two methods for the preparation and use of a diverse set of amine-containing MS tags are outlined below. In both methods, solid phase synthesis is employed to enable simultaneous parallel synthesis of a large number of tagged linkers, using the techniques of combinatorial chemistry. In the first method, the eventual cleavage of the tag from the oligonucleotide results in liberation of a carboxyl amide. In the second method, cleavage of the tag produces a carboxylic acid. The chemical components and linking elements used in these methods are abbreviated as follows:

| | | |
|---|---|---|
| R | = | resin |
| FMOC | = | fluorenylmethoxycarbonyl protecting group |
| All | = | allyl protecting group |
| $CO_2H$ | = | carboxylic acid group |
| $CONH_2$ | = | carboxylic amide group |
| $NH_2$ | = | amino group |
| OH | = | hydroxyl group |
| CONH | = | amide linkage |
| COO | = | ester linkage |
| $NH_2$—Rink—$CO_2H$ | = | 4-[($\alpha$-amino)-2,4-dimethoxybenzyl]-phenoxybutyric acid (Rink linker) |
| OH—1MeO—$CO_2H$ | = | (4-hydroxymethyl)phenoxybutyric acid |
| OH—2MeO—$CO_2H$ | = | (4-hydroxymethyl-3-methoxy)phenoxyacetic acid |
| $NH_2$—A—COOH | = | amino acid with aliphatic or aromatic amine functionality in side chain |
| X1 . . . Xn—COOH | = | set of n diverse carboxylic acids with unique molecular weights |
| oligo1 . . . oligo(n) | = | set of n oligonucleotides |
| HBTU | = | O-benzotriazol-1-yl-N,N,N',N'-tetramethyluronium hexafluorophosphate |

The sequence of steps in Method 1 is as follows:

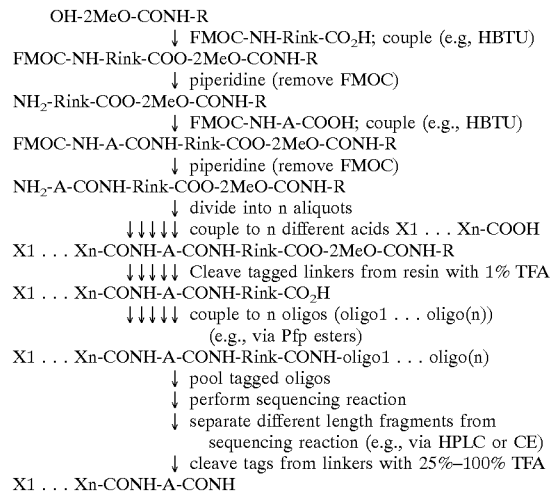

analyze by mass spectrometry

The sequence of steps in Method 2 is as follows:

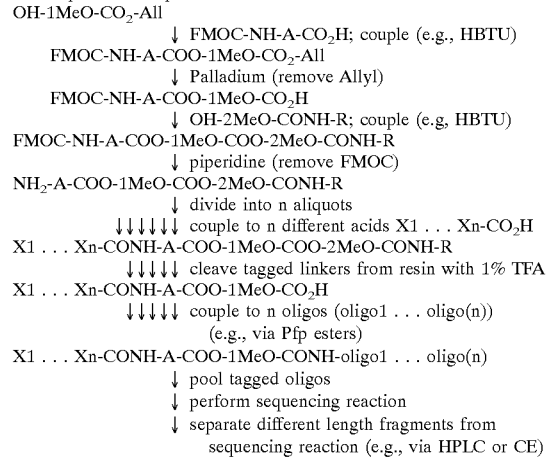

-continued

↓ cleave tags from linkers with 25–100% TFA

X1 ... Xn-CONH-A-CO₂H analyze by mass spectrometry

↓

2. Linkers

A "linker" component (or L), as used herein, means either a direct covalent bond or an organic chemical group which is used to connect a "tag" (or T) to a "molecule of interest" (or MOI) through covalent chemical bonds. In addition, the direct bond itself, or one or more bonds within the linker component is cleavable under conditions which allows T to be released (in other words, cleaved) from the remainder of the T—L—X compound (including the MOI component). The tag variable component which is present within T should be stable to the cleavage conditions. Preferably, the cleavage can be accomplished rapidly; within a few minutes and preferably within about 15 seconds or less.

In general, a linker is used to connect each of a large set of tags to each of a similarly large set of MOIs. Typically, a single tag-linker combination is attached to each MOI (to give various T—L—MOI), but in some cases, more than one tag-linker combination may be attached to each individual MOI (to give various (T—L)n—MOI). In another embodiment of the present invention, two or more tags are bonded to a single linker through multiple, independent sites on the linker, and this multiple tag-linker combination is then bonded to an individual MOI (to give various (T)n—L—MOI).

After various manipulations of the set of tagged MOIs, special chemical and/or physical conditions are used to cleave one or more covalent bonds in the linker, resulting in the liberation of the tags from the MOIs. The cleavable bond(s) may or may not be some of the same bonds that were formed when the tag, linker, and MOI were connected together. The design of the linker will, in large part, determine the conditions under which cleavage may be accomplished. Accordingly, linkers may be identified by the cleavage conditions they are particularly susceptible too. When a linker is photolabile (i.e., prone to cleavage by exposure to actinic radiation), the linker may be given the designation $L^{hv}$. Likewise, the designations $L^{acid}$, $L^{base}$, $L^{[O]}$, $L^{[R]}$, $L^{enz}$, $L^{elc}$, $L^{\Delta}$ and $L^{SS}$ may be used to refer to linkers that are particularly susceptible to cleavage by acid, base, chemical oxidation, chemical reduction, the catalytic activity of an enzyme (more simply "enzyme"), electrochemical oxidation or reduction, elevated temperature ("thermal") and thiol exchange, respectively.

Certain types of linker are labile to a single type of cleavage condition, whereas others are labile to several types of cleavage conditions. In addition, in linkers which are capable of bonding multiple tags (to give (T)n—L—MOI type structures), each of the tag-bonding sites may be labile to different cleavage conditions. For example, in a linker having two tags bonded to it, one of the tags may be labile only to base, and the other labile only to photolysis.

A linker which is useful in the present invention possesses several attributes:

1) The linker possesses a chemical handle ($L_h$) through which it can be attached to an MOI.

2) The linker possesses a second, separate chemical handle ($L_h$) through which the tag is attached to the linker. If multiple tags are attached to a single linker ((T)n—L—MOI type structures), then a separate handle exists for each tag.

3) The linker is stable toward all manipulations to which it is subjected, with the exception of the conditions which allow cleavage such that a T-containing moiety is released from the remainder of the compound, including the MOI. Thus, the linker is stable during attachment of the tag to the linker, attachment of the linker to the MOI, and any manipulations of the MOI while the tag and linker (T—L) are attached to it.

4) The linker does not significantly interfere with the manipulations performed on the MOI while the T—L is attached to it. For instance, if the T—L is attached to an oligonucleotide, the T—L must not significantly interfere with any hybridization or enzymatic reactions (e.g., PCR) performed on the oligonucleotide. Similarly, if the T—L is attached to an antibody, it must not significantly interfere with antigen recognition by the antibody.

5) Cleavage of the tag from the remainder of the compound occurs in a highly controlled manner, using physical or chemical processes that do not adversely affect the detectability of the tag.

For any given linker, it is preferred that the linker be attachable to a wide variety of MOIs, and that a wide variety of tags be attachable to the linker. Such flexibility is advantageous because it allows a library of T—L conjugates, once prepared, to be used with several different sets of MOIs.

As explained above, a preferred linker has the formula $$L_h—L^1—L^2—L^3—L_h$$

wherein each $L_h$ is a reactive handle that can be used to link the linker to a tag reactant and a molecule of interest reactant. $L^2$ is an essential part of the linker, because $L^2$ imparts lability to the linker. $L^1$ and $L^3$ are optional groups which effectively serve to separate $L^2$ from the handles $L_h$.

$L^1$ (which, by definition, is nearer to T than is $L^3$), serves to separate T from the required labile moiety $L^2$. This separation may be useful when the cleavage reaction generates particularly reactive species (e.g., free radicals) which may cause random changes in the structure of the T-containing moiety. As the cleavage site is further separated from the T-containing moiety, there is a reduced likelihood that reactive species formed at the cleavage site will disrupt the structure of the T-containing moiety. Also, as the atoms in L1 will typically be present in the T-containing moiety, these $L^1$ atoms may impart a desirable quality to the T-containing moiety. For example, where the T-containing moiety is a $T^{ms}$-containing moiety, and a hindered amine is desirably present as part of the structure of the $T^{ms}$-contaiing moiety (to serve, e.g., as a MSSE), the hindered amine may be present in $L^1$ labile moiety.

In other instances, $L^1$ and/or $L^3$ may be present in a linker component merely because the commercial supplier of a linker chooses to sell the linker in a form having such a $L^1$ and/or $L^3$ group. In such an instance, there is no harm in using linkers having $L^1$ and/or $L^3$ groups, (so long as these group do not inhibit the cleavage reaction) even though they may not contribute any particular performance advantage to the compounds that incorporate them. Thus, the present invention allows for $L^1$ and/or $L^3$ groups to be present in the linker component.

$L^1$ and/or $L^3$ groups may be a direct bond (in which case the group is effectively not present), a hydrocarbylene group (e.g., alkylene, arylene, cycloalkylene, etc.), —O-hydrocarbylene (e.g., —O—$CH_2$—, O—$CH_2$CH ($CH_3$)—, etc.) or hydrocarbylene-(O-hydrocarbylene)$_w$— wherein w is an integer ranging from 1 to about 10 (e.g., —$CH_2$—O—Ar—, —$CH_2$—(O—$CH_2CH_2$)$_4$—, etc.).

With the advent of solid phase synthesis, a great body of literature has developed regarding linkers that are labile to specific reaction conditions. In typical solid phase synthesis, a solid support is bonded through a labile linker to a reactive site, and a molecule to be synthesized is generated at the reactive site. When the molecule has been completely synthesized, the solid support-linker-molecule construct is subjected to cleavage conditions which releases the molecule from the solid support. The labile linkers which have been developed for use in this context (or which may be used in this context) may also be readily used as the linker reactant in the present invention.

Lloyd-Williams, P., et al., "Convergent Solid-Phase Peptide Synthesis", Tetrahedron Report No. 347, 49(48) :11065–11133 (1993) provides an extensive discussion of linkers which are labile to actinic radiation (i.e., photolysis), as well as acid, base and other cleavage conditions. Additional sources of information about labile linkers are well known in the art.

As described above, different linker designs will confer cleavability ("lability") under different specific physical or chemical conditions. Examples of conditions which serve to cleave various designs of linker include acid, base, oxidation, reduction, fluoride, thiol exchange, photolysis, and enzymatic conditions.

Examples of cleavable linkers that satisfy the general criteria for linkers listed above will be well known to those in the art and include those found in the catalog available from Pierce (Rockford, Ill.). Examples include:

ethylene glycobis(succinimidylsuccinate) (EGS), an amine reactive cross-linking reagent which is cleavable by hydroxylamine (1 M at 37° C. for 3–6 hours);

disuccinimidyl tartarate (DST) and sulfo-DST, which are amine reactive cross-linking reagents, cleavable by 0.015 M sodium periodate;

bis[2-(succinimidyloxycarbonyloxy)ethyl]sulfone (BSOCOES) and sulfo-BSOCOES, which are amine reactive cross-linking reagents, cleavable by base (pH 11.6);

1,4-di-[3'-(2'-pyridyldithio(propionamido))butane (DPDPB), a pyridyldithiol crosslinker which is cleavable by thiol exchange or reduction;

N-[4-(p-azidosalicylamido)-butyl]-3'-(2'-pyridydithio) propionamide (APDP), a pyridyldithiol crosslinker which is cleavable by thiol exchange or reduction;

bis-[beta-4-(azidosalicylamido)ethyl]-disulfide, a photoreactive crosslinker which is cleavable by thiol exchange or reduction;

N-succinimidyl-(4-azidophenyl)-1,3'dithiopropionate (SADP), a photoreactive crosslinker which is cleavable by thiol exchange or reduction;

sulfosuccinimidyl-2-(7-azido-4-methylcoumarin-3-acetamide)ethyl-1,3'-dithiopropionate (SAED), a photoreactive crosslinker which is cleavable by thiol exchange or reduction;

sulfosuccinimidyl-2-(m-azido-o-nitrobenzamido)-ethyl-1,3'dithiopropionate (SAND), a photoreactive crosslinker which is cleavable by thiol exchange or reduction.

Other examples of cleavable linkers and the cleavage conditions that can be used to release tags are as follows. A silyl linking group can be cleaved by fluoride or under acidic conditions. A 3-, 4-, 5-, or 6-substituted-2-nitrobenzyloxy or 2-, 3-, 5-, or 6-substituted-4-nitrobenzyloxy linking group can be cleaved by a photon source (photolysis). A 3-, 4-, 5-, or 6-substituted-2-alkoxyphenoxy or 2-, 3-, 5-, or 6-substituted-4-alkoxyphenoxy linking group can be cleaved by Ce($NH_4$)$_2$($NO_3$)$_6$ (oxidation). A $NCO_2$ (urethane) linker can be cleaved by hydroxide (base), acid, or $LiAlH_4$ (reduction). A 3-pentenyl, 2-butenyl, or 1-butenyl linking group can be cleaved by $O_3$, $O_sO_4$/$IO_4^-$, or $KMnO_4$ (oxidation). A 2-[3-, 4-, or 5-substituted-furyl]oxy linking group can be cleaved by $O_2$, $Br_2$, MeOH, or acid.

Conditions for the cleavage of other labile linking groups include: t-alkyloxy linking groups can be cleaved by acid; methyl(dialkyl)methoxy or 4-substituted-2-alkyl-1,3-dioxlane-2-yl linking groups can be cleaved by $H_3O^+$; 2-silylethoxy linking groups can be cleaved by fluoride or acid; 2-(X)-ethoxy (where X=keto, ester amide, cyano, $NO_2$, sulfide, sulfoxide, sulfone) linking groups can be cleaved under alkaline conditions; 2-, 3-, 4-, 5-, or 6-substituted-benzyloxy linking groups can be cleaved by acid or under reductive conditions; 2-butenyloxy linking groups can be cleaved by ($Ph_3P$)$_3$RhCl(H), 3-, 4-, 5-, or 6-substituted-2-bromophenoxy linking groups can be cleaved by Li, Mg, or BuLi; methylthiomethoxy linking groups can be cleaved by $Hg^{2+}$; 2-(X)-ethyloxy (where X=a halogen) linking groups can be cleaved by Zn or Mg; 2-hydroxyethyloxy linking groups can be cleaved by oxidation (e.g., with Pb(OAc)$_4$).

Preferred linkers are those that are cleaved by acid or photolysis. Several of the acid-labile linkers that have been developed for solid phase peptide synthesis are useful for linking tags to MOls. Some of these linkers are described in a recent review by Lloyd-Williams et al. (*Tetrahedron* 49:11065–11133, 1993). One useful type of linker is based upon p-alkoxybenzyl alcohols, of which two, 4-hydroxymethylphenoxyacetic acid and 4-(4-hydroxymethyl-3-methoxyphenoxy)butyric acid, are commercially available from Advanced ChemTech (Louisville, Ky.). Both linkers can be attached to a tag via an ester linkage to the benzylalcohol, and to an amine-containing MOI via an amide linkage to the carboxylic acid. Tags linked by these molecules are released from the MOI with varying concentrations of trifluoroacetic acid. The cleavage of these linkers results in the liberation of a carboxylic acid on the tag. Acid cleavage of tags attached through related linkers, such as 2,4-dimethoxy-4'-(carboxymethyloxy)-benzhydrylamine (available from Advanced ChemTech in FMOC-protected form), results in liberation of a carboxylic amide on the released tag.

The photolabile linkers useful for this application have also been for the most part developed for solid phase peptide synthesis (see Lloyd-Williams review).

These linkers are usually based on 2-nitrobenzylesters or 2-nitrobenzylamides. Two examples of photolabile linkers that have recently been reported in the literature are 4-(4-(1-Fmoc-amino)ethyl)-2-methoxy-5-nitrophenoxy)butanoic acid (Holmes and Jones, *J. Org. Chem.* 60:2318–2319, 1995) and 3-(Fmoc-amino)-3-(2-nitrophenyl)propionic acid (Brown et al., *Molecular Diversity* 1:4–12, 1995). Both linkers can be attached via the carboxylic acid to an amine on the MOI. The attachment of the tag to the linker is made by forming an amide between a carboxylic acid on the tag and the amine on the linker. Cleavage of photolabile linkers is usually performed with UV light of 350 nm wavelength at intensities and times known to those in the art. Cleavage of the linkers results in liberation of a primary amide on the tag. Examples of photocleavable linkers include nitrophenyl glycine esters, exo- and endo-2-benzonorbomeyl chlorides and methane sulfonates, and 3-amino-3(2-nitrophenyl) propionic acid. Examples of enzymatic cleavage include esterases which will cleave ester bonds, nucleases which will cleave phosphodiester bonds, proteases which cleave peptide bonds, etc.

A preferred linker component has an ortho-nitrobenzyl structure as shown below:

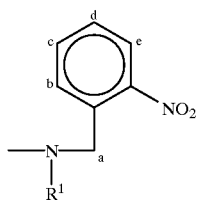

wherein one carbon atom at positions a, b, c, d or e is substituted with —$L^3$—X, and $L^1$ (which is preferably a direct bond) is present to the left of N($R^1$) in the above structure. Such a linker component is susceptible to selective photo-induced cleavage of the bond between the carbon labeled "a" and N($R^1$). The identity of $R^1$ is not typically critical to the cleavage reaction, however $R^1$ is preferably selected from hydrogen and hydrocarbyl. The present invention provides that in the above structure, —N($R^1$)— could be replaced with —O—. Also in the above structure, one or more of positions b, c, d or e may optionally be substituted with alkyl, alkoxy, fluoride, chloride, hydroxyl, carboxylate or amide, where these substituents are independently selected at each occurrence.

A further preferred linker component with a chemical handle $L_h$ has the following structure:

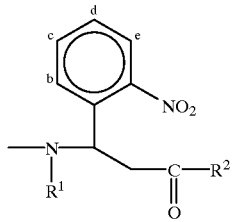

wherein one or more of positions b, c, d or e is substituted with hydrogen, alkyl, alkoxy, fluoride, chloride, hydroxyl, carboxylate or amide, $R^1$ is hydrogen or hydrocarbyl, and $R^2$ is —OH or a group that either protects or activates a carboxylic acid for coupling with another moiety. Fluorocarbon and hydrofluorocarbon groups are preferred groups that activate a carboxylic acid toward coupling with another moiety.

3. Molecule of Interest (MOI)

Examples of MOIs include nucleic acids or nucleic acid analogues (e.g., PNA), fragments of nucleic acids (i.e., nucleic acid fragments), synthetic nucleic acids or fragments, oligonucleotides (e.g., DNA or RNA), proteins, peptides, antibodies or antibody fragments, receptors, receptor ligands, members of a ligand pair, cytokines, hormones, oligosaccharides, synthetic organic molecules, drugs, and combinations thereof.

Preferred MOIs include nucleic acid fragments. Preferred nucleic acid fragments are primer sequences that are complementary to sequences present in vectors, where the vectors are used for base sequencing. Preferably a nucleic acid fragment is attached directly or indirectly to a tag at other than the 3' end of the fragment; and most preferably at the 5' end of the fragment. Nucleic acid fragments may be purchased or prepared based upon genetic databases (e.g., Dib et al., Nature 380:152–154, 1996 and CEPH Genotype Database, http://www.cephb.fr) and commercial vendors (e.g., Promega, Madison, Wis.).

As used herein, MOI includes derivatives of an MOI that contain fumctionality useful in joining the MOI to a T—L—$L_h$ compound. For example, a nucleic acid fragment that has a phosphodiester at the 5' end, where the phosphodiester is also bonded to an alkyleneamine, is an MOI. Such an MOI is described in, e.g., U.S. Pat. No. 4,762,779 which is incorporated herein by reference. A nucleic acid fragment with an internal modification is also an MOI. An exemplary internal modification of a nucleic acid fragment is where the base (e.g., adenine, guanine, cytosine, thymidine, uracil) has been modified to add a reactive functional group. Such internally modified nucleic acid fragments are commercially available from, e.g., Glen Research, Herndon, Va. Another exemplary internal modification of a nucleic acid fragment is where an abasic phosphoramidate is used to synthesize a modified phosphodiester which is interposed between a sugar and phosphate group of a nucleic acid fragment. The abasic phosphoramidate contains a reactive group which allows a nucleic acid fragment that contains this phosphoramidate-derived moiety to be joined to another moiety, e.g., a T—L—$L_h$ compound. Such abasic phosphoramidates are commercially available from, e.g., Clonetech Laboratories, Inc., Palo Alto, Calif.

4. Chemical Handles ($L_h$)

A chemical handle is a stable yet reactive atomic arrangement present as part of a first molecule, where the handle can undergo chemical reaction with a complementary chemical handle present as part of a second molecule, so as to form a covalent bond between the two molecules. For example, the chemical handle may be a hydroxyl group, and the complementary chemical handle may be a carboxylic acid group (or an activated derivative thereof, e.g., a hydrofluroaryl ester), whereupon reaction between these two handles forms a covalent bond (specifically, an ester group) that joins the two molecules together.

Chemical handles may be used in a large number of covalent bond-forming reactions that are suitable for attaching tags to linkers, and linkers to MOIs. Such reactions include alkylation (e.g., to form ethers, thioethers), acylation (e.g., to form esters, amides, carbamates, ureas, thioureas), phosphorylation (e.g., to form phosphates, phosphonates, phosphoramides, phosphonamides), sulfonylation (e.g., to form sulfonates, sulfonamides), condensation (e.g., to form imines, oximes, hydrazones), silylation, disulfide formation, and generation of reactive intermediates, such as nitrenes or carbenes, by photolysis. In general, handles and bond-forming reactions which are suitable for attaching tags to linkers are also suitable for attaching linkers to MOIs, and vice-versa. In some cases, the MOI may undergo prior modification or derivitization to provide the handle needed for attaching the linker.

One type of bond especially useful for attaching linkers to MOIs is the disulfide bond. Its formation requires the presence of a thiol group ("handle") on the linker, and another thiol group on the MOI. Mild oxidizing conditions then suffice to bond the two thiols together as a disulfide. Disulfide formation can also be induced by using an excess of an appropriate disulfide exchange reagent, e.g., pyridyl disulfides. Because disulfide formation is readily reversible, the disulfide may also be used as the cleavable bond for liberating the tag, if desired. This is typically accomplished under similarly mild conditions, using an excess of an appropriate thiol exchange reagent, e.g., dithiothreitol.

Of particular interest for linking tags (or tags with linkers) to oligonucleotides is the formation of amide bonds. Primary aliphatic amine handles can be readily introduced onto synthetic oligonucleotides with phosphoramidites such as 6-monomethoxytritylhexylcyanoethyl-N,N-diisopropyl phosphoramidite (available from Glenn Research, Sterling, Va.). The amines found on natural nucleotides such as adenosine and guanosine are virtually unreactive when compared to the introduced primary amine. This difference in reactivity forms the basis of the ability to selectively form amides and related bonding groups (e.g., ureas, thioureas, sulfonamides) with the introduced primary amine, and not the nucleotide amines.

As listed in the Molecular Probes catalog (Eugene, Oreg.), a partial enumeration of amine-reactive functional groups includes activated carboxylic esters, isocyanates, isothiocyanates, sulfonyl halides, and dichlorotriazenes. Active esters are excellent reagents for amine modification since the amide products formed are very stable. Also, these reagents have good reactivity with aliphatic amines and low reactivity with the nucleotide amines of oligonucleotides. Examples of active esters include N-hydroxysuccinimide esters, pentafluorophenyl esters, tetrafluorophenyl esters, and p-nitrophenyl esters. Active esters are useful because they can be made from virtually any molecule that contains a carboxylic acid. Methods to make active esters are listed in Bodansky (*Principles of Peptide Chemistry* (2d ed.), Springer Verlag, London, 1993).

5. Linker Attachment

Typically, a single type of linker is used to connect a particular set or family of tags to a particular set or family of MOIs. In a preferred embodiment of the invention, a single, uniform procedure may be followed to create all the various T—L—MOI structures. This is especially advantageous when the set of T—L—MOI structures is large, because it allows the set to be prepared using the methods of combinatorial chemistry or other parallel processing technology. In a similar manner, the use of a single type of linker allows a single, uniform procedure to be employed for cleaving all the various T—L—MOI structures. Again, this is advantageous for a large set of T—L—MOI structures, because the set may be processed in a parallel, repetitive, and/or automated manner.

There are, however, other embodiment of the present invention, wherein two or more types of linker are used to connect different subsets of tags to corresponding subsets of MOIs. In this case, selective cleavage conditions may be used to cleave each of the linkers independently, without cleaving the linkers present on other subsets of MOIs.

A large number of covalent bond-forming reactions are suitable for attaching tags to linkers, and linkers to MOIs. Such reactions include alkylation (e.g., to form ethers, thioethers), acylation (e.g., to form esters, amides, carbamates, ureas, thioureas), phosphorylation (e.g., to form phosphates, phosphonates, phosphoramides, phosphonamides), sulfonylation (e.g., to form sulfonates, sulfonamides), condensation (e.g., to form imines, oximes, hydrazones), silylation, disulfide formation, and generation of reactive intermediates, such as nitrenes or carbenes, by photolysis. In general, handles and bond-forming reactions which are suitable for attaching tags to linkers are also suitable for attaching linkers to MOIs, and vice-versa. In some cases, the MOI may undergo prior modification or derivitization to provide the handle needed for attaching the linker.

One type of bond especially useful for attaching linkers to MOIs is the disulfide bond. Its formation requires the presence of a thiol group ("handle") on the linker, and another thiol group on the MOI. Mild oxidizing conditions then suffice to bond the two thiols together as a disulfide. Disulfide formation can also be induced by using an excess of an appropriate disulfide exchange reagent, e.g., pyridyl disulfides. Because disulfide formation is readily reversible, the disulfide may also be used as the cleavable bond for liberating the tag, if desired. This is typically accomplished under similarly mild conditions, using an excess of an appropriate thiol exchange reagent, e.g., dithiothreitol.

Of particular interest for linking tags to oligonucleotides is the formation of amide bonds. Primary aliphatic amine handles can be readily introduced onto synthetic oligonucleotides with phosphoramidites such as 6-monomethoxytritylhexylcyanoethyl-N,N-diisopropyl phosphoramidite (available from Glenn Research, Sterling, Va.). The amines found on natural nucleotides such as adenosine and guanosine are virtually unreactive when compared to the introduced primary amine. This difference in reactivity forms the basis of the ability to selectively form amides and related bonding groups (e.g., ureas, thioureas, sulfonamides) with the introduced primary amine, and not the nucleotide amines.

As listed in the Molecular Probes catalog (Eugene, Oreg.), a partial enumeration of amine-reactive functional groups includes activated carboxylic esters, isocyanates, isothiocyanates, sulfonyl halides, and dichlorotriazenes. Active esters are excellent reagents for amine modification since the amide products formed are very stable. Also, these reagents have good reactivity with aliphatic amines and low reactivity with the nucleotide amines of oligonucleotides. Examples of active esters include N-hydroxysuccinimide esters, pentafluorophenyl esters, tetrafluorophenyl esters, and p-nitrophenyl esters. Active esters are useful because they can be made from virtually any molecule that contains a carboxylic acid. Methods to make active esters are listed in Bodansky (*Principles of Peptide Chemistry* (2d ed.), Springer Verlag, London, 1993).

Numerous commercial cross-linking reagents exist which can serve as linkers (e.g., see Pierce Cross-linkers, Pierce Chemical Co., Rockford, Ill.). Among these are homobifunctional amine-reactive cross-linking reagents which are exemplified by homobiftnctional imidoesters and N-hydroxysuccinimidyl (NHS) esters. There also exist heterobifunctional cross-linking reagents possess two or more different reactive groups that allows for sequential reactions. Imidoesters react rapidly with amines at alkaline pH. NHS-esters give stable products when reacted with primary or secondary amines. Maleimides, alkyl and aryl halides, alpha-haloacyls and pyridyl disulfides are thiol reactive. Maleimides are specific for thiol (sulfhydryl) groups in the pH range of 6.5 to 7.5, and at alkaline pH can become amine reactive. The thioether linkage is stable under physiological conditions. Alpha-haloacetyl cross-linking reagents contain the iodoacetyl group and are reactive towards sulfhydryls. Imidazoles can react with the iodoacetyl moiety, but the reaction is very slow. Pyridyl disulfides react with thiol groups to form a disulfide bond. Carbodiimides couple carboxyls to primary amines of hydrazides which give rises to the formation of an acyl-hydrazine bond. The arylazides are photoaffinity reagents which are chemically inert until exposed to UV or visible light. When such compounds are photolyzed at 250–460 nm, a reactive aryl nitrene is formed. The reactive aryl nitrene is relatively non-specific. Glyoxals are reactive towards guanidinyl portion of arginine.

In one typical embodiment of the present invention, a tag is first bonded to a linker, then the combination of tag and linker is bonded to a MOI, to create the structure T—L—MOI. Alternatively, the same structure is formed by first bonding a linker to a MOI, and then bonding the combination of linker and MOI to a tag. An example is where the MOI is a DNA primer or oligonucleotide. In that case, the tag is typically first bonded to a linker, then the T—L is bonded to a DNA primer or oligonucleotide, which is then used, for example, in a sequencing reaction.

One useful form in which a tag could be reversibly attached to an MOI (e.g., an oligonucleotide or DNA sequencing primer) is through a chemically labile linker. One preferred design for the linker allows the linker to be cleaved when exposed to a volatile organic acid, for example, trifluoroacetic acid (TFA). TFA in particular is compatible with most methods of MS ionization, including electrospray.

As described in detail below, the invention provides a method for determining the sequence of a nucleic acid molecule. A composition which may be formed by the inventive method comprises a plurality of compounds of the formula:

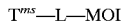

$T^{ms}$—L—MOI wherein $T^{ms}$ is an organic group detectable by mass spectrometry. $T^{ms}$ contains carbon, at least one of hydrogen and fluoride, and may contain optional atoms including oxygen, nitrogen, sulfur, phosphorus and iodine. In the formula, L is an organic group which allows a $T^{ms}$-containing moiety to be cleaved from the remainder of the compound upon exposure of the compound to cleavage condition. The cleaved $T^{ms}$-containing moiety includes a functional group which supports a single ionized charge state when each of the plurality of compounds is subjected to mass spectrometry. The functional group may be a tertiary amine, quaternary amine or an organic acid. In the formula, MOI is a nucleic acid fragment which is conjugated to L via the 5' end of the MOI. The term "conjugated" means that there may be chemical groups intermediate L and the MOI, e.g., a phosphodiester group and/or an alkylene group. The nucleic acid fragment may have a sequence complementary to a portion of a vector, wherein the fragment is capable of priming nucleotide synthesis.

In the composition, no two compounds have either the same $T^{ms}$ or the same MOI. In other words, the composition includes a plurality of compounds, wherein each compound has both a unique $T^{ms}$ and a unique nucleic acid fragment (unique in that it has a unique base sequence). In addition, the composition may be described as having a plurality of compounds wherein each compound is defined as having a unique $T^{ms}$, where the $T^{ms}$ is unique in that no other compound has a $T^{ms}$ that provides the same signal by mass spectrometry. The composition therefore contains a plurality of compounds, each having a $T^{ms}$ with a unique mass. The composition may also be described as having a plurality of compounds wherein each compound is defined as having a unique nucleic acid sequence. These nucleic acid sequences are intentionally unique so that each compound will serve as a primer for only one vector, when the composition is combined with vectors for nucleic acid sequencing. The set of compounds having unique $T^{ms}$ groups is the same set of compounds which has unique nucleic acid sequences.

Preferably, the $T^{ms}$ groups are unique in that there is at least a 2 amu, more preferably at least a 3 amu, and still more preferably at least a 4 amu mass separation between the $T^{ms}$ groups of any two different compounds. In the composition, there are at least 2 different compounds, preferably there are more than 2 different compounds, and more preferably there are more than 4 different compounds. The composition may contain 100 or more different compounds, each compound having a unique $T^{ms}$ and a unique nucleic acid sequence.

Another composition that is useful in, e.g., determining the sequence of a nucleic acid molecule, includes water and a compound of the formula $T^{ms}$—L—MOI, wherein $T^{ms}$ is an organic group detectable by mass spectrometry. $T^{ms}$ contains carbon, at least one of hydrogen and fluoride, and may contain optional atoms including oxygen, nitrogen, sulfur, phosphorus and iodine. In the formula, L is an organic group which allows a $T^{ms}$-containing moiety to be cleaved from the remainder of the compound upon exposure of the compound to cleavage condition. The cleaved $T^{ms}$-containing moiety includes a functional group which supports a single ionized charge state when each of the plurality of compounds is subjected to mass spectrometry. The functional group may be a tertiary amine, quaternary amine or an organic acid. In the formula, MOI is a nucleic acid fragment attached at its 5' end.

In addition to water, this composition may contain a buffer, in order to maintain the pH of the aqueous composition within the range of about 5 to about 9. Furthermore, the composition may contain an enzyme, salts (such as MgCl$_2$ and NaCl) and one of dATP, dGTP, dCTP, and dTTP. A preferred composition contains water, $T^{ms}$—L—MOI and one (and only one) of ddATP, ddGTP, ddCTP, and ddTTP. Such a composition is suitable for use in the dideoxy sequencing method.

The invention also provides a composition which contains a plurality of sets of compounds, wherein each set of compounds has the formula:

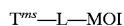

$T^{ms}$—L—MOI wherein $T^{ms}$ is an organic group detectable by mass spectrometry, comprising carbon, at least one of hydrogen and fluoride, and optional atoms selected from oxygen, nitrogen, sulfur, phosphorus and iodine. L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid. The MOI is a nucleic acid fragment wherein L is conjugated to MOI at the MOI's 5' end.

Within a set, all members have the same $T^{ms}$ group, and the MOI fragments have variable lengths that terminate with the same dideoxynucleotide selected from ddAMP, ddGMP, ddCMP and ddTMP; and between sets, the $T^{ms}$ groups differ by at least 2 amu, preferably by at least 3 amu. The plurality of sets is preferably at least 5 and may number 100 or more.

In a preferred composition comprising a first plurality of sets as described above, there is additionally present a second plurality of sets of compounds having the formula

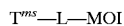

$T^{ms}$—L—MOI wherein $T^{ms}$ is an organic group detectable by mass spectrometry, comprising carbon, at least one of hydrogen and fluoride, and optional atoms selected from oxygen, nitrogen, sulfur, phosphorus and iodine. L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid. MOI is a nucleic acid fragment wherein L is conjugated to MOI at the MOI's 5' end. All members within the second plurality have an MOI sequence which terminates with the same dideoxynucleotide selected from ddAMP, ddGMP, ddCMP and ddTMP; with the proviso that the dideoxynucleotide present in the compounds of the first plurality is not the same dideoxynucleotide present in the compounds of the second plurality.

The invention also provides a kit for DNA sequencing analysis. The kit comprises a plurality of container sets, where each container set includes at least five containers. The first container contains a vector. The second, third, fourth and fifth containers contain compounds of the formula:

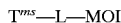

$T^{ms}$—L—MOI wherein $T^{ms}$ is an organic group detectable by mass spectrometry, comprising carbon, at least one of hydrogen and fluoride, and optional atoms selected from oxygen, nitrogen, sulfur, phosphorus and iodine. L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid. MOI is a nucleic acid fragment wherein L is conjugated to MOI at the MOI's 5' end. The MOI for the second, third, fourth and fifth containers is identical and complementary to a portion of the vector within the set of containers, and the $T^{ms}$ group within each container is different from the other $T^{ms}$ groups in the kit.

Preferably, within the kit, the plurality is at least 3, i.e., there are at least three sets of containers. More preferably, there are at least 5 sets of containers.

As noted above, the present invention provides compositions and methods for determining the sequence of nucleic acid molecules. Briefly, such methods generally comprise the steps of (a) generating tagged nucleic acid fragments which are complementary to a selected nucleic acid molecule (e.g., tagged fragments) from a first terminus to a second terminus of a nucleic acid molecule), wherein a tag is correlative with a particular or selected nucleotide, and may be detected by any of a variety of methods, (b) separating the tagged fragments by sequential length, (c) cleaving a tag from a tagged fragment, and (d) detecting the tags, and thereby determining the sequence of the nucleic acid molecule. Each of the aspects will be discussed in more detail below.

B. Sequencing Methods and Strategies

As noted above, the present invention provides methods for determining the sequence of a nucleic acid molecule. Briefly, tagged nucleic acid fragments are prepared. The nucleic acid fragments are complementary to a selected target nucleic acid molecule. In a preferred embodiment, the nucleic acid fragments are produced from a first terminus to a second terminus of a nucleic acid molecule, and more preferably from a 5' terminus to a 3' terminus. In other preferred embodiments, the tagged fragments are generated from 5'-tagged oligonucleotide primers or tagged dideoxynucleotide terminators. A tag of a tagged nucleic acid fragment is correlative with a particular nucleotide and is detectable by spectrometry (including fluorescence, but preferably other than fluorescence), or by potentiometry. In a preferred embodiment, at least five tagged nucleic acid fragments are generated and each tag is unique for a nucleic acid fragment. More specifically, the number of tagged fragments will generally range from about 5 to 2,000. The tagged nucleic acid fragments may be generated from a variety of compounds, including those set forth above. It will be evident to one in the art that the methods of the present invention are not limited to use only of the representative compounds and compositions described herein.

Following generation of tagged nucleic acid fragments, the tagged fragments are separated by sequential length. Such separation may be performed by a variety of techniques. In a preferred embodiment, separation is by liquid chromatography (LC) and particularly preferred is HPLC. Next, the tag is cleaved from the tagged fragment. The particular method for breaking a bond to release the tag is selected based upon the particular type of susceptibility of the bond to cleavage. For example, a light-sensitive bond (i.e., one that breaks by light) will be exposed to light. The released tag is detected by spectrometry or potentiometry. Preferred detection means are mass spectrometry, infrared spectrometry, ultraviolet spectrometry and potentiostatic amperometry (e.g., with an amperometric detector or coulemetric detector).

It will be appreciated by one in the art that one or more of the steps may be automated, e.g, by use of an instrument. In addition, the separation, cleavage and detection steps may be performed in a continuous manner (e.g., continuous flow/continuous fluid path of tagged fragments through separation to cleavage to tag detection). For example, the various steps may be incorporated into a system, such that the steps are performed in a continuous manner. Such a system is typically in an instrument or combination of instruments format. For example, tagged nucleic acid fragments that are separated (e.g., by HPLC) may flow into a device for cleavage (e.g., a photo-reactor) and then into a tag detector (e.g., a mass spectrometer or coulometric or amperometric detector). Preferably, the device for cleavage is tunable so that an optimum wavelength for the cleavage reaction can be selected.

It will be apparent to one in the art that the methods of the present invention for nucleic acid sequencing may be performed for a variety of purposes. For example, such use of the present methods include primary sequence determination for viral, bacterial, prokaryotic and eukaryotic (e.g., mammalian) nucleic acid molecules; mutation detection; diagnostics; forensics; identity; and polymorphism detection.

1. Sequencing Methods

As noted above, compounds including those of the present invention may be utilized for a variety of sequencing methods, including both enzymatic and chemical degradation methods. Briefly, the enzymatic method described by Sanger (*Proc. Natl. Acad. Sci.* (*USA*) 74:5463, 1977) which utilizes dideoxy-terminators, involves the synthesis of a DNA strand from a single-stranded template by a DNA polymerase. The Sanger method of sequencing depends on the fact that that dideoxynucleotides (ddNTPs) are incorporated into the growing strand in the same way a normal deoxynucleotides (albeit at a lower efficiency). However, ddNTPs differ from normal deoxynucleotides (dNTPs) in that they lack the 3'-OH group necessary for chain elongation. When a ddNTP is incorporated into the DNA chain, the absence the 3'-hydroxy group prevents the formation of a new phosphodiester bond and the DNA fragment is terminated with the ddNTP complementary to the base in the template DNA. The Maxam and Gilbert method (Maxam and Gilbert, *Proc. Natl. Acad. Sci.* (*USA*) 74:560, 1977) employs a chemical degradation method of the original DNA (in both cases the DNA must be clonal). Both methods produce populations of fragments that begin from a particular point and terminate in every base that is found in the DNA fragment that is to be sequenced. The termination of each fragment is dependent on the location of a particular base within the original DNA fragment. The DNA fragments are separated by polyacrylamide gel electrophoresis and the order of the DNA bases (A,C,T,G) is read from a autoradiograph of the gel.

2. Exonuclease DNA Sequencing

A procedure for determining DNA nucleotide sequences was reported by Labeit et al. (S. Labeit, H. Lehrach & R. S. Goody, *DNA* 5: 173–7, 1986; A new method of DNA sequencing using deoxynucleoside alpha-thiotriphosphates). In the first step of the method, four DNAs, each separately substituted with a different deoxynucleoside phosphorothioate in place of the corresponding monophosphate, are prepared by template-directed polymerization catalyzed by DNA polymerase. In the second step, these DNAs are subjected to stringent exonuclease III treatment, which produces only fragments terminating with a phosphorothioate internucleotide linkage. These can then be separated by standard gel electrophoresis techniques and the sequence can be read directly as in presently used sequencing methods. Porter et al. (K. W. Porter, J. Tomasz, F. Huang, A. Sood & B. R. Shaw, *Biochemistry* 34: 11963–11969, 1995; N7-cyanoborane-2'-deoxyguanosine 5'-triphosphate is a good substrate for DNA polymerase) described a new set of boron-substituted nucleotide analogs which are also exonuclease resistant and good substrates for a number of polymerases: these base are also suitable for exonuclease DNA sequencing.

3. A Simplified Strategy for Sequencing Large Numbers of Full Length cDNAs cDNA sequencing has been suggested as an alternative to generating the complete human genomic sequence. Two approaches have been attempted. The first involves generation of expressed sequence tags (ESTs) through a single DNA sequence pass at one end of each cDNA clone. This method has given insights into the distribution of types of expressed sequences and has revealed occasional useful homology with genomic fragments, but overall has added little to our knowledge base since insufficient data from each clone is provided. The second approach is to generate complete cDNA sequence which can indicate the possible function of the cDNAs. Unfortunately most cDNAs are of a size range of 1–4 kilobases which hinders the automation of full-length sequence determination. Currently the most efficient method for large scale, high throughput sequence production is from sequencing from a vector/primer site, which typically yields less than 500 bases of sequence from each flank. The synthesis of new oligonucleotide primers of length 15–18 bases for 'primer walking' can allow closure of each sequence. An alternative strategy for full length cDNA sequencing is to generate modified templates that are suitable for sequencing with a universal primer, but provide overlapping coverage of the molecules.

Shotgun sequencing methods can be applied to cDNA sequencing studies by preparing a separate library from each cDNA clone. These methods have not been used extensively for the analysis of the 1.5–4.0 kilobase fragments, however, as they are very labor intensive during the initial cloning phase. Instead they have generally been applied to projects where the target sequence is of the order of 15 to 40 kilobases, such as in lambda or cosmid inserts.

4. Analogy of cDNA with Genomic Sequencing

Despite the typically different size of the individual clones to be analyzed in cDNA sequencing, there are similarities with the requirements for large scale genomic DNA sequencing. In addition to a low cost per base, and a high throughput, the ideal strategy for full length cDNA sequencing will have a high accuracy. The favored current methodology for genomic DNA sequencing involves the preparation of shotgun sequencing libraries from cosmids, followed by random sequencing using ABI fluorescent DNA sequencing instruments, and closure (finishing) by directed efforts. Overall there is agreement that the fluorescent shotgun approach is superior to current alternatives in terms of efficiency and accuracy. The initial shotgun library quality is a critical determinant of the ease and quality of sequence assembly. The high quality of the available shotgun library procedure has prompted a strategy for the production of multiplex shotgun libraries containing mixtures of the smaller cDNA clones. Here the individual clones to be sequenced are mixed prior to library construction and then identified following random sequencing, at the stage of computer analysis. Junctions between individual clones are labeled during library production either by PCR or by identification of vector arm sequence.

Clones may be prepared both by microbial methods or by PCR. When using PCR, three reactions from each clone are used in order to minimize the risk for errors.

One pass sequencing is a new technique designed to speed the identification of important sequences within a new region of genomic DNA. Briefly, a high quality shotgun library is prepared and then the sequences sampled to obtain 80–95% coverage. For a cosmid this would typically be about 200 samples. Essentially all genes are likely to have at least one exon detected in this sample using either sequence similarity (BLAST) or exon structure (GRAIL2) screening.

"Skimming" has been successfully applied to cosmids and P1s. One pass sequencing is potentially the fastest and least expensive way to find genes in a positional cloning project. The outcome is virtually assured. Most investigators are currently developing cosmid contigs for exon trapping and related techniques. Cosmids are completely suitable for sequence skimming. P1 and other BACs could be considerably cheaper since there is savings both in shotgun library construction and minimization of overlaps.

5. Shotgun Sequencing

Shotgun DNA sequencing starts with random fragmentation of the target DNA. Random sequencing is then used to generate the majority of the data. A directed phase then completes gaps, ensuring coverage of each strand in both directions. Shotgun sequencing offers the advantage of high accuracy at relatively low cost. The procedure is best suited to the analysis of relatively large fragments and is the method of choice in large scale genomic DNA sequencing.

There are several factors that are important in making shotgun sequencing accurate and cost effective. A major consideration is the quality of the shotgun library that is generated, since any clones that do not have inserts, or have chimeric inserts, will result in subsequent inefficient sequencing. Another consideration is the careful balancing of the random and the directed phases of the sequencing, so that high accuracy is obtained with a minimal loss of efficiency through unnecessary sequencing.

6. Sequencing Chemistry: Tagged-Terminator Chemistry

There are two types of fluorescent sequencing chemistries currently available: dye primer, where the primer is fluorescently labeled, and dye terminator, where the dideoxy terminators are labeled. Each of these chemistries can be used with either Taq DNA polymerase or sequenase enzymes. Sequenase enzyme seems to read easily through G-C rich regions, palindromes, simple repeats and other difficult to read sequences. Sequenase is also good for sequencing mixed populations. Sequenase sequencing requires 5 µg of template, one extension and a multi-step cleanup process. Tagged-primer sequencing requires four separate reactions, one for each of A, C, G and T and then a laborious cleanup protocol. Taq terminator cycle sequencing chemistry is the most robust sequencing method. With this method any sequencing primer can be used. The amount of template needed is relatively small and the whole reaction process from setup to cleanup is reasonably easy, compared to sequenase and dye primer chemistries. Only 1.5 µg of DNA template and 4 pm of primer are needed. To this a ready reaction mix is added. This mix consists of buffer, enzyme, dNTPs and labeled dideoxynucleotides. This reaction can be done in one tube as each of the four dideoxies is labeled with a different fluorescent dye. These labeled terminators are present in this mix in excess because they are difficult to incorporate during extension. With unclean DNA the incorporation of these high molecular weight dideoxies can be inhibited. The premix includes dITP to minimize band compression. The use of Taq as the DNA polymerase allows the reactions to be run at high temperatures to minimize secondary structure problems as well as non-specific primer binding. The whole cocktail goes through 25 cycles of denaturation, annealing and extension in a thermal cycler and the completed reaction is spun through a Sephadex G50 (Pharmacia, Piscataway, N.J.) column and is ready for gel loading after five minutes in a vacuum dessicator.

7. Designing Primers

When designing primers, the same criteria should be used as for designing PCR primers. In particular, primers should preferably be 18 to 20 nucleotides long and the 3-prime end base should be a G or a C. Primers should also preferably have a Tm of more than 50° C. Primers shorter than 18 nucleotides will work but are not recommended. The shorter the primer the greater the probability of it binding at more than one site on the template DNA, and the lower its Tm. The sequence should have 100% match with the template. Any mismatch, especially towards the 3-prime end will greatly diminish sequencing ability. However primers with 5-prime tails can be used as long as there is about 18 bases at 3-prime that bind. If one is designing a primer from a sequence chromatogram, an area with high confidence must be used. As one moves out past 350 to 400 bases on a standard chromatogram, the peaks get broader and the base calls are not as accurate. As described herein, the primer may possess a 5' handle through which a linker or linker tag may be attached.

8. Nucleic Acid Template Preparation

The most important factor in tagged-primer DNA sequencing is the quality of the template. Briefly, one common misconception is that if a template works in manual sequencing, it should work in automated sequencing. In fact, if a reaction works in manual sequencing it may work in automated sequencing, however, automated sequencing is much more sensitive and a poor quality template may result in little or no data when fluorescent sequencing methods are utilized. High salt concentrations and other cell material not properly extracted during template preparation, including RNA, may likewise prevent the ability to obtain accurate sequence information. Many mini and maxi prep protocols produce DNA which is good enough for manual sequencing or PCR, but not for automated (tagged-primer) sequencing.

Also the use of phenol is not at all recommended as phenol can intercalate in the helix structure. The use of 100% chloroform is sufficient. There are a number of DNA preparation methods which are particularly preferred for the tagged primer sequencing methods provided herein. In particular, maxi preps which utilize cesium chloride preparations or Qiagen (Chatsworth, Calif.) maxi prep. columns (being careful not to overload) are preferred. For mini preps, columns such as Promega's Magic Mini prep (Madison, Wis.), may be utilized. When sequencing DNA fragments such as PCR fragments or restriction cut fragments, it is generally preferred to cut the desired fragment from a low melt argarose gel and then purify with a product such as GeneClean (La Jolla, Calif.). It is very important to make sure that only one band is cut from the gel. For PCR fragments the PCR primers or internal primers can be used in order to ensure that the appropriate fragment was sequenced. To get optimum performance from the sequence analysis software, fragments should be larger than 200 bases. Double stranded or single stranded DNA can be sequenced by this method.

An additional factor generally taken into account when preparing DNA for sequencing is the choice of host strain. Companies selling equipment and reagents for sequencing, such as ABI (Foster City, Calif.) and Qiagen (Chatsworth, Calif.), typically recommend preferred host strains, and have previously recommended strains such as DH5 alpha, HB101, XL-1 Blue, JM109, MV1190. Even when the DNA preparations are very clean, there are other inherent factors which can make it difficult to obtain sequence. G-C rich templates are always difficult to sequence through, and secondary structure can also cause problems. Sequencing through a long repeats often proves to be difficult. For instance as Taq moves along a poly T stretch, the enzyme often falls off the template and jumps back on again, skipping a T. This results in extension products with X amount of Ts in the poly T stretch and fragments with X-1, X-2 etc. amounts of Ts in the poly T stretch. The net effect is that more than one base appears in each position making the sequence impossible to read.

9. Use of Molecularly Distinct Cloning Vectors

Sequencing may also be accomplished utilizing universal cloning vector (M13) and complementary sequencing primers. Briefly, for present cloning vectors the same primer sequence is used and only 4 tags are employed (each tag is a different fluorophore which represents a different terminator (ddNTP)), every amplification process must take place in different containers (one DNA sample per container). That is, it is impossible to mix two or different DNA samples in the same amplification process. With only 4 tags available, only one DNA sample can be run per gel lane. There is no convenient means to deconvolute the sequence of more than one DNA sample with only 4 tags. (In this regard, workers in the field take great care not to mix or contaminate different DNA samples when using current technologies.)

A substantial advantage is gained when multiples of 4 tags can be run per gel lane or respective separation process. In particular, utilizing tags of the present invention, more than one DNA sample in a single amplification reaction or container can be processed. When multiples of 4 tags are available for use, each tag set can be assigned to a particular DNA sample that is to be amplified. (A tag set is composed of a series of 4 different tags each with a unique property. Each tag is assigned to represent a different dideoxy-terminator, ddATP, ddGTP, ddCTP, or ddTTP. To employ this advantage a series of vectors must be generated in which a unique priming site is inserted. A unique priming site is simply a stretch of 18 nucleotides which differs from vector to vector. The remaining nucleotide sequence is conserved from vector to vector. A sequencing primer is prepared (synthesized) which corresponds to each unique vector. Each unique primer is derived (or labeled) with a unique tag set.

With these respective molecular biology tools in hand, it is possible in the present invention to process multiple samples in a single container. First, DNA samples which are to be sequenced are cloned into the multiplicity of vectors. For example, if 100 unique vectors are available, 100 ligation reactions, plating steps, and picking of plaques are performed. Second, one sample from each vector type is pooled making a pool of 100 unique vectors containing 100 unique DNA fragments or samples. A given DNA sample is therefore identified and automatically assigned a primer set with the associated tag set. The respective primers, buffers, polymerase(s), ddNTPs, dNTPs and co-factors are added to the reaction container and the amplification process is carried out. The reaction is then subjected to a separation step and the respective sequence is established from the temporal appearance of tags. The ability to pool multiple DNA samples has substantial advantages. The reagent cost of a typical PCR reaction is about $2.00 per sample. With the method described herein the cost of amplification on a per sample basis could be reduced at least by a factor of 100. Sample handling could be reduced by a factor of at least 100, and materials costs could be reduced. The need for large scale amplification robots would be obviated.

10. Sequencing Vectors for Cleavable Mass Spectroscopy Tagging

Using cleavable mass spectroscopy tagging (CMST) of the present invention, each individual sequencing reaction can be read independently and simultaneously as the separation proceeds. In CMST sequencing, a different primer is used for each cloning vector: each reaction has 20 different primers when 20 clones are used per pool. Each primer corresponds to one of the vectors, and each primer is tagged with a unique CMST molecule. Four reactions are performed on each pooled DNA sample (one for each base), so every vector has four oligonucleotide primers, each one identical in sequence but tagged with a different CMS tag. The four separate sequencing reactions are pooled and run together. When 20 samples are pooled, 80 tags are used (4 bases per sample times 20 samples), and all 80 are detected simultaneously as the gel is run.

The construction of the vectors may be accomplished by cloning a random 20-mer on either side of a restriction site. The resulting clones are sequenced and a number chosen for use as vectors. Two oligonucleotides are prepared for each vector chosen, one homologous to the sequence at each side of the restriction site, and each orientated so that the 3'-end is towards the restriction site. Four tagged preparations of each primer are prepared, one for each base in the sequencing reactions and each one labeled with a unique CMS tag.

11. Advantages of Sequencing by the Use of Reversible Tags

There are substantial advantages when cleavable tags are used in sequencing and related technologies. First, an increase in sensitivity will contribute to longer read lengths, as will the ability to collect tags for a specified period of time prior to measurement. The use of cleavable tags permits the development of a system that equalizes bandwidth over the entire range of the gel (1–1500 nucleotides (nt), for example). This will greatly impact the ability to obtain read lengths greater than 450 nt.

The use of cleavable multiple tags (MW identifiers) also has the advantage that multiple DNA samples can be run on a single gel lane or separation process. For example, it is possible using the methodologies disclosed herein to combine at least 96 samples and 4 sequencing reactions (A,G, T,C) on a single lane or fragment sizing process. If multiple vectors are employed which possess unique priming sites, then at least 384 samples can be combined per gel lane (the different terminator reactions cannot be amplified together with this scheme). When the ability to employ cleavable tags is combined with the ability to use multiple vectors, an apparent 10,000-fold increase in DNA sequencing throughput is achieved. Also, in the schemes described herein, reagent use is decreased, disposables decrease, with a resultant decrease in operating costs to the consumer.

An additional advantage is gained from the ability to process internal controls throughout the entire methodologies described here. For any set of samples, an internal control nucleic acid can be placed in the sample(s). This is not possible with the current configurations. This advantage permits the control of the amplification process, the separation process, the tag detection system and sequence assembly. This is an immense advantage over current systems in which the controls are always separated from the samples in all steps.

The compositions and methods described herein also have the advantage that they are modular in nature and can be fitted on any type of separation process or method and in addition, can be fitted onto any type of detection system as improvements are made in either types of respective technologies. For example, the methodologies described herein can be coupled with "bundled" CE arrays or microfabricated devices that enable separation of DNA fragments.

C. Separation of DNA Fragments

A sample that requires analysis is often a mixture of many components in a complex matrix. For samples containing unknown compounds, the components must be separated from each other so that each individual component can be identified by other analytical methods. The separation properties of the components in a mixture are constant under constant conditions, and therefore once determined they can be used to identify and quantify each of the components. Such procedures are typical in chromatographic and electrophoretic analytical separations.

1. High-Performance Liquid Chromatography (HPLC)

High-Performance liquid chromatography (HPLC) is a chromatographic separations technique to separate compounds that are dissolved in solution. HPLC instruments consist of a reservoir of mobile phase, a pump, an injector, a separation columni, and a detector. Compounds are separated by injecting an aliquot of the sample mixture onto the column. The different components in the mixture pass through the column at different rates due to differences in their partitioning behavior between the mobile liquid phase and the stationary phase.

Recently, IP-RO-HPLC on non-porous PS/DVB particles with chemically bonded alkyl chains have been shown to be rapid alternatives to capillary electrophoresis in the analysis of both single and double-strand nucleic acids providing similar degrees of resolution (Huber et al, 1993, *Anal. Biochem.*, 212, p351; Huber et al., 1993, *Nuc. Acids Res.*, 21, p1061; Huber et al., 1993, *Biotechniques*, 16, p898). In contrast to ion-exchange chromatography, which does not always retain double-strand DNA as a function of strand length (Since AT base pairs interact with the positively charged stationary phase, more strongly than GC basepairs), IP-RP-HPLC enables a strictly size-dependent separation.

A method has been developed using 100 mM triethylammonium acetate as ion-pairing reagent, phosphodiester oligonucleotides could be successfully separated on alkylated non-porous 2.3 μM poly(styrene-divinylbenzene) particles by means of high performance liquid chromatography (Oefner et al., 1994, *Anal. Biochem.*, 223, p39). The technique described allowed the separation of PCR products differing only 4 to 8 base pairs in length within a size range of 50 to 200 nucleotides.

2. Electrophoresis

Electrophoresis is a separations technique that is based on the mobility of ions (or DNA as is the case described herein) in an electric field. Negatively charged DNA charged migrate towards a positive electrode and positively-charged ions migrate toward a negative electrode. For safety reasons one electrode is usually at ground and the other is biased positively or negatively. Charged species have different migration rates depending on their total charge, size, and shape, and can therefore be separated.

An electrode apparatus consists of a high-voltage power supply, electrodes, buffer, and a support for the buffer such as a polyacrylamide gel, or a capillary tube. Open capillary tubes are used for many types of samples and the other gel supports are usually used for biological samples such as protein mixtures or DNA fragments.

3. Capillary Electrophoresis (CE)

Capillary electrophoresis (CE) in its various manifestations (free solution, isotachophoresis, isoelectric focusing, polyacrylamide gel, micellar electrokinetic "chromatography") is developing as a method for rapid high resolution separations of very small sample volumes of complex mixtures. In combination with the inherent sensitivity and selectivity of MS, CE-MS is a potential powerful technique for bioanalysis. In the novel application disclosed herein, the interfacing of these two methods will lead to superior DNA sequencing methods that eclipse the current rate methods of sequencing by several orders of magnitude.

The correspondence between CE and electrospray ionization (ESI) flow rates and the fact that both are facilitated by (and primarily used for) ionic species in solution provide the basis for an extremely attractive combination. The combination of both capillary zone electrophoresis (CZE) and capillary isotachophoresis with quadrapole mass spectrometers based upon ESI have been described (Olivares et al., *Anal. Chem.* 59:1230, 1987; Smith et al., *Anal. Chem.* 60:436, 1988; Loo et al., *Anal. Chem.* 179:404, 1989; Edmonds et al., *J. Chroma.* 474:21, 1989; Loo et al., *J. Microcolumn Sep.* 1:223, 1989; Lee et al., *J. Chromatog.* 458:313, 1988; Smith et al., *J. Chromatog.* 480:211, 1989; Grese et al., *J. Am. Chem. Soc.* 111:2835, 1989). Small peptides are easily amenable to CZE analysis with good (femtomole) sensitivity.

The most powerful separation method for DNA fragments is polyacrylamide gel electrophoresis (PAGE), generally in a slab gel format. However, the major limitation of the current technology is the relatively long time required to perform the gel electrophoresis of DNA fragments produced in the sequencing reactions. An increase magnitude (10-fold) can be achieved with the use of capillary electrophoresis which utilize ultrathin gels. In free solution to a first approximation all DNA migrate with the same mobility as the addition of a base results in the compensation of mass and charge. In polyacrylamide gels, DNA fragments sieve and migrate as a function of length and this approach has now been applied to CE. Remarkable plate number per meter has now been achieved with cross-linked polyacrylamide ($10^{+7}$ plates per meter, Cohen et al., *Proc. Natl. Acad. Sci., USA* 85:9660, 1988). Such CE columns as described can be employed for DNA sequencing. The method of CE is in principle 25 times faster than slab gel electrophoresis in a standard sequencer. For example, about 300 bases can be read per hour. The separation speed is limited in slab gel electrophoresis by the magnitude of the electric field which can be applied to the gel without excessive heat production. Therefore, the greater speed of CE is achieved through the use of higher field strengths (300 V/cm in CE versus 10 V/cm in slab gel electrophoresis). The capillary format reduces the amperage and thus power and the resultant heat generation.

Smith and others (Smith et al., *Nuc. Acids. Res.* 18:4417, 1990) have suggested employing multiple capillaries in parallel to increase throughput. Likewise, Mathies and Huang (Mathies and Huang, *Nature* 359:167, 1992) have introduced capillary electrophoresis in which separations are performed on a parallel array of capillaries and demonstrated high through-put sequencing (Huang et al., *Anal. Chem.* 64:967, 1992, Huang et al., *Anal. Chem.* 64:2149, 1992). The major disadvantage of capillary electrophoresis is the limited amount of sample that can be loaded onto the capillary. By concentrating a large amount of sample at the beginning of the capillary, prior to separation, loadability is increased, and detection levels can be lowered several orders of magnitude. The most popular method of preconcentration in CE is sample stacking. Sample stacking has recently been reviewed (Chien and Burgi, *Anal. Chem.* 64:489A, 1992). Sample stacking depends of the matrix difference, (pH, ionic strength) between the sample buffer and the capillary buffer, so that the electric field across the sample zone is more than in the capillary region. In sample stacking, a large volume of sample in a low concentration buffer is introduced for preconcentration at the head of the capillary column. The capillary is filled with a buffer of the same composition, but at higher concentration. When the sample ions reach the capillary buffer and the lower electric field, they stack into a concentrated zone. Sample stacking has increased detectabilities 1–3 orders of magnitude.

Another method of preconcentration is to apply isotachophoresis (ITP) prior to the free zone CE separation of analytes. ITP is an electrophoretic technique which allows microliter volumes of sample to be loaded on to the capillary, in contrast to the low nL injection volumes typically associated with CE. The technique relies on inserting the sample between two buffers (leading and trailing electrolytes) of highel and lower mobility respectively, than the analyte. The technique is inherently a concentration technique, where the analytes concentrate into pure zones migrating with the same speed. The technique is currently less popular than the stacking methods described above because of the need for several choices of leading and trailing electrolytes, and the ability to separate only cationic or anionic species during a separation process.

The heart of the DNA sequencing process is the remarkably selective electrophoretic separation of DNA or oligonucleotide fragments. It is remarkable because each fragment is resolved and differs by only nucleotide. Separations of up to 1000 fragments (1000 bp) have been obtained. A further advantage of sequencing with cleavable tags is as follows. There is no requirement to use a slab gel format when DNA fragments are separated by polyacrylamide gel electrophoresis when cleavable tags are employed. Since numerous samples are combined (4 to 2000) there is no need to run samples in parallel as is the case with current dye-primer or dye-terminator methods (i.e., ABI373 sequencer). Since there is no reason to run parallel lanes, there is no reason to use a slab gel. Therefore, one can employ a tube gel format for the electrophoretic separation method. Grossman (Grossman et al., *Genet. Anal. Tech. Appl.* 9:9, 1992) have shown that considerable advantage is gained when a tube gel format is used in place of a slab gel format. This is due to the greater ability to dissipate Joule heat in a tube format compared to a slab gel which results in faster run times (by 50%), and much higher resolution of high molecular weight DNA fragments (greater than 1000 nt). Long reads are critical in genomic sequencing. Therefore, the use of cleavable tags in sequencing has the additional advantage of allowing the user to employ the most efficient and sensitive DNA separation method which also possesses the highest resolution.

4. Microfabricated Devices

Capillary electrophoresis (CE) is a powerful method for DNA sequencing, forensic analysis, PCR product analysis and restriction fragment sizing. CE is far faster than traditional slab PAGE since with capillary gels a far higher potential field can be applied. However, CE has the drawback of allowing only one sample to be processed per gel. The method combines the faster separations times of CE with the ability to analyze multiple samples in parallel. The underlying concept behind the use of microfabricated devices is the ability to increase the information density in electrophoresis by miniaturizing the lane dimension to about 100 micrometers. The electronics industry routinely uses microfabrication to make circuits with features of less than one micron in size. The current density of capillary arrays is limited the outside diameter of the capillary tube. Microfabrication of channels produces a higher density of arrays. Microfabrication also permits physical assemblies not possible with glass fibers and links the channels directly to other devices on a chip. Few devices have been constructed on microchips for separation technologies. A gas chromatograph (Terry et al., *IEEE Trans. Electron Device*, ED-26:1880, 1979) and a liquid chromatograph (Manz et al., *Sens. Actuators* B1:249, 1990) have been fabricated on silicon chips, but these devices have not been widely used. Several groups have reported separating fluorescent dyes and amino acids on microfabricated devices (Manz et al., *J. Chromatography* 593:253, 1992, Effenhauser et al., *Anal. Chem.* 65:2637, 1993). Recently Woolley and Mathies (Woolley and Mathies, *Proc. Natl. Acad. Sci.* 91:11348, 1994) have shown that photolithography and chemical etching can be used to make large numbers of separation channels on glass substrates. The channels are filled with hydroxyethyl cellulose (HEC) separation matrices. It was shown that DNA restriction fragments could be separated in as little as two minutes.

D. Cleavage of Tags

As described above. different linker designs will confer cleavability ("lability") under different specific physical or chemical conditions. Examples of conditions which serve to cleave various designs of linker include acid, base, oxidation, reduction, fluoride, thiol exchange, photolysis, and enzymatic conditions.

Examples of cleavable linkers that satisfy the general criteria for linkers listed above will be well known to those in the art and include those found in the catalog available from Pierce (Rockford, Ill.). Examples include:

ethylene glycobis(succinimidylsuccinate) (EGS), an amine reactive cross-linking reagent which is cleavable by hydroxylamine (1 M at 37° C. for 3–6 hours);

disuccinimidyl tartarate (DST) and sulfo-DST, which are amine reactive cross-linking reagents, cleavable by 0.015 M sodium periodate;

bis[2-(succinimidyloxycarbonyloxy)ethyl]sulfone (BSOCOES) and sulfo-BSOCOES, which are amine reactive cross-linking reagents, cleavable by base (pH 11.6);

1,4-di-[3'-(2'-pyridyldithio(propionamido))butane (DPDPB), a pyridyldithiol crosslinker which is cleavable by thiol exchange or reduction;

N-[4-(p-azidosalicylamido)-butyl]-3'-(2'-pyridydithio) propionamide (APDP), a pyridyldithiol crosslinker which is cleavable by thiol exchange or reduction;

bis-[beta-4-(azidosalicylamido)ethyl]-disulfide, a photoreactive crosslinker which is cleavable by thiol exchange or reduction;

N-succinimidyl-(4-azidophenyl)-1,3'dithiopropionate (SADP), a photoreactive crosslinker which is cleavable by thiol exchange or reduction;

sulfosuccinimidyl-2-(7-azido-4-methylcoumarin-3-acetamide)ethyl-1,3'-dithiopropionate (SAED), a photoreactive crosslinker which is cleavable by thiol exchange or reduction;

sulfosuccinimidyl-2-(m-azido-o-nitrobenzamido)-ethyl-1,3'dithiopropionate (SAND), a photoreactive crosslinker which is cleavable by thiol exchange or reduction.

Other examples of cleavable linkers and the cleavage conditions that can be used to release tags are as follows. A silyl linking group can be cleaved by fluoride or under acidic conditions. A 3-, 4-, 5-, or 6-substituted-2-nitrobenzyloxy or 2-, 3-, 5-, or 6-substituted-4-nitrobenzyloxy linking group can be cleaved by a photon source (photolysis). A 3-, 4-, 5-, or 6-substituted-2-alkoxyphenoxy or 2-, 3-, 5-, or 6-substituted-4-alkoxyphenoxy linking group can be cleaved by $Ce(NH_4)_2(NO_3)_6$ (oxidation). A $NCO_2$ (urethane) linker can be cleaved by hydroxide (base), acid, or $LiAlH_4$ (reduction). A 3-pentenyl, 2-butenyl, or 1-butenyl linking group can be cleaved by $O_3$, $O_sO_4/IO_4^-$, or $KMnO_4$ (oxidation). A 2-[3-, 4-, or 5-substituted-furyl]oxy linking group can be cleaved by $O_2$, $Br_2$, MeOH, or acid.

Conditions for the cleavage of other labile linking groups include: t-alkyloxy linking groups can be cleaved by acid; methyl(dialkyl)methoxy or 4-substituted-2-alkyl-1,3-dioxlane-2-yl linking groups can be cleaved by $H_3O^+$; 2-silylethoxy linking groups can be cleaved by fluoride or acid; 2-(X)-ethoxy (where X=keto, ester amide, cyano, $NO_2$, sulfide, sulfoxide, sulfone) linking groups can be cleaved under alkaline conditions; 2-, 3-, 4-, 5-, or 6-substituted-benzyloxy linking groups can be cleaved by acid or under reductive conditions; 2-butenyloxy linking groups can be cleaved by $(Ph_3P)_3RhCl(H)$, 3-, 4-, 5-, or 6-substituted-2-bromophenoxy linking groups can be cleaved by Li, Mg, or BuLi; methylthiomethoxy linking groups can be cleaved by $Hg^{2+}$; 2-(X)-ethyloxy (where X=a halogen) linking groups can be cleaved by Zn or Mg; 2-hydroxyethyloxy linking groups can be cleaved by oxidation (e.g., with $Pb(OAc)_4$).

Preferred linkers are those that are cleaved by acid or photolysis. Several of the acid-labile linkers that have been developed for solid phase peptide synthesis are useful for linking tags to MOIs. Some of these linkers are described in a recent review by Lloyd-Williams et al. (*Tetrahedron* 49:11065–11133, 1993). One useful type of linker is based upon p-alkoxybenzyl alcohols, of which two, 4-hydroxymethylphenoxyacetic acid and 4-(4-hydroxymethyl-3-methoxyphenoxy)butyric acid, are commercially available from Advanced ChemTech (Louisville, Ky.). Both linkers can be attached to a tag via an ester linkage to the benzylalcohol, and to an amine-containing MOI via an amide linkage to the carboxylic acid. Tags linked by these molecules are released from the MOI with varying concentrations of trifluoroacetic acid. The cleavage of these linkers results in the liberation of a carboxylic acid on the tag. Acid cleavage of tags attached through related linkers, such as 2,4-dimethoxy-4'-(carboxymethyloxy)-benzhydrylamine (available from Advanced ChemTech in FMOC-protected form), results in liberation of a carboxylic amide on the released tag.

The photolabile linkers useful for this application have also been for the most part developed for solid phase peptide synthesis (see Lloyd-Williams review). These linkers are usually based on 2-nitrobenzylesters or 2-nitrobenzylamides. Two examples of photolabile linkers that have recently been reported in the literature are 4-(4-(1-Fmoc-amino)ethyl)-2-methoxy-5-nitrophenoxy)butanoic acid (Holmes and Jones, *J. Org. Chem.* 60:2318–2319, 1995) and 3-(Fmoc-amino)-3-(2-nitrophenyl)propionic acid (Brown et al., *Molecular Diversity* 1:4–12, 1995). Both linkers can be attached via the carboxylic acid to an amine on the MOI. The attachment of the tag to the linker is made by forming an amide between a carboxylic acid on the tag and the amine on the linker. Cleavage of photolabile linkers is usually performed with UV light of 350 nm wavelength at intensities and times known to those in the art. Examples of conmmercial sources of instruments for photochemical cleavage are Aura Industries Inc. (Staten Island, N.Y. and Agrenetics (Wilmington, Mass.). Cleavage of the linkers results in liberation of a primary amide on the tag. Examples of photocleavable linkers include nitrophenyl glycine esters, exo- and endo-2-benzonorbomeyl chlorides and methane sulfonates, and 3-amino-3(2-nitrophenyl) propionic acid. Examples of enzymatic cleavage include esterases which will cleave ester bonds, nucleases which will cleave phosphodiester bonds, proteases which cleave peptide bonds, etc.

E. Detection of Tags

Detection methods typically rely on the absorption and emission in some type of spectral field. When atoms or molecules absorb light, the incoming energy excites a quantized structure to a higher energy level. The type of excitation depends on the wavelength of the light. Electrons are promoted to higher orbitals by ultraviolet or visible light, molecular vibrations are excited by infrared light, and rotations are excited by microwaves. An absorption spectrum is the absorption of light as a finction of wavelength. The spectrum of an atom or molecule depends on its energy level structure. Absorption spectra are usefuil for identification of compounds. Specific absorption spectroscopic methods include atomic absorption spectroscopy (AA), infrared spectroscopy (IR), and UV-vis spectroscopy (uv-vis).

Atoms or molecules that are excited to high energy levels can decay to lower levels by emitting radiation. This light emission is called fluorescence if the transition is between states of the same spin, and phosphorescence if the transition occurs between states of different spin. The emission intensity of an analyte is linearly proportional to concentration (at low concentrations), and is useful for quantifying the emitting species. Specific emission spectroscopic methods include atomic emission spectroscopy (AES), atomic fluorescence spectroscopy (AFS), molecular laser-induced fluorescence (LIF), and X-ray fluorescence (XRF).

When electromagnetic radiation passes through matter, most of the radiation continues in its original direction but a small fraction is scattered in other directions. Light that is scattered at the same wavelength as the incoming light is called Rayleigh scattering. Light that is scattered in transparent solids due to vibrations (phonons) is called Brillouin scattering. Brillouin scattering is typically shifted by 0.1 to 1 wave number from the incident light. Light that is scattered due to vibrations in molecules or optical phonons in opaque solids is called Raman scattering. Raman scattered light is shifted by as much as 4000 wavenumbers from the incident light. Specific scattering spectroscopic methods include Raman spectroscopy.

IR spectroscopy is the measurement of the wavelength and intensity of the absorption of mid-infrared light by a sample. Mid-infrared light (2.5–50 $\mu$m, 4000–200 $cm^{-1}$) is energetic enough to excite molecular vibrations to higher energy levels. The wavelength of IR absorption bands are characteristic of specific types of chemical bonds and IR spectroscopy is generally most useful for identification of organic and organometallic molecules.

Near-infrared absorption spectroscopy (NIR) is the measurement of the wavelength and intensity of the absorption of near-infrared light by a sample. Near-infrared light spans the 800 nm–2.5 $\mu$m (12,500–4000 $cm^{-1}$) range and is energetic enough to excite overtones and combinations of molecular vibrations to higher energy levels. NIR spectroscopy is typically used fot quantitative measurement of organic functional groups, especially O—H, N—H, and C=O. The components and design of NIR instrumentation are similar to uv-vis absorption spectrometers. The light source is usually a tungsten lamp and the detector is usually a PbS solid-state detector. Sample holders can be glass or quartz and typical solvents are $CCl_4$ and $CS_2$. The convenient instrumentation of NIR spectroscopy makes it suitable for on-line monitoring and process control.

Ultraviolet and Visible Absorption Spectroscopy (uv-vis) spectroscopy is the measurement of the wavelength and intensity of absorption of near-ultraviolet and visible light by a sample. Absorption in the vacuum UV occurs at 100–200 nm; ($10^5$–50,000 $cm^{-1}$) quartz UV at 200–350 nm; (50,000–28,570 $cm^{-1}$) and visible at 350–800 nm; (28,570–12,500 $cm^{-1}$) and is described by the Beer-Lambert-Bouguet law. Ultraviolet and visible light are energetic enough to promote outer electrons to higher energy levels. UV-vis spectroscopy can be usually applied to molecules and inorganic ions or complexes in solution. The uv-vis spectra are limited by the broad features of the spectra. The light source is usually a hydrogen or deuterium lamp for uv measurements and a tungsten lamp for visible measurements. The wavelengths of these continuous light sources are selected with a wavelength separator such as a prism or grating monochromator. Spectra are obtained by scanning the wavelength separator and quantitative measurements can be made from a spectrum or at a single wavelength.

Mass spectrometers use the difference in the mass-to-charge ratio (m/z) of ionized atoms or molecules to separate them from each other. Mass spectrometry is therefore useful for quantitation of atoms or molecules and also for determining chemical and structural information about molecules. Molecules have distinctive fragmentation patterns that provide structural information to identify compounds. The general operations of a mass spectrometer are as follows. Gas-phase ions are created, the ions are separated in space or time based on their mass-to-charge ratio, and the quantity of ions of each mass-to-charge ratio is measured. The ion separation power of a mass spectrometer is described by the resolution, which is defined as R=m/delta m, where m is the ion mass and delta m is the difference in mass between two resolvable peaks in a mass spectrum. For example, a mass spectrometer with a resolution of 1000 can resolve an ion with a m/z of 100.0 from an ion with a m/z of 100.1.

In general, a mass spectrometer (MS) consists of an ion source, a mass-selective analyzer, and an ion detector. The magnetic-sector, quadrupole, and time-of-flight designs also require extraction and acceleration ion optics to transfer ions from the source region into the mass analyzer. The details of several mass analyzer designs (for magnetic-sector MS, quadrupole MS or time-of-flight MS) are discussed below. Single Focusing analyzers for magnetic-sector MS utilize a particle beam path of 180, 90, or 60 degrees. The various forces influencing the particle separate ions with different mass-to-charge ratios. With double-focusing analyzers, an electrostatic analyzer is added in this type of instrument to separate particles with difference in kinetic energies.

A quadrupole mass filter for quadrupole MS consists of four metal rods arranged in parallel. The applied voltages affect the trajectory of ions traveling down the flight path centered between the four rods. For given DC and AC voltages, only ions of a certain mass-to-charge ratio pass through the quadrupole filter and all other ions are thrown out of their original path. A mass spectrum is obtained by monitoring the ions passing through the quadrupole filter as the voltages on the rods are varied.

A time-of-flight mass spectrometer uses the differences in transit time through a "drift region" to separate ions of different masses. It operates in a pulsed mode so ions must be produced in pulses and/or extracted in pulses. A pulsed electric field accelerates all ions into a field-free drift region with a kinetic energy of qV, where q is the ion charge and V is the applied voltage. Since the ion kinetic energy is 0.5 $mV^2$, lighter ions have a higher velocity than heavier ions and reach the detector at the end of the drift region sooner. The output of an ion detector is displayed on an oscilloscope as a function of time to produce the mass spectrum.

The ion formation process is the starting point for mass spectrometric analyses. Chemical ionization is a method that employs a reagent ion to react with the analyte molecules (tags) to form ions by either a proton or hydride transfer. The reagent ions are produced by introducing a large excess of methane (relative to the tag) into an electron impact (EI) ion source. Electron collisions produce $CH_4^+$ and $CH_3^+$ which further react with methane to form $CH_5^+$ and $C_2H_5^+$. Another method to ionize tags is by plasma and glow discharge. Plasma is a hot, partially-ionized gas that effectively excites and ionizes atoms. A glow discharge is a low-pressure plasma maintained between two electrodes. Electron impact ionization employs an electron beam, usually generated from a tungsten filament, to ionize gas-phase atoms or molecules. An electron from the beam knocks an electron off analyte atoms or molecules to create ions. Electrospray ionization utilizes a very fine needle and a series of skimmers. A sample solution is sprayed into the source chamber to form droplets. The droplets carry charge when the exit the capillary and as the solvent vaporizes the droplets disappear leaving highly charged analyte molecules. ESI is particularly useful for large biological molecules that are difficult to vaporize or ionize. Fast-atom bombardment (FAB) utilizes a high-energy beam of neutral atoms, typically Xe or Ar, that strikes a solid sample causing desorption and ionization. It is used for large biological molecules that are difficult to get into the gas phase. FAB causes little fragmentation and usually gives a large molecular ion peak, making it useful for molecular weight determination. The atomic beam is produced by accelerating ions from an ion source though a charge-exchange cell. The ions pick up an electron in collisions with neutral atoms to form a beam of high energy atoms. Laser ionization (LIMS) is a method in which a laser pulse ablates material from the surface of a sample and creates a microplasma that ionizes some of the sample constituents. Matrix-assisted laser desorption ionization (MALDI) is a LIMS method of vaporizing and ionizing large biological molecules such as proteins or DNA fragments. The biological molecules are dispersed in a solid matrix such as nicotinic acid. A UV laser pulse ablates the matrix which carries some of the large molecules into the gas phase in an ionized form so they can be extracted into a mass spectrometer. Plasma-desorption ionization (PD) utilizes the decay of $^{252}Cf$ which produces two fission fragments that travel in opposite directions. One fragment strikes the sample knocking out 1–10 analyte ions. The other fragment strikes a detector and triggers the start of data acquisition. This ionization method is especially useful for large biological molecules. Resonance ionization (RIMS) is a method in which one or more laser beams are tuned in resonance to transitions of a gas-phase atom or molecule to promote it in a stepwise fashion above its ionization potential to create an ion. Secondary ionization (SIMS) utilizes an ion beam; such as $^3He^+$, $^{16}O^+$, or $^{40}Ar^+$; is focused onto the surface of a sample and sputters material into the gas phase. Spark source is a method which ionizes analytes in solid samples by pulsing an electric current across two electrodes.

A tag may become charged prior to, during or after cleavage from the molecule to which it is attached. Ionization methods based on ion "desorption", the direct formation or emission of ions from solid or liquid surfaces have allowed increasing application to nonvolatile and thermally labile compounds. These methods eliminate the need for neutral molecule volatilization prior to ionization and generally minimize thermal degradation of the molecular species. These methods include field desorption (Becky, *Principles of Field Ionization and Field Desorption Mass Spectrometry*, Pergamon, Oxford, 1977), plasma desorption (Sundqvist and Macfarlane, *Mass Spectrom. Rev.* 4:421, 1985), laser desorption (Karas and Hillenkamp, *Anal. Chem.* 60:2299, 1988; Karas et al., *Angew. Chem.* 101:805, 1989), fast particle bombardment (e.g., fast atom bombardment, FAB, and secondary ion mass spectrometry, SIMS, Barber et al., *Anal. Chem.* 54:645A, 1982), and thermospray (TS) ionization (Vestal, *Mass Spectrom. Rev.* 2:447, 1983). Thermospray is broadly applied for the on-line combination with liquid chromatography. The continuous flow FAB methods (Caprioli et al., *Anal. Chem.* 58:2949, 1986) have also shown significant potential. A more complete listing of ionization/mass spectrometry combinations is ion-trap mass spectrometry, electrospray ionization mass spectrometry, ion-spray mass spectrometry, liquid ionization mass spectrometry, atmospheric pressure ionization mass spectrometry, electron ionization mass spectrometry, metastable atom bombardment ionization mass spectrometry, fast atom bombard ionization mass spectrometry, MALDI mass spectrometry, photo-ionization time-of-flight mass spectrometry, laser droplet mass spectrometry, MALDI-TOF mass spectrometry, APCI mass spectrometry, nanospray mass spectrometry, nebulised spray ionization mass spectrometry, chemical ionization mass spectrometry., resonance ionization mass spectrometry, secondary ionization mass spectrometry, thermospray mass spectrometry.

The ionization methods amenable to nonvolatile biological compounds have overlapping ranges of applicability. Ionization efficiencies are highly dependent on matrix composition and compound type. Currently available results indicate that the upper molecular mass for $T^{ms}$ is about 8000 daltons (Jones and Krolik, *Rapid Comm. Mass Spectrom.* 1:67, 1987). Since $T^{ms}$ is practiced mainly with quadrapole mass spectrometers, sensitivity typically suffers disproportionately at higher mass-to-charge ratios (m/z). Time-of-flight (TOF) mass spectrometers are commercially available and possess the advantage that the m/z range is limited only by detector efficiency. Recently, two additional ionization methods have been introduced. These two methods are now referred to as matrix-assisted laser desorption (MALDI, Karas and Hillenkamp, *Anal. Chem.* 60:2299, 1988; Karas et al., *Angew. Chem.* 101:805, 1989) and electrospray ionization (ESI). Both methodologies have very high ionization efficiency (i.e., very high [molecular ions produced]/[molecules consumed]). Sensitivity, which defines the ultimate potential of the technique, is dependent on sample size, quantity of ions, flow rate, detection efficiency and actual ionization efficiency.

Electrospray-MS is based on an idea first proposed in the 1960s (Dole et al., *J. Chem. Phys.* 49:2240, 1968). Electrospray ionization (ESI) is one means to produce charged molecules for analysis by mass spectroscopy. Briefly, electrospray ionization produces highly charged droplets by nebulizing liquids in a strong electrostatic field. The highly charged droplets, generally formed in a dry bath gas at atmospheric pressure, shrink by evaporation of neutral solvent until the charge repulsion overcomes the cohesive forces, leading to a "Coulombic explosion". The exact mechanism of ionization is controversial and several groups have put forth hypotheses (Blades et al., *Anal. Chem.* 63:2109–14, 1991; Kebarle et al., *Anal. Chem.* 65:A972–86, 1993; Fenn, *J. Am. Soc. Mass. Spectrom.* 4:524–35, 1993). Regardless of the ultimate process of ion formation, ESI produces charged molecules from solution under mild conditions.

The ability to obtain useful mass spectral data on small amounts of an organic molecule relies on the efficient production of ions. The efficiency of ionization for ESI is related to the extent of positive charge associated with the molecule. Improving ionization experimentally has usually involved using acidic conditions. Another method to improve ionization has been to use quaternary amines when possible (see Aebersold et al., *Protein Science* 1:494–503, 1992; Smith et al., *Anal. Chem.* 60:436–41, 1988).

Electrospray ionization is described in more detail as follows. Electrospray ion production requires two steps: dispersal of highly charged droplets at near atmospheric pressure, followed by conditions to induce evaporation. A solution of analyte molecules is passed through a needle that is kept at high electric potential. At the end of the needle, the solution disperses into a mist of small highly charged droplets containing the analyte molecules. The small droplets evaporate quickly and by a process of field desorption or residual evaporation, protonated protein molecules are released into the gas phase. An electrospray is generally produced by application of a high electric field to a small flow of liquid (generally 1–10 uL/min) from a capillary tube. A potential difference of 3–6 kV is typically applied between the capillary and counter electrode located 0.2–2 cm away (where ions, charged clusters, and even charged droplets, depending on the extent of desolvation, may be sampled by the MS through a small orifice). The electric field results in charge accumulation on the liquid surface at the capillary terminus; thus the liquid flow rate, resistivity, and surface tension are important factors in droplet production. The high electric field results in disruption of the liquid surface and formation of highly charged liquid droplets. Positively or negatively charged droplets can be produced depending upon the capillary bias. The negative ion mode requires the presence of an electron scavenger such as oxygen to inhibit electrical discharge.

A wide range of liquids can be sprayed electrostatically into a vacuum, or with the aid of a nebulizing agent. The use of only electric fields for nebulization leads to some practical restrictions on the range of liquid conductivity and dielectric constant. Solution conductivity of less than $10^{-5}$ ohms is required at room temperature for a stable electrospray at useful liquid flow rates corresponding to an aqueous electrolyte solution of $<10^{-4}$ M. In the mode found most useful for ESI-MS, an appropriate liquid flow rate results in dispersion of the liquid as a fine mist. A short distance from the capillary the droplet diameter is often quite uniform and on the order of 1 $\mu$m. Of particular importance is that the total electrospray ion current increases only slightly for higher liquid flow rates. There is evidence that heating is useful for manipulating the electrospray. For example, slight heating allows aqueous solutions to be readily electrosprayed, presumably due to the decreased viscosity and surface tension. Both thermally-assisted and gas-nebulization-assisted electrosprays allow higher liquid flow rates to be used, but decrease the extent of droplet charging. The formation of molecular ions requires conditions effecting evaporation of the initial droplet population. This can be accomplished at higher pressures by a flow of dry gas at moderate temperatures ($<60°$ C.), by heating during transport through the interface, and (particularly in the case of ion trapping methods) by energetic collisions at relatively low pressure.

Although the detailed processes underlying ESI remain uncertain, the very small droplets produced by ESI appear to allow almost any species carrying a net charge in solution to be transferred to the gas phase after evaporation of residual solvent. Mass spectrometric detection then requires that ions have a tractable m/z range (<4000 daltons for quadrupole instruments) after desolvation, as well as to be produced and transmitted with sufficient efficiency. The wide range of solutes already found to be amenable to ESI-MS, and the lack of substantial dependence of ionization efficiency upon molecular weight, suggest a highly non-discriminating and broadly applicable ionization process.

The electrospray ion "source" functions at near atmospheric pressure. The electrospray "source" is typically a metal or glass capillary incorporating a method for electrically biasing the liquid solution relative to a counter electrode. Solutions, typically water-methanol mixtures containing the analyte and often other additives such as acetic acid, flow to the capillary terminus. An ESI source has been described (Smith et al., *Anal. Chem.* 62:885, 1990) which can accommodate essentially any solvent system. Typical flow rates for ESI are 1–10 uL/min. The principal requirement of an ESI-MS interface is to sample and transport ions from the high pressure region into the MS as efficiently as possible.

The efficiency of ESI can be very high, providing the basis for extremely sensitive measurements, which is useful for the invention described herein. Current instrumental performance can provide a total ion current at the detector of about $2 \times 10^{-12}$ A or about $10^7$ counts/s for singly charged species. On the basis of the instrumental performance, concentrations of as low as $10^{-10}$ M or about $10^{-18}$ mol/s of a singly charged species will give detectable ion current (about 10 counts/s) if the analyte is completely ionized. For example, low attomole detection limits have been obtained for quaternary ammonium ions using an ESI interface with capillary zone electrophoresis (Smith et al., *Anal. Chem.* 59:1230, 1988). For a compound of molecular weight of 1000, the average number of charges is 1, the approximate number of charge states is 1, peak width (m/z) is 1 and the maximum intensity (ion/s) is $1 \times 10^{12}$.

Remarkably little sample is actually consumed in obtaining an ESI mass spectrum (Smith et al., *Anal. Chem.* 60:1948, 1988). Substantial gains might be also obtained by the use of array detectors with sector instruments, allowing simultaneous detection of portions of the spectrum. Since currently only about $10^{-5}$ of all ions formed by ESI are detected, attention to the factors limiting instrument performance may provide a basis for improved sensitivity. It will be evident to those in the art that the present invention contemplates and accommodates for improvements in ionization and detection methodologies.

An interface is preferably placed between the separation instrumentation (e.g., gel) and the detector (e.g., mass spectrometer). The interface preferably has the following properties: (1) the ability to collect the DNA fragments at discreet time intervals, (2) concentrate the DNA fragments, (3) remove the DNA fragments from the electrophoresis buffers and milieu, (4) cleave the tag from the DNA fragment, (5) separate the tag from the DNA fragment, (6) dispose of the DNA fragment, (7) place the tag in a volatile solution, (8) volatilize and ionize the tag, and (9) place or transport the tag to an electrospray device that introduces the tag into mass spectrometer.

The interface also has the capability of "collecting" DNA fragments as they elute from the bottom of a gel. The gel may be composed of a slab gel, a tubular gel, a capillary, etc. The DNA fragments can be collected by several methods. The first method is that of use of an electric field wherein DNA fragments are collected onto or near an electrode. A second method is that wherein the DNA fragments are collected by flowing a stream of liquid past the bottom of a gel. Aspects of both methods can be combined wherein DNA collected into a flowing stream which can be later concentrated by use of an electric field. The end result is that DNA fragments are removed from the milieu under which the separation method was performed. That is, DNA fragments can be "dragged" from one solution type to another by use of an electric field.

Once the DNA fragments are in the appropriate solution (compatible with electrospray and mass spectrometry) the tag can be cleaved from the DNA fragment. The DNA fragment (or remnants thereof) can then be separated from the tag by the application of an electric field (preferably, the tag is of opposite charge of that of the DNA tag). The tag is then introduced into the electrospray device by the use of an electric field or a flowing liquid.

Fluorescent tags can be identified and quantitated most directly by their absorption and fluorescence emission wavelengths and intensities.

While a conventional spectrofluorometer is extremely flexible, providing continuous ranges of excitation and emission wavelengths ($l_{EX}$, $l_{S1}$, $l_{S2}$), more specialized instruments such as flow cytometers and laser-scanning microscopes require probes that are excitable at a single fixed wavelength. In contemporary instruments, this is usually the 488-nm line of the argon laser.

Fluorescence intensity per probe molecule is proportional to the product of e and QY. The range of these parameters among fluorophores of current practical importance is approximately 10,000 to 100,000 $cm^{-1}M^{-1}$ for $\epsilon$ and 0.1 to 1.0 for QY. When absorption is driven toward saturation by high-intensity illumination, the irreversible destruction of the excited fluorophore (photobleaching) becomes the factor limiting fluorescence detectability. The practical impact of photobleaching depends on the fluorescent detection technique in question.

It will be evident to one in the art that a device (an interface) may be interposed between the separation and detection steps to permit the continuous operation of size separation and tag detection (in real time). This unites the separation methodology and instrumentation with the detection methodology and instrumentation forming a single device. For example, an interface is interposed between a separation technique and detection by mass spectrometry or potentiostatic amperometry.

The function of the interface is primarily the release of the (e.g., mass spectrometry) tag from analyte. There are several representative implementations of the interface. The design of the interface is dependent on the choice of cleavable linkers. In the case of light or photo-cleavable linkers, an energy or photon source is required. In the case of an acid-labile linker, a base-labile linker, or a disulfide linker, reagent addition is required within the interface. In the case of heat-labile linkers, an energy heat source is required. Enzyme addition is required for an enzyme-sensitive linker such as a specific protease and a peptide linker, a nuclease and a DNA or RNA linker, a glycosylase, HRP or phosphatase and a linker which is unstable after cleavage (e.g., similar to chemiluminescent substrates). Other characteristics of the interface include minimal band broadening, separation of DNA from tags before injection into a mass spectrometer. Separation techniques include those based on electrophoretic methods and techniques, affinity techniques, size retention (dialysis), filtration and the like.

It is also possible to concentrate the tags (or nucleic acid-linker-tag construct), capture electrophoretically, and then release into alternate reagent stream which is compatible with the particular type of ionization method selected. The interface may also be capable of capturing the tags (or nucleic acid-linker-tag construct) on microbeads, shooting the bead(s) into chamber and then performing laser desorption/vaporization. Also it is possible to extract in flow into alternate buffer (e.g., from capillary electrophoresis buffer into hydrophobic buffer across a permeable membrane). It may also be desirable in some uses to deliver tags into the mass spectrometer intermittently which would comprise a further function of the interface. Another function of the interface is to deliver tags from multiple columns into a mass spectrometer, with a rotating time slot for each column. Also. it is possible to deliver tags from a single column into multiple MS detectors, separated by time, collect each set of tags for a few milliseconds, and then deliver to a mass spectrometer.

The following is a list of representative vendors for separation and detection technologies which may be used in the present invention. Hoefer Scientific Instruments (San Francisco, Calif.) manufactures electrophoresis equipment (Two Step™, Poker Face™ II) for sequencing applications. Pharmacia Biotech (Piscataway, N.J.) manufactures electrophoresis equipment for DNA separations and sequencing (PhastSystem for PCR-SSCP analysis, MacroPhor System for DNA sequencing). Perkin Elmer/Applied Biosystems Division (ABI, Foster City, Calif.) manufactures semi-automated sequencers based on fluorescent-dyes (ABI373 and ABI377). Analytical Spectral Devices (Boulder, Colo.) manufactures UV spectrometers. Hitachi Instruments (Tokyo, Japan) manufactures Atomic Absorption spectrometers, Fluorescence spectrometers, LC and GC Mass Spectrometers, NMR spectrometers, and UV-VIS Spectrometers. PerSeptive Biosystems (Framingham, Mass.) produces Mass Spectrometers (Voyager™ Elite). Bruker Instruments Inc. (Manning Park, Mass.) manufactures FTIR Spectrometers (Vector 22), FT-Raman Spectrometers, Time of Flight Mass Spectrometers (Reflex II™), Ion Trap Mass Spectrometer (Esquire™) and a Maldi Mass Spectrometer. Analytical Technology Inc. (ATI, Boston, Mass.) makes Capillary Gel Electrophoresis units, UV detectors, and Diode Array Detectors. Teledyne Electronic Technologies (Mountain View, Calif.) manufactures an Ion Trap Mass Spectrometer (3DQ Discovery™ and the 3DQ Apogee™). Perkin Elmer/Applied Biosystems Division (Foster City, Calif.) manufactures a Sciex Mass Spectrometer (triple quadrupole LC/MS/MS, the API 100/300) which is compatible with electrospray. Hewlett-Packard (Santa Clara, Calif.) produces Mass Selective Detectors (HP 5972A), MALDI-TOF Mass Spectrometers (HP G2025A), Diode Array Detectors, CE units, HPLC units (HP1090) as well as UV Spectrometers. Finnigan Corporation (San Jose, Calif.) manufactures mass spectrometers (magnetic sector (MAT 95 S™), quadrapole spectrometers (MAT 95 SQ™) and four other related mass spectrometers). Rainin (Emeryville, Calif.) manufactures HPLC instruments.

The methods and compositions described herein permit the use of cleaved tags to serve as maps to particular sample type and nucleotide identity. At the beginning of each sequencing method, a particular (selected) primer is assigned a particular unique tag. The tags map to either a sample type, a dideoxy terminator type (in the case of a Sanger sequencing reaction) or preferably both. Specifically, the tag maps to a primer type which in turn maps to a vector type which in turn maps to a sample identity. The tag may also may map to a dideoxy terminator type (ddTTP, ddCTP, ddGTP, ddATP) by reference into which dideoxynucleotide reaction the tagged primer is placed. The sequencing reaction is then performed and the resulting fragments are sequentially separated by size in time.

The tags are cleaved from the fragments in a temporal frame and measured and recorded in a temporal frame. The sequence is constructed by comparing the tag map to the temporal frame. That is, all tag identities are recorded in time after the sizing step and related become related to one another in a temporal frame. The sizing step separates the nucleic acid fragments by a one nucleotide increment and hence the related tag identities are separated by a one nucleotide increment. By foreknowledge of the dideoxy-terminator or nucleotide map and sample type, the sequence is readily deduced in a linear fashion.

Figure 15:
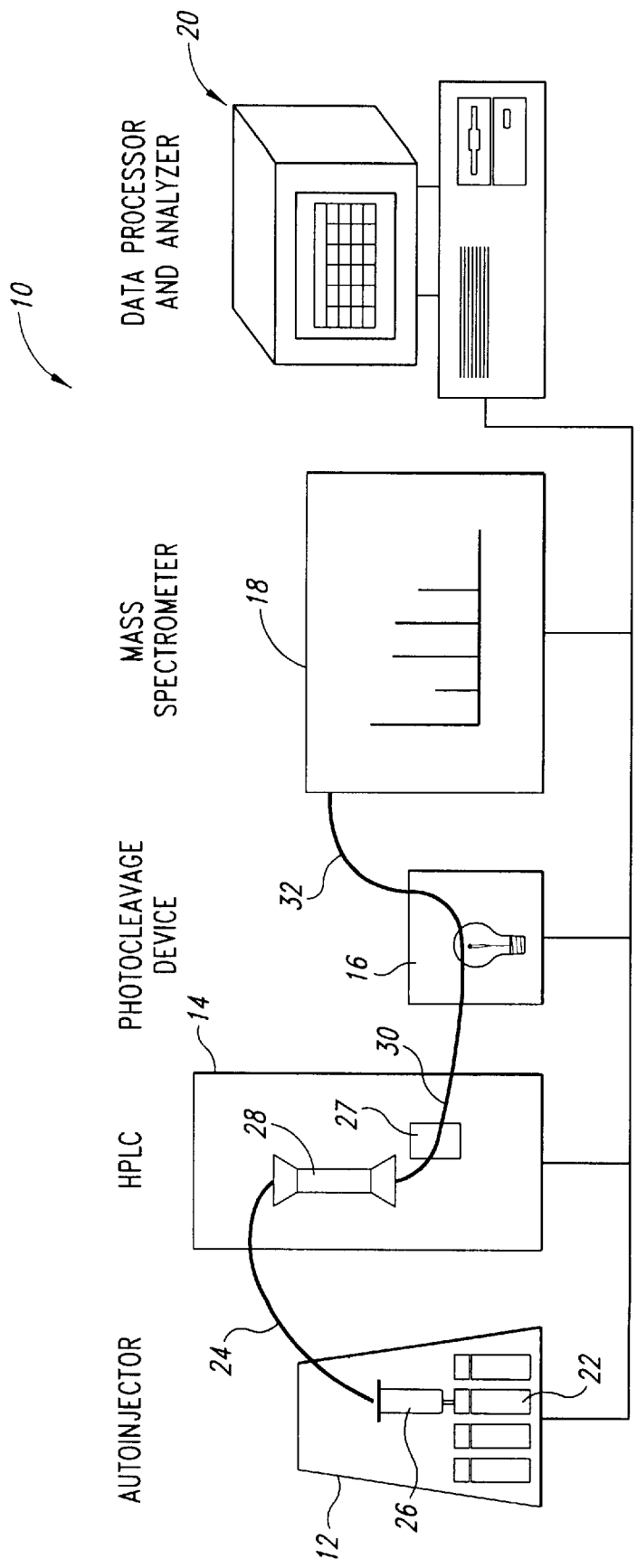
FIG. 15 is a schematic representation of a DNA sequencing system in accordance with an exemplary embodiment of the present invention.

A DNA sequencing system of an exemplary embodiment of the present invention consists of, in general, a sample introduction device, a device to separate the tagged samples of interest, a device to cleave the tags from the samples of interest, a device for detecting the tag, and a software program to analyze the data collected. It will be evident to one of ordinary skill in the art when in possession of the present disclosure that this general description may have many variances for each of the components listed. As best seen in FIG. 15, an exemplary embodiment of the DNA sequencing system 10 of the present invention consists of a sample introduction device 12, a separation device 14 that separates the samples by high-performance liquid chromatography (HPLC), a photocleavage device 16 to cleave the tags from the samples of interest, a detection device 18 that detects the tags by mass spectrometry, and a data processing device 20 with a data analysis software program that analyzes the results from the detection device 16. Each component is discussed in more detail below.

The sample introduction device 12 automatically takes a measured aliquot 22 (e.g., of the PCR product generated by the Sanger sequencing method) and delivers it through a conventional tube 24 to the separation device 14 (generally an HPLC). The sample introduction device 12 of the exemplary embodiment consists of a temperature-controlled autosampler 26 that can accommodate micro-titer plates. The autosampler 26 must be temperature controlled to maintain the integrity of the nucleic acid samples generated and be able to inject 25 μl or less of sample. Manufacturers of this type of sample introduction device 12 are represented, for example, by Gilson (Middleton, Wis.).

The sample introduction device 12 is operatively connected in series to the separation device 14 by the tube 24. The sequencing reaction products (which may be produced by PCR) in the measured aliquot 22 are received in the separation device 14 and separated temporally by high-performance liquid chromatography to provide separated DNA fragments. The high-performance liquid chromatograph may have an isocratic, binary, or quaternary pump(s) 27 and can be purchased from multiple manufacturers (e.g., Hewlett Packard (Palo Alto, Calif.) HP 1100 or 1090 series, Beckman Instruments Inc. (800-742-2345), Bioanalytical Systems, Inc. (800-845-4246), ESA, Inc. (508) 250-700), Perkin-Elmer Corp. (800-762-4000), Varian Instruments (800-926-3000), Waters Corp. (800-254-4752)).

The separation device 14 includes an analytical HPLC column 28 suitable for use to separate the nucleic acid fragments. The column 28 is an analytical HPLC, for example, is non-porous polystyrene divinylbenzene (2.2μ particle size) solid support which can operate within a pH range of 2 to 12, pressures of up to 3000 psi and a temperature range of about 10 to 70° C. A temperature-control device (e.g., a column oven) (not shown) may be used to control the temperature of the column. Such temperature-control devices are known in the art, and may be obtained from, for example, Rainin Instruments (subsidiary of Varian Instruments, Palo Alto, Calif.). A suitable column 28 is available under the commercial name of DNAsep® and is available from Serasep (San Jose, Calif.). Other suitable analytical HPLC columns are available from other manufacturers (e.g., Hewlett Packard (Palo Alto, Calif.), Beckman Instruments Inc. (Brea, Calif.), Waters Corp. (Milford, Mass.)).

A stream of the separated DNA fragments (e.g., sequencing reaction products) flows through a conventional tube 30 from the separation device 14 to the cleavage device 16. Each of the DNA fragments is labeled with a unique cleavable (e.g., photocleavable) tag. The flowing stream of separated DNA fragments pass through or past the cleaving device 16 where the tag is removed for detection (e.g., by mass spectrometry or with an electrochemical detector). In the exemplary embodiment, the cleaving device 16 is a photocleaving unit such that the flowing stream of sample is exposed to selected light energy and wavelength. In one embodiment, the sample enters the photocleaving unit and is exposed to the selected light source for a selected duration of time. In an alternate embodiment, the stream of separated DNA fragments is carried adjacent to the light source along a path that provides a sufficient exposure to the light energy to cleave the tags from the separated DNA fragments.

A photocleaving unit is available from Supelco (Bellefonte, Pa.). Photocleaving can be performed at multiple wavelengths with a mercury/xenon arc lamp. The wavelength accuracy is about 2 nm with a bandwidth of 10 nm. The area irradiated is circular and typically of an area of 10–100 square centimeters. In alternate embodiments, other cleaving devices, which cleave by acid, base, oxidation, reduction, floride, thiol exchange, photolysis, or enzymatic conditions, can be used to remove the tags from the separated DNA fragments.

After the cleaving device 16 cleaves the tags from the separated DNA fragments, the tags flow through a conventional tube 32 to the detection device 18 for detection of each tag. Detection of the tags can be based upon the difference in molecular weight between each of the tags used to label each kind of DNA generated in the PCR step. The best detector based upon differences in mass is the mass spectrometer. For this use, the mass spectrometer typically will have an atmospheric pressure ionization (API) interface with either electrospray or chemical ionization, a quadrupole mass analyzer, and a mass range of at least 50 to 2600 m/z. Examples of manufacturers of a suitable mass spectrometer are: Hewlett Packard (Palo Alto, Calif.) HP 1100 LC/MSD, Hitachi Instruments (San Jose, Calif.) M-1200H LC/MS, Perkin Elmer Corporation, Applied Biosystems Division (Foster City, Calif.) API 100 LC/MS or API 300 LC/MS/MS, Finnigan Corporation (San Jose, Calif.) LCQ, Bruker Analytical Systems, Inc. (Billerica, Mass.) ESQUIRE and MicroMass (UK).

The detection device 18 is electrically connected to a data processor and analyzer 20 that receives data from the detection device. The data processor and analyzer 20 includes a software program that identifies the detected tag. The data processor and analyzer 20 in alternate embodiments is operatively connected to the sample introduction device 12, the separation device 14, and/or the cleaving device 16 to control the different components of the DNA sequencing system 10.

Figure 16:
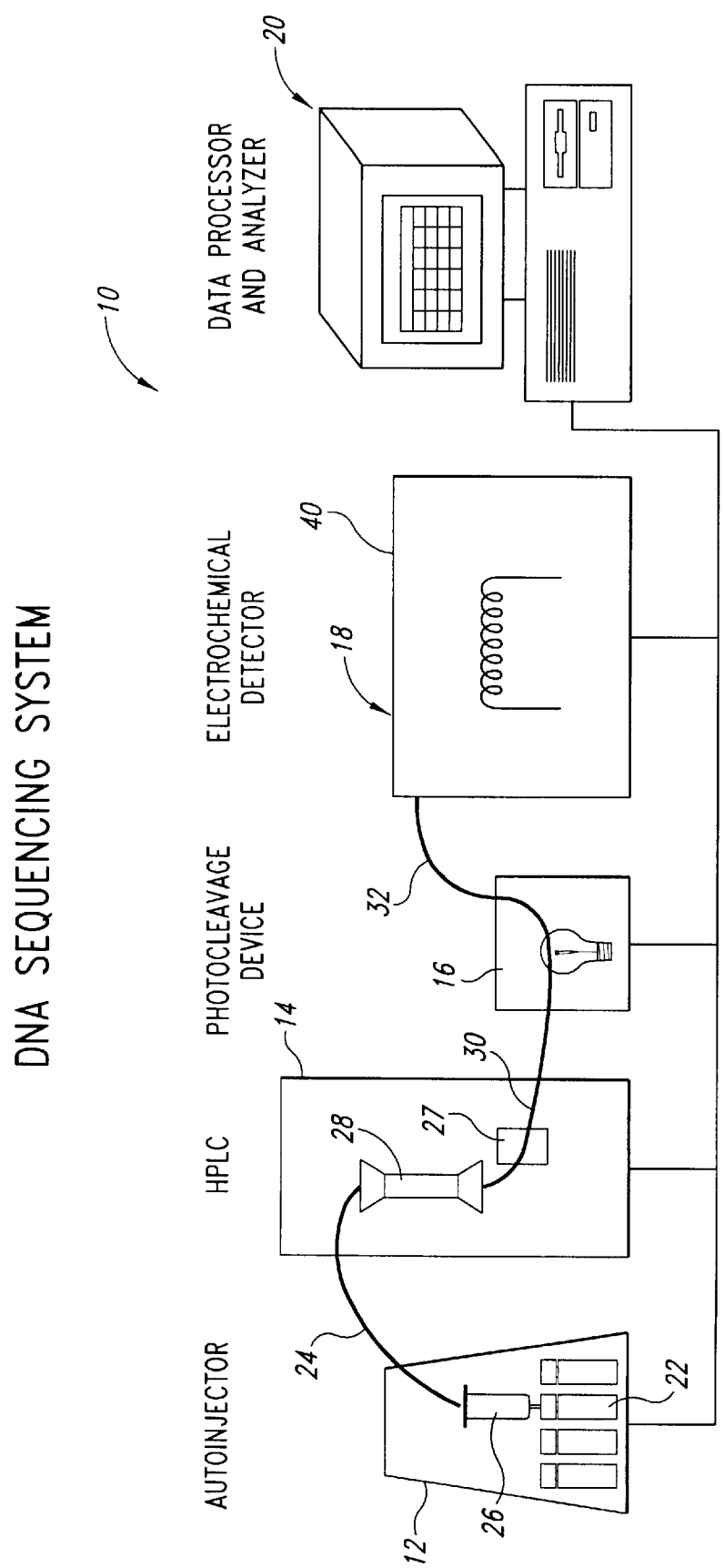
FIG. 16 is a schematic representation of a DNA sequencing system in accordance with an alternate embodiment of the present invention.

In an alternate embodiment illustrated schematically in FIG. 16, the sample introduction device 12, the separating device 14, and the cleavage device 16 are serially connected as discussed above for maintaining the flow of the sample. The cleavage device 16 is serially connected to detection device 18 that is an electrochemical detecting device 40 rather than a mass spectrometer. Detection of the tags in this alternate embodiment is based upon the difference in electrochemical potential between each of the tags used to label each kind of DNA generated in the sequencing reaction step. The electrochemical detector 40 can operate on either coulometric or amperometric principles. The preferred electrochemical detector 40 is the coulometric detector, which consists of a flow-through or porous-carbon graphite amperometric detector where the column eluent passes through the electrode resulting in 100% detection efficiency. To fully detect each component, an array of 16 coulometric detectors each held at a different potential (generally at 60 mV increments) is utilized. Examples of manufacturers of this type of detector are ESA (Bedford, Mass.) and Bioanalytical Systems Inc. (800-845-4246).

The electrochemical detector 40 is electrically connected to the data processor and analyzer 20 with the software package. The software package maps the detected property (e.g., the electrochemical signature or mass as discussed above) of a given tag to a specific sample ID. The software is able to display the DNA sequence determined and load the sequence information into respective databases.

The DNA sequencing system 10 is provided by operatively interconnecting the system's multiple components. Accordingly, one or more system components, such as the sample introducing device 12 and the detecting device 18 that are in operation in a lab can be combined with the system's other components (e.g., the separating device 14, cleaving device 16, and the data processor and analyzer 20 in order to equip the lab with the DNA sequencing system 10 of the present invention.

In a preferred embodiment, five or more (and more preferably sixteen or more) samples are introduced simultaneously in a system according to the present invention. Each sample has a unique tag for each type of nucleotide and the system has a data processor device that correlates the detection of a tag (e.g., tag mass or tag electrochemical signature) to a particular nucleotide and to a specific sample. For example, where five samples are introduced into the system, the data processor is able to associate a tag detected by the system with both the particular nucleotide (to which the tag was attached prior to cleavage) and one of the five specific samples (to which the tag was introduced to generate tagged nucleic acid fragments).

Tagged Probes in Array-Based Assays

Arrays with covalently attached oligonucleotides have been made used to perform DNA sequence analysis by hybridization (Southern et al., *Genomics* 13: 1008, 1992; Drmanac et al., *Science* 260: 1649, 1993), determine expression profiles, screen for mutations and the like. In general, detection for these assays uses fluorescent or radioactive labels. Fluorescent labels can be identified and quantitated most directly by their absorption and fluorescence emission wavelengths and intensity. A microscope/camera setup using a fluorescent light source is a convenient means for detecting fluorescent label. Radioactive labels may be visualized by standard autoradiography, phosphor image analysis or CCD detector. For such labels the number of different reactions that can be detected at a single time is limited. For example, the use of four fluorescent molecules, such as commonly employed in DNA sequence analysis, limits anaylsis to four samples at a time. Essentially, because of this limitation, each reaction must be individually assessed when using these detector methods.

A more advantageous method of detection allows pooling of the sample reactions on at least one array and simultaneous detection of the products. By using a tag, such as the ones described herein, having a different molecular weight or other physical attribute in each reaction, the entire set of reaction products can be harvested together and analyzed.

As noted above, the methods described herein are applicable for a variety of purposes. For example, the arrays of oligonucleotides may be used to control for quality of making arrays, for quantitation or qualitative analysis of nucleic acid molecules, for detecting mutations, for determining expression profiles, for toxicology testing, and the like.

Probe quantitation or typing

In this embodiment, oligonucleotides are immobilized per element in an array where each oligonucleotide in the element is a different or related sequence. Preferably, each element possesses a known or related set of sequences. The hybridization of a labeled probe to such an array permits the characterization of a probe and the identification and quantification of the sequences contained in a probe population.

A generalized assay format that may be used in the particular applications discussed below is a sandwich assay format. In this format, a plurality of oligonucleotides of known sequence are immobilized on a solid substrate. The immobilized oligonucleotide is used to capture a nucleic acid (e.g., RNA, rRNA, a PCR product, fragmented DNA) and then a signal probe is hybridized to a different portion of the captured target nucleic acid.

Another generalized assay format is a secondary detection system. In this format, the arrays are used to identify and quantify labeled nucleic acids that have been used in a primary binding assay. For example, if an assay results in a labeled nucleic acid, the identity of that nucleic acid can be determined by hybridization to an array. These assay formats are particularly useful when combined with cleavable mass spectometry tags.

Mutation detection

Mutations involving a single nucleotide can be identified in a sample by scanning techniques, which are suitable to identify previously unknown mutations, or by techniques designed to detect, distinguish, or quantitate known sequence variants. Several scanning techniques for mutation detection have been developed based on the observation that heteroduplexes of mismatched complementary DNA strands, derived from wild type and mutant sequences, exhibit an abnormal migratory behavior.

The methods described herein may be used for mutation screening. One strategy for detecting a mutation in a DNA strand is by hybridization of the test sequence to target sequences that are wild-type or mutant sequences. A mismatched sequence has a destabilizing effect on the hybridization of short oligonucleotide probes to a target sequence (see Wetmur, *Crit. Rev. Biochem. Mol. Biol.*, 26:227, 1991). The test nucleic acid source can be genomic DNA, RNA, cDNA, or amplification of any of these nucleic acids. Preferably, amplification of test sequences is first performed, followed by hybridization with short oligonucleotide probes immobilized on an array. An amplified product can be scanned for many possible sequence variants by determining its hybridization pattern to an array of immobilized oligonucleotide probes.

A label, such as described herein, is generally incorporated into the final amplification product by using a labeled nucleotide or by using a labeled primer. The amplification product is denatured and hybridized to the array. Unbound product is washed off and label bound to the array is detected by one of the methods herein. For example, when cleavable mass spectrometry tags are used, multiple products can be simultaneously detected.

Expression profiles/differential display

Mammals, such as human beings, have about 100,000 different genes in their genome, of which only a small fraction, perhaps 15%, are expressed in any individual cell. Differential display techniques permit the identification of genes specific for individual cell types. Briefly, in differential display, the 3'terminal portions of mRNAs are amplified and identified on the basis of size. Using a primer designed to bind to the 5' boundary of a poly(A) tail for reverse transcription, followed by amplification of the cDNA using upstream arbitrary sequence primers, mRNA subpopulations are obtained.

As disclosed herein, a high throughput method for measuring the expression of numerous genes (e.g., 1–2000) is provided. Within one embodiment of the invention, methods are provided for analyzing the pattern of gene expression from a selected biological sample, comprising the steps of (a) amplifying cDNA from a biological sample using one or more tagged primers, wherein the tag is correlative with a particular nucleic acid probe and detectable by non-fluorescent spectrometry or potentiometry, (b) hybridizing amplified fragments to an array of oligonucleotides as described herein, (c) washing away non-hybridized material, and (d) detecting the tag by non-fluorescent spectrometry or potentiometry, and therefrom determining the pattern of gene expression of the biological sample. Tag-based differential display, especially using cleavable mass spectometry tags, on solid substrates allows characterization of differentially expressed genes.

Single nucleotide extension assay

The primer extension technique may be used for the detection of single nucleotide changes in a nucleic acid template (Sokolov, *Nucleic Acids Res.*, 18:3671, 1989). The technique is generally applicable to detection of any single base mutation (Kuppuswamy et al., *Proc. Natl, Acad. Sci. USA*, 88:1143–1147, 1991). Briefly, this method first hybridizes a primer to a sequence adjacent to a known single nucleotide polymorphism. The primed DNA is then subjected to conditions in which a DNA polymerase adds a labeled dNTP, typically a ddNTP, if the next base in the template is complementary to the labeled nucleotide in the reaction mixture. In a modification, cDNA is first amplified for a sequence of interest containing a single-base difference between two alleles. Each amplified product is then analyzed for the presence, absence, or relative amounts of each allele by annealing a primer that is 1 base 5' to the polymorphism and extending by one labeled base (generally a dideoxynucleotide). Only when the correct base is available in the reaction will a base to incorporated at the 3'-end of the primer. Extension products are then analyzed by hybridization to an array of oligonucleotides such that a non-extended product will not hybridize.

Briefly, in the present invention, each dideoxynucleotide is labeled with a unique tag. Of the four reaction mixtures, only one will add a dideoxy-terminator on to the primer sequence. If the mutation is present, it will be detected through the unique tag on the dideoxynucleotide after hybridization to the array. Multiple mutations can be simultaneously determined by tagging the DNA primer with a unique tag as well. Thus, the DNA fragments are reacted in four separate reactions each including a different tagged dideoxyterminator, wherein the tag is correlative with a particular dideoxynucleotide and detectable by non-fluorescent spectrometry, or potentiometry. The DNA fragments are hybridized to an array and non-hybridized material is washed away. The tags are cleaved from the hybridized fragments and detected by the respective detection technology (e.g., mass spectrometry, infrared spectrometry, potentiostatic amperometry or UV/visible spectrophotometry). The tags detected can be correlated to the particular DNA fragment under investigation as well as the identity of the mutant nucleotide.

Oligonucleotide ligation assay

The oligonucleotide ligation assay (OLA). (Landegen et al., *Science* 241:487, 1988) is used for the identification of known sequences in very large and complex genomes. The principle of OLA is based on the ability of ligase to covalently join two diagnostic oligonucleotides as they hybridize adjacent to one another on a given DNA target. If the sequences at the probe junctions are not perfectly based-paired, the probes will not be joined by the ligase. When tags are used, they are attached to the probe, which is ligated to the amplified product. After completion of OLA, fragments are hybridized to an array of complementary sequences, the tags cleaved and detected by mass spectrometry.

Within one embodiment of the invention methods are provided for determining the identity of a nucleic acid molecule, or for detecting a selecting nucleic acid molecule, in, for example a biological sample, utilizing the technique of oligonucleotide ligation assay. Briefly, such methods generally comprise the steps of performing amplification on the target DNA followed by hybridization with the 5' tagged reporter DNA probe and a 5' phosphorylated probe. The sample is incubated with T4 DNA ligase. The DNA strands with ligated probes are captured on the array by hybridization to an array, wherein non-ligated products do not hybridize. The tags are cleaved from the separated fragments, and then the tags are detected by the respective detection technology (e.g., mass spectrometry, infrared spectrophotometry, potentiostatic amperometry or UV/visible spectrophotometry.

Other assays

The methods described herein may also be used to genotype or identification of viruses or microbes. For example, F+RNA coliphages may be useful candidates as indicators for enteric virus contamination. Genotyping by nucleic acid amplification and hybridization methods are reliable, rapid, simple, and inexpensive alternatives to serotyping (Kafatos et. al., *Nucleic Acids Res.* 7:1541, 1979). Amplification techniques and nucleic aid hybridization techniques have been successfully used to classify a variety of microorganisms including *E. coli* (Feng, *Mol. Cell Probes* 7:151, 1993), rotavirus (Sethabutr et. al., *J. Med Virol.* 37:192, 1992), hepatitis C virus (Stuyver et. al., *J. Gen Virol.* 74:1093, 1993), and herpes simplex virus (Matsumoto et. al., *J. Virol. Methods* 40:119, 1992).

Genetic alterations have been described in a variety of experimental mammalian and human neoplasms and represent the morphological basis for the sequence of morphological alterations observed in carcinogenesis (Vogelstein et al., NEJM319:525, 1988). In recent years with the advent of molecular biology techniques, allelic losses on certain chromosomes or mutation of tumor suppressor genes as well as mutations in several oncogenes (e.g., c-myc, c-jun, and the ras family) have been the most studied entities. Previous work (Finkelstein et al., *Arch Surg.* 128:526, 1993) has identified a correlation between specific types of point mutations in the K-ras oncogene and the stage at diagnosis in colorectal carcinoma. The results suggested that mutational analysis could provide important information of tumor aggressiveness, including the pattern and spread of metastasis. The prognostic value of TP53 and K-ras-2 mutational analysis in stage III carconoma of the colon has more recently been demonstrated (Pricolo et al., *Am. J. Surg.* 171:41, 1996). It is therefore apparent that genotyping of tumors and pre-cancerous cells, and specific mutation detection will become increasingly important in the treatment of cancers in humans.

The tagged biomolecules as disclosed herein may be used to interrogate (untagged) arrays of biomolecules. Preferred arrays of biomolcules contain a solid substrate comprising a surface, where the surface is at least partially covered with a layer of poly(ethylenimine) (PEI). The PEI layer comprises a plurality of discrete first regions abutted and surrounded by a contiguous second region. The first regions are defined by the presence of a biomolecule and PEI, while the second region is defined by the presence of PEI and the substantial absence of the biomolecule. Preferably, the substrate is a glass plate or a silicon wafer. However, the substrate may be, for example, quartz, gold, nylon-6,6, nylon or polystyrene, as well as composites thereof, as described above.

The PEI coating preferably contains PEI having a molecular weight ranging from 100 to 100,000. The PEI coating may be directly bonded to the substrate using, for example, silylated PEI. Alternatively, a reaction product of a biftinctional coupling agent may be disposed between the substrate surface and the PEI coating, where the reaction product is covalently bonded to both the surface and the PEI coating, and secures the PEI coating to the surface. The bifunctional coupling agent contains a first and a second reactive functional group, where the first reactive functional group is, for example, a tri(O—$C_1$–$C_5$alkyl)silane, and the second reactive functional group is, for example, an epoxide, isocyanate, isothiocyanate and anhydride group. Preferred bifuictional coupling agents include 2-(3,4-epoxycyclohexyl)ethyltrimethoxysilane; 3,4-epoxybutyltrimethoxysilane; 3-isocyanatopropyltriethoxysilane, 3-(triethoxysilyl)-2-methylpropylsuccinic anhydride and 3-(2,3-epoxypropoxy)propyltrimethoxysilane.

The array of the invention contains first, biomolecule-containing regions, where each region has an area within the range of about 1,000 square microns to about 100,000 square microns. In a preferred embodiment, the first regions have areas that range from about 5,000 square microns to about 25,000 square microns.

The first regions are preferably substantially circular, where the circles have an average diameter of about 10 microns to 200 microns. Whether circular or not, the boundaries of the first regions are preferably separated from one another (by the second region) by an average distance of at least about 25 microns, however by not more than about 1 cm (and preferably by no more than about 1,000 microns). In a preferred array, the boundaries of neighboring first regions are separated by an average distance of about 25 microns to 100 microns, where that distance is preferably constant throughout the array, and the first regions are preferably positioned in a repeating geometric pattern as shown in the Figures attached hereto. In a preferred repeating geometric pattern, all neighboring first regions are separated by approximately the same distance (about 25 microns to about 100 microns).

In preferred arrays, there are from 10 to 50 first regions on the substrate. In another embodiment, there are 50 to 400 first regions on a substrate. In yet another preferred embodiment, there are 400 to 800 first regions on the substrate.

The biomolecule located in the first regions is preferably a nucleic acid polymer. A preferred nucleic acid polymer is an oligonucleotide having from about 15 to about 50 nucleotides. The biomolecule may be amplification reaction products having from about 50 to about 1,000 nucleotides.

In each first region, the biomolecule is preferably present at an average concentration ranging from $10^5$ to $10^9$ biomolecules per 2,000 square microns of a first region. More preferably, the average concentration of biomolecule ranges from $10^7$ to $10^9$ biomolecules per 2,000 square microns. In the second region, the biomolecule is preferably present at an average concentration of less than $10^3$ biomolecules per 2,000 square microns of said second region, and more preferably at an average concentration of less than $10^2$ biomolecules per 2,000 square microns. Most preferably, the second regions does not contain any biomolecule.

The chemistry used to adhere the layer of PEI to the substrate depends, in substantial part, upon the chemical identity of the substrate. The prior art provides numerous examples of suitable chemistries that may adhere PEI to a solid support. For example, when the substrate is nylon-6,6, the PEI coating may be applied by the methods disclosed in Van Ness, J. et al. *Nucleic Acids Res.* 19:3345–3350, 1991 and PCT International Publication WO 94/00600, both of which are incorporated herein by reference. When the solid support is glass or silicon, suitable methods of applying a layer of PEI are found in, e.g., Wasserman, B. P. *Biotechnology and Bioengineering* XXII:271–287, 1980; and D'Souza, S. F. *Biotechnology Letters* 8:643–648, 1986.

Preferably, the PEI coating is covalently attached to the solid substrate. When the solid substrate is glass or silicon, the PEI coating may be covalently bound to the substrate using silylating chemistry. For example, PEI having reactive siloxy endgroups is commercially available from Gelest, Inc. (Tullytown, Pa.). Such reactive PEI may be contacted with a glass slide or silicon wafer, and after gentle agitation, the PEI will adhere to the substrate. Alternatively, a bifunctional silylating reagent may be employed. According to this process, the glass or silicon substrate is treated with the bifunctional silylating reagent to provide the substrate with a reactive surface. PEI is then contacted with the reactive surface, and covalently binds to the surface through the bifunctional reagent.

The biomolecules being placed into the array format are originally present in a so-called "arraying solution". In order to place biomolecule in discrete regions on the PEI-coated substrate, the arraying solution preferably contains a thickening agent at a concentration of about 35 vol % to about 80 vol % based on the total volume of the composition, a biomolecule which is preferably an oligonucleotide at a concentration ranging from 0.001 µg/mL to 10 µg/mL, and water.

The concentration of the thickening agent is 35% V/V to 80% V/V for liquid thickening agents such as glycerol. The preferred concentration of thickening agent in the composition depends, to some extent, on the temperature at which the arraying is performed. The lower the arraying temperature, the lower the concentration of thickening agent that needs to be used. The combination of temperature and liquid thickening agent concentration control permits arrays to be made on most types of solid supports (e.g., glass, wafers, nylon 6/6, nylon membranes, etc.).

The presence of a thickening agent has the additional benefit of allowing the concurrent presence of low concentrations of various other materials to be present in combination with the biomolecule. For example 0.001% V.V to 1% V/V of detergents may be present in the arraying solution. This is useful because PCR buffer contains a small amount of Tween-20 or NP-40, and it is frequently desirable to array sample nucleic acids directly from a PCR vial without prior purification of the amplicons. The use of a thickening agent permits the presence of salts (for example NaCl, KCl, or $MgCl_2$), buffers (for example Tris), and/or chelating reagents (for example EDTA) to also be present in the arraying solution. The use of a thickening agent also has the additional benefit of permitting the use of cross-linking reagents and/or organic solvents to be present in the arraying solution. As commercially obtained, cross-linking reagents are commonly dissolved in organic solvent such as DMSO, DMF, NMP, methanol, ethanol and the like. Commonly used organic solvents can be used in arraying solutions of the invention at levels of 0.05% to 20% (V/V) when thickening agents are used.

In general, the thickening agents impart increased viscosity to the arraying solution. When a proper viscosity is achieved in the arraying solution, the first drop is the substantially the same size as, for example, the 100th drop deposited. When an improper viscosity is used in the arraying solution, the first drops deposited are significantly larger than latter drops which are deposited. The desired viscosity is between those of pure water and pure glycerin.

The biomolecule in the array may be a nucleic acid polymer or analog thereof, such as PNA, phosphorothioates and methylphosphonates. Nucleic acid refers to both ribonucleic acid and deoxyribonucleic acid. The biomolecule may comprise unnatural and/or synthetic bases. The biomolecule may be single or double stranded nucleic acid polymer.

A preferred biomolecule is an nucleic acid polymer, which includes oligonucleotides (up to about 100 nucleotide bases) and polynucleotides (over about 100 bases). A preferred nucleic acid polymer is formed from 15 to 50 nucleotide bases. Another preferred nucleic acid polymer has 50 to 1,000 nucleotide bases. The nucleic acid polymer may be a PCR product, PCR primer, or nucleic acid duplex, to list a few examples. However, essentially any nucleic acid type can be covalently attached to a PEI-coated surface when the nucleic acid contains a primary amine, as disclosed below. The typical concentration of nucleic acid polymer in the arraying solution is 0.001–10 µg/mL, preferably 0.01–1 µg/mL, and more preferably 0.05–0.5 µg/mL.

Preferred nucleic acid polymers are "amine-modified" in that they have been modified to contain a primary amine at the 5'-end of the nucleic acid polymer, preferably with one or more methylene ($—CH_2—$) groups disposed between the primary amine and the nucleic acid portion of the nucleic acid polymer. Six is a preferred number of methylene groups. Amine-modified nucleic acid polymers are preferred because they can be covalently coupled to a solid support through the 5'-amine group. PCR products can be arrayed using 5'-hexylamine modified PCR primers. Nucleic acid duplexes can be arrayed after the introduction of amines by nick translation using aminoallyl-dUTP (Sigma, St. Louis, Mo.). Amines can be introduced into nucleic acids by polymerases such as terminal transferase with amino allyl-dUTP or by ligation of short amine-containing nucleic acid polymers onto nucleic acids by ligases.

Preferably, the nucleic acid polymer is activated prior to be contacted with the PEI coating. This can be conveniently accomplished by combining amine-functionalized nucleic acid polymer with a multi-finctional amine-reactive chemical such as trichlorotriazine. When the nucleic acid polymer contains a 5'-amine group, that 5'-amine can be reacted with trichlorotriazine, also known as cyanuric chloride (Van Ness et al., *Nucleic Acids Res.* 19(2):3345–3350, 1991) Preferably, an excess of cyanuric chloride is added to the nucleic acid polymer solution, where a 10- to 1000-fold molar excess of cyanuric chloride over the number of amines in the nucleic acid polymer in the arraying solution is preferred. In this way, the majority of amine-terminated nucleic acid polymers have reacted with one molecule of trichlorotriazine, so that the nucleic acid polymer becomes terminated with dichlorotriazine.

Preferably, the arraying solution is buffered using a common buffer such as sodium phosphate, sodium borate, sodium carbonate, or Tris HCl. A preferred pH range for the arraying solution is 7 to 9, with a preferred buffer being freshly prepared sodium borate at pH 8.3 to pH 8.5. To prepare a typical arraying solution, hexylamine-modified nucleic acid polymer is placed in 0.2 M sodium borate, pH 8.3, at 0.1 µg/mL, to a total volume of 50 µl. Ten µl of a 15 mg/mL solution of cyanuric chloride is then added, and the reaction is allowed to proceed for 1 hour at 25 C with constant agitation. Glycerol (Gibco Brl®, Grand Island, N.Y. is added to a final concentration of 56%.

The biomolecular arraying solutions may be applied to the PEI coating by any of the number of techniques currently used in microfabrication. For example, the solutions may be placed into an ink jet print head, and ejected from such a head onto the coating.

A preferred approach to delivering biomolecular solution onto the PEI coating employs a modified spring probe. Spring probes are available from several vendors including Everett Charles (Pomona, Calif.), Interconnect Devices Inc. (Kansas City, Kans.) and Test Connections Inc., (Upland, Calif.). In order for the commercially available spring probes as described above to satisfactorily function as liquid deposition devices according to the present invention, approximately $\frac{1}{1000}$th to $\frac{5}{1000}$th of an inch of metal material must be removed from the tip of the probe. The process must result in a flat surface which is perpendicular to the longitudinal axis of the spring probe. The removal of approximately ¹⁄₁₀₀₀th to ⁵⁄₁₀₀₀th of an inch of material from the bottom of the tip is preferred and can be accomplished easily with a very fine grained wet stone. Specific spring probes which are commercially available and may be modified to provide a planar tip as described above include the XP54 probe manufactured by Ostby Barton (a division of Everett Charles (Pomona, Calif.)); the SPA 25P probe manufactured by Everett Charles (Pomona, Calif.) and 43-P fluted spring probe from Test Connections Inc., (Upland, Calif.).

The arraying solutions as described above may be used directly in an arraying process. That is, the activated nucleic acid polymers need not be purified away from unreacted cyanuric chloride prior to the printing step. Typically the reaction which attaches the activated nucleic acid to the solid support is allowed to proceed for 1 to 20 hours at 20 to 50 C. Preferably, the reaction time is 1 hour at 25 C.

The arrays as described herein are particularly useful in conducting hybridization assays, for example, using CMST labeled probes. However, in order to perform such assays, the amines on the solid support must be capped prior to conducting the hybridization step. This may be accomplished by reacting the solid support with 0.1–2.0 M succinic anhydride. The preferred reaction conditions are 1.0 M succinic anhydride in 70% m-pyrol and 0.1 M sodium borate. The reaction typically is allowed to occur for 15 minutes to 4 hours with a preferred reaction time of 30 minutes at 25 C. Residual succinic anhydride is removed with a 3×water wash.

The solid support is then incubated with a solution containing 0.1–5 M glycine in 0.1–10.0 M sodium borate at pH 7–9. This step "caps" any dichloro-triazine which may be covalently bound to the PEI surface by conversion into monochlorotriazine. The preferred conditions are 0.2 M glycine in 0.1 M sodium borate at pH 8.3. The solid support may then be washed with detergent-containing solutions to remove unbound materials, for example, trace NMP. Preferably, the solid support is heated to 95 C in 0.01 M NaCl, 0.05 M EDTA and 01 M Tris pH 8.0 for 5 minutes. This heating step removes non-covalently attached nucleic acid polymers, such as PCR products. In the case where double strand nucleic acid are arrayed, this step also has the effect of converting the double strand to single strand form (denaturation).

The arrays are may be interrogated by probes (e.g., oligonucleotides, nucleic acid fragments, PCR products, etc.) which may be tagged with, for example CMST tags as described herein, radioisotopes, fluorophores or biotin. The methods for biotinylating nucleic acids are well known in the art and are adequately described by Pierce (Avidin-Biotin Chemistry: A Handbook, Pierce Chemical Company, 1992, Rockford Ill.). Probes are generally used at 0.1 ng/mL to 10/μg/mL in standard hybridization solutions that include GuSCN, GuHCl, formamide, etc. (see Van Ness and Chen, *Nucleic Acids Res.*, 19:5143–5151, 1991).

To detect the hybridization event (i.e., the presence of the biotin), the solid support is incubated with streptavidin/horseradish peroxidase conjugate. Such enzyme conjugates are commercially available from, for example, Vector Laboratories (Burlingham, Calif.). The streptavidin binds with high affinity to the biotin molecule bringing the horseradish peroxidase into proximity to the hybridized probe. Unbound streptavidin/horseradish peroxidase conjugate is washed away in a simple washing step. The presence of horseradish peroxidase enzyme is then detected using a precipitating substrate in the presence of peroxide and the appropriate buffers.

A blue enzyme product deposited on a reflective surface such as a wafer has a many-fold lower level of detection (LLD) compared to that expected for a calorimetric substrate. Furthermore, the LLD is vastly different for different colored enzyme products. For example, the LLD for 4-methoxynapthol (which produces a precipitated blue product) per 50 μM diameter spot is approximately 1000 molecules, whereas a red precipitated substrate gives an LLD about 1000-fold higher at 1,000,000 molecules per 50 μM diameter spot. The LLD is determined by interrogating the surface with a microscope (such as the Axiotech microscope commercially available from Zeiss) equipped with a visible light source and a CCD camera (Princeton Instruments, Princeton, N.J.). An image of approximately 10,000 μM×10,000 μM can be scanned at one time.

In order to use the blue colorimetric detection scheme, the surface must be very clean after the enzymatic reaction and the wafer or slide must be scanned in a dry state. In addition, the enzymatic reaction must be stopped prior to saturation of the reference spots. For horseradish peroxidase this is approximately 2–5 minutes.

It is also possible to use chemiluminescent substrates for alkaline phosphatase or horesradish peroxidase (HRP), or fluoroescence substrates for HRP or alkaline phosphatase. Examples include the dioxetane substrates for alkaline phosphatase available from Perkin Elmer or Attophos HRP substrate from JBL Scientific (San Luis Obispo, Calif.).

The following examples are offered by way of illustration, and not by way of limitation.

Unless otherwise stated, chemicals as used in the examples may be obtained from Aldrich Chemical Company, Milwaukee, Wis. The following abbreviations, with the indicated meanings, are used herein:

ANP=3-(Fmoc-amino)-3-(2-nitrophenyl)propionic acid
NBA=4-(Fmoc-aminomethyl)-3-nitrobenzoic acid
HATU=O-7-azabenzotriazol-1-yl-NN,N',N'-tetramethyluronium hexafluorophosphate
DIEA=diisopropylethylamine
MCT=monochlorotriazine
NMM=4-methylmorpholine
NMP=N-methylpyrrolidone
ACT357=ACT357 peptide synthesizer from Advanced ChemTech, Inc., Louisville, Ky.
ACT=Advanced ChemTech, Inc., Louisville, Ky.
NovaBiochem=CalBiochem-NovaBiochem International, San Diego, Calif.
TFA=Trifluoroacetic acid
Tfa=Trifluoroacetyl
iNIP=N-Methylisonipecotic acid
Tfp=Tetrafluorophenyl
DIAEA=2-(Diisopropylamino)ethylamine
MCT=monochlorotriazene
5'-AH-ODN=5'-aminohexyl-tailed oligodeoxynucleotide

EXAMPLES

Example 1

PREPARATION OF ACID LABILE LINKERS FOR USE IN CLEAVABLE-MW-IDENTIFIER SEQUENCING

Figure 1B:
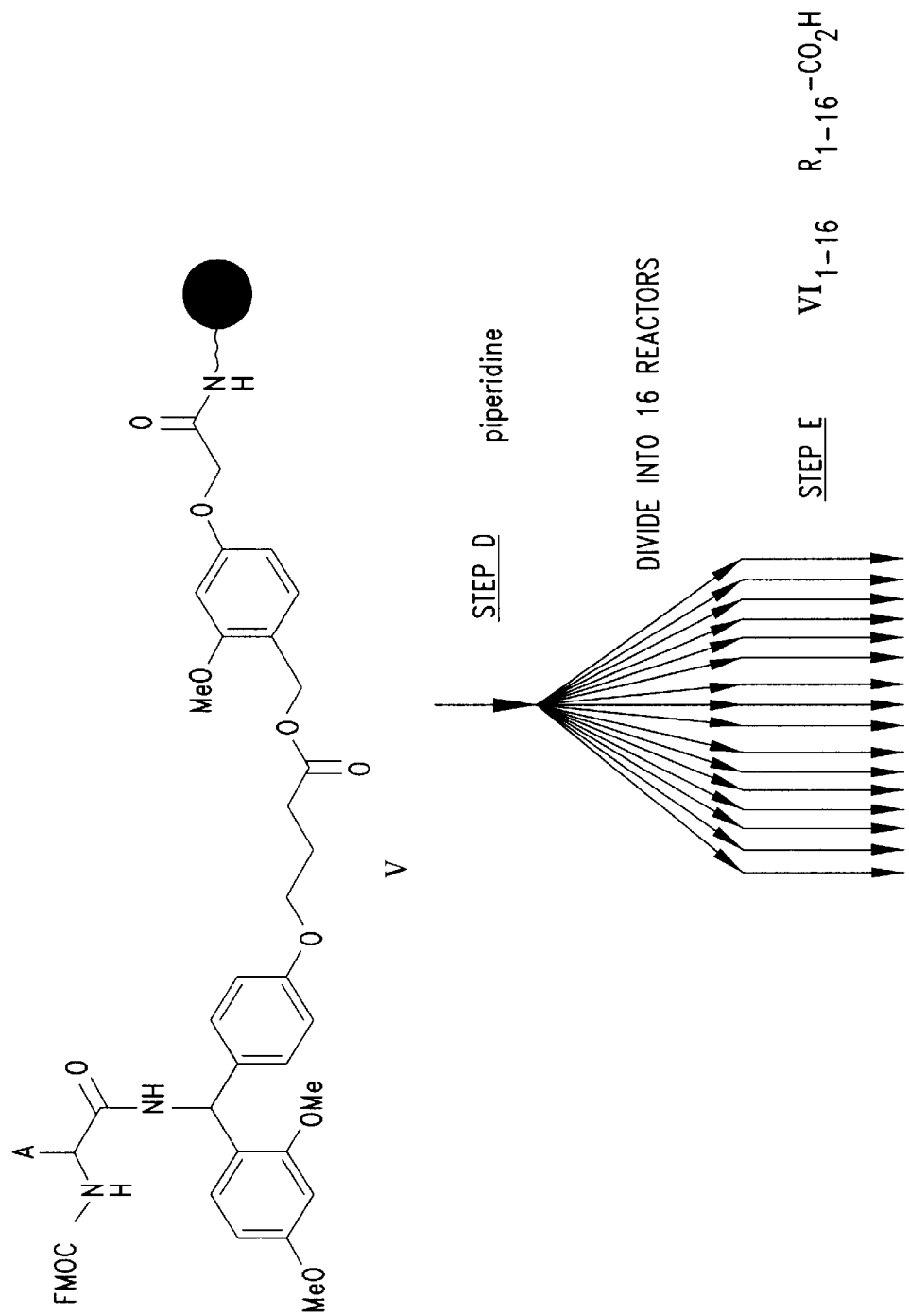
Figure 1C:
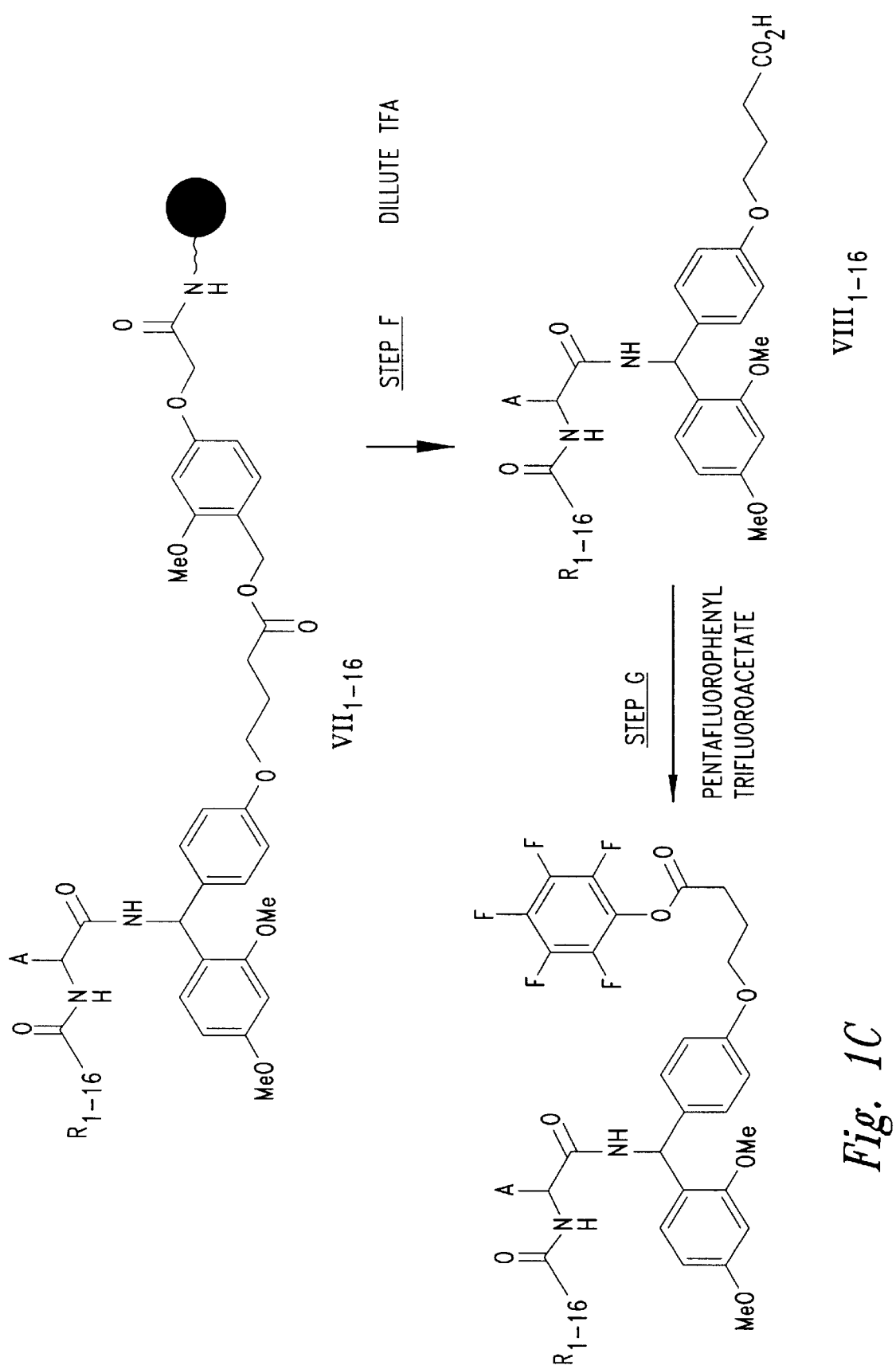

A. Synthesis of Pentafluorophenyl Esters of Chemically Cleavable Mass Spectroscopy Tags, to Liberate Tags with Carboxyl Amide Termini FIG. 1 shows the reaction scheme.

Step A. TentaGel S AC resin (compound II; available from ACT; 1 eq.) is suspended with DMF in the collection vessel of the ACT357 peptide synthesizer (ACT). Compound I (3 eq.), HATU (3 eq.) and DIEA (7.5 eq.) in DMF are added and the collection vessel shaken for 1 hr. The solvent is removed and the resin washed with NMP (2×), MeOH (2×), and DMF (2×). The coupling of I to the resin and the wash steps are repeated, to give compound III.

Step B. The resin (compound III) is mixed with 25% piperidine in DMF and shaken for 5 min. The resin is filtered, then mixed with 25% piperidine in DMF and shaken for 10 min. The solvent is removed, the resin washed with NMP (2×), MeOH (2×), and DMF (2×), and used directly in step C.

Step C. The deprotected resin from step B is suspended in DMF and to it is added an FMOC-protected amino acid, containing amine finctionality in its side chain (compound IV, e.g. alpha-N-FMOC-3-(3-pyridyl)-alanine, available from Synthetech, Albany, Oreg.; 3 eq.), HATU (3 eq.), and DIEA (7.5 eq.) in DMF. The vessel is shaken for 1 hr. The solvent is removed and the resin washed with NMP (2×), MeOH (2×), and DMF (2×). The coupling of IV to the resin and the wash steps are repeated, to give compound V.

Step D. The resin (compound V) is treated with piperidine as described in step B to remove the FMOC group. The deprotected resin is then divided equally by the ACT357 from the collection vessel into 16 reaction vessels.

Step E. The 16 aliquots of deprotected resin from step D are suspended in DMF. To each reaction vessel is added the appropriate carboxylic acid $VI_{1-16}$ ($R_{1-16}CO_2H$; 3 eq.), HATU (3 eq.), and DIEA (7.5 eq.) in DMF. The vessels are shaken for 1 hr. The solvent is removed and the aliquots of resin washed with NMP (2×), MeOH (2×), and DMF (2×). The coupling of $VI_{1-16}$ to the aliquots of resin and the wash steps are repeated, to give compounds $VIII_{1-16}$.

Step F. The aliquots of resin (compounds $VII_{1-16}$) are washed with $CH_2Cl_2$ (3×). To each of the reaction vessels is added 1% TFA in $CH_2Cl_2$ and the vessels shaken for 30 min. The solvent is filtered from the reaction vessels into individual tubes. The aliquots of resin are washed with $CH_2Cl_2$ (2×) and MeOH (2×) and the filtrates combined into the individual tubes. The individual tubes are evaporated in vacuo, providing compounds $VIII_{1-16}$.

Step G. Each of the free carboxylic acids $VIII_{1-16}$ is dissolved in DMF. To each solution is added pyridine (1.05 eq.), followed by pentafluorophenyl trifluoroacetate (1.1 eq.). The mixtures are stirred for 45 min. at room temperature. The solutions are diluted with EtOAc, washed with 1 M aq. citric acid (3×) and 5% aq. $NaHCO_3$ (3×), dried over $Na_2SO_4$, filtered, and evaporated in vacuo, providing compounds $IX_{1-16}$.

Figure 2A:
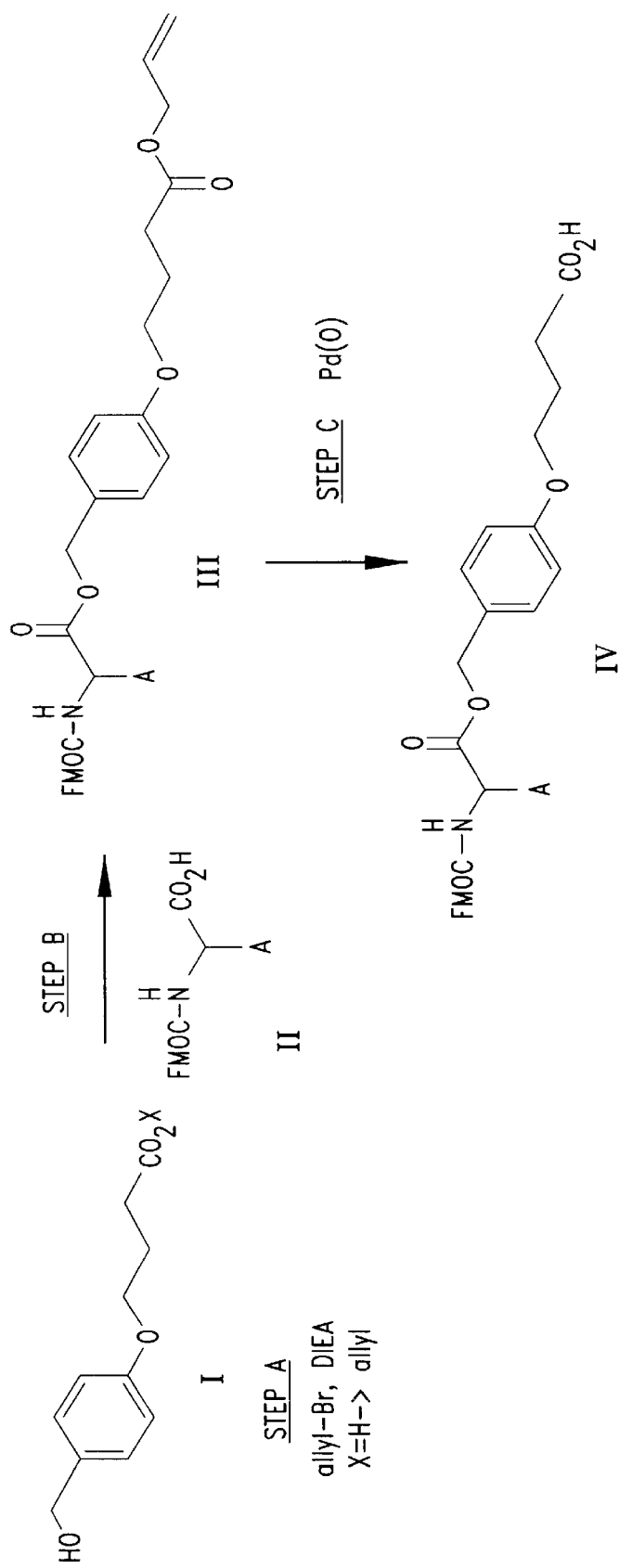
FIG. 2 depicts the flowchart for the synthesis of pentafluorophenyl esters of chemically cleavable mass spectroscopy tags, to liberate tags with carboxyl acid termini.
Figure 2B:
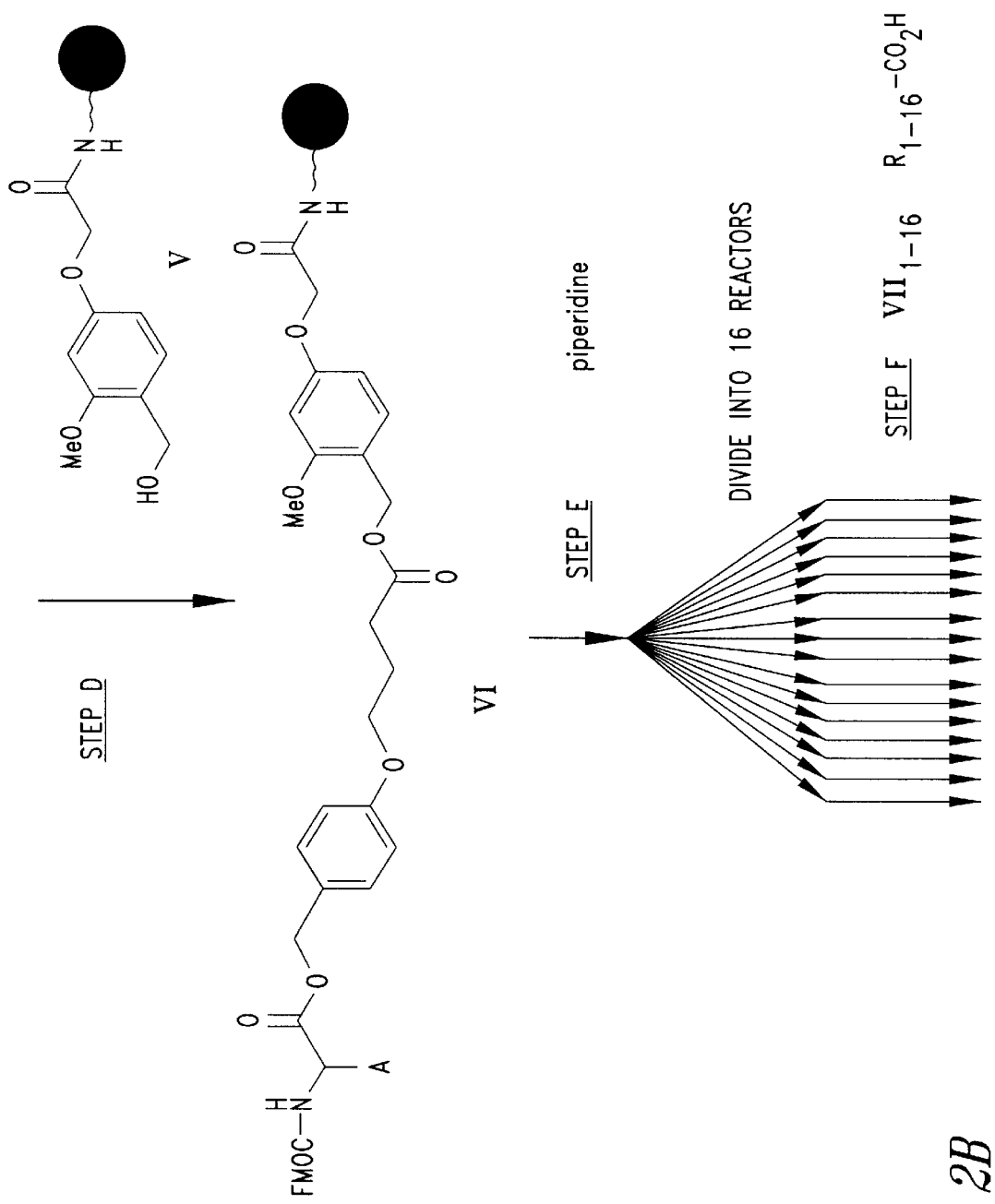
Figure 2C:
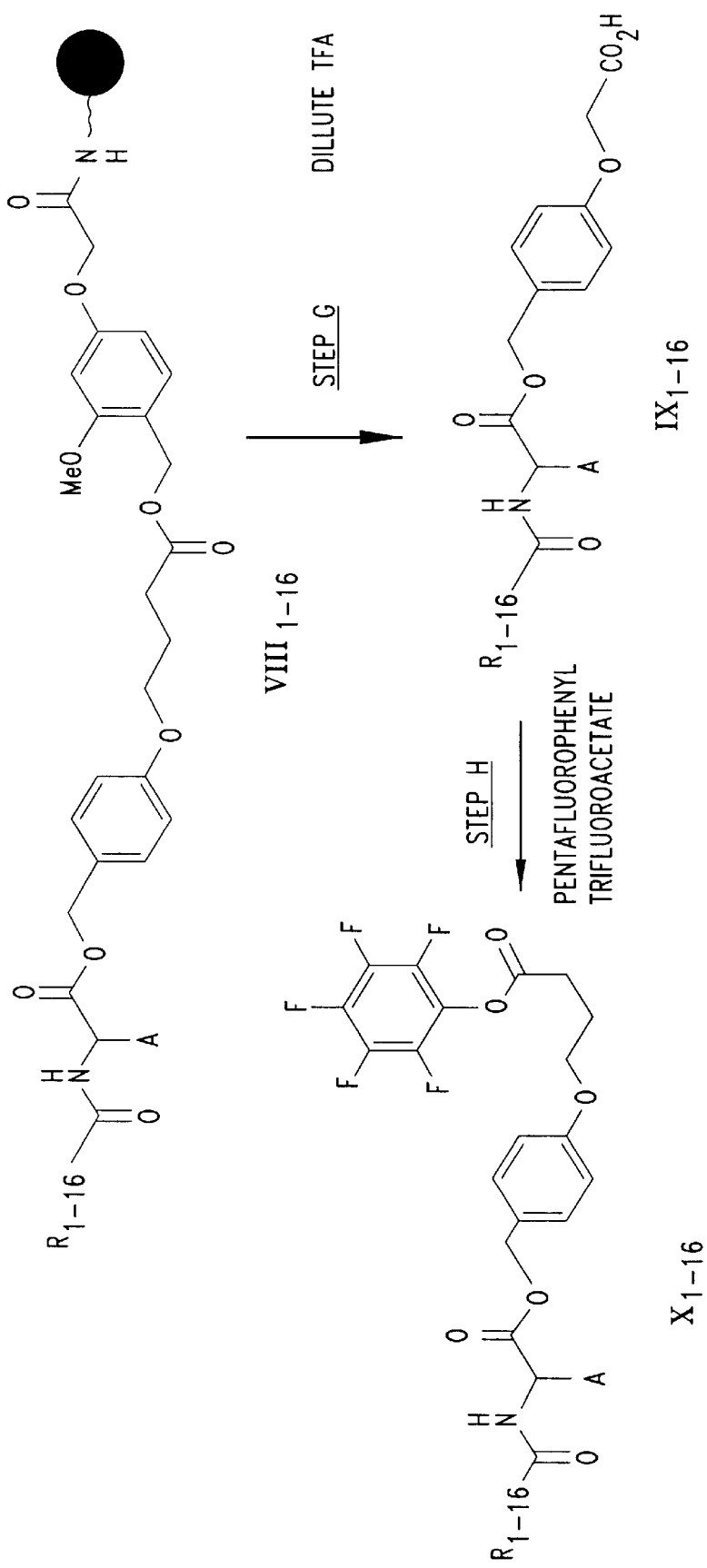

B. Synthesis of Pentafluorophenyl Esters of Chemically Cleavable Mass Spectroscopy Tags, to Liberate Tags with Carboxyl Acid Termini FIG. 2 shows the reaction scheme.

Step A. 4-(Hydroxymethyl)phenoxybutyric acid (compound I; 1 eq.) is combined with DIEA (2.1 eq.) and allyl bromide (2.1 eq.) in $CHCl_3$ and heated to reflux for 2 hr. The mixture is diluted with EtOAc, washed with 1 N HCl (2×), pH 9.5 carbonate buffer (2×), and brine (1×), dried over $Na_2SO_4$, and evaporated in vacuo to give the allyl ester of compound I.

Step B. The allyl ester of compound I from step A (1.75 eq.) is combined in $CH_2Cl_2$ with an FMOC-protected amino acid containing amine functionality in its side chain (compound II, e.g. alpha-N-FMOC-3-(3-pyridyl)-alanine, available from Synthetech, Albany, Oreg.; 1 eq.), N-methylmorpholine (2.5 eq.), and HATU (1.1 eq.), and stirred at room temperature for 4 hr. The mixture is diluted with $CH_2Cl_2$, washed with 1 M aq. citric acid (2×), water (1×), and 5% aq. $NaHCO_3$ (2×), dried over $Na_2SO_4$, and evaporated in vacuo. Compound III is isolated by flash chromatography ($CH_2Cl_2 \rightarrow EtOAc$).

Step C. Compound III is dissolved in $CH_2Cl_2$, $Pd(PPh_3)_4$ (0.07 eq.) and N-methylaniline (2 eq.) are added, and the mixture stirred at room temperature for 4 hr. The mixture is diluted with $CH_2Cl_2$, washed with 1 M aq. citric acid (2×) and water (1×), dried over $Na_2SO_4$, and evaporated in vacuo. Compound IV is isolated by flash chromatography ($CH_2Cl_2 \rightarrow EtOAc+HOAc$).

Step D. TentaGel S AC resin (compound V; 1 eq.) is suspended with DMF in the collection vessel of the ACT357 peptide synthesizer (Advanced ChemTech Inc. (ACT), Louisville, Ky.). Compound IV (3 eq.), HATU (3 eq.) and DIEA (7.5 eq.) in DMF are added and the collection vessel shaken for 1 hr. The solvent is removed and the resin washed with NMP (2×), MeOH (2×), and DMF (2×). The coupling of IV to the resin and the wash steps are repeated, to give compound VI.

Step E. The resin (compound VI) is mixed with 25% piperidine in DMF and shaken for 5 min. The resin is filtered, then mixed with 25% piperidine in DMF and shaken for 10 min. The solvent is removed and the resin washed with NMP (2×), MeOH (2×), and DMF (2×). The deprotected resin is then divided equally by the ACT357 from the collection vessel into 16 reaction vessels.

Step F. The 16 aliquots of deprotected resin from step E are suspended in DMF. To each reaction vessel is added the appropriate carboxylic acid $VII_{1-16}$ ($R_{1-16}CO_2H$; 3 eq.), HATU (3 eq.), and DIEA (7.5 eq.) in DMF. The vessels are shaken for 1 hr. The solvent is removed and the aliquots of resin washed with NMP (2×), MeOH (2×), and DMF (2×). The coupling of $VII_{1-16}$ to the aliquots of resin and the wash steps are repeated, to give compounds $VIII_{1-16}$.

Step G. The aliquots of resin (compounds $VIII_{1-16}$) are washed with $CH_2Cl_2$ (3×). To each of the reaction vessels is added 1% TFA in $CH_2Cl_2$ and the vessels shaken for 30 min. The solvent is filtered from the reaction vessels into individual tubes. The aliquots of resin are washed with $CH_2Cl_2$ (2×) and MeOH (2×) and the filtrates combined into the individual tubes. The individual tubes are evaporated in vacuo, providing compounds $IX_{1-16}$.

Step H. Each of the free carboxylic acids $IX_{1-16}$ is dissolved in DMF. To each solution is added pyridine (1.05 eq.), followed by pentafluorophenyl trifluoroacetate (1.1 eq.). The mixtures are stirred for 45 min. at room temperature. The solutions are diluted with EtOAc, washed with 1 M aq. citric acid (3×) and 5% aq. $NaHCO_3$ (3×), dried over $Na_2SO_4$, filtered, and evaporated in vacuo, providing compounds $X_{1-16}$.

Example 2

DEMONSTRATION OF PHOTOLYTIC CLEAVAGE OF T—L—X

A T—L—X compound as prepared in Example 13 was irradiated with near-UV light for 7 min at room temperature. A Rayonett fluorescence UV lamp (Southern New England Ultraviolet Co., Middletown, Conn.) with an emission peak at 350 nm is used as a source of UV light. The lamp is placed at a 15-cm distance from the Petri dishes with samples. SDS gel electrophoresis shows that >85% of the conjugate is cleaved under these conditions.

Example 3

PREPARATION OF FLUORESCENT LABELED PRIMERS AND DEMONSTRATION OF CLEAVAGE OF FLUOROPHORE

Synthesis and Purification of Oligonucleotides

The oligonucleotides (ODNs) are prepared on automated DNA synthesizers using the standard phosphoramidite chemistry supplied by the vendor, or the H-phosphonate chemistry (Glenn Research Sterling, Va.). Appropriately blocked dA, dG, dC, and T phosphoramnidites are commercially available in these forms, and synthetic nucleosides may readily be converted to the appropriate form. The oligonucleotides are prepared using the standard phosphoramidite supplied by the vendor, or the H-phosphonate chemistry. Oligonucleotides are purified by adaptations of standard methods. Oligonucleotides with 5'-trityl groups are chromatographed on HPLC using a 12 micrometer, 300 # Rainin (Emeryville, Calif.) Dynamax C-8 4.2×250 mm reverse phase column using a gradient of 15% to 55% MeCN in 0.1 N $Et_3NH^+OAc^-$, pH 7.0, over 20 min. When detritylation is performed, the oligonucleotides are further purified by gel exclusion chromatography. Analytical checks for the quality of the oligonucleotides are conducted with a PRP-column (Alltech, Deerfield, Ill.) at alkaline pH and by PAGE.

Preparation of 2,4,6-trichlorotriazine derived oligonucleotides: 10 to 1000 μg of 5'-terminal amine linked oligonucleotide are reacted with an excess recrystallized cyanuric chloride in 10% n-methyl-pyrrolidone in alkaline (pH 8.3 to 8.5 preferably) buffer at 19° C. to 25° C. for 30 to 120 minutes. The final reaction conditions consist of 0.15 M sodium borate at pH 8.3, 2 mg/ml recrystallized cyanuric chloride and 500 ug/ml respective oligonucleotide. The unreacted cyanuric chloride is removed by size exclusion chromatography on a G-50 Sephadex (Pharmacia, Piscataway, N.J.) column.

The activated purified oligonucleotide is then reacted with a 100-fold molar excess of cystamine in 0.15 M sodium borate at pH 8.3 for 1 hour at room temperature. The unreacted cystamine is removed by size exclusion chromatography on a G-50 Sephadex column. The derived ODNs are then reacted with amine-reactive fluorochromes. The derived ODN preparation is divided into 3 portions and each portion is reacted with either (a) 20-fold molar excess of Texas Red sulfonyl chloride (Molecular Probes, Eugene, Oreg.), with (b) 20-fold molar excess of Lissamine sulfonyl chloride (Molecular Probes, Eugene, Oreg.), (c) 20-fold molar excess of fluorescein isothiocyanate. The final reaction conditions consist of 0.15 M sodium borate at pH 8.3 for 1 hour at room temperature. The unreacted fluorochromes are removed by size exclusion chromatography on a G-50 Sephadex column.

To cleave the fluorochrome from the oligonucleotide, the ODNs are adjusted to $1 \times 10^{-5}$ molar and then dilutions are made (12, 3-fold dilutions) in TE (TE is 0.01 M Tris, pH 7.0, 5 mM EDTA). To 100 μl volumes of ODNs 25 μl of 0.01 M dithiothreitol (DTT) is added To an identical set of controls no DDT is added. The mixture is incubated for 15 minutes at room temperature. Fluorescence is measured in a black microtiter plate. The solution is removed from the incubation tubes (150 microliters) and placed in a black microtiter plate (Dynatek Laboratories, Chantilly, Va.). The plates are then read directly using a Fluoroskan II fluorometer (Flow Laboratories, McLean, Va.) using an excitation wavelength of 495 nm and monitoring emission at 520 nm for fluorescein, using an excitation wavelength of 591 nm and monitoring emission at 612 nm for Texas Red, and using an excitation wavelength of 570 nm and monitoring emission at 590 nm for lissamine.

| Moles of Fluorochrome | RFU non-cleaved | RFU cleaved | RFU free |
| --- | --- | --- | --- |
| $1.0 \times 10^5$ M | 6.4 | 1200 | 1345 |
| $3.3 \times 10^6$ M | 2.4 | 451 | 456 |
| $1.1 \times 10^6$ M | 0.9 | 135 | 130 |
| $3.7 \times 10^7$ M | 0.3 | 44 | 48 |
| $1.2 \times 10^7$ M | 0.12 | 15.3 | 16.0 |
| $4.1 \times 10^7$ M | 0.14 | 4.9 | 5.1 |
| $1.4 \times 10^8$ M | 0.13 | 2.5 | 2.8 |
| $4.5 \times 10^9$ M | 0.12 | 0.8 | 0.9 |

The data indicate that there is about a 200-fold increase in relative fluorescence when the fluorochrome is cleaved from the ODN.

Example 4

PREPARATION OF TAGGED M13 SEQUENCE PRIMERS AND DEMONSTRATION OF CLEAVAGE OF TAGS

Preparation of 2,4,6-trichlorotriazine derived oligonucleotides: 1000 μg of 5'-terminal amine linked oligonucleotide (5'-hexylamine-TGTAAAACGACGGCCAGT-3") (Seq. ID No. 1) are reacted with an excess recrystallized cyanuric chloride in 10% n-methyl-pyrrolidone alkaline (pH 8.3 to 8.5 preferably) buffer at 19 to 25- C for 30 to 120 minutes. The final reaction conditions consist of 0.15 M sodium borate at pH 8.3, 2 mg/ml recrystallized cyanuric chloride and 500 ug/ml respective oligonucleotide. The unreacted cyanuric chloride is removed by size exclusion chromatography on a G-50 Sephadex column.

The activated purified oligonucleotide is then reacted with a 100-fold molar excess of cystamine in 0.15 M sodium borate at pH 8.3 for 1 hour at room temperature. The unreacted cystamine is removed by size exclusion chromatography on a G-50 Sephadex column. The derived ODNs are then reacted with a variety of amides. The derived ODN preparation is divided into 12 portions and each portion is reacted (25 molar excess) with the pentafluorophenyl-esters of either: (1) 4-methoxybenzoic acid, (2) 4-fluorobenzoic acid, (3) toluic acid, (4) benzoic acid, (5) indole-3-acetic acid, (6) 2,6-difluorobenzoic acid, (7) nicotinic acid N-oxide, (8) 2-nitrobenzoic acid, (9) 5-acetylsalicylic acid, (10) 4-ethoxybenzoic acid, (11) cinnamic acid, (12) 3-aminonicotinic acid. The reaction is for 2 hours at 37° C. in 0.2 M NaBorate pH 8.3. The derived ODNs are purified by gel exclusion chromatography on G-50 Sephadex.

To cleave the tag from the oligonucleotide, the ODNs are adjusted to $1 \times 10^{-5}$ molar and then dilutions are made (12, 3-fold dilutions) in TE (TE is 0.01 M Tris, pH 7.0, 5 mM EDTA) with 50% EtOH (V/V). To 100 μl volumes of ODNs 25 μl of 0.01 M dithiothreitol (DTT) is added. To an identical set of controls no DDT is added. Incubation is for 30 minutes at room temperature. NaCl is then added to 0.1 M and 2 volumes of EtOH is added to precipitate the ODNs. The ODNs are removed from solution by centrifugation at 14,000×G at 4° C. for 15 minutes. The supernatants are reserved, dried to completeness. The pellet is then dissolved in 25 μl MeOH. The pellet is then tested by mass spectrometry for the presence of tags.

The mass spectrometer used in this work is an external ion source Fourier-transform mass spectrometer (FTMS). Samples prepared for MALDI analysis are deposited on the tip of a direct probe and inserted into the ion source. When the sample is irradiated with a laser pulse, ions are extracted from the source and passed into a long quadrupole ion guide that focuses and transports them to an FTMS analyzer cell located inside the bore of a superconducting magnet.

The spectra yield the following information. Peaks varying in intensity from 25 to 100 relative intensity units at the following molecular weights: (1) 212.1 amu indicating 4-methoxybenzoic acid derivative, (2) 200.1 indicating 4-fluorobenzoic acid derivative, (3) 196.1 amu indicating toluic acid derivative, (4) 182.1 amu indicating benzoic acid derivative, (5) 235.2 amu indicating indole-3-acetic acid derivative, (6) 218.1 amu indicating 2,6-difluorobenzoic derivative, (7) 199.1 amu indicating nicotinic acid N-oxide derivative, (8) 227.1 amu indicating 2-nitrobenzamide, (9) 179.18 amu indicating 5-acetylsalicylic acid derivative, (10) 226.1 amu indicating 4-ethoxybenzoic acid derivative, (11) 209.1 amu indicating cinnamic acid derivative, (12) 198.1 amu indicating 3-aminonicotinic acid derivative.

The results indicate that the MW-identifiers are cleaved from the primers and are detectable by mass spectrometry.

Example 5

DEMONSTRATION OF SEQUENCING USING AN HPLC SEPARATION METHOD, COLLECTING FRACTIONS, CLEAVING THE MW IDENTIFIERS, DETERMINING THE MASS (AND THUS THE IDENTITY) OF THE MW-IDENTIFIER AND THEN DEDUCING THE SEQUENCE

The following oligonucleotides are prepared as described in Example 4:

DMO 767: '5-hexylamine-TGTAAAACGACGGCCAGT-3' (Seq. ID No. 1)
DMO 768: '5-hexylamine-TGTAAAACGACGGCCAGTA-3' (Seq. ID No. 2)
DMO 769: '5-hexylamine-TGTAAAACGACGGCCAGTAT-3' (Seq. ID No. 3)
DMO 770: '5-hexylanine-TGTAAAACGACGGCCAGTATG-3' (Seq. ID No. 4)
DMO 771: '5-hexylamine-TGTAAAACGACGGCCAGTArGC-3' (Seq. ID No. 5)
DMO 772: '5-hexylamine-TGTAAAACGACGGCCAGTATGCA-3' (Seq. ID No. 6)
DMO 773: '5-hexylamine-TGTAAAACGACGGCCAGTATGCAT-3' (Seq. ID No. 7)
DMO 774: '5-hexylamine-TGTAAAACGACGGCCAGTATGCATG-3' (Seq. ID No. 8)

100 $\mu$g of each of the 5'-terminal amnine-linked oligonucleotides described above are reacted with an excess recrystallized cyanuric chloride in 10% n-methyl-pyrrolidone alkaline (pH 8.3 to 8.5 preferably) buffer at 19° C. to 25° C. for 30 to 120 minutes. The final reaction conditions consist of 0.15 M sodium borate at pH 8.3, 2 mg/ml recrystallized cyanuric chloride and 500 ug/ml respective oligonucleotide. The unreacted cyanuric chloride is removed by size exclusion chromatography on a G-50 Sephadex column.

The activated purified oligonucleotide is then reacted with a 100-fold molar excess of cystamine in 0.15 M sodium borate at pH 8.3 for 1 hour at room temperature. The unreacted cystamine is removed by size exclusion chromatography on a G-50 Sephadex column. The derived ODNs are then reacted with a particular pentafluorophenyl-ester of the following: (1) DMO 767 with 4-methoxybenzoic acid, (2) DMO 768 with 4-fluorobenzoic acid, (3) toluic acid, (4) DMO 769 with benzoic acid, (5) DMO 770 with indole-3-acetic acid, (6) DMO 771 with 2,6-difluorobenzoic acid, (7) DMO 772 with nicotinic acid N-oxide, (8) DMO 773 with 2-nitrobenzoic acid.

10 ng of each of the eight derived ODNs are mixed together and then size separated by HPLC. The mixture is placed in 25 $\mu$l of distilled water. The entire sample is injected on to the following column. A LiChrospher 4000 DMAE, 50–10 mm column is used (EM Separations, Wakefield, R.I.). Eluent A is 20 mM $Na_2HPO_4$ in 20% ACN, pH7.4; Eluent B is Eluent A+1 M NaCl, pH7.4. The flowrate is for 1 ml/min and detection is UV@280 nm. The gradient is as follows: 0 min.@100% A and 0% B, 3 min.@100% A and 0% B. 15 min.@80% A and 20% B, 60 min.@0% A and 100% B, 63 min.@0% A and 100% B, 65 min.@100% A and 0% B, 70 min.@100% A and 0% B. Fractions are collected at 0.5 minute intervals.

To cleave the tags from the oligonucleotide, 100 $\mu$l of 0.05 M dithiothreitol (DTT) is added to each fraction. Incubation is for 30 minutes at room temperature. NaCl is then added to 0.1 M and 2 volumes of EtOH is added to precipitate the ODNs. The ODNs are removed from solution by centrifugation at 14,000×G at 4° C. for 15 minutes. The supematents are reserved, dried to completeness under a vacuum with centrifugation. The pellets are then dissolved in 25 $\mu$l MeOH. The pellet is then tested by mass spectrometry for the presence of MW-identifiers. The same MALDI technique is employed as described in Example 4. The following MWs (tags) are observed in the mass spectra as a function of time:

| Fraction # | Time | MWs |
|---|---|---|
| 1 | 0.5 | none |
| 2 | 1.0 | none |
| 3 | 1.5 | none |
| 4 | 2.0 | none |
| 5 | 2.5 | none |
| 6 | 3.0 | none |
| 7 | 3.5 | none |
| 8 | 4.0 | none |
| 9 | 4.5 | none |
| 10 | 5.0 | none |
| 11 | 5.5 | none |
| 12 | 6.0 | none |
| 13 | 6.5 | none |
| 14 | 7.0 | none |
| 15 | 7.5 | none |
| 16 | 8.0 | none |
| 17 | 8.5 | none |
| 18 | 9.0 | none |
| 19 | 9.5 | none |
| 20 | 10.0 | none |
| 21 | 10.5 | none |
| 22 | 11 | none |
| 23 | 11.5 | none |
| 24 | 12 | none |
| 25 | 12.5 | none |
| 26 | 13 | none |
| 27 | 13.5 | none |
| 28 | 14 | none |
| 29 | 14.5 | none |
| 30 | 15 | none |
| 31 | 15.5 | 212.1 |
| 32 | 16 | 212.1 |
| 33 | 16.5 | 212.1 |
| 34 | 17 | 212.1; 200.1 |
| 35 | 17.5 | 200.1 |
| 36 | 18 | 200.1 |
| 37 | 18.5 | 200.1 |
| 38 | 19 | 200.1; 196.1 |
| 39 | 19.5 | 200.1; 196.1 |

| Fraction # | Time | MWs |
|---|---|---|
| 40 | 20 | 196.1 |
| 41 | 20.5 | 196.1 |
| 42 | 21 | 196.1; 182.1 |
| 43 | 21.5 | 182.1 |
| 44 | 22 | 182.1 |
| 45 | 22.5 | 182.1; 235.2 |
| 46 | 23 | 235.2 |
| 47 | 23.5 | 235.2 |
| 48 | 24 | 235.2; 218.1 |
| 49 | 24.5 | 218.1 |
| 50 | 25 | 218.1 |
| 51 | 25.5 | 218.1; 199.1 |
| 52 | 26 | 199.1 |
| 53 | 26.5 | 199.1; 227.1 |
| 54 | 27 | 227.1 |
| 55 | 27.5 | 227.1 |
| 56 | 28 | none |
| 57 | 28.5 | none |
| 58 | 29 | none |
| 59 | 29.5 | none |
| 60 | 30 | none |

The temporal appearance of the tags is thus 212.1, 200.1, 196.1, 182.1, 235.2, 218.1, 199.1, 227.1. Since 212.1 amu indicates the 4-methoxybenzoic acid derivative, 200.1 indicates the 4-fluorobenzoic acid derivative, 196.1 amu indicates the toluic acid derivative, 182.1 amu indicates the benzoic acid derivative, 235.2 amu indicates the indole-3-acetic acid derivative, 218.1 amu indicates the 2,6-difluorobenzoic derivative, 199.1 amu indicates the nicotinic acid N-oxide derivative, 227.1 amu indicates the 2-nitrobenzamide, the sequence can be deduced as -5'-ATGCATG-3'-.

Example 6

DEMONSTRATION OF SEQUENCING OF TWO DNA SAMPLES IN A SINGLE HPLC SEPARATION METHOD

In this example, two DNA samples are sequenced in a single separation method.

The following oligonucleotides are prepared as described in Example 1.

DMO 767: '5-hexylamine-TGTAAAACGACGGCCAGT-3' (Seq. ID No. 1)
DMO 768: '5-hexylaiine-TGTAAAACGACGGCCAGTA-3' (Seq. ID No. 2)
DMO 769: '5-hexylamine-TGTAAAACGACGGCCAGTAT-3' (Seq. ID No. 3)
DMO 770: '5-hexylamine-TGTAAAACGACGGCCAGTATG-3' (Seq. ID No. 4)
DMO 771: '5-hexylamine-TGTAAAACGACGGCCAGTATGC-3' (Seq. ID No. 5)
DMO 772: '5-hexylamine-TGTAAAACGACGGCCAGTATGCA-3' (Seq. ID No. 6)
DMO 775: '5-hexylamine-TGTAAAACGACGGCCAGC-3' (Seq. ID No. 9)
DMO 776: '5-hexylamine-TGTAAAACGACGGCCAGCG-3' (Seq. ID No. 10)
DMO 777: '5-hexylamine-TGTAAAACGACGGCCAGCGT-3' (Seq. ID No. 11)
DMO 778: '5-hexylamine-TGTAAAACGACGGCCAGCGTA-3' (Seq. ID No. 12)
DMO 779: '5-hexylamine-TGTAAAACGACGGCCAGCGTAC-3' (Seq. ID No. 13)
DMO 780: '5-hexylamine-TGTAAAACGACGGCCAGCGTACC-3' (Seq. ID No. 14)

100 µg of each of the 5'-terminal amine-linked oligonucleotides described above are reacted with an excess recrystallized cyanuric chloride in 10% n-methyl-pyrrolidone alkaline (pH 8.3 to 8.5 preferably) buffer at 19° C. to 25° C. for 30 to 120 minutes. The final reaction conditions consist of 0.15 M sodium borate at pH 8.3, 2 mg/ml recrystallized cyanuric chloride and 500 ug/ml respective oligonucleotide. The unreacted cyanuric chloride is removed by size exclusion chromatography on a G-50 Sephadex column.

The activated purified oligonucleotide is then reacted with a 100-fold molar excess of cystamine in 0.15 M sodium borate at pH 8.3 for 1 hour at room temperature. The unreacted cystamine is removed by size exclusion chromatography on a G-50 Sephadex column. The derived ODNs are then reacted with a particular pentafluorophenyl-ester of the following: (1) DMO 767 with 4-methoxybenzoic acid and DMO 773 with nicotinic acid N-oxide, (2) DMO 768 with 4-fluorobenzoic acid and DMO 774 with 2-nitrobenzoic acid, (3) toluic acid and DMO 775 with acetylsalicylic acid, (4) DMO 769 with benzoic acid and DMO 776 with 4-ethoxybenzoic acid, (5) DMO 770 with indole-3-acetic acid and DMO 777 with cinnamic acid, (6) DMO 771 with 2,6-difluorobenzoic acid and DMO 778 with 3-aminonicotinic acid. Therefore, there is one of tags for each set of ODNs.

10 ng of each of the 12 derived ODNs are mixed together and then size separated by HPLC. The mixture is placed in 25 µl of distilled water. The entire sample is injected on to the following column. A LiChrospher 4000 DMAE, 50–10 mm column is used (EM Separations, Wakefield, R.I.). Eluent A is 20 mM $Na_2HPO_4$ in 20% ACN, pH7.4; Eluent B is Eluent A+1 M NaCl, pH7.4. The flowrate is for 1 ml/min and detection is UV@280 nm. The gradient is as follows: 0 min.@100% A and 0% B, 3 min.@100% A and 0% B, 15 min.@80% A and 20% B, 60 min.@0% A and 100% B, 63 min.@0% A and 100% B, 65 min.@100% A and 0% B, 70 min.@100% A and 0% B. Fractions are collected at 0.5 minute intervals.

To cleave the tags from the oligonucleotide, 100 µl of 0.05 M dithiothreitol (DTT) is added to each fraction. Incubation is for 30 minutes at room temperature. NaCl is then added to 0.1 M and 2 volumes of EtOH is added to precipitate the ODNs. The ODNs are removed from solution by centrifugation at 14,000×G at 4° C. for 15 minutes. The supernatents are reserved, dried to completeness under a vacuum with centrifugation. The pellets are then dissolved in 25 µl MeOH. The pellet is then tested by mass spectrometry for the presence of tags. The same MALDI technique is employed as described in Example 4. The following MWs (tags) are observed in the mass spectra as a function of time:

| Fraction # | Time | MWs | Fraction # | Time | MWs |
|---|---|---|---|---|---|
| 1 | 0.5 | none | 31 | 15.5 | 212.1, 199.1 |
| 2 | 1.0 | none | 32 | 16 | 212.1, 199.1 |
| 3 | 1.5 | none | 33 | 16.5 | 212.1, 199.1 |
| 4 | 2.0 | none | 34 | 17 | 212.1; 200.1, 199.1, 227.1 |
| 5 | 2.5 | none | 35 | 17.5 | 200.1, 199.1, 227.1 |
| 6 | 3.0 | none | 36 | 18 | 200.1, 227.1 |
| 7 | 3.5 | none | 37 | 18.5 | 200.1, 227.1, 179.18 |
| 8 | 4.0 | none | 38 | 19 | 200.1; 196.1, 179.18 |
| 9 | 4.5 | none | 39 | 19.5 | 200.1; 196.1, 179.18 |
| 10 | 5.0 | none | 40 | 20 | 196.1, 179.18, 226.1 |
| 11 | 5.5 | none | 41 | 20.5 | 196.1, 226.1 |
| 12 | 6.0 | none | 42 | 21 | 196.1; 182.1, 226.1 |
| 13 | 6.5 | none | 43 | 21.5 | 182.1, 226.1, 209.1 |

-continued

| Fraction # | Time | MWs | Fraction # | Time | MWs |
|---|---|---|---|---|---|
| 14 | 7.0 | none | 44 | 22 | 182.1, 209.1 |
| 15 | 7.5 | none | 45 | 22.5 | 182.1; 235.2, 209.1, 198.1 |
| 16 | 8.0 | none | 46 | 23 | 235.2, 198.1 |
| 17 | 8.5 | none | 47 | 23.5 | 235.2, 198.1 |
| 18 | 9.0 | none | 48 | 24 | 235.2;, 198.1, 218.1 |
| 19 | 9.5 | none | 49 | 24.5 | 218.1 |
| 20 | 10.0 | none | 50 | 25 | 218.1 |
| 21 | 10.5 | none | 51 | 25.5 | none |
| 22 | 11 | none | 52 | 26 | none |
| 23 | 11.5 | none | 53 | 26.5 | none |
| 24 | 12 | none | 54 | 27 | none |
| 25 | 12.5 | none | 55 | 27.5 | none |
| 26 | 13 | none | 56 | 28 | none |
| 27 | 13.5 | none | 57 | 28.5 | none |
| 28 | 14 | none | 58 | 29 | none |
| 29 | 14.5 | none | 59 | 29.5 | none |
| 30 | 15 | none | 60 | 30 | none |

The temporal appearance of the tags for set #1 is 212.1, 200.1, 196.1, 182.1, 235.2, 218.1, 199.1, 227.1, and the temporal appearance of tags for set #2 is 199.1, 227.1, 179.1, 226.1, 209.1, 198.1. Since 212.1 amu indicates the 4-methoxybenzoic acid derivative, 200.1 indicates the 4-fluorobenzoic acid derivative, 196.1 amu indicates the toluic acid derivative, 182.1 amu indicates the benzoic acid derivative, 235.2 amu indicates the indole-3-acetic acid derivative, 218.1 amu indicates the 2,6-difluorobenzoic derivative, 199.1 amu indicates the nicotinic acid N-oxide derivative, 227.1 amu indicates the 2-nitrobenzamide, 179.18 amu indicates the 5-acetylsalicylic acid derivative, 226.1 amu indicates the 4-ethoxybenzoic acid derivative, 209.1 amu indicates the cinnamic acid derivative, and 198.1 amu indicates the 3-aminonicotinic acid, the first sequence can be deduced as -5'-TATGCA-3'- and the second sequence can be deduced as -5'-CGTACC-3'-. Thus, it is possible to sequence more than one DNA sample per separation step.

Example 7

Figure 3A:
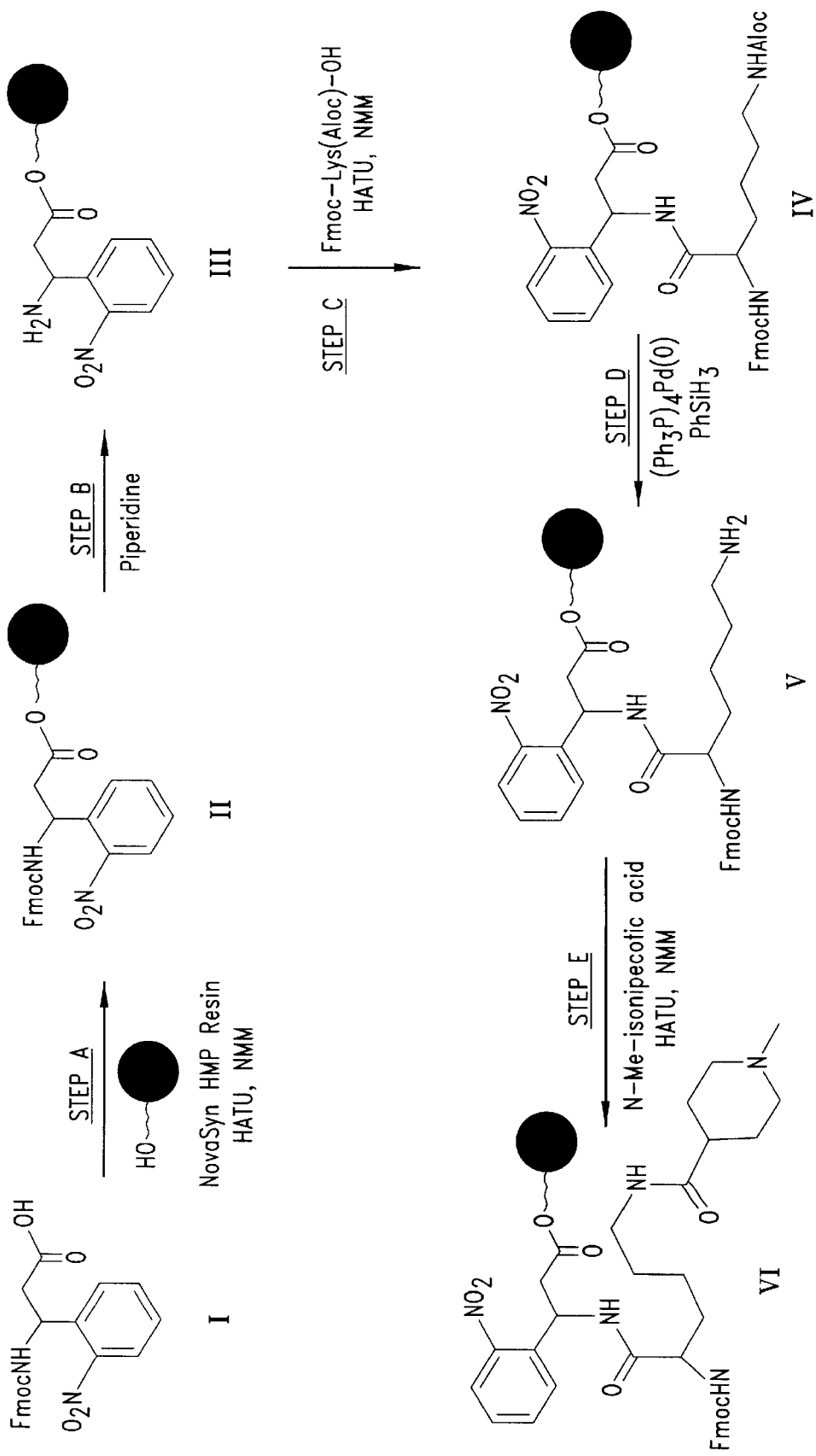
FIGS. 3–6 and 8 depict the flowchart for the synthesis of tetrafluorophenyl esters of a set of 36 photochemically cleavable mass spec. tags.
Figure 3B:
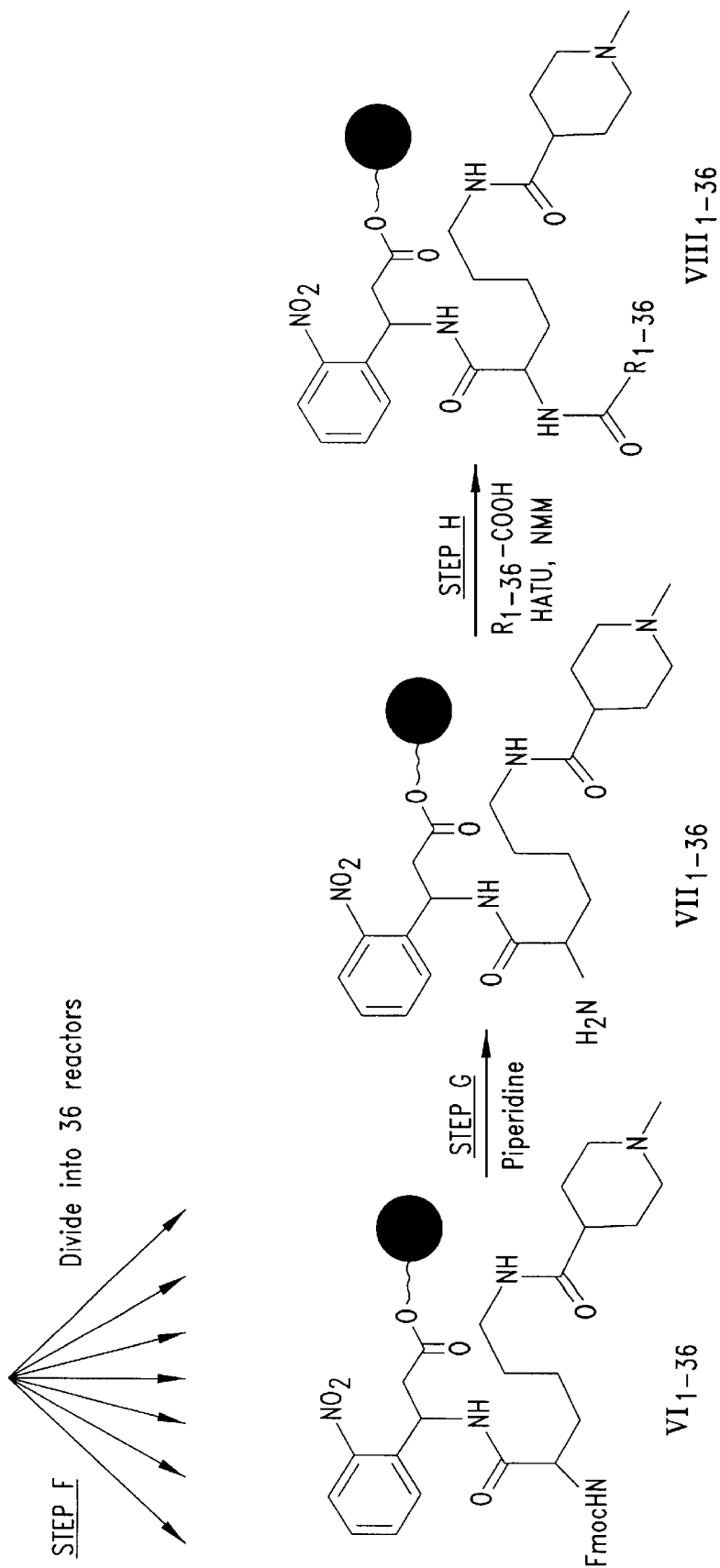
Figure 3C:
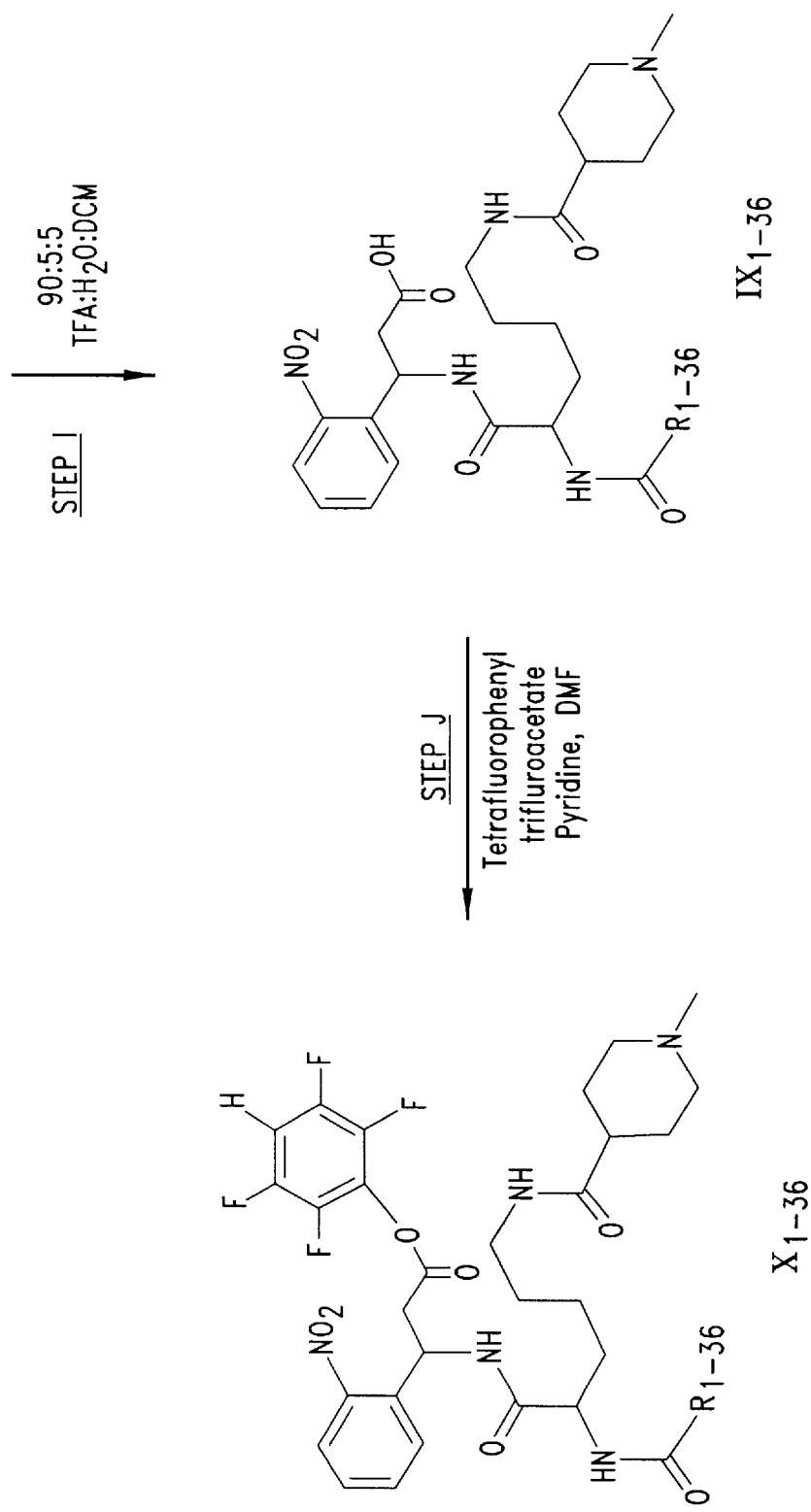

PREPARATION OF A SET OF COMPOUNDS OF THE FORMULA $R_{1-36}$-LYS($\epsilon$-INIP)-ANP-TFP FIG. 3 illustrates the parallel synthesis of a set of 36 T—L—X compounds (X=$L_h$), where $L_h$ is an activated ester (specifically, tetrafluorophenyl ester), $L^2$ is an ortho-nitrobenzylamine group with $L^3$ being a methylene group that links $L_h$ and $L^2$, T has a modular structure wherein the carboxylic acid group of lysine has been joined to the nitrogen atom of the $L^2$ benzylamine group to form an amide bond, and a variable weight component $R_{1-36}$, (where these R groups correspond to $T^2$ as defined herein, and may be introduced via any of the specific carboxylic acids listed herein) is bonded through the α-amino group of the lysine, while a mass spec sensitivity enhancer group (introduced via N-methylisonipecotic acid) is bonded through the C-amino group of the lysine.

Referring to FIG. 3:

Step A. NovaSyn HMP Resin (available from NovaBiochem; 1 eq.) is suspended with DMF in the collection vessel of the ACT357. Compound I (ANP available from ACT; 3 eq.), HATU (3 eq.) and NMM (7.5 eq.) in DMF are added and the collection vessel shaken for 1 hr. The solvent is removed and the resin washed with NMP (2×), MeOH (2×), and DMF (2×). The coupling of I to the resin and the wash steps are repeated, to give compound II.

Step) B. The resin (compound II) is mixed with 25% piperidine in DMF and shaken for 5 min. The resin is filtered, then mixed with 25% piperidine in DMF and shaken for 10 min. The solvent is removed, the resin washed with NMP (2×), MeOH (2×), and DMF (2×), and used directly in step C.

Step C. The deprotected resin from step B is suspended in DMF and to it is added an FMOC-protected amino acid, containing a protected amine functionality in its side chain (Fmoc-Lysine(Aloc)-OH, available from PerSeptive Biosystems; 3 eq.), HATU (3 eq.), and NMM (7.5 eq.) in DMF. The vessel is shaken for 1 hr. The solvent is removed and the resin washed with NMP (2×), MeOH (2×), and DMF (2×). The coupling of Fmoc-Lys(Aloc)-OH to the resin and the wash steps are repeated, to give compound IV.

Step D. The resin (compound IV) is washed with $CH_2Cl_2$ (2×), and then suspended in a solution of $(PPh_3)_4Pd$ (0) (0.3 eq.) and $PhSiH_3$ (10 eq.) in $CH_2Cl_2$. The mixture is shaken for 1 hr. The solvent is removed and the resin is washed with $CH_2Cl_2$ (2×). The palladium step is repeated. The solvent is removed and the resin is washed with $CH_2Cl_2$ (2×), N,N-diisopropylethylammonium diethyldithiocarbamate in DMF (2×), DMF (2×) to give compound V.

Step E. The deprotected resin from step D is coupled with N-methylisonipecotic acid as described in step C to give compound VI.

Step) F. The Fmoc protected resin VI is divided equally by the ACT357 from the collection vessel into 36 reaction vessels to give compounds $VI_{1-36}$.

Step G. The resin (compounds $VII_{1-36}$) is treated with piperidine as described in step B to remove the FMOC group.

Step H. The 36 aliquots of deprotected resin from step G are suspended in DMF. To each reaction vessel is added the appropriate carboxylic acid ($R_{1-36}CO_2H$; 3 eq.), HATU (3 eq.), and NMM (7.5 eq.) in DMF. The vessels are shaken for 1 hr. The solvent is removed and the aliquots of resin washed with NMP (2×), MeOH (2×), and DMF (2×). The coupling of $R_{1-36}CO_2H$ to the aliquots of resin and the wash steps are repeated, to give compounds $VIII_{1-36}$.

Step I. The aliquots of resin (compounds $VIII_{1-36}$) are washed with $CH_2Cl_2$ (3×). To each of the reaction vessels is added 90:5:5 TFA:H20:$CH_2Cl_2$ and the vessels shaken for 120 min. The solvent is filtered from the reaction vessels into individual tubes. The aliquots of resin are washed with $CH_2Cl_2$ (2×) and MeOH (2×) and the filtrates combined into the individual tubes. The individual tubes are evaporated in vacuo, providing compounds $IX_{1-36}$.

Step J. Each of the free carboxylic acids $IX_{1-36}$ is dissolved in DMF. To each solution is added pyridine (1.05 eq.), followed by tetrafluorophenyl trifluoroacetate (1.1 eq.). The mixtures are stirred for 45 min. at room temperature. The solutions are diluted with EtOAc, washed with 5% aq. $NaHCO_3$ (3×), dried over $Na_2SO_4$, filtered, and evaporated in vacuo, providing compounds $X_{1-36}$.

Example 8

Figure 4A:
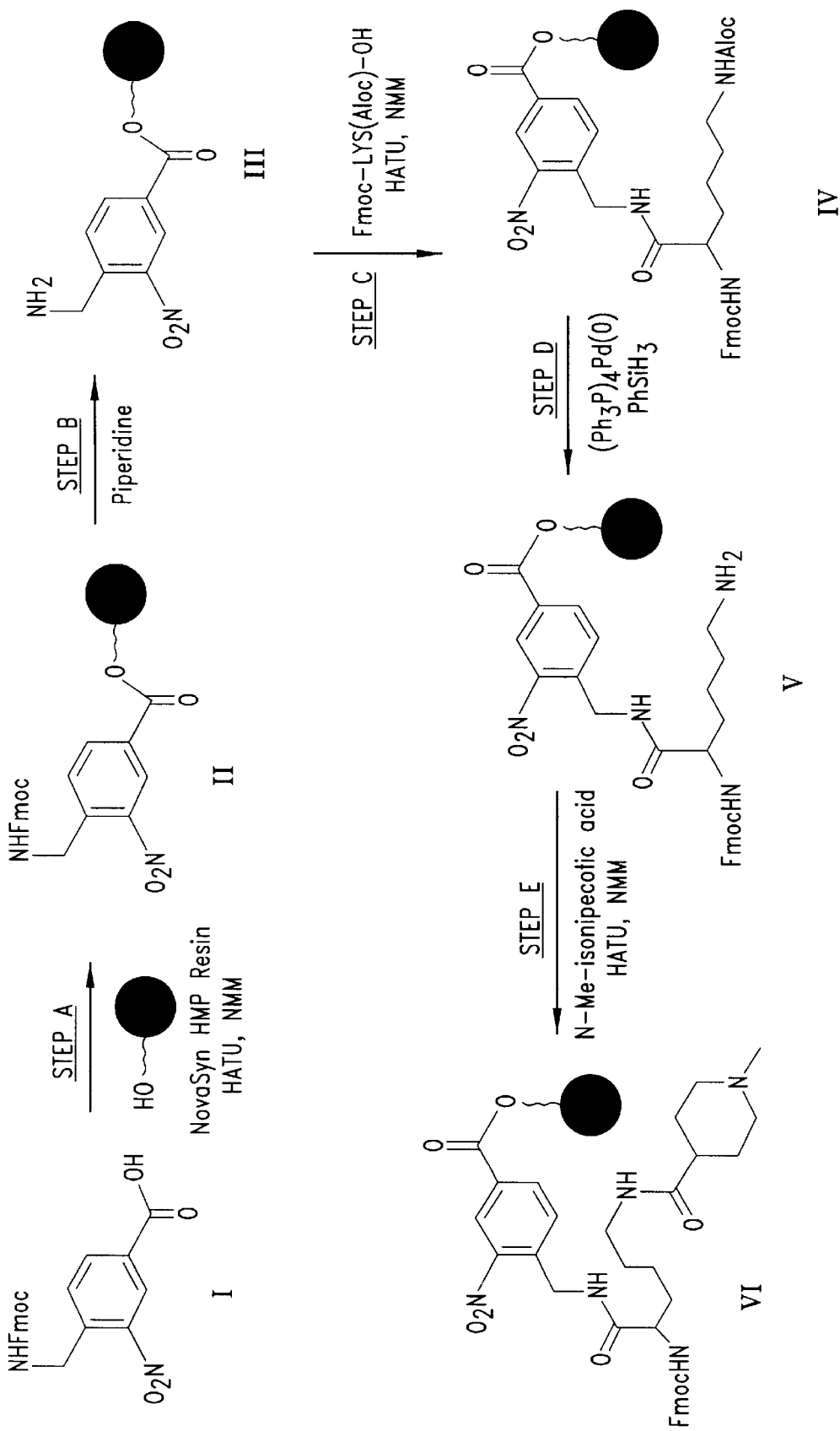
Figure 4B:
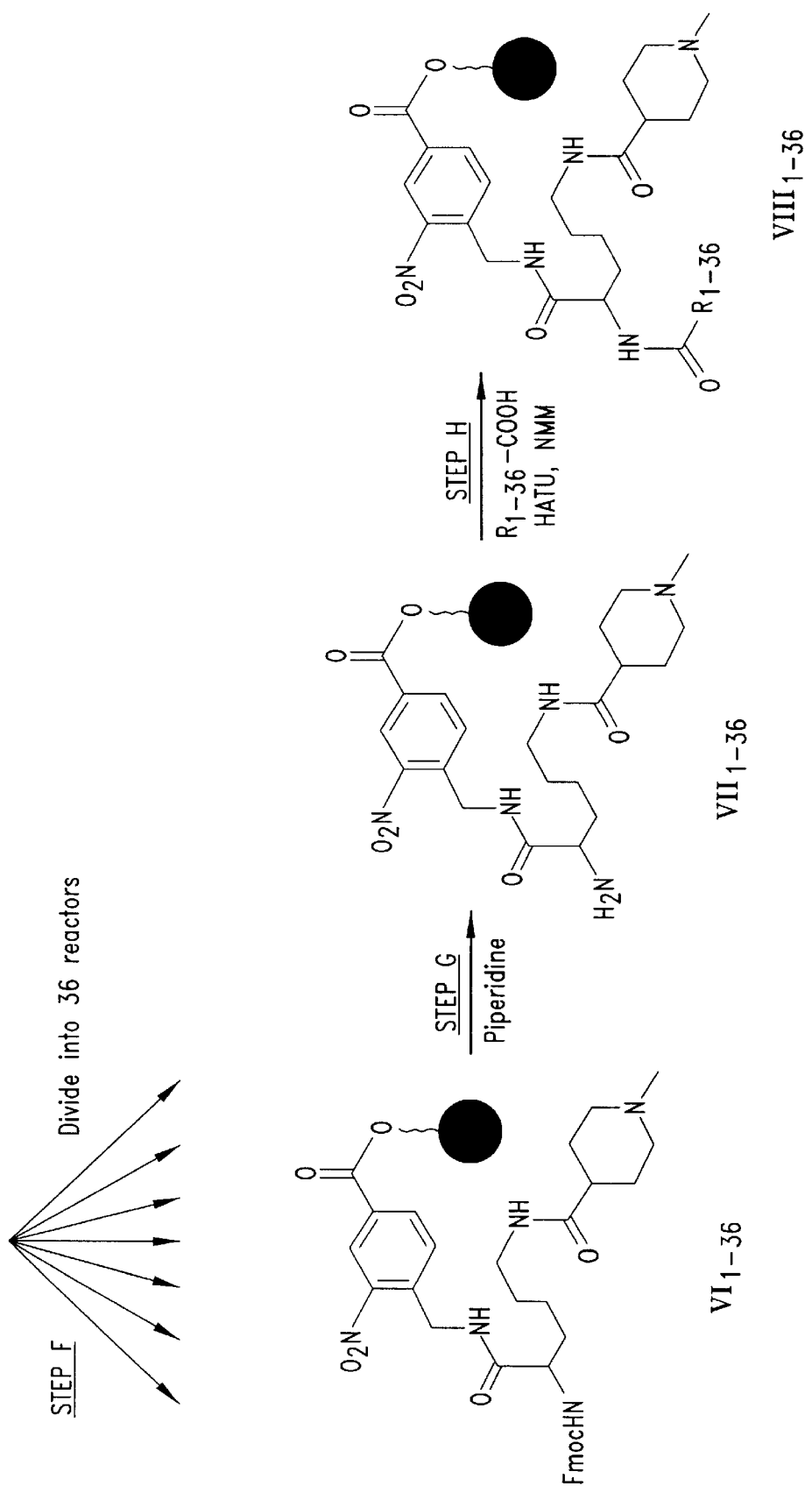
Figure 4C:
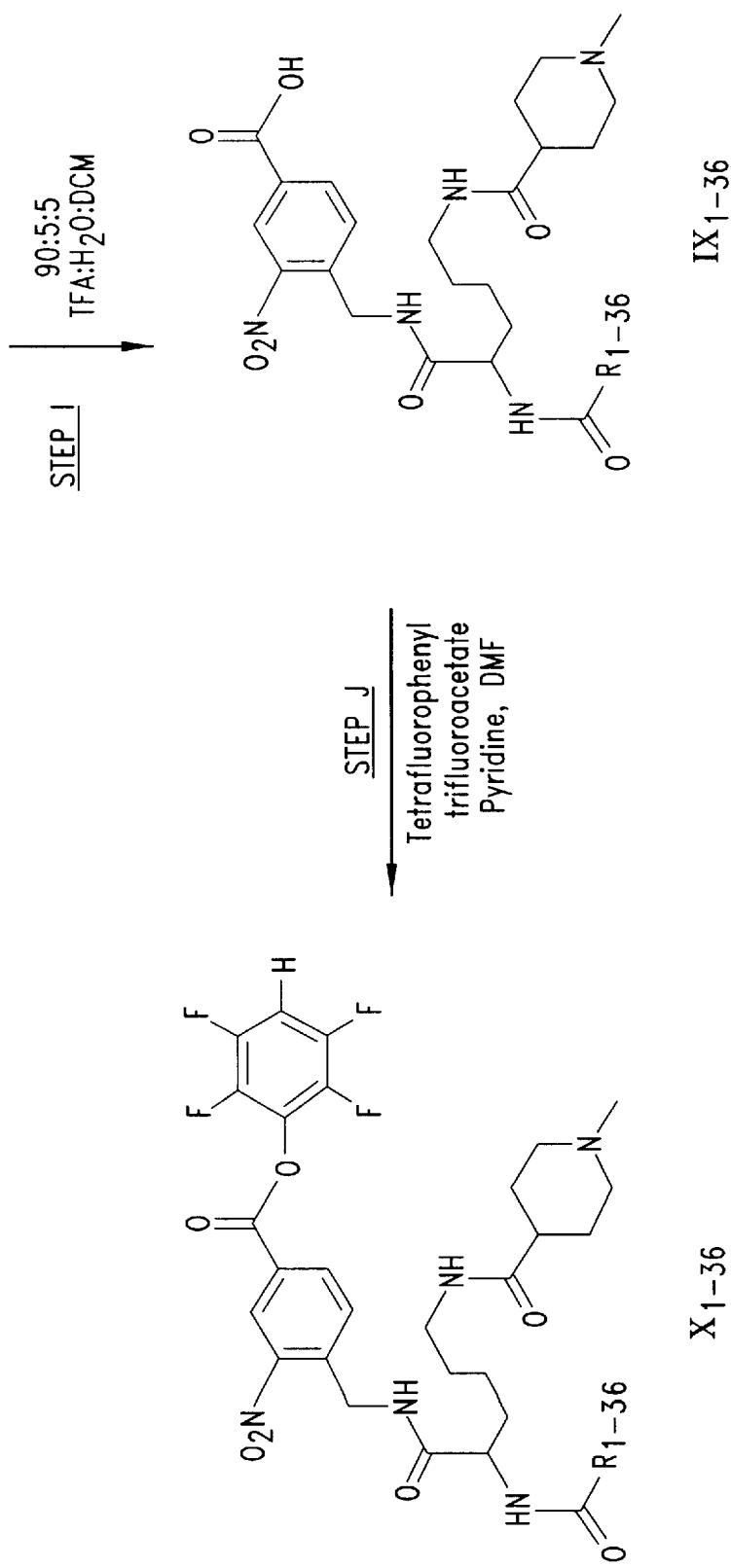

PREPARATION OF A SET OF COMPOUNDS OF THE FORMULA $R_{1-36}$-LYS($\epsilon$-INIP)-NBA-TFP FIG. 4 illustrates the parallel synthesis of a set of 36 T—L—X compounds (X=$L_h$), where $L_h$ is an activated ester (specifically, tetrafluorophenyl ester), $L^2$ is an ortho-nitrobenzylamine group with $L^3$ being a direct bond between $L_h$ and $L^2$, where $L_h$ is joined directly to the aromatic ring of the L² group, T has a modular structure wherein the carboxylic acid group of lysine has been joined to the nitrogen atom of the L² benzylamine group to form an amide bond, and a variable weight component $R_{1-36}$, (where these R groups correspond to T² as defined herein, and may be introduced via any of the specific carboxylic acids listed herein) is bonded through the ax-amino group of the lysine, while a mass spec enhancer group (introduced via N-methylisonipecotic acid) is bonded through the E-amino group of the lysine.

Referring to FIG. 4:

Step A. NovaSyn HMP Resin is coupled with compound I (NBA prepared according to the procedure of Brown et al., Molecular Diversity, 1, 4 (1995)) according to the procedure described in step A of Example 7, to give compound II.

Steps B–J. The resin (compound II) is treated as described in steps B–J of Example 7 to give compounds $X_{1-36}$.

Example 9

Figure 5A:
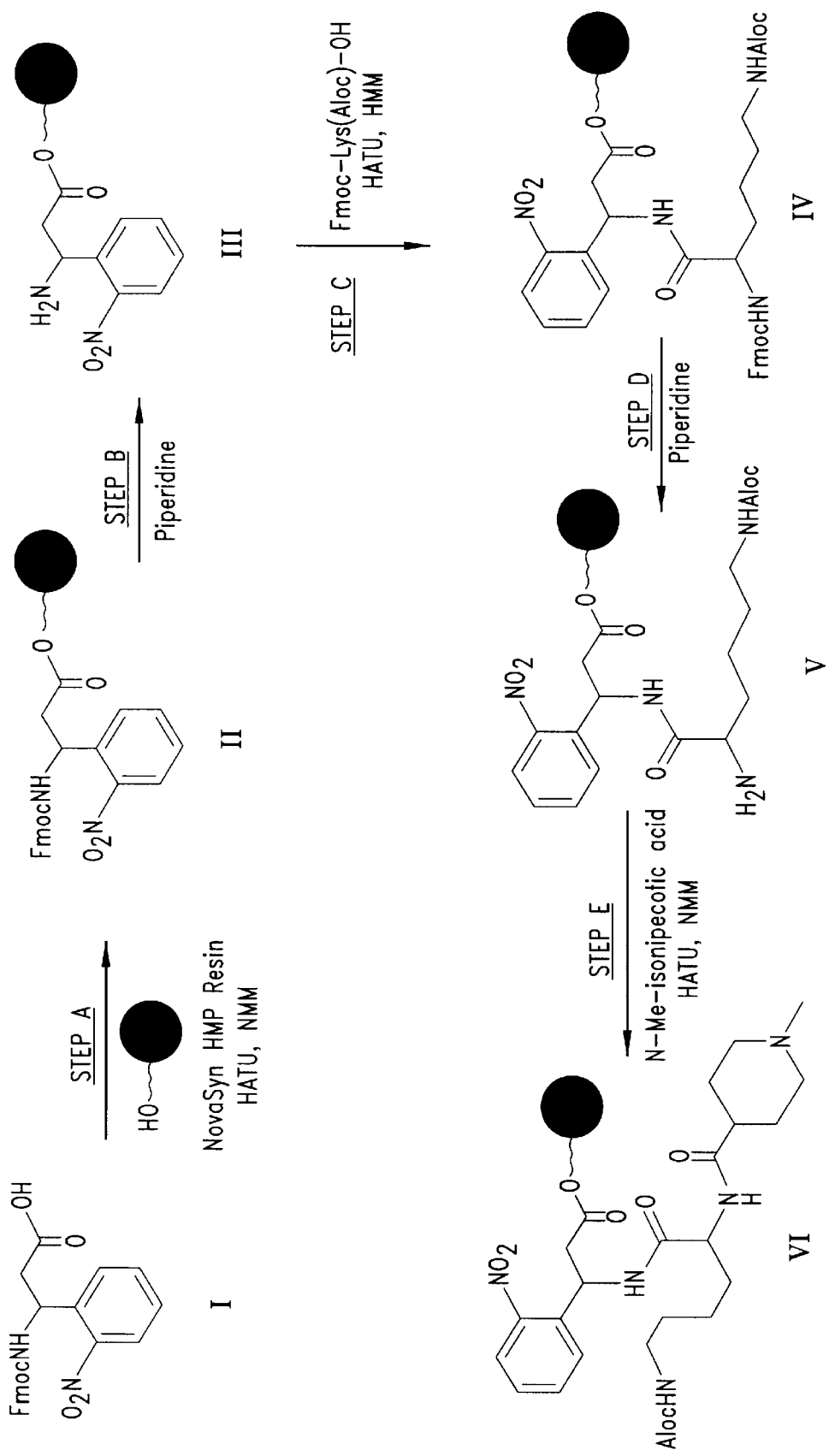
Figure 5B:
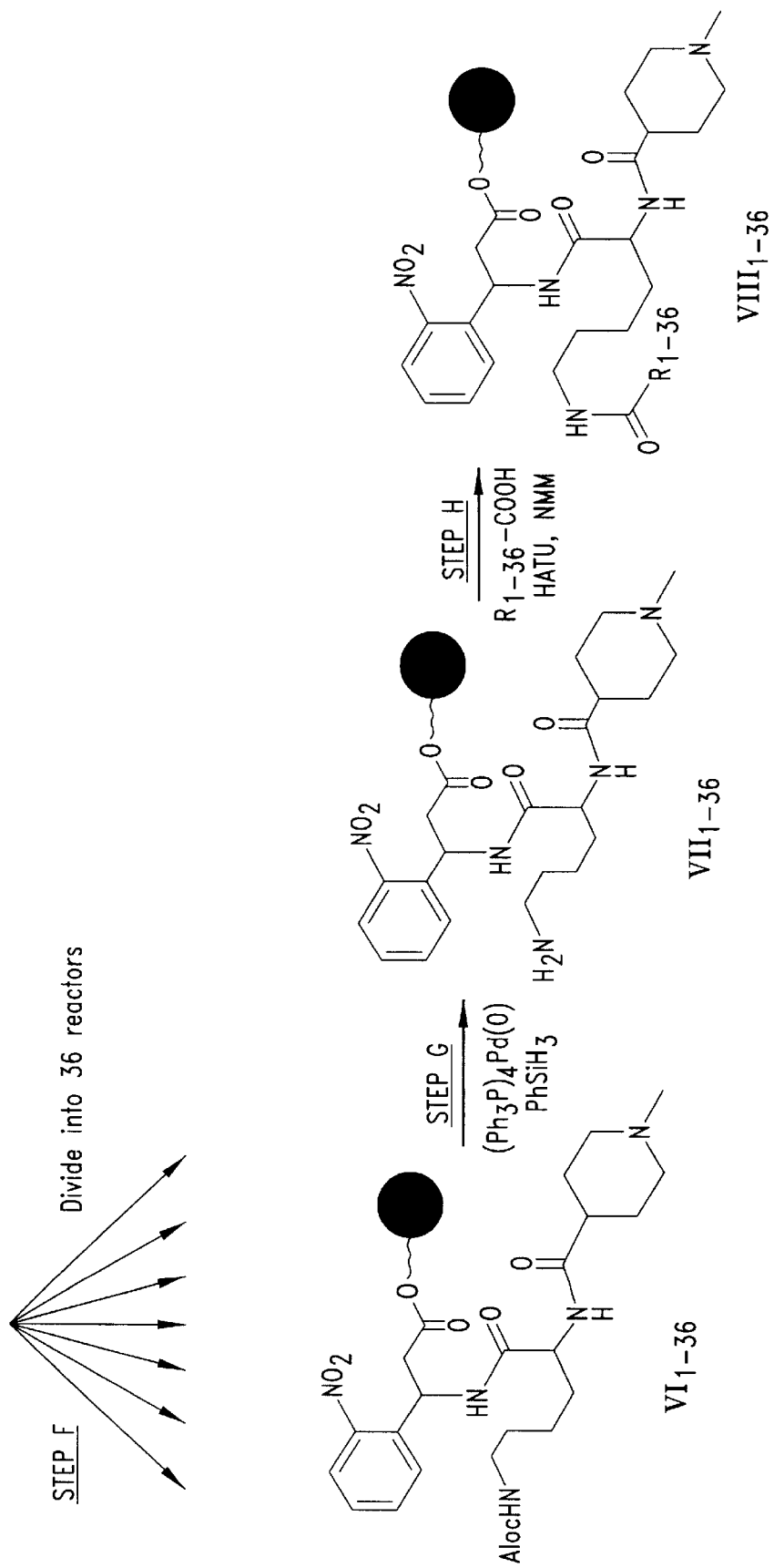
Figure 5C:
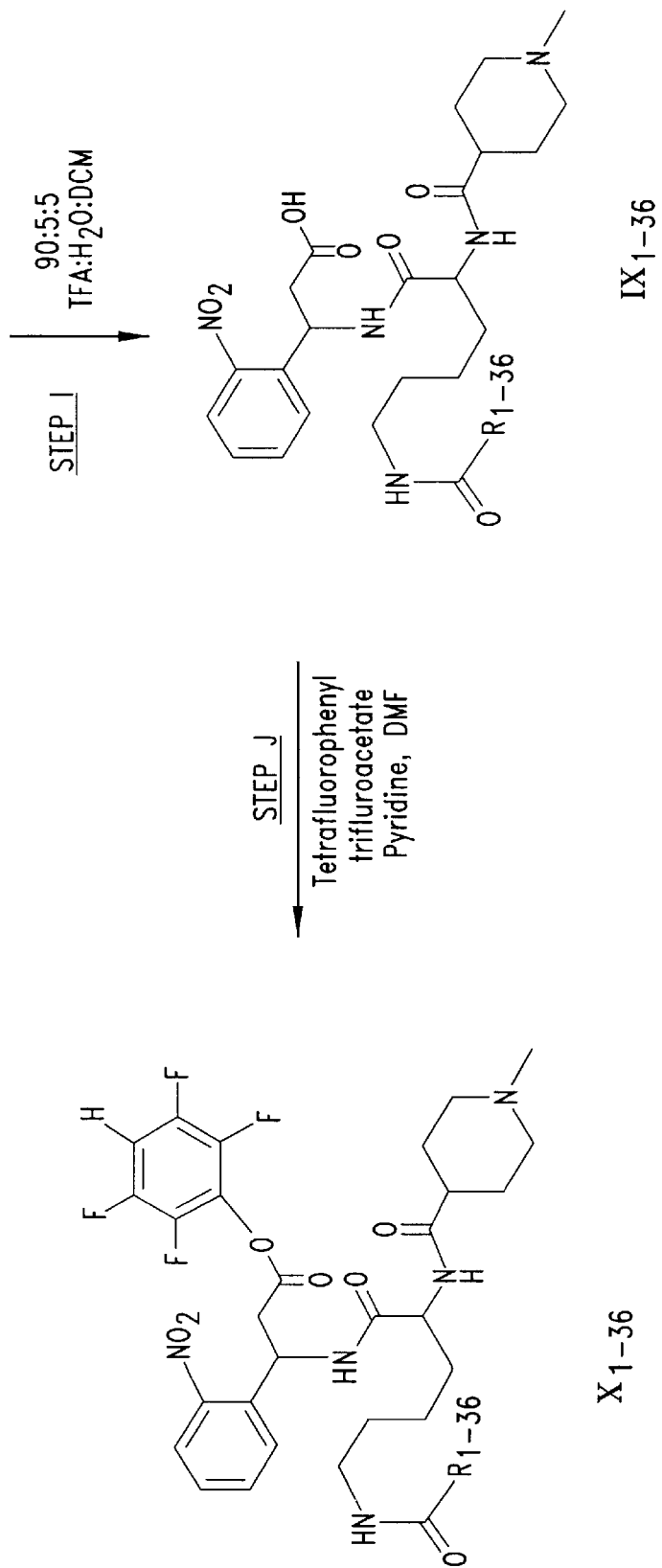

PREPARATION OF A SET OF COMPOUNDS OF THE FORMULA $I_{NIP-LYS (\epsilon-R_{1-36})-ANP-TFP}$ FIG. 5 illustrates the parallel synthesis of a set of 36 T—L—X compounds ($X=L_h$), where $L_h$ is an activated ester (specifically, tetrafluorophenyl ester), L² is an ortho-nitrobenzylamine group with L³ being a methylene group that links $L_h$ and L², T has a modular structure wherein the carboxylic acid group of lysine has been joined to the nitrogen atom of the L² benzylamine group to form an amide bond, and a variable weight component $R_{1-36}$, (where these R groups correspond to T² as defined herein, and may be introduced via any of the specific carboxylic acids listed herein) is bonded through the ε-amino group of the lysine, while a mass spec sensitivity enhancer group (introduced via N-methylisonipecotic acid) is bonded through the α-amino group of the lysine.

Referring to FIG. 5:

Steps A–C. Same as in Example 7.

Step D. The resin (compound IV) is treated with piperidine as described in step B of Example 7 to remove the FMOC group.

Step E. The deprotected α-amine on the resin in step D is coupled with N-30 methylisonipecotic acid as described in step C of Example 7 to give compound V.

Step F. Same as in Example 7.

Step G. The resin (compounds $VI_{1-36}$) are treated with palladium as described in step D of Example 7 to remove the Aloc group.

Steps H–J. The compounds $X_{1-36}$ are prepared in the same manner as in Example 7.

Example 10

PREPARATION OF A SET OF COMPOUNDS OF THE FORMULA $R_{1-36}$-GLU(γ-DIAEA)-ANP-TFP

Figure 6A:
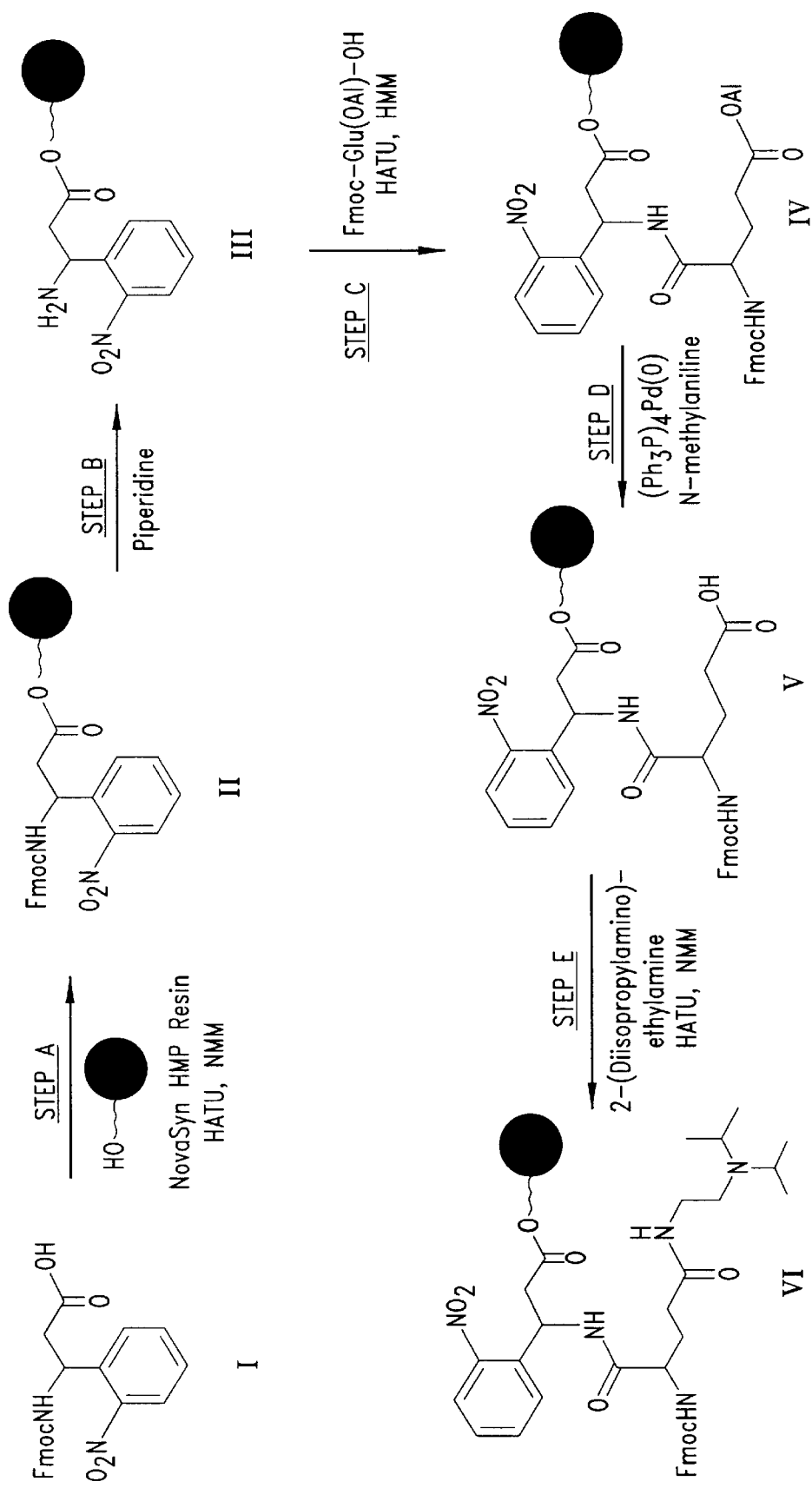
Figure 6B:
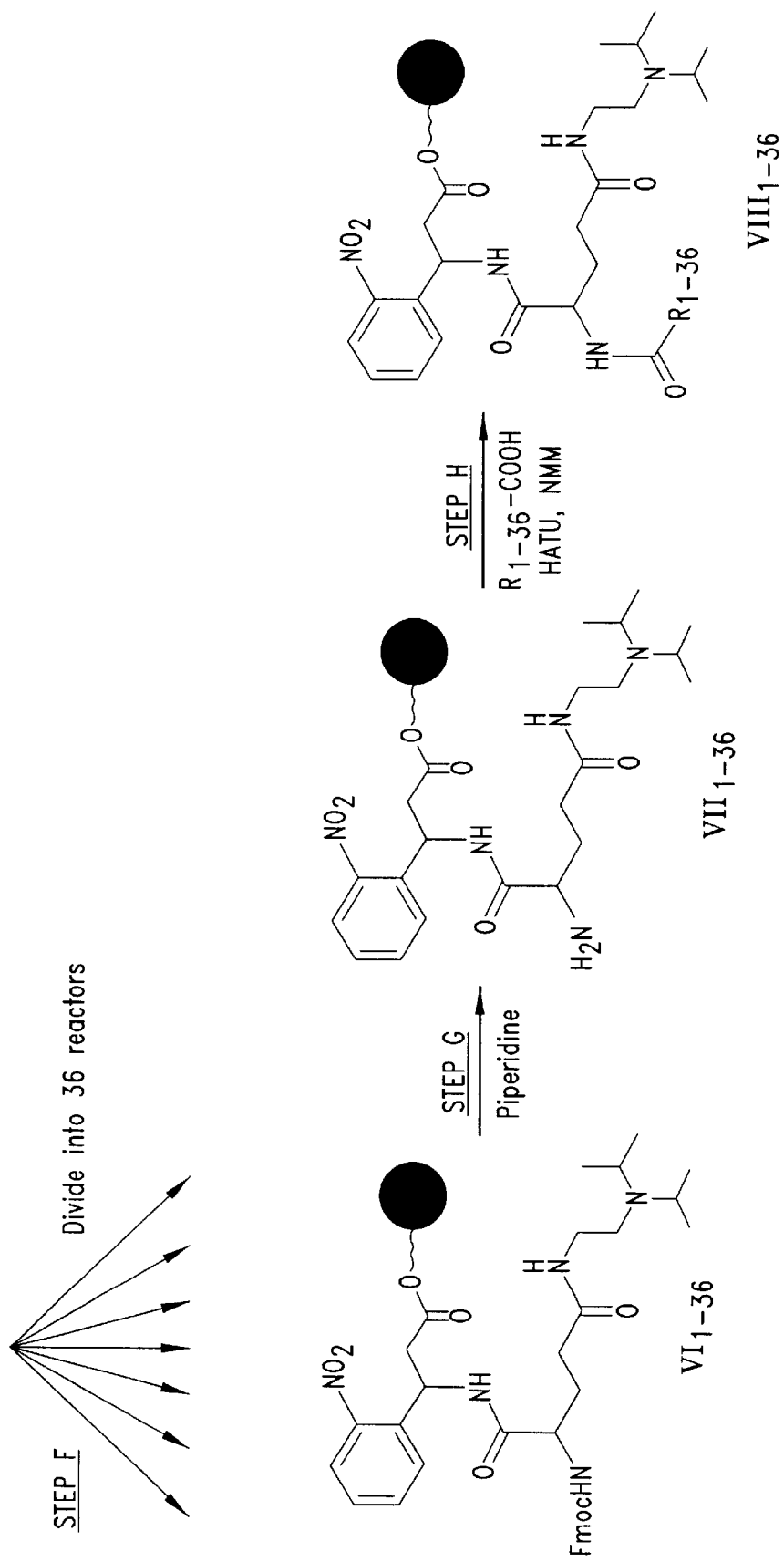
Figure 6C:
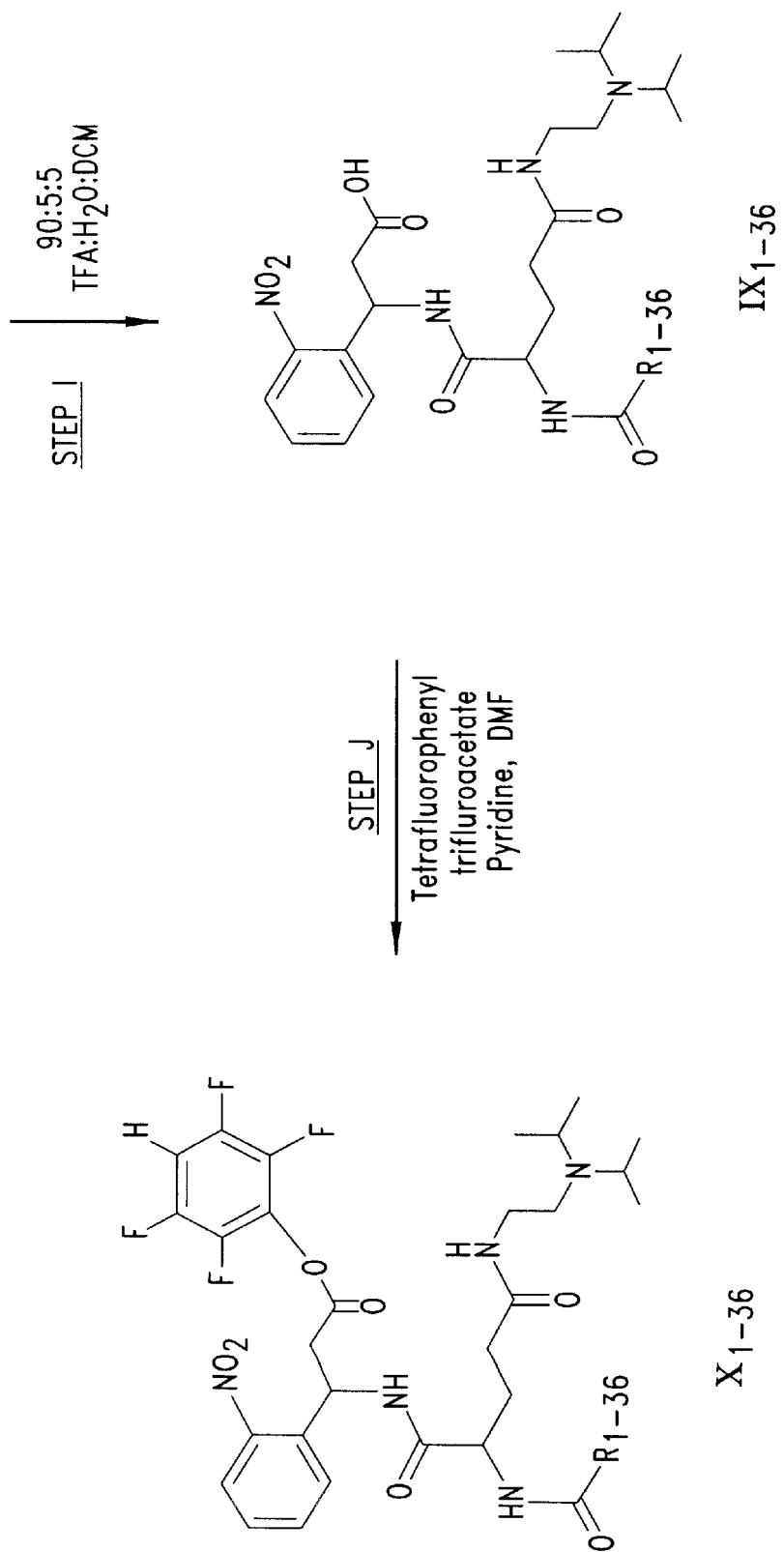

FIG. 6 illustrates the parallel synthesis of a set of 36 T—L—X compounds ($X=L_h$), where $L_h$ is an activated ester (specifically, tetrafluorophenyl ester), L² is an ortho-nitrobenzylamine group with L³ being a methylene group that links $L_h$ and L², T has a modular structure wherein the α-carboxylic acid group of glutamatic acid has been joined to the nitrogen atom of the L² benzylamine group to form an amide bond, and a variable weight component $R_{1-36}$, (where these R groups correspond to T² as defined herein, and may be introduced via any of the specific carboxylic acids listed herein) is bonded through the αα-amino group of the glutamic acid, while a mass spec sensitivity enhancer group (introduced via 2-(diisopropylamino)ethylamine) is bonded through the γ-carboxylic acid of the glutamic acid.

Referring to FIG. 6:

Steps A–B. Same as in Example 7.

Step C. The deprotected resin (compound III) is coupled to Fmoc-Glu-(OAI)-OH using the coupling method described in step C of Example 7 to give compound IV.

Step D. The allyl ester on the resin (compound IV) is washed with $CH_2Cl_2$ (2×) and mixed with a solution of $(PPh_3)_4Pd$ (0) (0.3 eq.) and N-methylaniline (3 eq.) in $CH_2Cl_2$. The mixture is shaken for 1 hr. The solvent is removed and the resin is washed with $CH_2Cl_2$ (2×). The palladium step is repeated. The solvent is removed and the resin is washed with $CH_2Cl_2$ (2×), N,N-diisopropylethylammonium diethyldithiocarbamate in DMF (2×), DMF (2×) to give compound V.

Step E. The deprotected resin from step D is suspended in DMF and activated by mixing HATU (3 eq.), and NMM (7.5 eq.). The vessels are shaken for 15 minutes. The solvent is removed and the resin washed with NMP (1×). The resin is mixed with 2-(diisopropylamino)ethylamine (3 eq.) and NMM (7.5 eq.). The vessels are shaken for 1 hour. The coupling of 2-(diisopropylamino)ethylamine to the resin and the wash steps are repeated, to give compound VI.

Steps F–J. Same as in Example 7.

Example 11

PREPARATION OF A SET OF COMPOUNDS OF THE FORMULA $R_{1-36}$-LYS(ε-IN1P)-ANP-LYS(ε-$NH_2$)—$NH_2$

Figure 7A:
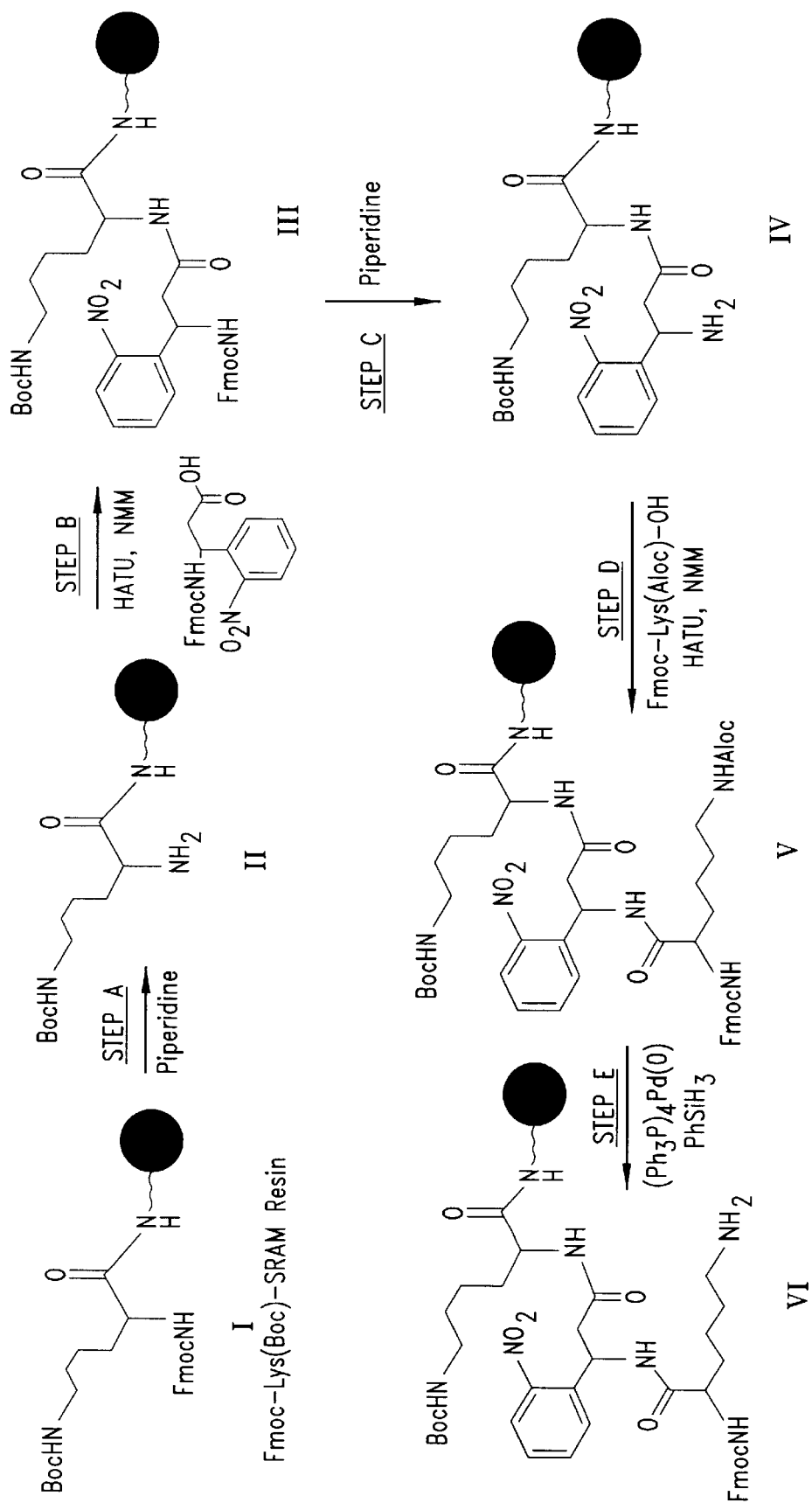
FIG. 7 depicts the flowchart for the synthesis of a set of 36 amine-terminated photochemically cleavable mass spectroscopy tags.
Figure 7B:
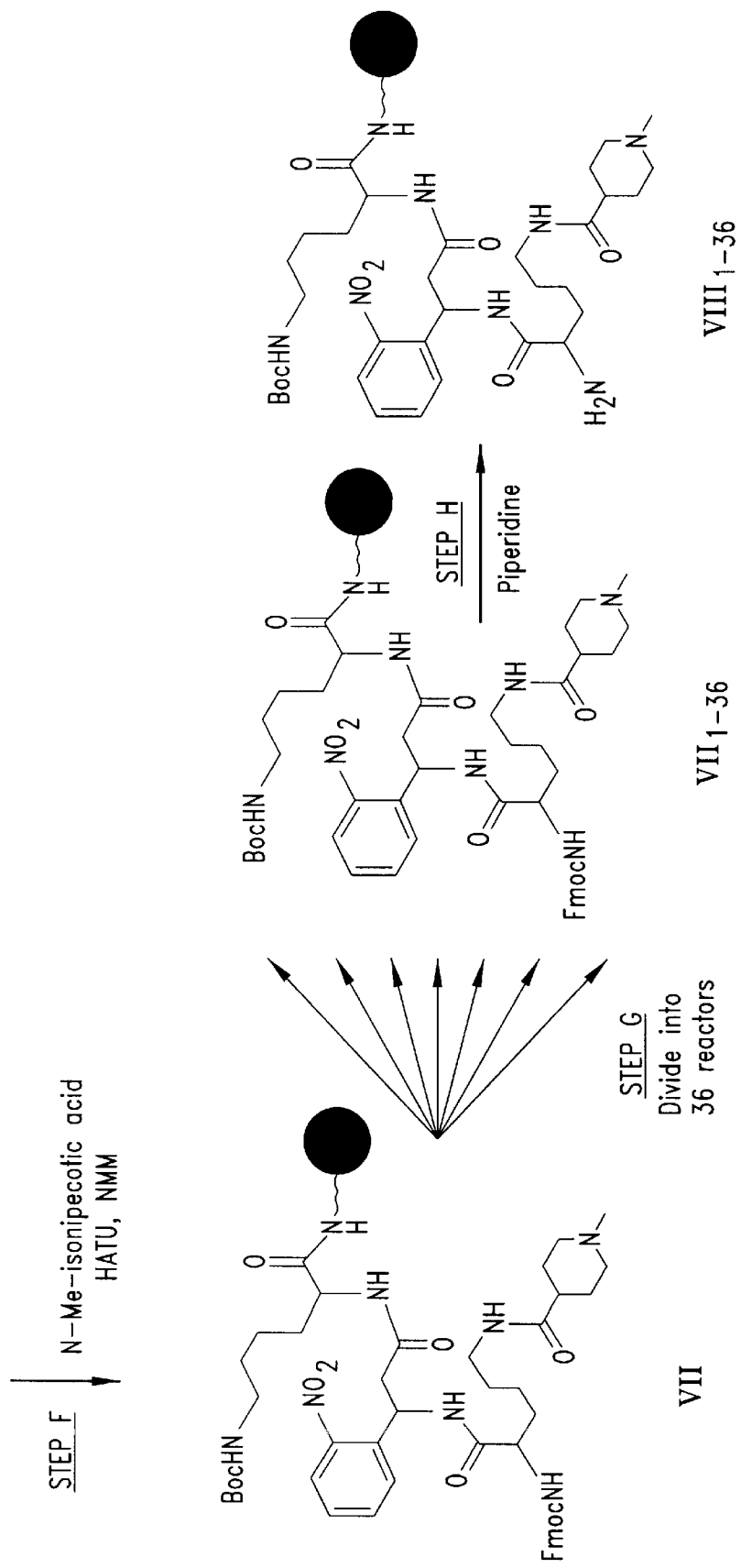
Figure 7C:
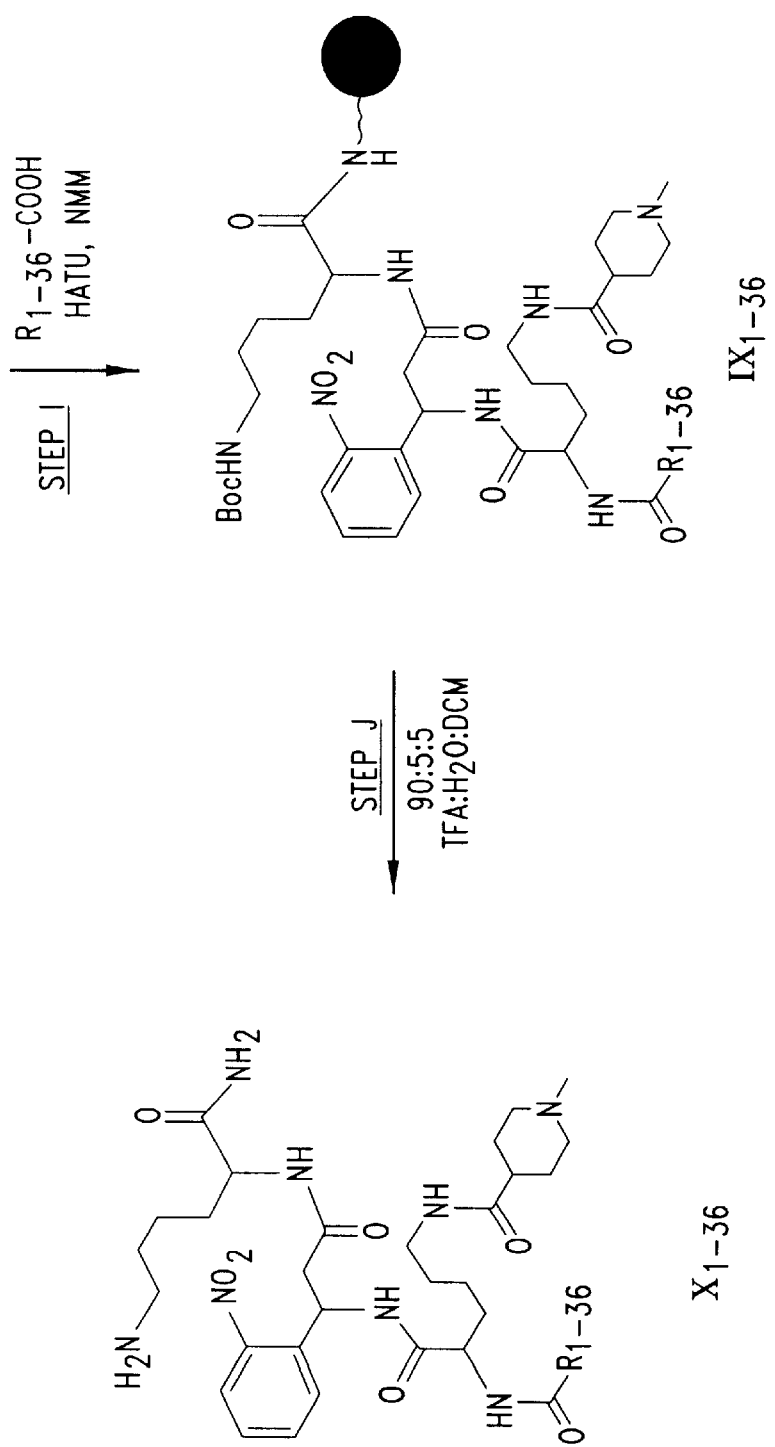

FIG. 7 illustrates the parallel synthesis of a set of 36 T—L—X compounds ($X=L_h$), where $L_h$ is an amine (specifically, the ε-amino group of a lysine-derived moiety), L² is an ortho-nitrobenzylamine group with L³ being a carboxamido-substituted alkyleneaminoacylalkylene group that links $L_h$ and L², T has a modular structure wherein the carboxylic acid group of lysine has been joined to the nitrogen atom of the L² benzylamine group to form an amide bond, and a variable weight component $R_{1-36}$, (where these R groups correspond to T² as defined herein, and may be introduced via any of the specific carboxylic acids listed herein) is bonded through the α-amino group of the lysine, while a mass spec sensitivity enhancer group (introduced via N-methylisonipecotic acid) is bonded through the ε-amino group of the lysine.

Referring to FIG. 7:

Step A. Fmoc-Lys(Boc)-SRAM Resin (available from ACT; compound I) is mixed with 25% piperidine in DMF and shaken for 5 min. The resin is filtered, then mixed with 25% piperidine in DMF and shaken for 10 min. The solvent is removed, the resin washed with NMP (2×), MeOH (2×), and DMF (2×), and used directly in step B.

Step B. The resin (compound II), ANP (available from ACT; 3 eq.), HATU (3 eq.) and NMM (7.5 eq.) in DMF are added and the collection vessel shaken for 1 hr. The solvent is removed and the resin washed with NMP (2×), MeOH (2×), and DMF (2×). The coupling of I to the resin and the wash steps are repeated, to give compound III.

Steps C–J. The resin (compound III) is treated as in steps B–I in Example 7 to give compounds $X_{1-36}$.

Example 12

PREPARATION OF A SET OF COMPOUNDS OF THE FORMULA $R_{1-36}$-LYS(ε-TFA)-LYS(ε-IN1P)-ANP-TFP

Figure 8A:
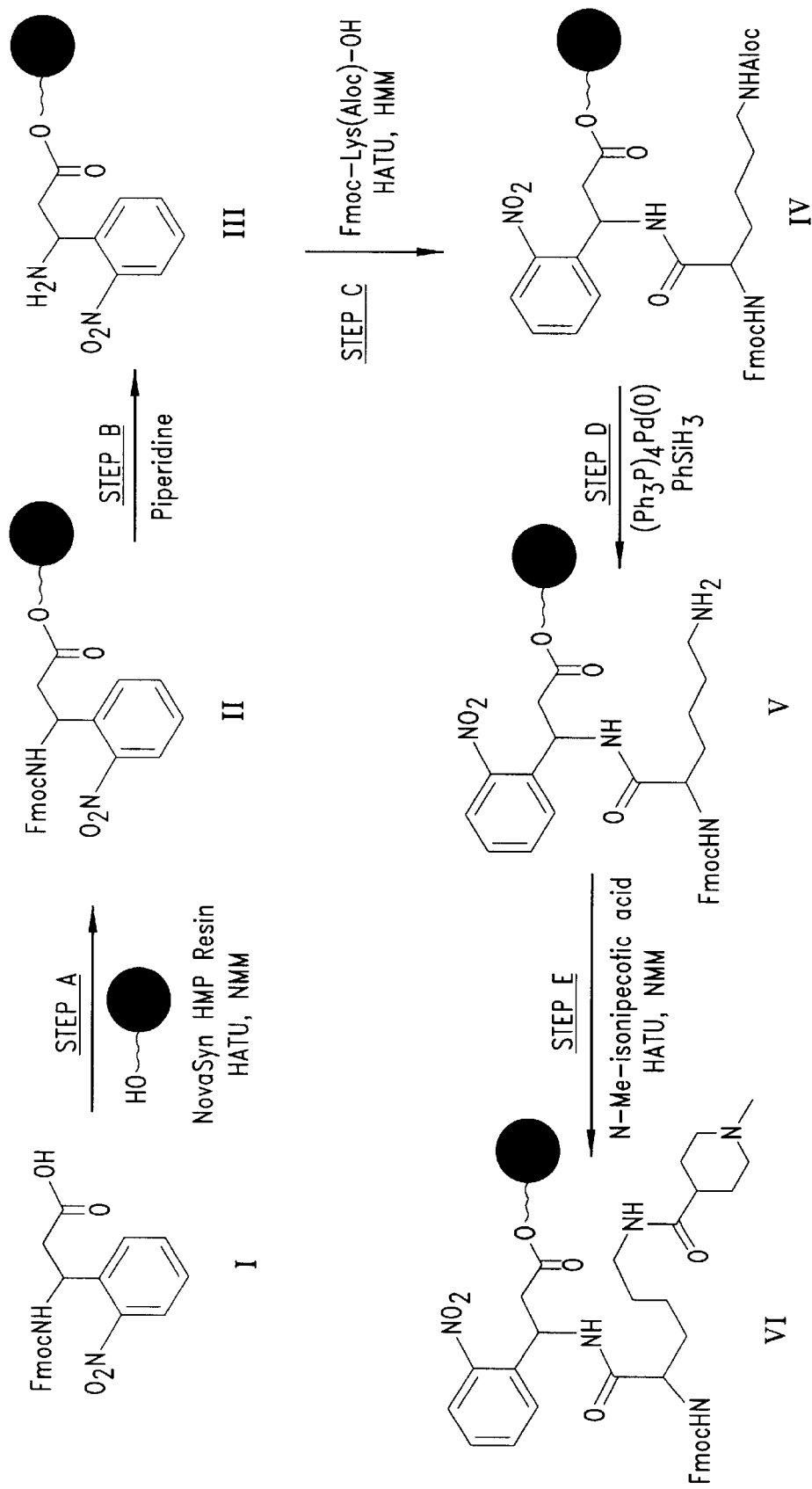
Figure 8B:
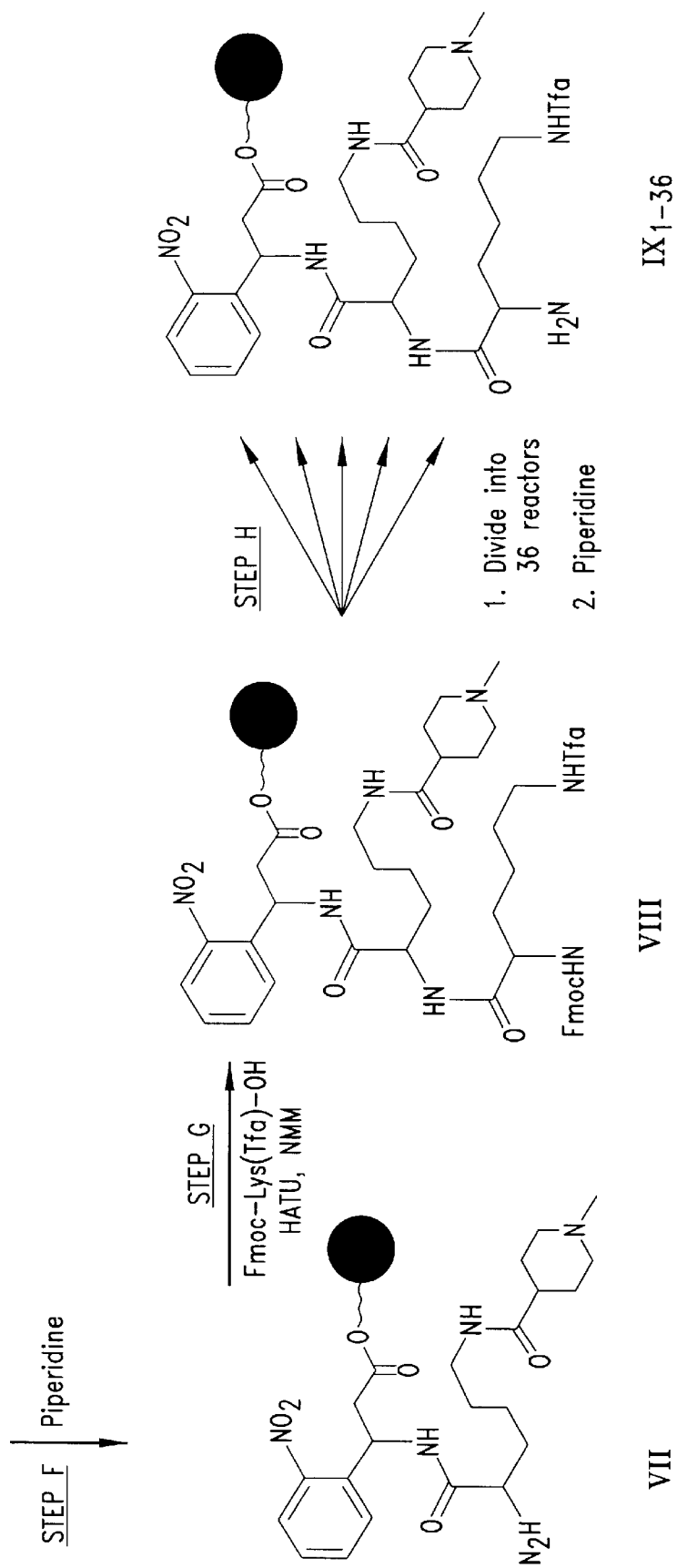
Figure 8C:
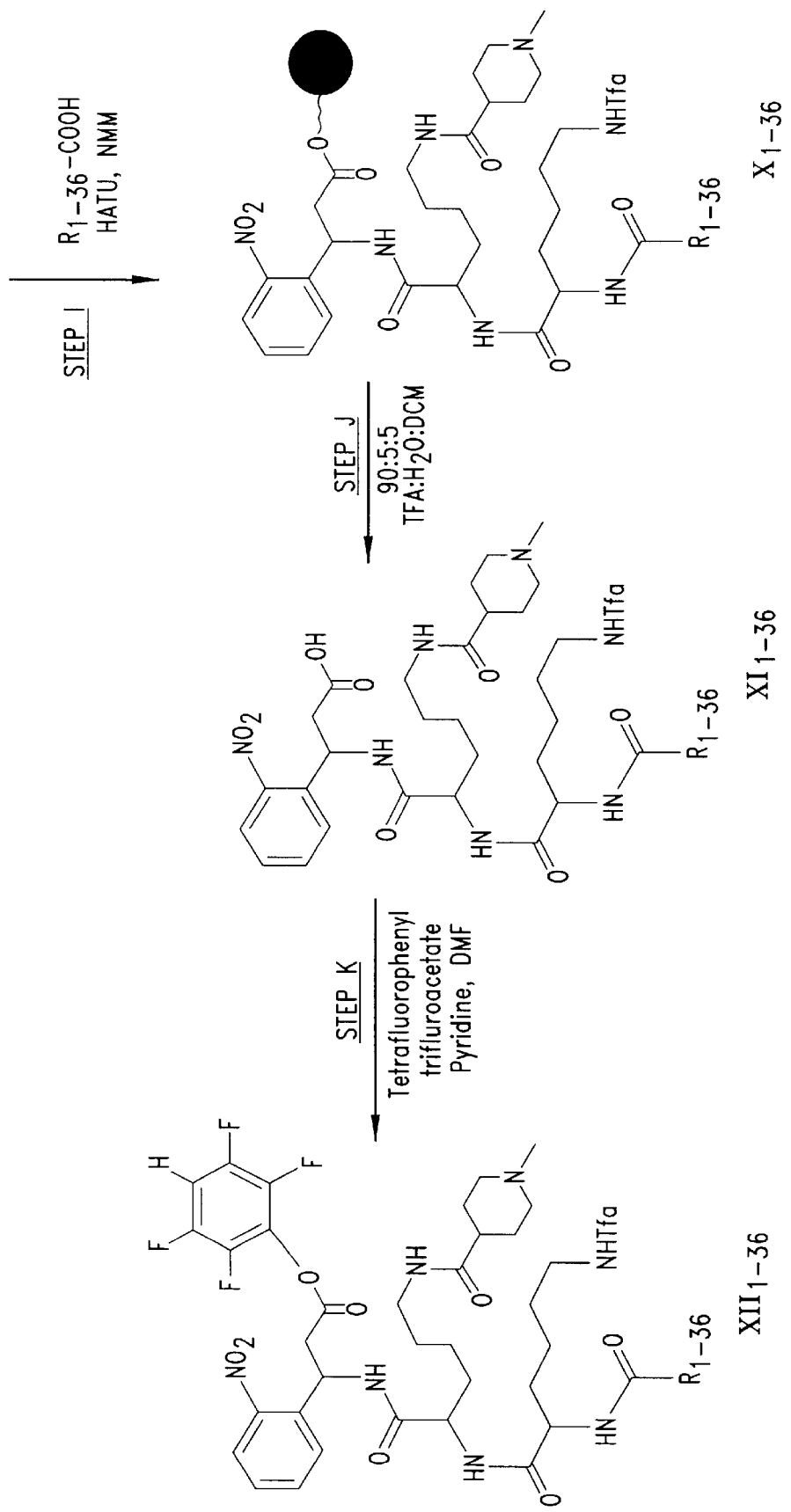

FIG. 8 illustrates the parallel synthesis of a set of 36 T—L—X compounds ($X=L_h$), where $L_h$ is an activated ester (specifically, tetrafluorophenyl ester), $L^2$ is an ortho-nitrobenzylamine group with $L^3$ being a methylene group that links $L_h$ and $L^2$, T has a modular structure wherein the carboxylic acid group of a first lysine has been joined to the nitrogen atom of the $L^2$ benzylamine group to form an amide bond, a mass spec sensitivity enhancer group (introduced via N-methylisonipecotic acid) is bonded through the ε-amino group of the first lysine, a second lysine molecule has been joined to the first lysine through the α-amino group of the first lysine, a molecular weight adjuster group (having a trifluoroacetyl structure) is bonded through the ε-amino group of the second lysine, and a variable weight component $R_{1-36}$, (where these R groups correspond to $T^2$ as defined herein, and may be introduced via any of the specific carboxylic acids listed herein) is bonded through the α-amino group of the second lysine.

Referring to FIG. 8:

Steps A–E. These steps are identical to steps A–E in Example 7.

Step F. The resin (compound VI) is treated with piperidine as described in step B in Example 7 to remove the FMOC group.

Step G. The deprotected resin (compound VII) is coupled to Fmoc-Lys(Tfa)—OH using the coupling method described in step C of Example 7 to give compound VIII.

Steps H–K. The resin (compound VIII) is treated as in steps F–J in Example 7 to give compounds $XI_{1-36}$.

Example 13

PREPARATION OF A SET OF COMPOUNDS OF THE FORMULA $R_{1-36}$-LYS(ε-iNIP)-ANP-5'-AH-ODN

Figure 9:
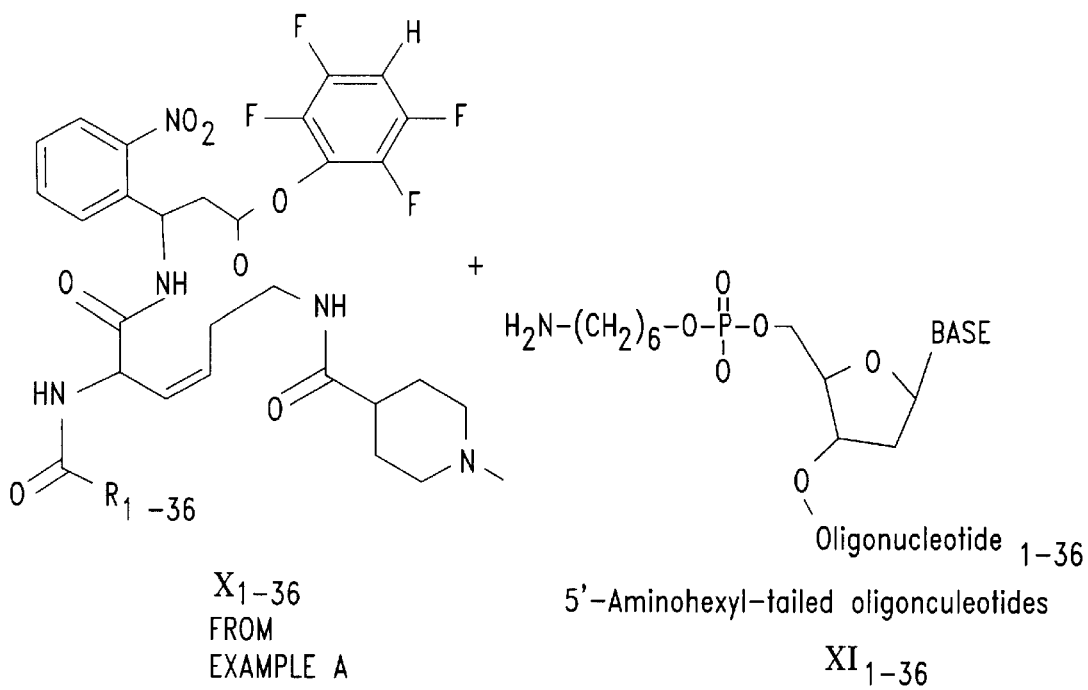
FIG. 9 depicts the synthesis of 36 photochemically cleavable mass spectroscopy tagged oligonucleotides made from the corresponding set of 36 tetrafluorophenyl esters of photochemically cleavable mass spectroscopy tag acids.
Figure 9:
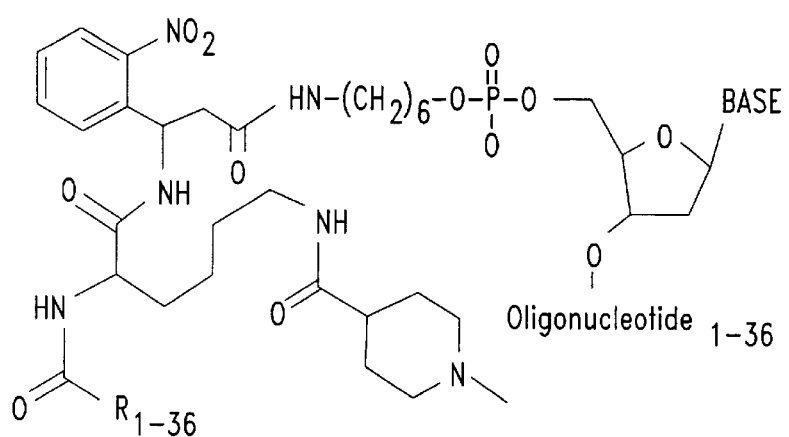

FIG. 9 illustrates the parallel synthesis of a set of 36 T—L—X compounds (X=MOI, where MOI is a nucleic acid fragment, ODN) derived from the esters of Example 7 (the same procedure could be used with other T—L—X compounds wherein X is an activated ester). The MOI is conjugated to T—L through the 5' end of the MOI, via a phosphodiester—alkyleneamine group.

Referring to FIG. 9:

Step A. Compounds $XII_{1-36}$ are prepared according to a modified biotinylation procedure in Van Ness et al., Nucleic Acids Res., 19, 3345 (1991). To a solution of one of the 5'-aminohexyl oligonucleotides (compounds $XI_{1-36}$, 1 mg) in 200 mM sodium borate (pH 8.3, 250 mL) is added one of the Tetrafluorophenyl esters (compounds $X_{1-36}$ from Example A, 100-fold molar excess in 250 mL of NMP). The reaction is incubated overnight at ambient temperature. The unreacted and hydrolyzed tetrafluorophenyl esters are removed from the compounds $XII_{1-36}$ by Sephadex G-50 chromatography.

Example 14

PREPARATION OF A SET OF COMPOUNDS OF THE FORMULA $R_{1-36}$-LYS(ε-iNIP)-ANP-LYS(ε-(MCT-5'-AH-ODN))—$NH_2$

Figure 10A:
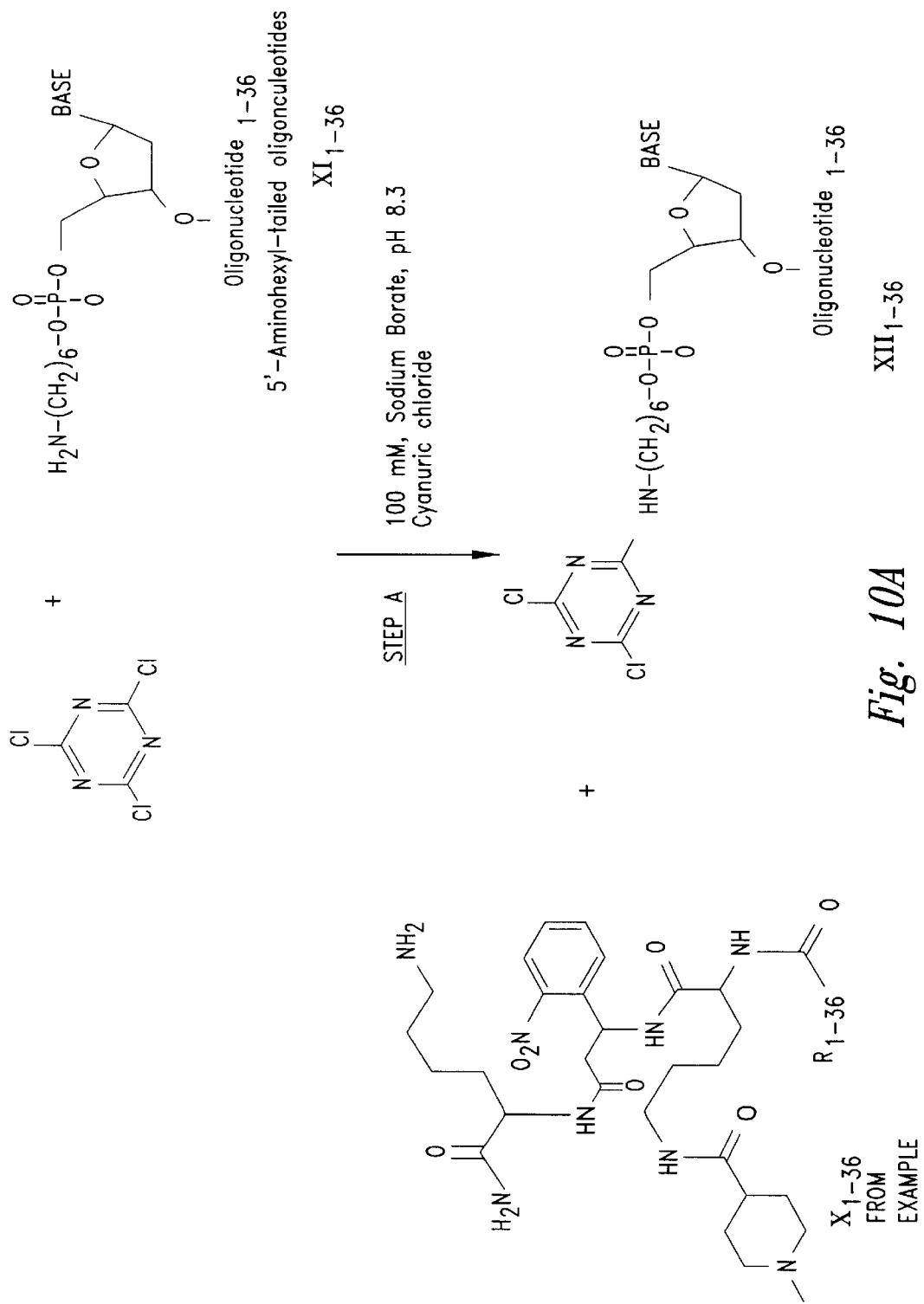
FIG. 10 depicts the synthesis of 36 photochemically cleavable mass spectroscopy tagged oligonucleotides made from the corresponding set of 36 amine-terminated photochemically cleavable mass spectroscopy tags.
Figure 10B:
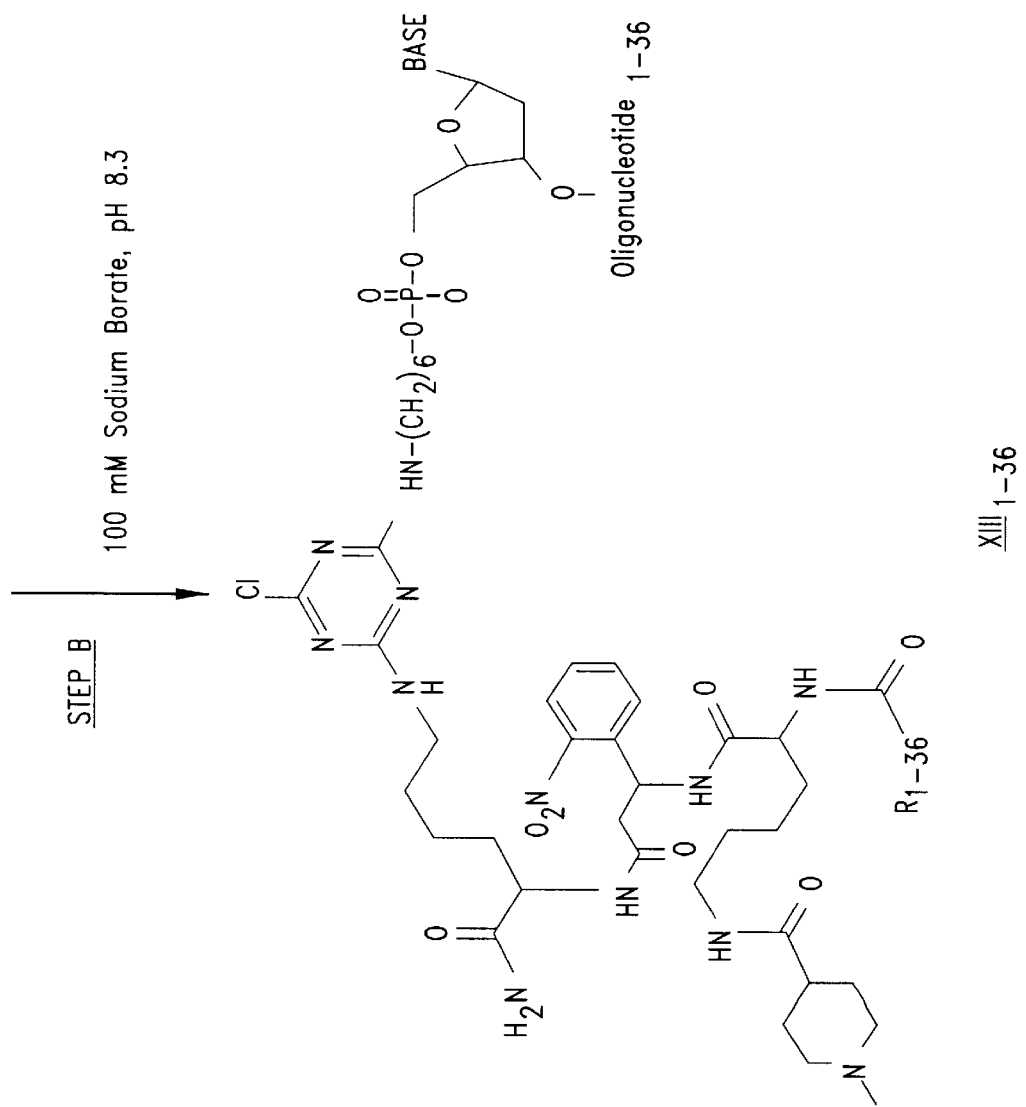

FIG. 10 illustrates the parallel synthesis of a set of 36 T—L—X compounds (X=MOI, where MOI is a nucleic acid fragment, ODN) derived from the amines of Example 11 (the same procedure could be used with other T—L—X compounds wherein X is an amine). The MOI is conjugated to T—L through the 5' end of the MOI, via a phosphodiester—alkyleneamine group.

Referring to FIG. 10:

Step A. The 5'-[6-(4,6-dichloro-1,3,5-triazin-2-ylamino) hexyl]oligonucleotides $XII_{1-36}$ are prepared as described in Van Ness et al., Nucleic Acids Res., 19, 3345 (1991).

Step B. To a solution of one of the 5'-[6-(4,6-dichloro-1, 3,5-triazin-2-ylamino)hexyl]oligonucleotides (compounds $XII_{1-36}$) at a concentration of 1 mg/ml in 100 mM sodium borate (pH 8.3) was added a 100-fold molar excess of a primary amine selected from $R_{1-36}$-Lys(ε-iNIP)-ANP-Lys(ε-$NH_2$)—$NH_2$ (compounds $X_{1-36}$ from Example 11). The solution is mixed overnight at ambient temperature. The unreacted amine is removed by ultrafiltration through a 3000 MW cutoff membrane (Amicon, Beverly, Mass.) using $H_2O$ as the wash solution (3×). The compounds $XIII_{1-36}$ are isolated by reduction of the volume to 100 mL.

Example 15

DEMONSTRATION OF SEQUENCING USING A CE SEPARATION METHOD, COLLECTING FRACTIONS, CLEAVING THE TAG, DETERMINING THE MASS (AND THUS THE IDENTITY) OF THE TAG AND THEN DEDUCING THE SEQUENCE

In this example, two DNA samples are sequenced in a single separation method.

CE Instrumentation

The CE instrument is a breadboard version of the instrument available commercially from Applied Biosystems, Inc. (Foster City, Calif.). It consists of Plexiglas boxes enclosing two buffer chambers, which can be maintained at constant temperature with a heat control unit. The voltage necessary for electrophoresis is provided by a high-voltage power supply (Gamma High Voltage Research, Ormond Beach, Fla.) with a magnetic safety interlock, and a control unit to vary the applied potential. Sample injections for open tube capillaries are performed by use of a hand vacuum pump to generate a pressure differential across the capillary (vacuum injection). For gel-filled capillaries, samples are electrophoresed into the tube by application of an electric field (electrokinetic injection).

Preparation of Gel-Filled Capillaries

Fifty-centimeter fused silica capillaries (375 mm o.d., 50 mm i.d., Polymicro Technologies, Phoenix, Ariz.) with detector windows (where the polyimide coating has been removed from the capillary) at 25 cm are used in the separations. The inner surface of the capillaries are derivatized with (methyacryloxypropyl)trimethoxysilane (MAPS) (Sigma, St. Louis, Mo.) to permit covalent attachment of the gel to the capillary wall (Nashabeh et al., *Anal Chem* 63:2148, 1994). Briefly, the capillaries are cleaned by successively flowing trifluoracetic acid, deionized water, and acetone through the column. After the acetone wash, 0.2% solution of MAPS in 50/50 water/ethanol solution is passed through the capillary and left at room temperature for 30 min. The solution is removed by aspiration and the tubes are dried for 30 min under an infrared heat lamp.

Gel-filled capillaries are prepared under high pressure by a modification of the procedure described by Huang et al. (*J. Chromatography* 600:289, 1992). Four percent poly (acrylamide) gels with 5% cross linker and 8.3 urea are used for all the studies reported here. A stock solution is made by dissolving 3.8 g of acrylamide, 0.20 g of N,N'-methylenebis (acrylamide), and 50 g of urea into 100 mL of TBE buffer (90 mM Tris borate, pH 8.3, 0.2 mM EDTA). Cross linking is initiated with 10 mL of N,N,N',N'-tetramethylethylenediamine (TEMED) and 250 mL of 10% ammonium persulfate solution. The polymerizing solution is quickly passed into the derivatized column. Filled capillaries are then placed in a steel tube 1×m×⅛ in. i.d.×¼ in. o.d. filled with water, and the pressure is raised to 400 bar by using a HPLC pump and maintained at that pressure overnight. The pressure is gradually released and the capillaries are removed. A short section of capillary from each end of the column is removed before use.

Separation and Detection of DNA Fragments

Analysis of DNA sequencing reactions separated by conventional electrophoresis is performed on an ABI 370A DNA sequencer. This instrument uses a slab denaturing urea poly(acrylamide) gel 0.4 mm thick with a distance of 26 cm from the sample well to the detection region, prepared according to the manufacturers instructions. DNA sequencing reactions are prepared as described by the manufacturer utilizing Taq polymerase (Promega Corp., Madison, Wis.) and are performed on M13mp19 single-stranded DNA template prepared by standard procedures. Sequencing reactions are stored at −20° C. in the dark and heated at 90° C. for 3 min in formamide just prior to sample loading. They are loaded on the 370A with a pipetman according to the manufacturers instructions and on the CE by electrokinetic injection at 10,000 V for 10 seconds. Ten µl fractions are collected during the run by removing the all the liquid at the bottom electrode and replacing it with new electolyte.

To cleave the tag from the oligonucleotide, 100 µl of 0.05 M dithiothreitol (DTT) is added to each fraction. Incubation is for 30 minutes at room temperature. NaCl is then added to 0.1 M and 2 volumes of EtOH is added to precipitate the ODNs. The ODNs are removed from solution by centrifugation at 14,000×G at 4° C. for 15 minutes. The supernatents are reserved, dried to completeness under a vacuum with centrifugation. The pellets are then dissolved in 25 µl MeOH. The pellet is then tested by mass spectrometry for the presence of tags. The same MALDI technique is employed as described in Example 4. The following MWs (tags) are observed in the mass spectra as a function of time:

| Fraction # | Time | MWs | Fraction # | Time | MWs |
|---|---|---|---|---|---|
| 1 | 1 | none | 31 | 31 | 212.1, |
| 2 | 2 | none | 32 | 32 | 212.1, 199.1 |
| 3 | 3 | none | 33 | 33 | 212.1, 199.1 |
| 4 | 4 | none | 34 | 34 | 212.1; 200.1, 199.1, 227.1 |
| 5 | 5 | none | 35 | 35 | 200.1, 199.1, 227.1 |
| 6 | 6 | none | 36 | 36 | 200.1, 227.1 |
| 7 | 7 | none | 37 | 37 | 200.1, 227.1, 179.18 |
| 8 | 8 | none | 38 | 38 | 200.1; 196.1, 179.18 |
| 9 | 9 | none | 39 | 39 | 200.1; 196.1, 179.18 |
| 10 | 10 | none | 40 | 40 | 196.1, 179.18, 226.1 |
| 11 | 11 | none | 41 | 41 | 196.1, 226.1 |
| 12 | 12 | none | 42 | 42 | 196.1; 182.1, 226.1 |
| 13 | 13 | none | 43 | 43 | 182.1, 226.1, 209.1 |
| 14 | 14 | none | 44 | 44 | 182.1, 209.1 |
| 15 | 15 | none | 45 | 45 | 182.1; 235.2, 209.1, 198.1 |
| 16 | 16 | none | 46 | 46 | 235.2, 198.1 |
| 17 | 17 | none | 47 | 47 | 235.2, 198.1 |
| 18 | 18 | none | 48 | 48 | 235.2;, 198.1, 218.1 |
| 19 | 19 | none | 49 | 49 | 218.1 |
| 20 | 20 | none | 50 | 50 | 218.1 |
| 21 | 21 | none | 51 | 51 | none |
| 22 | 22 | none | 52 | 52 | none |
| 23 | 23 | none | 53 | 53 | none |
| 24 | 24 | none | 54 | 54 | none |
| 25 | 25 | none | 55 | 55 | none |
| 26 | 26 | none | 56 | 56 | none |
| 27 | 27 | none | 57 | 57 | none |
| 28 | 28 | none | 58 | 58 | none |
| 29 | 29 | 212.1 | 59 | 59 | none |
| 30 | 30 | 212.1 | 60 | 60 | none |

The temporal appearance of the tags for set #1 is 212.1, 200.1, 196.1, 182.1, 235.2, 218.1, 199.1, 227.1, and the temporal appearance of tags for set #2 is 199.1, 227.1, 179.1, 226.1, 209.1, 198.1. Since 212.1 amu indicates the 4-methoxybenzoic acid derivative, 200.1 indicates the 4-fluorobenzoic acid derivative, 196.1 amu indicates the toluic acid derivative, 182.1 amu indicates the benzoic acid derivative, 235.2 amu indicates the indole-3-acetic acid derivative, 218.1 amu indicates the 2,6-difluorobenzoic derivative, 199.1 amu indicates the nicotinic acid N-oxide derivative, 227.1 arnu indicates the 2-nitrobenzamide, 179.18 amu indicates the 5-acetylsalicylic acid derivative, 226.1 amu indicates the 4-ethoxybenzoic acid derivative, 209.1 amu indicates the cinnamic acid derivative, and 198.1 amu indicates the 3-aminonicotinic acid, the first sequence can be deduced as -5'-TATGCA-3'- and the second sequence can be deduced as -5'-CGTACC-3'-. Thus, it is possible to sequence more than one DNA sample per separation step.

Example 16

DEMONSTRATION OF THE SIMULTANEOUS DETECTION OF MULTIPLE TAGS BY MASS SPECTROMETRY

This example provides a description of the ability to simultaneously detect multiple compounds (tags) by mass spectrometry. In this particular example, 31 compounds are mixed with a matrix, deposited and dried on to a solid support and then desorbed with a laser. The resultant ions are then introduced in a mass spectrometer.

The following compounds (purchased from Aldrich, Milwaukee, Wis.) are mixed together on an equal molar basis to a final concentration of 0.002 M (on a per compound) basis: benzamide (121.14), nicotinamide (122.13), pyrazinamide (123.12), 3-amino-4-pyrazolecarboxylic acid (127.10), 2-thiophenecarboxamide (127.17), 4-aminobenzamide (135.15), tolumide (135.17), 6-methylnicotinamide (136.15), 3-aminonicotinamide (137.14), nicotinamide N-oxide (138.12), 3-hydropicolinamide (138.13), 4-fluorobenzamide (139.13), cinnamamide (147.18), 4-methoxybenzamide (151.17), 2,6-difluorbenzamide (157.12), 4-amino-5-imidazole-carboxyamide (162.58), 3,4-pyridine-dicarboxyamide (165.16), 4-ethoxybenzamide (165.19), 2,3-pyrazinedicarboxamide (166.14), 2-nitrobenzamide (166.14), 3-fluoro-4-methoxybenzoic acid (170.4), indole-3-acetamide (174.2), 5-acetylsalicylamide (179.18), 3,5-dimethoxybenzamide (181.19), 1-naphthaleneacetamide (185.23), 8-chloro-3,5-diamino-2-pyrazinecarboxyamide (187.59), 4-trifluoromethyl-benzamide (189.00), 5-amino-5-phenyl-4-pyrazole-carboxamide (202.22), 1-methyl-2-benzyl-malonamate (207.33), 4-amino-2,3,5,6-tetrafluorobenzamide (208.11), 2,3-napthlenedicarboxylic acid (212.22). The compounds are placed in DMSO at the concentration described above. One µl of the material is then mixed with alpha-cyano-4-hydroxy cinnamic acid matrix (after a 1:10,000 dilution) and deposited on to a solid stainless steel support.

Figure 11:
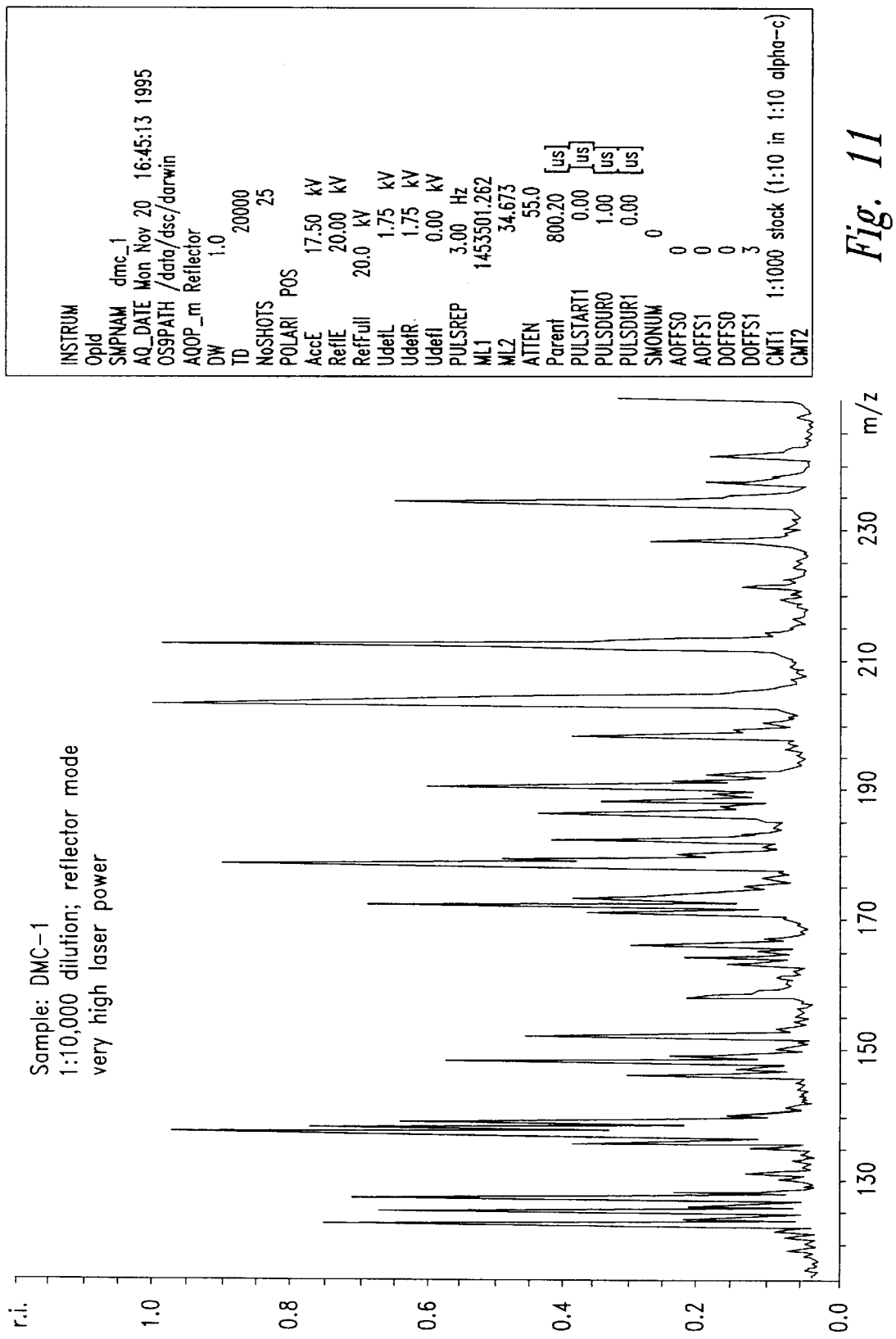
FIG. 11 illustrates the simultaneous detection of multiple tags by mass spectrometry.

The material is then desorbed by a laser using the Protein TOF Mass Spectrometer (Bruker, Manning Park, Mass.) and the resulting ions are measured in both the linear and reflectron modes of operation. The following m/z values are observed (FIG. 11):
121.1→benzamide (121.14)
122.1→nicotinamide (122.13)
123.1→pyrazinamide (123.12)
124.1
125.2
127.3→3-amino-4-pyrazolecarboxylic acid (127.10)
127.2→2-thiophenecarboxamide (127.17)
135.1→4-aminobenzamide (135.15)
135.1→tolumide (135.17)
136.2→6-methylnicotinamide (136.15)
137.1→3-aminonicotinamide (137.14)
138,2→nicotinamide N-oxide (138.12)
138.2→3-hydropicolinamide (138.13)
139.2→4-fluorobenzamide (139.13)
140.2
147.3→cinnamamide (147.18)
148.2
149.2 4-methoxybenzamide (151.17)
152.2 2,6-difluorbenzamide (157.12)
158.3 4-amino-5-imidazole-carboxyamide (162.58)
163.3
165.2→3,4-pyridine-dicarboxyamide (165.16)
165.2→4-ethoxybenzamide (165.19)
166.2→2,3-pyrazinedicarboxamide (166.14)
166.2→2-nitrobenzamide (166.14) 3-fluoro-4-methoxybenzoic acid (170.4)
171.1
172.2
173.4 indole-3-acetamide (174.2)
178.3
179.3→5-acetylsalicylamide (179.18)
181.2→3,5-dimethoxybenzamide (181.19)
182.2→1-naphthaleneacetamide (185.23)
186.2 8-chloro-3,5-diamino-2-pyrazinecarboxyamide (187.59)
188.2
189.2 →4-trifluoromethyl-benzamide (189.00)
190.2
191.2
192.3 5-amino-5-phenyl-4-pyrazole-carboxamide (202.22)
203.2
203.4 1-methyl-2-benzyl-malonamate (207.33) 4-amino-2,3,5,6-tetrafluorobenzamide (208.11)
212.2→2,3-napthlenedicarboxylic acid (212.22).
219.3
221.2
228.2
234.2
237.4
241.4

The data indicate that 22 of 31 compounds appeared in the spectrum with the anticipated mass, 9 of 31 compounds appeared in the spectrum with a n+H mass (1 atomic mass unit, amu) over the anticipated mass. The latter phenomenon is probably due to the protonation of an amine within the compounds. Therefore 31 of 31 compounds are detected by MALDI Mass Spectroscopy. More importantly, the example demonstrates that multiple tags can be detected simultaneously by a spectroscopic method.

Figure 12:
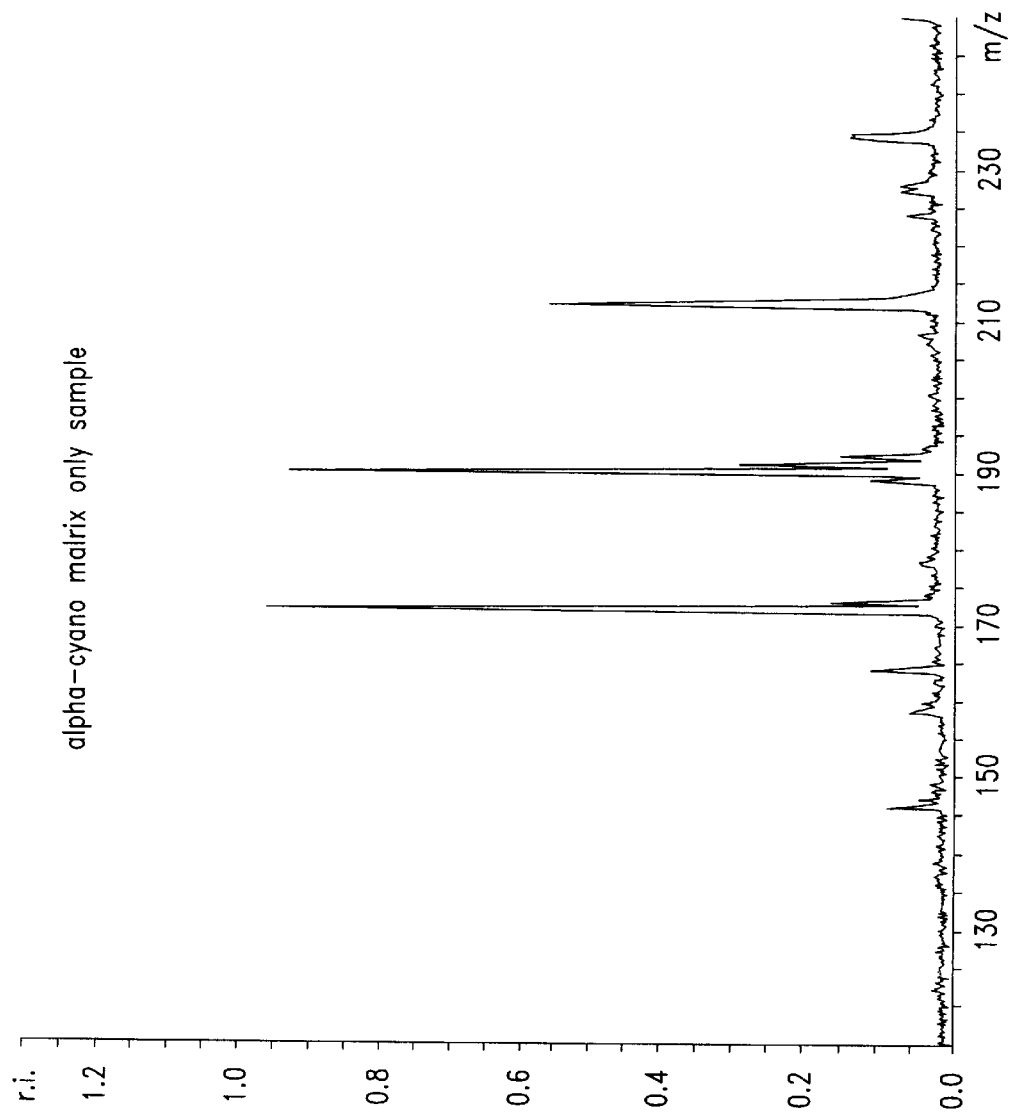
FIG. 12 shows the mass spectrogram of the alpha-cyano matrix alone.

The alpha-cyano matrix alone (FIG. 12) gave peaks at 146.2, 164.1, 172.1, 173.1, 189.1, 190.1, 191.1, 192.1, 212.1, 224.1, 228.0, 234.3. Other identified masses in the spectrum are due to contaminants in the purchased compounds as no effort was made to further purify the compounds.

Example 17

A PROCEDURE FOR SEQUENCING WITH MW-IDENTIFIER-LABELED PRIMERS, RADIOLABELED PRIMERS, MW-IDENTIFIER-LABELED-DIDEOXY-TERMINATORS, FLUORESCENT-PRIMERS AND FLUORESCENT-DIDEOXY-TERMINATORS

A. Preparation Sequencing Gels and Electrophoresis

The protocol is as follows. Prepare 8 M urea, polyacrylamide gels according to the following recipes (100 ml) for 4%, 6%, or 8% polyacrylamide.

|  | 4% | 5% | 6% |
|---|---|---|---|
| urea | 48 g | 48 | 48 g |
| 40% acrylamide/bisacrylamide | 10 ml | 12.5 ml | 15 ml |
| 10X MTBE | 10 ml | 10 ml | 10 ml |
| ddH$_2$O | 42 ml | 39.5 ml | 37 ml |
| 15% APS | 500 µl | 500 µl | 500 µl |
| TEMED | 50 µl | 50 µl | 50 µl |

Urea (5505UA) is obtained from Gibco/BRL (Gaithersburg, Md.). All other materials are obtained from Fisher (Fair Lawn, N.J.). Briefly, urea, MTBE buffer and water are combined, incubated for 5 minutes at 55° C., and stirred to dissolve the urea. The mixture is cooled briefly, acrylamide/bis-acrylamide solution is added and mixed, and the entire mixture is degassed under vacuum for 5 minutes. APS and TEMED polymerization agents are added with stirring. The complete gel mix is immediately poured in between the taped glass plates with 0.15 mm spacers. Plates are prepared by first cleaning with ALCONOX™ (New York, N.Y. detergent and hot water, are rinsed with double distilled water, and dried. Typically, the notched glass plate is treated with a silanizing reagent and then rinsed with double distilled water. After pouring, the gel is immediately laid horizontally, the well forming comb is inserted, clamped into place, and the gel allowed to polymerize for at least 30 minutes. Prior to loading, the tape around the bottom of the gel and the well-forming comb is removed. A vertical electrophoresis apparatus is then assembled by clamping the upper and lower buffer chambers to the gel plates, and adding 1× MTBE electrophoresis buffer to the chambers. Sample wells are flushed with a syringe containing running buffer, and immediately prior to loading each sample, the well is flushed with running buffer using gel loading tips to remove urea. One to two microliters of sample is loaded into each well using a Pipetteman (Rainin, Emeryville, Calif.) with gel-loading tips, and then electrophoresed according the following guidelines (during electrophoresis, the gel is cooled with a fan):

|  | termination reaction polyacrylamide gel | electrophoresis conditions |
|---|---|---|
| short | 5%, 0.15 mm × 50 cm × 20 cm | 2.25 hours at 22 mA |
| long | 4%, 0.15 mm × 70 cm × 20 cm | 8–9 hours at 15 mA |
| long | 4%, 0.15 mm × 70 cm × 20 cm | 20–24 hours at 15 mA |

Each base-specific sequencing reaction terminated (with the short termination) mix is loaded onto a 0.15 mm×50 cm×20 cm denaturing 5% polyacrylamide gel; reactions terminated with the long termination mix typically are divided in half and loaded onto two 0.15 mm×70 cm×20 cm denaturing 4% polyacrylamide gels.

After electrophoresis, buffer is removed from the wells, the tape is removed, and the gel plates separated. The gel is transferred to a 40 cm×20 cm sheet of 3MM Whatman paper, covered with plastic wrap, and dried on a Hoefer (San Francisco, Calif.) gel dryer for 25 minutes at 80° C. The dried gel is exposed to Kodak (New Haven, Conn.) XRP-1 film. Depending on the intensity of the signal and whether the radiolabel is $^{32}$P or $^{35}$S, exposure times vary from 4 hours to several days. After exposure, films are developed by processing in developer and fixer solutions, rinsed with water, and air dried. The autoradiogram is then placed on a light-box, the sequence is manually read, and the data typed into a computer.

Taq-polymerase catalyzed cycle sequencing using labeled primers. Each base-specific cycle sequencing reaction routinely included approximately 100 or 200 ng isolated single-stranded DNA for A and C or G and T reactions, respectively. Double-stranded cycle sequencing reactions similarly contained approximately 200 or 400 ng of plasmid DNA isolated using either the standard alkaline lysis or the diatomaceous earth-modified alkaline lysis procedures. All reagents except template DNA are added in one pipetting step from a premix of previously aliquoted stock solutions stored at −20° C. Reaction premixes are prepared by combining reaction buffer with the base-specific nucleotide mixes. Prior to use, the base-specific reaction premixes are thawed and combined with diluted Taq DNA polymerase and the individual end-labeled universal primers to yield the final reaction mixes. Once the above mixes are prepared, four aliquots of single or double-stranded DNA are pipetted into the bottom of each 0.2 ml thin-walled reaction tube, corresponding to the A, C, G, and T reactions, and then an aliquot of the respective reaction mixes is added to the side of each tube. These tubes are part of a 96-tube/retainer set tray in a microtiter plate format, which fits into a Perkin Elmer Cetus Cycler 9600 (Foster City, Calif.). Strip caps are sealed onto the tube/retainer set and the plate is centrifuged briefly. The plate then is placed in the cycler whose heat block had been preheated to 95° C., and the cycling program immediately started. The cycling protocol consists of 15–30 cycles of: 95° C. denaturation; 55° C. annealing; 72° C. extension; 95° C. denaturation; 72° C. extension; 95° C. denaturation, and 72° C. extension, linked to a 4° C. final soak file.

At this stage, the reactions may be frozen and stored at −20° C. for up to several days. Prior to pooling and precipitation, the plate is centriftiged briefly to reclaim condensation. The primer and base-specific reactions are pooled into ethanol, and the precipitated DNA is collected by centrifugation and dried. These sequencing reactions could be stored for several days at −20° C.

The protocol for the sequencing reactions is as follows. For A and C reactions, 1 μl, and for G and T reactions, 2 μl of each DNA sample (100 ng/ul for M13 templates and 200 ng/ul for pUC templates) are pipetted into the bottom of the 0.2 ml thin-walled reaction tubes. AmpliTaq polymerase (N801-0060) is from Perkin-Elmer Cetus (Foster City, Calif.).

A mix of 30 μl AmpliTaq (5U/μl), 30 μl 5× Taq reaction buffer, 130 μl ddH20, and 190 μl diluted Taq for 24 clones is prepared.

A, C, G, and T base specific mixes are prepared by adding base-specific primer and diluted Taq to each of the base specific nucleotide/buffer premixes:

| A,C/G,T | |
|---|---|
| 60/120 μl | 5X Taq cycle sequencing mix |
| 30/60 μl | diluted Taq polymerase |
| 30/60 μl | respective fluorescent end-labeled primer |
| 120/240 μl | |

B. Taq-polymerase Catalyzed Cycle Sequencing Using MW-identifier-labeled Terminator Reactions One problem in DNA cycle sequencing is that when primers are used the reaction conditions are such that the nested fragment set distribution is highly dependent upon the template concentration in the reaction mix. It has been recently observed that the nested fragment set distribution for the DNA cycle sequencing reactions using the labeled terminators is much less sensitive to DNA concentration than that obtained with the labeled primer reactions as described above. In addition, the terminator reactions require only one reaction tube per template while the labeled primer reactions require one reaction tube for each of the four terminators. The protocol described below is easily interfaced with the 96 well template isolation and 96 well reaction clean-up procedures also described herein.

Place 0.5 μg of single-stranded or 1 μg of double-stranded DNA in 0.2 ml PCR tubes. Add 1 μl (for single stranded templates) or 4 μl (for double-stranded templates) of 0.8 μM primer and 9.5 μl of ABI supplied premix to each tube, and bring the final volume to 20 μl with ddH$_2$O. Centrifuge briefly and cycle as usual using the terminator program as described by the manufacturer (i.e., preheat at 96° C. followed by 25 cycles of 96° C. for 15 seconds, 50° C. for 1 second, 60° C. for 4 minutes, and then link to a 4° C. hold). Proceed with the spin column purification using either the Centri-Sep columns (Amicon, Beverly, Mass.) or G-50 microtiter plate procedures given below.

C. Terminator Reaction Clean-Up via Centri-Sep Columns

A column is prepared by gently tapping the column to cause the gel material to settle to the bottom of the column. The column stopper is removed and 0.75 ml dH$_2$O is added. Stopper the column and invert it several times to mix. Allow the gel to hydrate for at least 30 minutes at room temperature. Columns can be stored for a few days at 4° C. Allow columns that have been stored at 4° C. to warm to room temperature before use. Remove any air bubbles by inverting the column and allowing the gel to settle. Remove the upper-end cap first and then remove the lower-end cap. Allow the column to drain completely, by gravity. (Note: If flow does not begin immediately apply gentle pressure to the column with a pipet bulb.) Insert the column into the wash tube provided. Spin in a variable-speed microcentrifuge at 1300×g for 2 minutes to remove the fluid. Remove the column from the wash tube and insert it into a sample collection tube. Carefully remove the reaction mixture (20 μl) and load it on top of the gel material. If the samples were incubated in a cycling instrument that required overlaying with oil, carefully remove the reaction from beneath the oil. Avoid picking up oil with the sample, although small amounts of oil (<1 μl) in the sample will not affect results. Oil at the end of the pipet tip containing the sample can be removed by touching the tip carefully on a clean surface (e.g., the reaction tube). Use each column only once. Spin in a variable-speed microcentrifuge with a fixed angle rotor, placing the column in the same orientation as it was in for the first spin. Dry the sample in a vacuum centrifuge. Do not apply heat or over dry. If desired, reactions can be precipitated with ethanol.

D. Terminator Reaction Clean-Up via Sephadex G-50 Filled Microtiter Format Filter Plates Sephadex (Pharmacia, Piscataway, N.J.) settles out; therefore, you must resuspend before adding to the plate and also after filling every 8 to 10 wells. Add 400 μl of mixed Sephadex G-50 to each well of microtiter filter plate. Place microtiter filter plate on top of a microtiter plate to collect water and tape sides so they do not fly apart during centrifugation. Spin at 1500 rpm for 2 minutes. Discard water that has been collected in the microtiter plate. Place the microtiter filter plate on top of a microtiter plate to collect water and tape sides so they do not fly apart during centrifugation. Add an additional 100–200 μl of Sephadex G-50 to fill the microtiter plate wells. Spin at 1500 rpm for 2 minutes. Discard water that has been collected in the microtiter plate. Place the microtiter filter plate on top of a microtiter plate with tubes to collect water and tape sides so they do not fly apart during centrifugation. Add 20 μl terminator reaction to each Sephadex G-50 containing wells. Spin at 1500 rpm for 2 minutes. Place the collected effluent in a Speed-Vac for approximately 1–2 hours.

Sequenase™ (UBS, Cleveland Ohio) catalyzed sequencing with labeled terminators. Single-stranded terminator reactions require approximately 2 μg of phenol extracted M13-based template DNA. The DNA is denatured and the primer annealed by incubating DNA, primer, and buffer at 65° C. After the reaction cooled to room temperature, alpha-thio-deoxynucleotides, labeled terminators, and diluted Sequenase TM DNA polymerase are added and the mixture is incubated at 37° C. The reaction is stopped by adding ammonium acetate and ethanol, and the DNA fragments are precipitated and dried. To aid in the removal of unincorporated terminators, the DNA pellet is rinsed twice with ethanol. The dried sequencing reactions could be stored up to several days at −20° C.

Double-stranded terminator reactions required approximately 5 μg of diatomaceous earth modified-alkaline lysis midi-prep purified plasmid DNA. The double-stranded DNA is denatured by incubating the DNA in sodium hydroxide at 65° C., and after incubation, primer is added and the reaction is neutralized by adding an acid-buffer. Reaction buffer, alpha-thio-deoxynucleotides, labeled dye-terminators, and diluted Sequenase TM DNA polymerase then are added and the reaction is incubated at 37° C. Ammonium acetate is added to stop the reaction and the DNA fragments are precipitated, rinsed, dried, and stored.

For Single-stranded reactions:

Add the following to a 1.5 ml microcentrifuge tube:

| | |
|---|---|
| 4 μl | ss DNA (2 μg) |
| 4 μl | 0.8 μM primer |
| 2 μl | 10x MOPS buffer |
| 2 μl | 10x Mn$^{2+}$/isocitrate buffer |

To denature the DNA and anneal the primer, incubate the reaction at 65° C.–70° C. for 5 minutes. Allow the reaction to cool at room temperature for 15 minutes, and then briefly centrifuge to reclaim condensation. To each reaction, add the following reagents and incubate for 10 minutes at 37° C.

| | |
|---|---|
| 7 μl | ABI terminator mix (Catalogue No. 401489) |
| 2 μl | diluted Sequenase TM (3.25 U/μl) |
| 1 μl | 2 mM α-S dNTPs |

The undiluted Sequenase TM (Catalogue No. 70775, United States Biochemicals, Cleveland, Ohio) is 13 U/μl and is diluted 1:4 with USB dilution buffer prior to use. Add 20 μl 9.5 M ammonium acetate and 100 μl 95% ethanol to stop the reaction and mix.

Precipitate the DNA in an ice-water bath for 10 minutes. Centrifuge for 15 minutes at 10,000×g in a microcentrifuge at 4° C. Carefully decant the supernatant, and rinse the pellet by adding 300 μl of 70–80% ethanol. Mix and centrifuge again for 15 minutes and carefully decant the supernatant.

Repeat the rinse step to insure efficient removal of the unincorporated terminators. Dry the DNA for 5–10 minutes (or until dry) in the Speed-Vac, and store the dried reactions at −20° C.

For double-stranded reactions:

Add the following to a 1.5 ml microcentrifuge tube:

| | |
|---|---|
| 5 μl | ds DNA (5 μg) |
| 4 μl | 1 N NaOH |
| 3 μl | ddH$_2$O |

Incubate the reaction at 65° C.–70° C. for 5 minutes, and then briefly centrifuge to reclaim condensation. Add the following reagents to each reaction, vortex, and briefly centrifuge:

| | |
|---|---|
| 3 μl | 8 μM primer |
| 9 μl | ddH$_2$O |
| 4 μl | MOPS-Acid buffer |

To each reaction, add the following reagents and incubate for 10 minutes at 37° C.

| | |
|---|---|
| 4 μl | 10X Mn$^{2+}$/isocitrate buffer |
| 6 μl | ABI terminator mi |
| 2 μl | diluted Sequenase TM (3.25 U/μl) |
| 1 μl | 2 mM [alpha]-S-dNTPS |

The undiluted SEQUENASE™ from United States Biochemicals is 13 U/μl and should be diluted 1:4 with USB dilution buffer prior to use. Add 60 μl 8 M ammonium acetate and 300 μl 95% ethanol to stop the reaction and vortex. Precipitate the DNA in an ice-water bath for 10 minutes. Centrifuge for 15 minutes at 10,000×g in a microcentrifuge at 4° C. Carefully decant the supernatant, and rinse the pellet by adding 300 μl of 80% ethanol. Mix the sample and centrifuge again for 15 minutes, and carefully decant the supernatant. Repeat the rinse step to insure efficient removal of the unincorporated terminators. Dry the DNA for 5–10 minutes (or until dry) in the Speed-Vac.

E. Sequence Gel Preparation, Pre-electrophoresis Sample Loading, Electrophoresis, Data Collection, and Analysis on the ABI 373A DNA Sequencer Polyacrylamide gels for DNA sequencing are prepared as described above, except that the gel mix is filtered prior to polymerization. Glass plates are carefully cleaned with hot water, distilled water, and ethanol to remove potential fluorescent contaminants prior to taping. Denaturing 6% polyacrylamide gels are poured into 0.3 mm×89 cm×52 cm taped plates and fitted with a 36 well comb. After polymerization, the tape and the comb are removed from the gel and the outer surfaces of the glass plates are cleaned with hot water, and rinsed with distilled water and ethanol. The gel is assembled into an ABI sequencer, and the checked by laser-scanning. If baseline alterations are observed on the ABI associated Macintosh computer display, the plates are recleaned. Subsequently, the buffer wells are attached, electrophoresis buffer is added, and the gel is pre-electrophoresed for 10–30 minutes at 30 W. Prior to sample loading, the pooled and dried reaction products are resuspended in formamide/EDTA loading buffer by vortexing and then heated at 90° C. A sample sheet is created within the ABI data collection software on the Macintosh computer which indicates the number of samples loaded and the fluorescent-labeled mobility file to use for sequence data processing. After cleaning the sample wells with a syringe, the odd-numbered sequencing reactions are loaded into the respective wells using a micropipettor equipped with a flat-tipped gel-loading tip. The gel is then electrophoresed for 5 minutes before the wells are cleaned again and the even numbered samples are loaded. The filter wheel used for dye-primers and dye-terminators is specified on the ABI 373A CPU. Typically electrophoresis and data collection are for 10 hours at 30 W on the ABI 373A that is fitted with a heat-distributing aluminum plate. After data collection, an image file is created by the ABI software that relates the fluorescent signal detected to the corresponding scan number. The software then determines the sample lane positions based on the signal intensities. After the lanes are tracked, the cross-section of data for each lane are extracted and processed by baseline subtraction, mobility calculation, spectral deconvolution, and time correction. After processing, the sequence data files are transferred to a SPARCstation 2 using NFS Share.

Protocol: prepare 8 M urea, 4.75% polyacrylamide gels, as described above, using a 36-well comb. Prior to loading, clean the outer surface of the gel plates. Assemble the gel plates into an ABI 373A DNA Sequencer (Foster City, Calif.) so that the lower scan (usually the blue) line corresponds to an intensity value of 800–1000 as displayed on the computer data collection window. If the baseline of four-color scan lines is not flat, reclean the glass plates. Affix the aluminum heat distribution plate. Pre-electrophorese the gel for 10–30 minutes. Prepare the samples for loading. Add 3 µl of FE to the bottom of each tube, vortex, heat at 90° C. for 3 minutes, and centrifuge to reclaim condensation. Flush the sample wells with electrophoresis buffer using a syringe. Using flat-tipped gel loading pipette tips. load each odd-numbered sample. Pre-electrophorese the gel for at least 5 minutes, flush the wells again, and then load each even-numbered sample. Begin the electrophoresis (30 W for 10 hours). After data collection, the ABI software will automatically open the data analysis software, which will create the imaged gel file, extract the data for each sample lane, and process the data.

F. Double-stranded Sequencing of cDNA Clones Containing Long Poly(A) Tails Using Anchored Poly(dT) Primers Double-stranded templates of cDNAs containing long poly(A) tracts are difficult to sequence with vector primers which anneal downstream of the poly(A) tail. Sequencing with these primers results in a long poly(T) ladder followed by a sequence which may be difficult to read. To circumvent this problem, three primers which contain $(dT)_{17}$ and either (dA) or (dC) or (dG) at the 3' end were designed to 'anchor' the primers and allow sequencing of the region immediately upstream of the poly(A) region. Using this protocol, over 300 bp of readable sequence could be obtained. The sequence of the opposite strand of these cDNAs was determined using insert-specific primers upstream of the poly(A) region. The ability to directly obtain sequence immediately upstream from the poly(A) tail of cDNAs should be of particular importance to large scale efforts to generate sequence-tagged sites (STSs) from cDNAs.

The protocol is as follows. Synthesize anchored poly $(dT)_{17}$ with anchors of (dA) or (dC) or (dG) at the 3' end on a DNA synthesizer and use after purification on Oligonucleotide Purification Cartridges (Amicon, Beverly, Mass.). For sequencing with anchored primers, denature 5–10 µg of plasmid DNA in a total volume of 50 µl containing 0.2 M sodium hydroxide and 0.16 mM EDTA by incubation at 65° C. for 10 minutes. Add the three poly(dT) anchored primers (2 pmol of each) and immediately place the mixture on ice. Neutralize the solution by adding 5 ml of 5 M ammonium acetate, pH 7.0.

Precipitate the DNA by adding 150 µl of cold 95% ethanol and wash the pellet twice with cold 70% ethanol. Dry the pellet for 5 minutes and then resuspend in MOPS buffer. Anneal the primers by heating the solution for 2 minutes at 65° C. followed by slow cooling to room temperature for 15–30 minutes. Perform sequencing reactions, using modified T7 DNA polymerase and $\alpha$-$[^{32}P]dATP$ (>1000 Ci/mmole) using the protocol described above.

G. cDNA Sequencing Based on PCR and Random Shotgun Cloning

The following is a method for sequencing cloned cDNAs based on PCR amplification, random shotgun cloning, and automated fluorescent sequencing. This PCR-based approach uses a primer pair between the usual "universal" forward and reverse priming sites and the multiple cloning sites of the Stratagene Bluescript vector. These two PCR primers, with the sequence 5'-TCGAGGTCGACGGTATCG-3' (Seq. ID No. 15) for the forward or −16 bs primer and 5'-GCCGCTCTAGAACTAG TG-3' (Seq. ID No. 16) for the reverse or +19 bs primer, may be used to amplify sufficient quantities of cDNA inserts in the 1.2 to 3.4 kb size range so that the random shotgun sequencing approach described below could be implemented.

The following is the protocol. Incubate four 100 µl PCR reactions, each containing approximately 100 ng of plasmid DNA, 100 pmoles of each primer, 50 mM KCl, 10 mM Tris-HCl pH 8.5, 1.5 mM $MgCl_2$, 0.2 mM of each dNTP, and 5 units of PE-Cetus Amplitaq in 0.5 ml snap cap tubes for 25 cycles of 95° C. for 1 minute, 55° C. for 1 minute and 72° C. for 2 minutes in a PE-Cetus 48 tube DNA Thermal Cycler. After pooling the four reactions, the aqueous solution containing the PCR product is placed in an nebulizer, brought to 2.0 ml by adding approximately 0.5 to 1.0 ml of glycerol, and equilibrated at −20° C. by placing it in either an isopropyl alcohol/dry ice or saturated aqueous NaCl/dry ice bath for 10 minutes. The sample is nebulized at −20° C. by applying 25–30 psi nitrogen pressure for 2.5 min. Following ethanol precipitation to concentrate the sheared PCR product, the fragments were blunt ended and phosphorylated by incubation with the Klenow fragment of *E. coli* DNA polymerase and T4 polynucleotide kinase as described previously. Fragments in the 0.4 to 0.7 kb range were obtained by elution from a low melting agarose gel.

Example 18

SEPARATION OF DNA FRAGMENTS

Instrumentation

The separation of DNA fragments can be performed using an HPLC system assembled from several standard components. These components include a minimum of two high pressure pumps which pump solvent through a high pressure gradient mixer, an injector, HPLC column, and a detector. The injector is an automated, programmable autosampler capable of storing typically between eighty and one hundred samples at or below ambient temperatures to maintain the stability of the sample components. The autoinjector also is capable of making uL size injections in a reproducible manner completely unattended. The HPLC column is contained in a heated column compartment capable of holding a defined temperature to within 0.1° C. The column used in the examples below was purchased from SeraSep (San Jose, Calif.) under the name DNASep. This column is a 55×4.6 mm column with a 2.2 um non-porous polystyrenedivinyl-benzene copolymer particle alkylated with C18. The packing material is stable within a pH range of 2–12 and tolerates temperatures as high as 70° C. Detection of analyte was performed using a single or multiple wavelength UV detector or diode array detector.

Methods

The methods applied in this example for separation of DNA fragments use ion-pair chromatography, a form of chromatography in which ions in solution can be paired or neutralized and separated as an ion pair on a reversed phase column. The lipophilic character and the concentration of the counterion determine the degree of retention of the analyte. In the case of a DNA molecule the lipophilic, cationic buffer component pairs with anionic phosphate groups of the DNA backbone. The buffer components also interact with the alkyl groups of the stationary phase. The paired DNA then elutes according to size as the mobile phase is made progressively more organic with increasing concentration of acetonitrile. Evaluation of the suitability of various amine salts was evaluated using enzymatic digests of plasmids or commercially available DNA ladders. The range of acetonitrile required to elute the DNA as well as the temperature of the column compartment varied with each buffer evaluated.

Buffers

The buffers evaluated for their ion-pairing capability were prepared from stock solutions. In order to keep the concentration of ion-pair reagent the same throughout the gradient, the ion-pair reagent was added to both the water and the acetonitrile mobile phases. The column was equilibrated with a new mobile phase for approximately 18 hours at a flow rate of 50 ul/minute before attempting any separation. Once a mobile phase had been evaluated, it was removed and the column cleaned with a flush of 800 mL 0.1% formic acid in 50% acetonitrile, followed by a flush with 800 mL 0.1% acetic acid in 50% acetonitrile before equilibration with a new mobile phase.

A. N,N-Dimethyloctylammonium trifluoroacetate

A stock solution of lmolar dimethyloctylammonium trifluoroacetate was prepared by mixing one half of an equivalent of trifluoroacetic acid in an appropriate volume of water and slowly adding one equivalent of nn-Dimethyloctylamine. The pH of this stock solution is 7. The stock solution was diluted with an appropriate volume of water or acetonitrile to working concentration.

B. N,N-Dimethylheptylammonium acetate

A stock solution of Imolar dimethylheptylammonium acetate was prepared by mixing one equivalent of glacial acetic acid in an appropriate volume of water and slowly adding one equivalent of nn-Dimethylheptylamine. The pH of this stock solution is 6.6. The stock solution was diluted with an appropriate amount of water or acetonitrile to working concentration.

C. N,N-Dimethylhexylammonium acetate

A stock solution of 1 molar dimethylhexylammonium acetate was prepared by mixing one equivalent of glacial acetic acid in an appropriate volume of water and slowly adding one equivalent of nn-Dimethylhexylamine. The pH of this stock solution is 6.5. The stock solution was diluted with an appropriate volume of water or acetonitrile to working concentration.

D. N,N-Dimethylbutylammonium acetate

A stock solution of Imolar dimethylbutylammonium acetate was prepared by mixing one equivalent of glacial acetic acid in an appropriate volume of water and slowly adding one equivalent of nn-Dimethylbutylamine. The pH of the stock solution is 6.9. The stock solution was diluted with an appropriate volume of water or acetonitrile to working concentration.

E. N,N-Dimethylisopropylammonium acetate

A stock solution of 1 molar dimethylisopropylammonium acetate was prepared by mixing one equivalent of glacial acetic acid in an appropriate volume of water and slowly adding one equivalent of nn-Dimethylisopropylamine. The pH of the stock solution is 6.9. The stock solution was diluted with an appropriate volume of water or acetonitrile to working concentration.

F. N,N-Dimethylcyclohexylammonium acetate

A stock solution of 1 molar dimethylcyclohexylammonium acetate was prepared by mixing one equivalent of glacial acetic acid in appropriate volume of water and slowly adding one equivalent of nn-Dimethylcyclohexylamine. The pH of the stock solution is 6.5. The stock solution was diluted with an appropriate volume of water or acetonitrile to working concentration.

G. Methylpiperidine acetate

A stock solution of 1 molar methylpiperidine acetate was prepared by mixing one equivalent of glacial acetic acid in an appropriate volume of water and slowly adding one equivalent of 1-methylpiperidine. The pH of the solution is 7. The stock solution was diluted with an appropriate volume of water or acetonitrile to working concentration.

H. Methylpyrrolidine acetate

A stock solution of 1 molar piperidine acetate was prepared by mixing one equivalent of glacial acetic acid in an appropriate volume of water and slowly adding one equivalent 1-methylpyrrolidine. The pH of the stock solution is 7. The stock solution was diluted in an appropriate volume of water or acetonitrile to working concentration.

I. Triethylammonium acetate

A stock solution of 2 molar triethylammonium acetate pH 7.0 was purchased from Glenn Research Sterling, Va. The stock solution was diluted in an appropriate volume of water or acetonitrile to working concentration.

Example 19

Figure 17A:
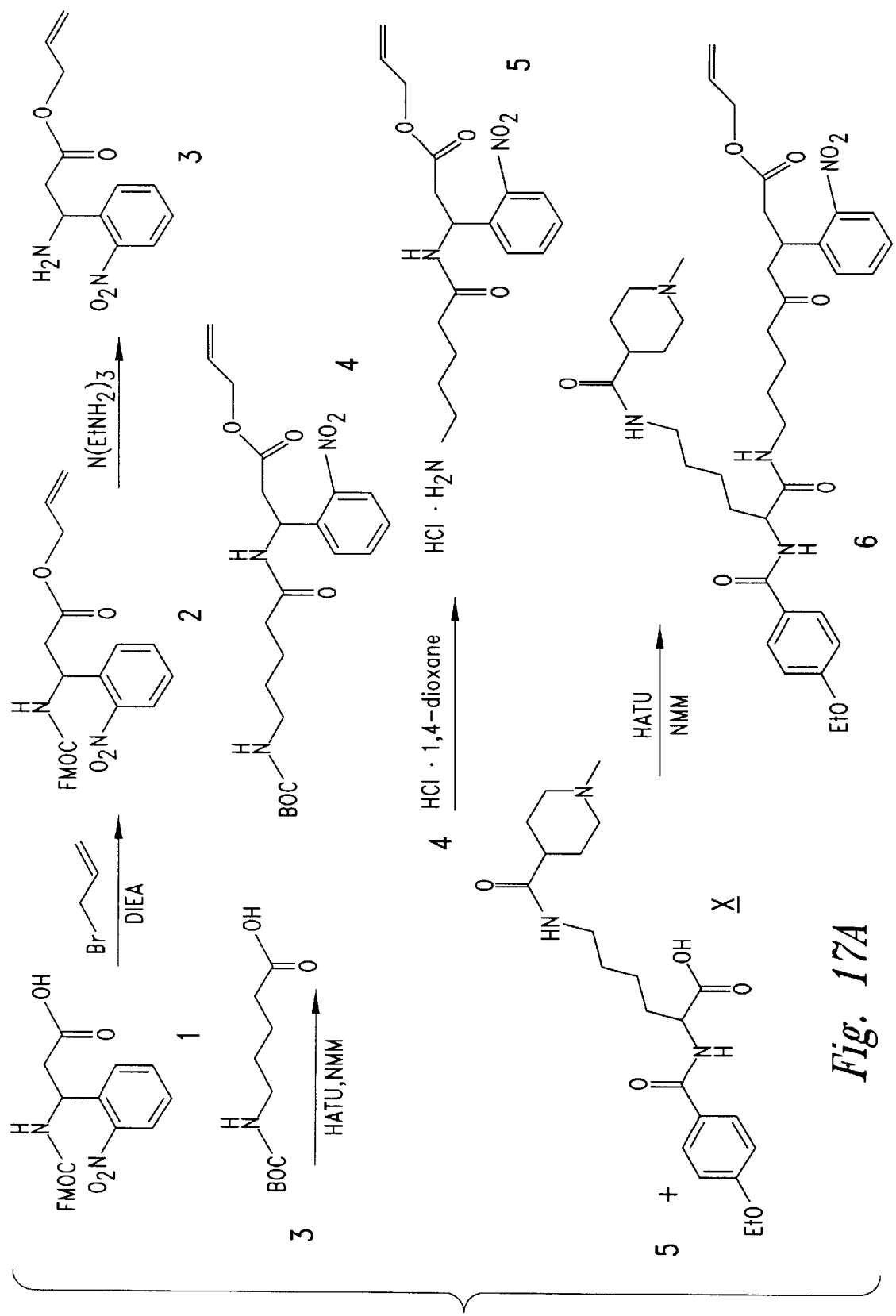
FIGS. 17A and 17B illustrate the preparation of a cleavable tag of the present invention.
Figure 17B:
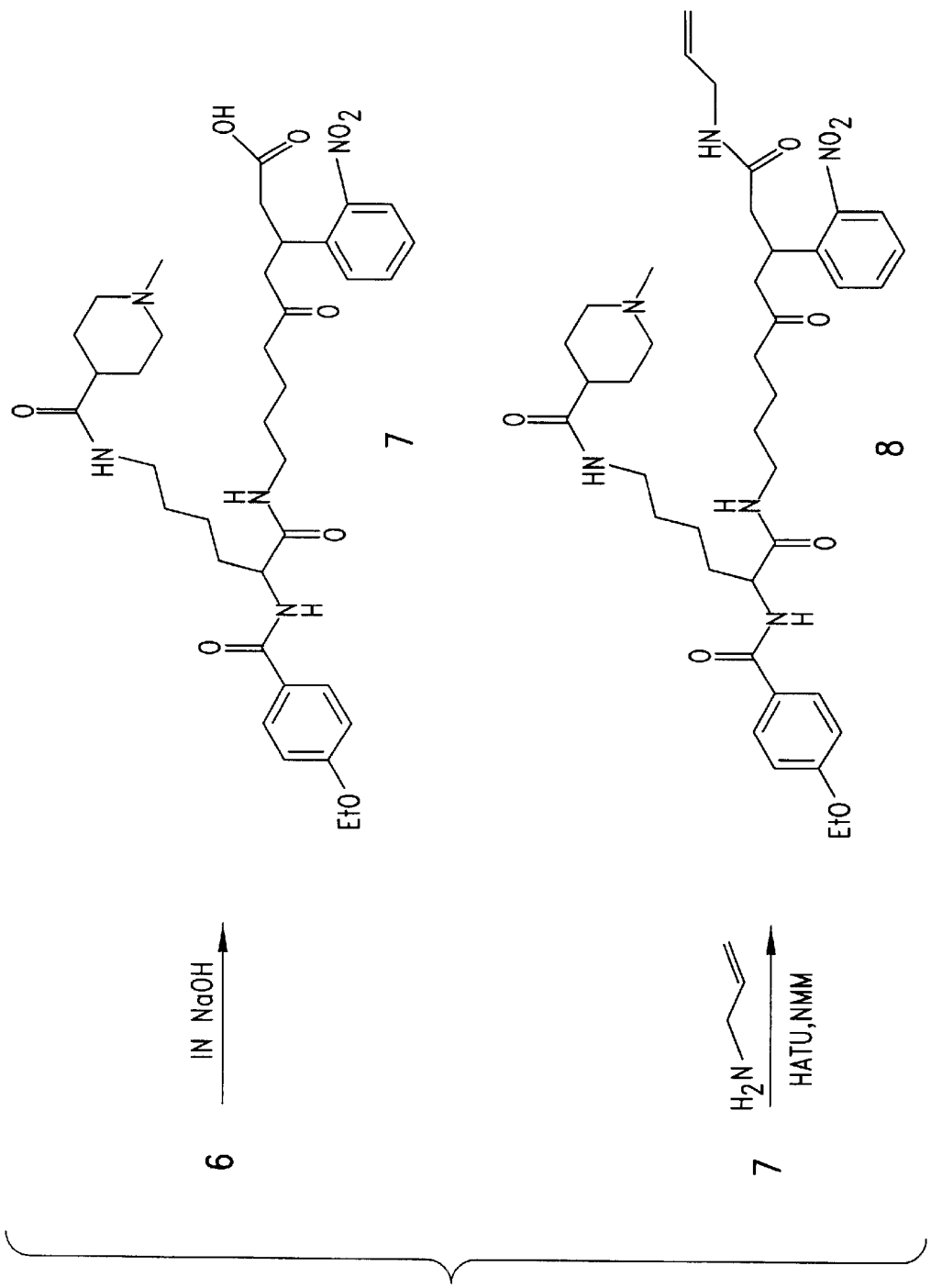

In this Example (19), all reactions were conducted in foil-covered flasks. The sequence of reactions A→F described in this Example is illustrated in FIGS. 17A and 17B. Compound numbers as set forth in this Example refer to the compounds of the same number in FIGS. 17A and 17B.

A. To a solution of ANP linker (compound 1, 11.2 mmol) and diisopropylethylamine (22.4 mmol) in $CHCl_3$ (60 ml) was added allyl bromide (22.4 mmol). The reaction mixture was refluxed for 3 hours, stirred at room temperature for 18 hours, diluted with $CHCl_3$ (200 ml), and washed with 1.0 M HCl (2×150 ml) and $H_2O$ (2×150 ml). The organic extracts were dried ($MgSO_4$) and the solvent evaporated to give compound 2 as a yellow solid.

To a mixture of compound 2 in $CH_2Cl_2$ (70 ml), tris (2-aminoethyl) amine (50 ml) was added and the reaction mixture stirred at room temperature for 18 hours. The reaction was diluted with $CH_2Cl_2$ (150 ml) and washed with pH 6.0 phosphate buffer (2×150 ml). The organic extracts were dried ($MgSO_4$) and the solvent evaporated. The residue was subjected to column chromatography (hexane/EtOAc) to give 1.63 g (58%/o) of compound 3: $^1H$ NMR (DMSO-$d_6$): δ 7.85 (dd, 2H), 7.70 (t, 1H), 7.43 (t, 1H), 5.85 (m, 1H), 5.20 (q, 2H), 4.58 (q, 1H), 4.50 (d, 2H), 2.70 (m, 2H), 2.20 (br s, 2H).

B. To a solution of Boc-5-aminopentanoic acid (1.09 mmol) and NMM (3.27 mmol) in dry DMF (6 ml), was added HATU (1.14 mmol) and the reaction mixture stirred at room temperature for 0.5 hours. A solution of compound 3 (1.20 mmol) in dry DMF (1 ml) was added and the reaction mixture stirred at room temperature for 18 hours. The reaction was diluted with EtOAc (50 ml) and washed with 1.0 M HCl (2×50 ml) and D.I. $H_2O$ (2×50 ml). The organic extracts were dried ($MgSO_4$) and evaporated to dryness. The residue was subjected to column chromatography to give 420 mg (91%) of compound 4: $^1H$ NMR (DMSO-$d_6$): δ 8.65 (d, 1H), 7.88 (d, 1H), 7.65 (m, 2H), 7.48 (t, 1H), 6.73 (br s, 1H), 5.85 (m, 1H), 5.55 (m, 1H), 5.23 (q, 2H), 4.55 (d, 2H), 2.80 (m, 2H), 2.05 (t, 2H), 1.33 (s, 9H), 1.20–1.30 (m, 4H).

C. A solution of compound 4 (0.9 mmol) in HCl•1,4-dioxane (20 mmol) was stirred at room temperature for 2 hours. The reaction mixture was concentrated, dissolved in MeOH and toluene, and concentrated again (5×5 ml) to give 398 mg (quantitative) of the compound 5: $^1H$ NMR (DMSO-$d_6$): δ 8.75 (d, 1H), 7.88 (d, 1H), 7.65 (m, 2H),7.51 (t, 1H), 7.22 (m, 2H),5.85 (m, 1H), 5.57 (m, 1H), 5.23 (q, 2H), 4.55 (d, 2H), 2.80 (m, 2H), 2.71 (m, 2H), 2.07 (s, 2H), 1.40–1.48 (br s, 4 H).

D. To a solution of compound 21 (0.48 mmol, prepared according to Example 21) and NMM (1.44 mmol) in dry DMF (3 ml), was added HATU (0.50 mmol) and the reaction mixture stirred at room temperature for 0.5 hours. A solution of compound 5 (0.51 mmol) in dry DMF (3 ml) was added and the reaction stirred at room temperature for 18 hours. The reaction mixture was diluted with EtOAc (75 ml) and washed with 5% $Na_2CO_3$ (3×50 ml). The organic extracts were dried ($MgSO_4$) and the solvent evaporated to give 281 mg (78%) of compound 6: $^1H$ NMR (DMSO-$d_6$): δ 8.65 (d, 1H), 8.17 (d, 1H), 7.82–7.95 (m, 4H), 7.68 (m, 3H), 7.50 (t, 1H), 6.92 (d, 1H), 5.85 (m, 1H), 5.57 (m, 1H), 5.20 (q, 2H), 4.55 (d, 2H), 4.30 (q, 1H), 4.05 (q, 2H), 2.95 (m, 4H), 2.80 (m, 2H), 2.72 (m, 2H), 2.05 (s, 3H), 2.01 (t, 2H), 1.58–1.77 (m, 3H), 1.50 (m, 4H), 1.30 (q, 3H), 1.17–1.40 (m, 9H).

E. To a mixture of compound 6 (0.36 mmol) in THF (4 ml), was added 1 M NaOH (1 mmol) and the reaction stirred at room temperature for 2 hours. The reaction mixture was acidified to pH 7.0 with 1.0 M HCl (1 ml) and the solvent evaporated to give compound 7 (quantitative): $^1H$ NMR (DMSO-$d_6$): δ 8.65 (d, 1H), 8.17 (d, 1H), 7.82–7.95 (m, 4H), 7.68 (m, 3H), 7.50 (t, 1H), 6.92 (d, 1H), 5.52 (m, 1H), 4.30 (q, 1H), 4.05 (q, 2H), 2.95 (m, 4H), 2.80 (m, 2H), 2.72 (m, 2H), 2.05 (s, 3H), 2.01 (t, 2H), 1.58–1.77 (m, 3H), 1.50 (m, 4H), 1.30 (q, 3H), 1.17–1.40 (m, 9H).

F. To a solution of compound 7 (0.04 mmol) and NMM (0.12 mmol) in dry DMF (0.4 ml), was added HATU (0.044 mmol) and the reaction stirred at room temperature for 0.5 hours. Allylamine (0.12 mmol) was added and the reaction mixture stirred at room temperature for 5 hours. The reaction mixture was diluted with EtOAc (15 ml) and washed with 5% $Na_2CO_3$ (3×10 ml). The organic extracts were dried ($MgSO_4$) and the solvent evaporated to yield 15 mg (49%) of compound 8: $^1H$ NMR (DMSO-$d_6$) δ 8.49 (d, 1H), 8.17 (d, 1H), 7.82–7.95 (m, 4H), 7.68 (m, 3H), 7.50 (t, 1H), 6.92 (d, 1H), 5.72 (m, 1H), 5.50 (m, 1H), 5.03 (q, 2H), 4.37 (d, 2H), 4.30 (q, 1H), 4.05 (q, 2H), 2.95 (m, 4H), 2.80 (m, 2H), 2.72 (m, 2H), 2.05 (s, 3H), 2.01 (t, 2H), 1.58–1.77 (m, 3H), 1.50 (m, 4H), 1.30 (q, 3H), 1.17–1.40 (m, 9H).

Example 20

Figure 18A:
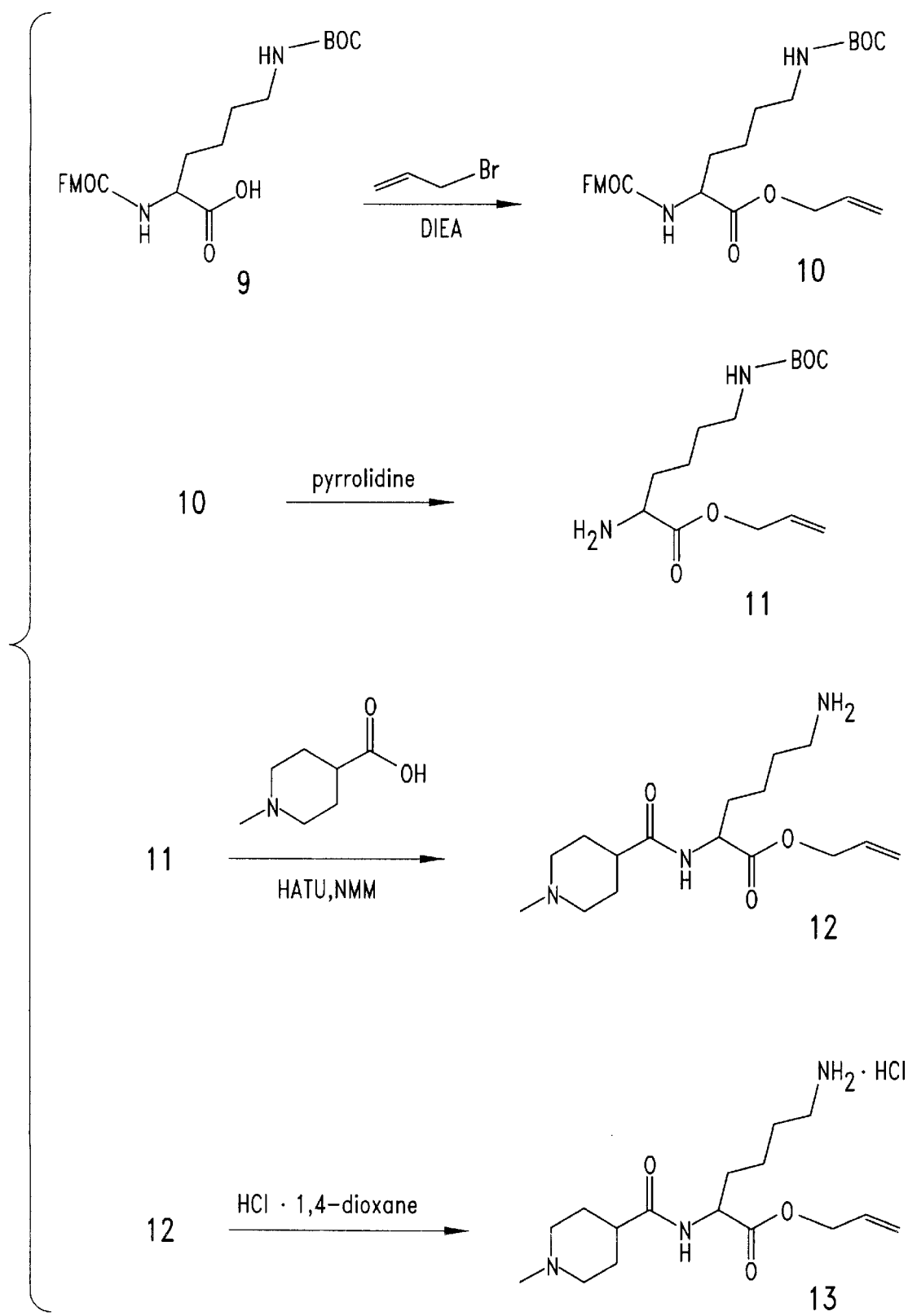
FIGS. 18A and 18B illustrate the preparation of a cleavable tag of the present invention.
Figure 18B:
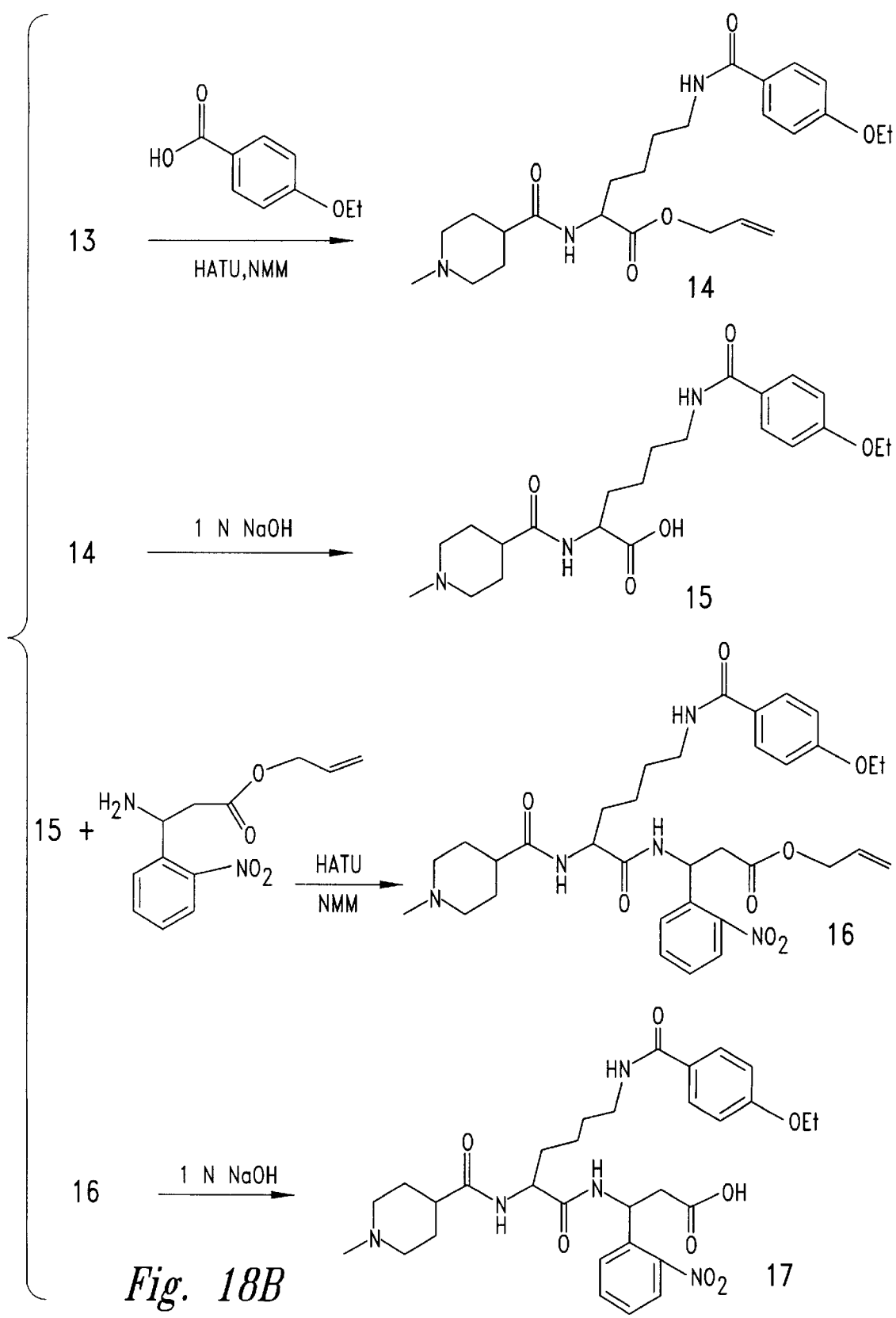

The sequence of reactions A→G as described in this Example 20 is illustrated in FIGS. 18A and 18B. Compound numbers as set forth in this Example refer to the compounds of the same number in FIGS. 18A and 18B.

A. To a solution of Fmoc-Lys(Boc)—OH (compound 9, 33.8 mmol) in $CHCl_3$ (200 ml), was added diisopropylethylamine (67.5 mmol) and allyl bromide (67.5 mmol). The reaction mixture was refluxed for 6 hours, stirred at room temperature for 16 hours, diluted with $CHCl_3$, washed with 1.0 M HCl (2×150 ml), saturated $NaHCO_3$ (1×150 ml) and D.I. $H_2O$ (2×150 ml). The organic extracts were dried ($MgSO_4$) and the solvent evaporated to yield compound 10.

To a solution of compound 10 in $CHCl_3$ (90 ml), was added pyrrolidine (10 eq.) and the reaction was stirred at room temperature for 2.5 hours. The reaction mixture was diluted with $CHCl_3$ (150 ml) and washed with saturated $NaHCO_3$ (3×250 ml). The organic extracts were dried ($MgSO_4$) and the solvent evaporated. The residue Nwas subjected to column chromatography (EtOAc/MeOH) to give 6.52 g (67%) of compound 11: $^1H$ NMR ($CDCl_3$): δ 5.90 (m, 1H), 5.27 (m, 2H), 4.60 (d, 2H), 3.48 (t, 1H), 3.10 (d, 2H), 1.40–1.78 (m, 9H), 1.40 (s, 9H).

B. To a solution of N-methylisonipecotic acid (1.60 mmol) and N-methyl morpholine (4.80 mmol) in dry DMF (5 ml), was added HATU (1.67 mmol). After 0.5 hours, a solution of compound 11 (1.75 mmol) in dry DMF (2 ml) was added and the reaction mixture stirred at room temperature for 18 hours. The reaction mixture was diluted with $CH_2CL_2$ (60 ml) and washed with saturated $Na_2CO_3$ (3×40 ml). The organic extracts were dried ($MgSO_4$) and the solvent evaporated. The residue was subjected to column chromatography ($CH_2Cl_2$/MeOH/triethylamine) to give 580 mg (88%) of compound 12: $^1H$ NMR (DMSO): δ 8.12 (d, 1H), 6.77 (t, 1H), 5.90 (m, 1H), 5.27 (m, 2H), 4.53 (d, 2H), 4.18 (m, 1H),2.62–2.90 (m, 5H), 2.13 (s, 3H), 1.85 (m, 2H), 1.57 (m, 5H), 1.35 (s, 9H), 1.00 (t, 2H).

C. A mixture of compound 12 (1.39 mmol) in HCl•1,4-dioxane (20 mmol) was stirred at room temperature for 4 hours. The reaction mixture was concentrated, dissolved in MeOH, coevaporated with toluene (5×5 ml) to give 527 mg (quantitative) of compound 13: $^1H$ NMR (DMSO-$d_6$): δ 8.12 (d, 1H), 6.77 (t, 1H), 5.90 (m, 1H), 5.27 (m, 2H), 4.53 (d, 2H), 4.18 (m, 1H), 2.65–3.00 (m, 8H), 2.23 (s, 3H), 1.85 (m, 2H), 1.57 (m, 5H), 1.00 (t, 2H).

D. To a solution of 4-ethoxybenzoic acid (1 eq.) in dry DMF, is added NMM (3 eq.) and HATU (1.05 eq.). After 0.5 hours, a solution of compound 13 in dry DMF is added. After the completion of the reaction and basic workup, the compound 14 is isolated and purified.

E. To a solution of compound 14 in THF, is added 1N NaOH and the reaction mixture stirred at room temperature. After the completion of the reaction and acidification, the compound 15 is isolated.

F. To a solution of compoumd 15 (1 eq.) in dry DMF, is added NIMM (3 eq.) and HATU (1.05 eq.). After 0.5 hours, a solution of compound 21 (ANP-allyl ester, prepared according to Example 21) in dry DMF is added. After the completion of the reaction and basic workup, the title compound 16 is isolated and purified.

G. To a solution of compound 16 in THF, is added 1N NaOH and the reaction mixture stirred at room temperature. After the completion of the reaction and acidification, the compound 17 is isolated.

Example 21

Figure 19:
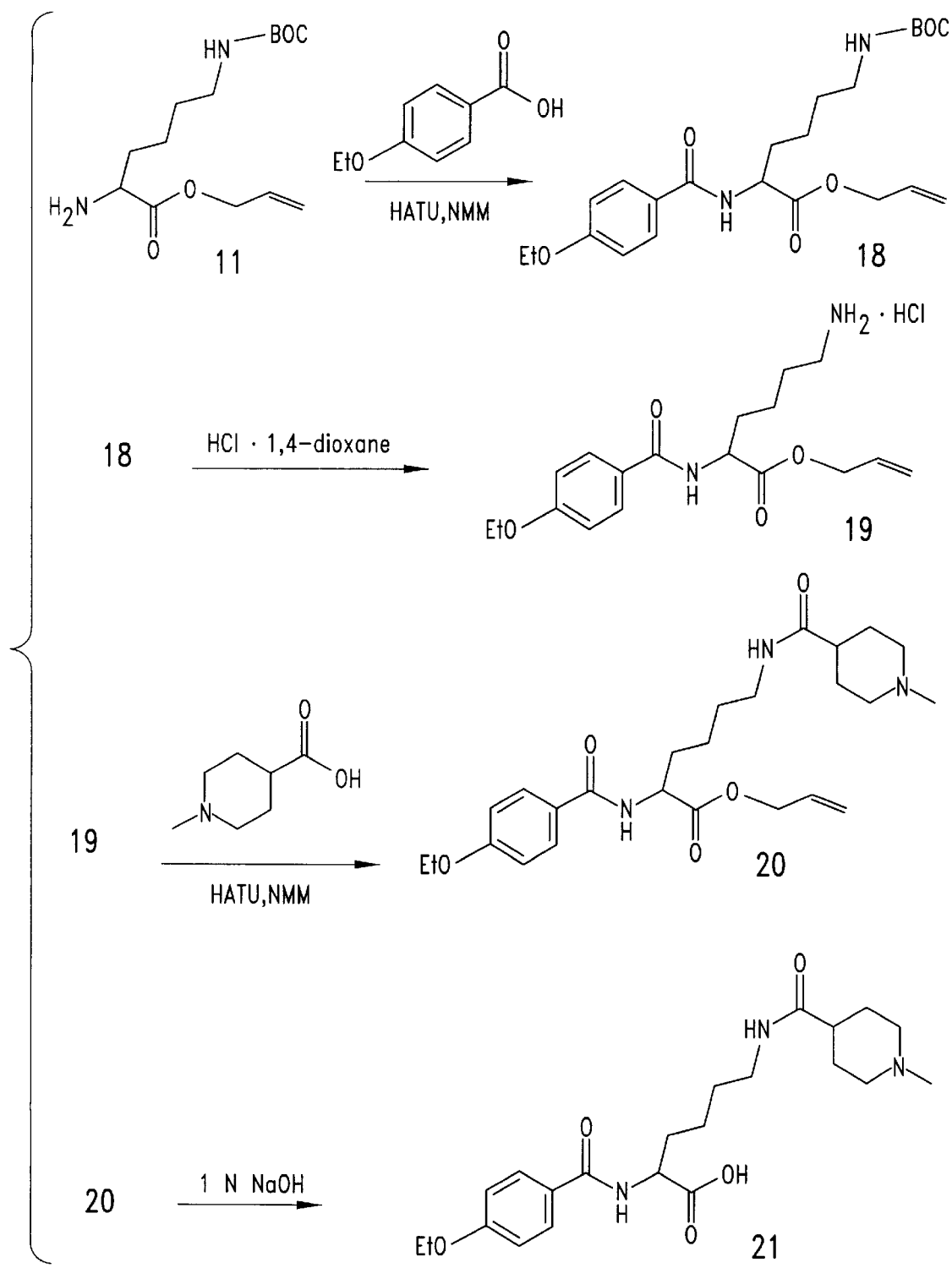
FIG. 19 illustrates the preparation of an intermediate compound useful in the preparation of a cleavable tag of the invention.

The sequence of reaction A through D as described in this Example 21 is illustrated in FIG. 19. Compound numbers as set forth in this Example, as well as Examples 19 and 20, refer to the compounds of the same number in FIG. 19.

A. To a solution of 4-ethoxybenzoic acid (7.82 mmol) and N-methyl morpholine (20.4 mmol) in $CH_2Cl_2$ (10 ml), was added HATU (7.14 mmol). After 0.25 hours, a solution of compound 11 (6.8 mmol) in $CH_2Cl_2$ (6 ml) was added and the reaction mixture stirred at room temperature for 18 hours. The reaction was diluted with $CH_2Cl_2$ (150 ml) and washed with 1.0 M HCl (3×50 ml) and saturated $NaHCO_3$ (3×50 ml). The organic extracts were dried ($MgSO_4$) and the solvent evaporated. The residue was subjected to column chromatography ($CH_2Cl_2$/MeOH) to give 2.42 g (82%) of compound 18: $^1$H NMR (CDCl): δ 7.78 (d, 2H), 6.91 (d, 2H), 6.88 (d, 1H), 5.83–5.98 (m, 1H), 5.21–5.38 (m, 2H), 4.80 (q, 1H), 4.66 (d, 2H), 4.06 (q, 2H), 3.11 (q, 2H), 1.90–2.04 (m, 1H), 1.68–1.87 (m, 1H), 1.39 (t, 3H), 1.34 (s, 9H), 1.32–1.58 (m, 4H).

B. A mixture of compound 18 (5.5 mmol) in HCl•1,4-dioxane (14.3 mmol) was stirred at room temperature for 1 hour. The reaction mixture was concentrated, dissolved in MeOH, azeotroped with toluene, and concentrated again (5×5 ml) to give a quantitative yield of compound 19.

C. To a solution of N-methylisonipecotic acid (6.21 mmol) in dry DMF (15 mL), was added NMM (21.6 mmol) and HATU (5.67 mmol). After 0.5 hours, a solution of compound 19 (5.4 mmol) in dry DMF (10 ml) was added and the reaction stirred at room temperature for 18 hours. The reaction mixture was brought to pH 12 with 1N NaOH (20 ml) and extracted with $CHCl_3$ (2×200 ml). The organic extracts were dried ($MgSO_4$) and the solvent evaporated to give 2.2 g (89%) of compound 20: $^1$H NMR (DMSO-$d_6$): δ 8.52 (d, 1H), 7.84 (d, 2H), 7.72 (t, 1H), 6.95 (d, 2H), 5.80–5.95 (m, 1H), 5.18–5.31 (dd, 2H), 4.58 (d, 2H), 4.37 (q, 1H), 4.08 (q, 2H), 3.01 (d, 2H), 2.08 (s, 3H), 1.95 (m, 1H), 1.63–1.82 (m, 4H), 1.51 (m, 4H), 1.32 (t,3H), 1.22–1.41 (m, 6H).

D. To a solution of compound 20 (4.4 mmol) in THF (10 ml), is added 1N NaOH (4.4 mmol) and the reaction mixture stirred at room temperature for 1 hour. The reaction was concentrated, dissolved in THF/toluene (2×5 ml), concentrated, dissolved in $CH_2Cl_2$/toluene (1×5 ml) and concentrated again to give a quantitative yield of compound 21: $^1$H NMR (DMSO-$d_6$): δ 7.76 (d, 2H), 6.96 (d, 2H), 4.04 (q, 2H), 3.97 (d, 1H), 2.97 (d, 2H), 2.64 (d, 2H), 2.08 (s, 3H), 1.95 (m, 1H), 1.58–1.79 (m, 4H), 1.44 (m, 6H), 1.30 (t, 3H), 1.11–1.35 (m, 4H).

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for determining the sequence of a nucleic acid molecule, comprising:
   (a) generating tagged nucleic acid fragments which are complementary to a selected target nucleic acid molecule, wherein a tag is an organic moiety that is correlative with a particular nucleotide and detectable by non-fluorescent spectrometry or potentiometry;
   (b) separating the tagged fragments by sequential length;
   (c) cleaving the tags from the tagged fragments; and
   (d) detecting the tags by non-fluorescent spectrometry or potentiometry, and therefrom determining the sequence of the nucleic acid molecule.

2. The method according to claim 1 wherein the detection of the tags is by mass spectrometry, infrared spectrometry, ultraviolet spectrometry or potentiostatic amperometry.

3. The method according to claims 1 or 2 wherein the tagged fragments are separated in step (b) by a method selected from gel electrophoresis, capillary electrophoresis, micro-channel electrophoresis and HPLC.

4. The method according to claims 1 or 2 wherein the tagged fragments are cleaved in step (c) by a method selected from oxidation, reduction, acid-labile, base-labile, enzymatic, electrochemical, thermal, thiol exchange and photolabile methods.

5. The method according to claim 2 wherein the tags are detected by time-of-flight mass spectrometry, quadrupole mass spectrometry, magnetic sector mass spectrometry or electric sector mass spectrometry.

6. The method according to claim 2 wherein the tags are detected by coulometric detectors or amperometric detectors.

7. The method according to claims 1 or 2 wherein the tagged nucleic acid fragments are generated in step (a) from a 5' terminus to a 3' terminus.

8. The method according to claims 1 or 2 wherein step (a) generates more than four of the tagged nucleic acid fragments and each tag is unique for a nucleic acid fragment.

9. The method according to claims 1 or 2 wherein steps (b), (c) and (d) are performed in a continuous manner.

10. The method according to claims 1 or 2 wherein steps (b), (c) and (d) are performed in a continuous manner on a system.

11. The method according to claims 1 or 2 wherein one or more of the steps is automated.

12. The method according to claims 1 or 2 wherein the tagged fragments are generated from oligonucleotide primers that are conjugated to a tag at other than the 3' end of the primer.

13. The method according to claims 1 or 2 wherein the tagged fragments are generated from tagged dideoxynucleotide terminators.

14. The method according to claims 1 or 2 wherein at least one tagged nucleic acid fragment is a compound according to any one of claims 15 to 33.

15. A compound of the formula:

$$T^{ms}\text{—L—X}$$

wherein, $T^{ms}$ is an organic group detectable by mass spectrometry, comprising carbon, at least one of hydrogen and fluoride, and optional atoms selected from oxygen, nitrogen, sulfur, phosphorus and iodine;

L is an organic group which allows a unique $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid;

X is a nucleic acid fragment attached to L at other than the 3' end of the nucleic acid fragment;

with the provisos that the compound is not bonded to a solid support nor has a mass of less than 250 daltons.

16. A compound according to claim 15 wherein $T^{ms}$ has a mass of from 15 to 10,000 daltons and a molecular formula of $C_{1-500}N_{0-100}O_{0-100}S_{0-10}P_{0-10}H_\alpha F_\beta I_\delta$ wherein the sum of $\alpha$, $\beta$ and $\delta$ is sufficient to satisfy the otherwise unsatisfied valencies of the C, N, O, P and S atoms.

17. A compound according to claim 15 wherein $T^{ms}$ and L are bonded together through a functional group selected from amide, ester, ether, amine, sulfide, thioester, disulfide, thioether, urea, thiourea, carbamate, thiocarbamate, Schiff base, reduced Schiff base, imine, oxime, hydrazone, phosphate, phosphonate, phosphoramide, phosphonamide, sulfonate, sulfonamide or carbon-carbon bond.

18. A compound according to claim 17 wherein the functional group is selected from amide, ester, amine, urea and carbamate.

19. A compound according to claim 15 wherein L is selected from $L^{hv}$, $L^{acid}$, $L^{base}$, $L^{[O]}$, $L^{[R]}$, $L^{enz}$, $L^{elc}$, $L^\Delta$ and $L^{ss}$, where actinic radiation, acid, base, oxidation, reduction, enzyme, electrochemical, thermal and thiol exchange, respectively, cause the $T^{ms}$-containing moiety to be cleaved from the remainder of the molecule.

20. A compound according to claim 19 wherein $L^{hv}$ has the formula $L^1-L^2-L^3$, wherein $L^2$ is a molecular fragment that absorbs actinic radiation to promote the cleavage of $T^{ms}$ from X, and $L^1$ and $L^3$ are independently a direct bond or an organic moiety, where $L^1$ separates $L^2$ from $T^{ms}$ and $L^3$ separates $L^2$ from X, and neither $L^1$ nor $L^3$ undergo bond cleavage when $L^2$ absorbs the actinic radiation.

21. A compound according to claim 20 wherein $-L^2-L^3$ has the formula:

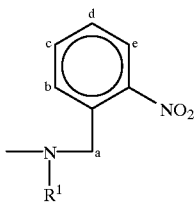

with one carbon atom at positions a, b, c, d or e being substituted with $-L^3-X$ and optionally one or more of positions b, c, d or e being substituted with alkyl, alkoxy, fluoride, chloride, hydroxyl, carboxylate or amide; and $R^1$ is hydrogen or hydrocarbyl.

22. A compound according to claim 21 wherein X is

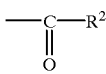

and $R^2$ is nucleic acid fragment.

23. A compound according to claim 20 wherein $L^3$ is selected from a direct bond, a hydrocarbylene, —O-hydrocarbylene, and hydrocarbylene-(O-hydrocarbylene)$_n$—H, and n is an integer ranging from 1 to 10.

24. A compound according to claim 15 wherein —L—X has the formula:

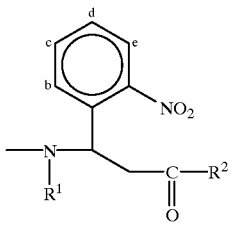

wherein one or more of positions b, c, d or e is substituted with hydrogen, alkyl, alkoxy, fluoride, chloride, hydroxyl, carboxylate or amide; $R^1$ is hydrogen or hydrocarbyl, and $R^2$ is a nucleic acid fragment.

25. A compound according to claim 15 wherein $T^{ms}$ has the formula:

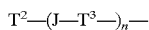

$T^2$ is an organic moiety formed from carbon and one or more of hydrogen, fluoride, iodide, oxygen, nitrogen, sulfur and phosphorus, having a mass of 15 to 500 daltons;

$T^3$ is an organic moiety formed from carbon and one or more of hydrogen, fluoride, iodide, oxygen, nitrogen, sulfur and phosphorus, having a mass of 50 to 1000 daltons;

J is a direct bond or a functional group selected from amide, ester, amine, sulfide, ether, thioester, disulfide, thioether, urea, thiourea, carbamate, thiocarbamate, Schiff base, reduced Schiff base, imine, oxime, hydrazone, phosphate, phosphonate, phosphoramide, phosphonamide, sulfonate, sulfonamide or carbon-carbon bond; and n is an integer ranging from 1 to 50, and when n is greater than 1, each $T^3$ and J is independently selected.

26. A compound according to claim 25 wherein $T^2$ is selected from hydrocarbyl, hydrocarbyl-O-hydrocarbylene, hydrocarbyl-S-hydrocarbylene, hydrocarbyl-NH-hydrocarbylene, hydrocarbyl-amide-hydrocarbylene, N-(hydrocarbyl)hydrocarbylene, N,N-di(hydrocarbyl)hydrocarbylene, hydrocarbylacyl-hydrocarbylene, heterocyclylhydrocarbyl wherein the heteroatom(s) are selected from oxygen, nitrogen, sulfur and phosphorus, substituted heterocyclylhydrocarbyl wherein the heteroatom(s) are selected from oxygen, nitrogen, sulfur and phosphorus and the substituents are selected from hydrocarbyl, hydrocarbyl-O-hydrocarbylene, hydrocarbyl-NH-hydrocarbylene, hydrocarbyl-S-hydrocarbylene, N-(hydrocarbyl)hydrocarbylene, N,N-di(hydrocarbyl)hydrocarbylene and hydrocarbylacyl-hydrocarbylene, as well as derivatives of any of the foregoing wherein one or more hydrogens is replaced with an equal number of fluorides.

27. A compound according to claim 25 wherein $T^3$ has the formula $-G(R^2)-$, G is $C_{1-6}$ alkylene having a single $R^2$ substituent, and $R^2$ is selected from alkyl, alkenyl, alkynyl, cycloalkyl, aryl-fused cycloalkyl, cycloalkenyl, aryl, aralkyl, aryl-substituted alkenyl or alkynyl, cycloalkyl-substituted alkyl, cycloalkenyl-substituted cycloalkyl, biaryl, alkoxy, alkenoxy, alkynoxy, aralkoxy, aryl-substituted alkenoxy or alkynoxy, alkylamino, alkenylamino or alkynylamino, aryl-substituted alkylamino, aryl-substituted alkenylamino or alkynylamino, aryloxy, arylamino, N-alkylurea-substituted alkyl, N-arylurea-substituted alkyl, alkylcarbonylamino-substituted alkyl, aminocarbonyl-substituted alkyl, heterocyclyl, heterocyclyl-substituted alkyl, heterocyclyl-substituted amino, carboxyalkyl substituted aralkyl, oxocarbocyclyl-fused aryl and heterocyclylalkyl; cycloalkenyl, aryl-substituted alkyl and, aralkyl, hydroxy-substituted alkyl, alkoxy-substituted alkyl, aralkoxy-substituted alkyl, alkoxy-substituted alkyl, aralkoxy-substituted alkyl, amino-substituted alkyl, (aryl-substituted alkyloxycarbonylamino)-substituted alkyl, thiol-substituted alkyl, alkylsulfonyl-substituted alkyl, (hydroxy-substituted alkylthio)-substituted alkyl, thioalkoxy-substituted alkyl, hydrocarbylacylamino-substituted alkyl, heterocyclylacylamino-substituted alkyl, hydrocarbyl-substituted-heterocyclylacylamino-substituted alkyl, alkylsulfonylamino-substituted alkyl, arylsulfonylamino-substituted alkyl, morpholino-alkyl, thiomorpholino-alkyl, morpholino carbonyl-substituted alkyl, thiomorpholinocarbonyl-substituted alkyl, [N-(alkyl, alkenyl or alkynyl)- or N,N-[dialkyl, dialkenyl, dialkynyl or (alkyl, alkenyl)-amino]carbonyl-substituted alkyl, heterocyclylaminocarbonyl, heterocylylalkyleneaminocarbonyl, heterocyclylaminocarbonyl-substituted alkyl, heterocylylalkyleneaminocarbonyl-substituted alkyl, N,N-[dialkyl]alkyleneaminocarbonyl, N,N-[dialkyl]alkyleneaminocarbonyl-substituted alkyl, alkyl-substituted heterocyclylcarbonyl, alkyl-substituted heterocyclylcarbonyl-alkyl, carboxyl-substituted alkyl, dialkylamino-substituted acylaminoalkyl and amino acid side chains selected from arginine, asparagine, glutamine, S-methyl cysteine, methionine and corresponding sulfoxide and sulfone derivatives thereof, glycine, leucine, isoleucine, allo-isoleucine, tert-leucine, norleucine, phenylalanine, tyrosine, tryptophan, proline, alanine, ornithine, histidine, glutamine, valine, threonine, serine, aspartic acid, beta-cyanoalanine, and allothreonine; alynyl, heterocyclylcarbonyl, aminocarbonyl, amido, mono- or dialkylaminocarbonyl, mono- or diarylaminocarbonyl, alkylarylaminocarbonyl, diarylaminocarbonyl, mono- or diacylaminocarbonyl, aromatic or aliphatic acyl, alkyl optionally substituted by substituents selected from amino, carboxy, hydroxy, mercapto, mono- or dialkylamino, mono- or diarylamino, alkylarylamino, diarylamino, mono- or diacylamino, alkoxy, alkenoxy, aryloxy, thioalkoxy, thioalkenoxy, thioalkynoxy, thioaryloxy and heterocyclyl.

28. A compound according to claim 25 having the formula:

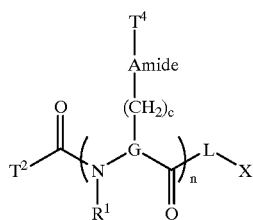

wherein

G is $(CH_2)_{1-6}$ wherein a hydrogen on one and only one of the $CH_2$ groups of each G is replaced with $-(CH_2)_c$-Amide-$T^4$;

$T^2$ and $T^4$ are organic moieties of the formula $C_{1-25}N_{0-9}S_{0-3}P_{0-3}H_\alpha F_\beta I_\delta$ wherein the sum of $\alpha$, $\beta$ and $\delta$ is sufficient to satisfy the otherwise unsatisfied valencies of the C, N, O, S and P atoms;

Amide is

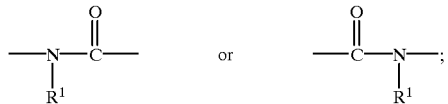

$R^1$ is hydrogen or $C_{1-10}$ alkyl;

c is an integer ranging from 0 to 4;

X is defined according to claim 1; and n is an integer ranging from 1 to 50 such that when n is greater than 1, G, c, Amide, $R^1$ and $T^4$ are independently selected.

29. A compound according to claim 28 having the formula:

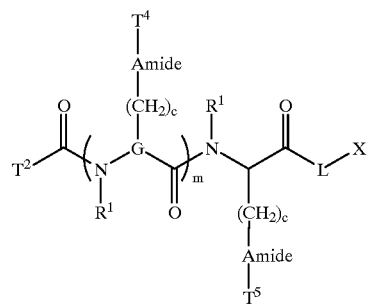

wherein $T^5$ is an organic moiety of the formula $C_{1-25}N_{0-9}O_{0-9}S_{0-3}P_{0-3}H_\alpha F_\beta I_\delta$ wherein the sum of $\alpha$, $\beta$ and $\delta$ is sufficient to satisfy the otherwise unsatisfied valencies of the C, N, O, S and P atoms; and $T^5$ includes a tertiary or quaternary amine or an organic acid; and m is an integer ranging from 0–49.

30. A compound according to claim 28 having the formula:

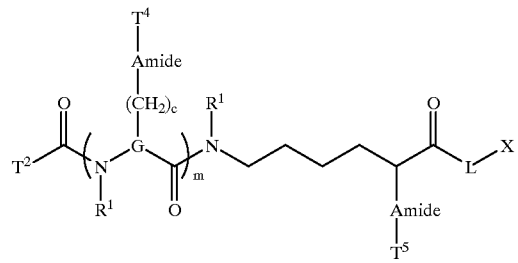

wherein $T^5$ is an organic moiety of the formula $C_{1-25}N_{0-9}O_{0-9}S_{0-3}P_{0-3}H_\alpha F_\beta I_\delta$ wherein the sum of $\alpha$, $\beta$ and $\delta$ is sufficient to satisfy the otherwise unsatisfied valencies of the C, N, O, S and P atoms; and $T^5$ includes a tertiary or quaternary amine or an organic acid; and m is an integer ranging from 0–49.

31. A compound according to any one of claims 29 and 30 wherein -Amide-$T^5$ is selected from:

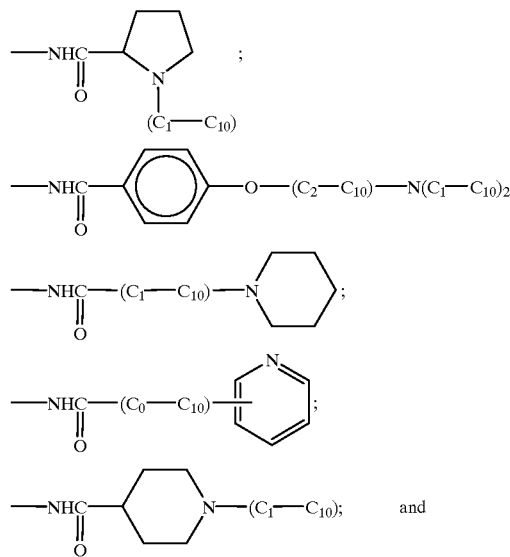

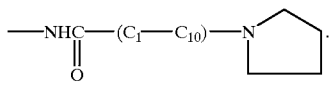

32. A compound according to any of claims 29 and 30 wherein -Amide-$T^5$ is selected from:

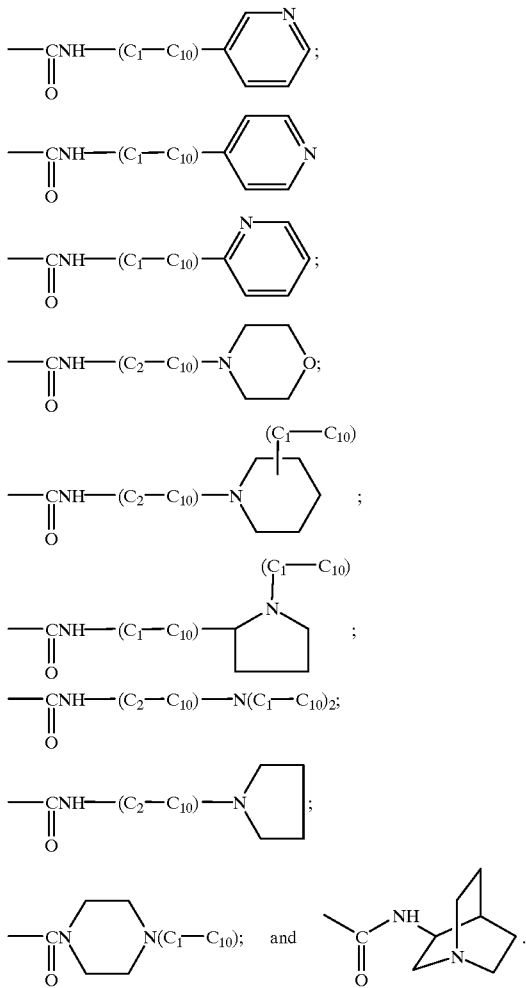

33. A compound according to any one of claims 25–29 wherein $T^2$ has the structure which results when one of the following organic acids is condensed with an amine group to form $T^2$—C(=O)—N($R^1$)—: Formic acid, Acetic acid, Propiolic acid, Propionic acid, Fluoroacetic acid, 2-Butynoic acid, Cyclopropanecarboxylic acid, Butyric acid, Methoxyacetic acid, Difluoroacetic acid, 4-Pentynoic acid, Cyclobutanecarboxylic acid, 3,3-Dimethylacrylic acid, Valeric acid, N,N-Dimethylglycine, N-Formyl-Gly-OH, Ethoxyacetic acid, (Methylthio)acetic acid, Pyrrole-2-carboxylic acid, 3-Furoic acid, Isoxazole-5-carboxylic acid, trans-3-Hexenoic acid, Trifluoroacetic acid, Hexanoic acid, Ac-Gly-OH, 2-Hydroxy-2-methylbutyric acid, Benzoic acid, Nicotinic acid, 2-Pyrazinecarboxylic acid, 1-Methyl-2-pyrrolecarboxylic acid, 2-Cyclopentene-1-acetic acid, Cyclopentylacetic acid, (S)-(–)-2-Pyrrolidone-5-carboxylic acid, N-Methyl-L-proline, Heptanoic acid, Ac-b-Ala-OH, 2-Ethyl-2-hydroxybutyric acid, 2-(2-Methoxyethoxy)acetic acid, p-Toluic acid, 6-Methylnicotinic acid, 5-Methyl-2-pyrazinecarboxylic acid, 2,5-Dimethylpyrrole-3-carboxylic acid, 4-Fluorobenzoic acid, 3,5-Dimethylisoxazole-4-carboxylic acid, 3-Cyclopentylpropionic acid, Octanoic acid, N,N-Dimethylsuccinamic acid, Phenylpropiolic acid, Cinnamic acid, 4-Ethylbenzoic acid, p-Anisic acid, 1,2,5-Trimethylpyrrole-3-carboxylic acid, 3-Fluoro-4-methylbenzoic acid, Ac-DL-Propargylglycine, 3-(Trifluoromethyl)butyric acid, 1-Piperidinepropionic acid, N-Acetylproline, 3,5-Difluorobenzoic acid, Ac-L-Val-OH, Indole-2-carboxylic acid, 2-Benzofurancarboxylic acid, Benzotriazole-5-carboxylic acid, 4-n-Propylbenzoic acid, 3-Dimethylaminobenzoic acid, 4-Ethoxybenzoic acid, 4-(Methylthio)benzoic acid, N-(2-Furoyl)glycine, 2-(Methylthio)nicotinic acid, 3-Fluoro-4-methoxybenzoic acid, Tfa-Gly-OH, 2-Napthoic acid, Quinaldic acid, Ac-L-Ile-OH, 3-Methylindene-2-carboxylic acid, 2-Quinoxalinecarboxylic acid, 1-Methylindole-2-carboxylic acid, 2,3,6-Trifluorobenzoic acid, N-Formyl-L-Met-OH, 2-[2-(2-Methoxyethoxy)ethoxy]acetic acid, 4-n-Butylbenzoic acid, N-Benzoylglycine, 5-Fluoroindole-2-carboxylic acid, 4-n-Propoxybenzoic acid, 4-Acetyl-3,5-dimethyl-2-pyrrolecarboxylic acid, 3,5-Dimethoxybenzoic acid, 2,6-Dimethoxynicotinic acid, Cyclohexanepentanoic acid, 2-Naphthylacetic acid, 4-(1H-Pyrrol-1-yl)benzoic acid, Indole-3-propionic acid, m-Trifluoromethylbenzoic acid, 5-Methoxyindole-2-carboxylic acid, 4-Pentylbenzoic acid, Bz-b-Ala-OH, 4-Diethylaminobenzoic acid, 4-n-Butoxybenzoic acid, 3-Methyl-5-CF3-isoxazole-4-carboxylic acid, (3,4-Dimethoxyphenyl)acetic acid, 4-Biphenylcarboxylic acid, Pivaloyl-Pro-OH, Octanoyl-Gly-OH, (2-Naphthoxy)acetic acid, Indole-3-butyric acid, 4-(Trifluoromethyl)phenylacetic acid, 5-Methoxyindole-3-acetic acid, 4-(Trifluoromethoxy)benzoic acid, Ac-L-Phe-OH, 4-Pentyloxybenzoic acid, Z-Gly-OH, 4-Carboxy-N-(fur-2-ylmethyl)pyrrolidin-2-one, 3,4-Diethoxybenzoic acid, 2,4-Dimethyl-5-$CO_2$Et-pyrrole-3-carboxylic acid, N-(2-Fluorophenyl)succinamic acid, 3,4,5-Trimethoxybenzoic acid, N-Phenylanthranilic acid, 3-Phenoxybenzoic acid, Nonanoyl-Gly-OH, 2-Phenoxypyridine-3-carboxylic acid, 2,5-Dimethyl-1-phenylpyrrole-3-carboxylic acid, trans-4-(Trifluoromethyl)cinnamic acid, (5-Methyl-2-phenyloxazol-4-yl)acetic acid, 4-(2-Cyclohexenyloxy)benzoic acid, 5-Methoxy-2-methylindole-3-acetic acid, trans-4-Cotininecarboxylic acid, Bz-5-Aminovaleric acid, 4-Hexyloxybenzoic acid, N-(3-Methoxyphenyl)succinamic acid, Z-Sar-OH, 4-(3,4-Dimethoxyphenyl)butyric acid, Ac-o-Fluoro-DL-Phe-OH, N-(4-Fluorophenyl)glutaramic acid, 4'-Ethyl-4-biphenylcarboxylic acid, 1,2,3,4-Tetrahydroacridinecarboxylic acid, 3-Phenoxyphenylacetic acid, N-(2,4-Difluorophenyl)succinamic acid, N-Decanoyl-Gly-OH, (+)-6-Methoxy-a-methyl-2-naphthaleneacetic acid, 3-(Trifluoromethoxy)cinnamic acid, N-Formyl-DL-Trp-OH, (R)-(+)-a-Methoxy-a-(trifluoromethyl) phenylacetic acid, Bz-DL-Leu-OH, 4-(Trifluoromethoxy) phenoxyacetic acid, 4-Heptyloxybenzoic acid, 2,3,4-Trimethoxycinnamic acid, 2,6-Dimethoxybenzoyl-Gly-OH, 3-(3,4,5-Trimethoxyphenyl)propionic acid, 2,3,4,5,6-Pentafluorophenoxyacetic acid, N-(2,4-Difluorophenyl) glutaramic acid, N-Undecanoyl-Gly-OH, 2-(4-Fluorobenzoyl)benzoic acid, 5-Trifluoromethoxyindole-2-carboxylic acid, N-(2,4-Difluorophenyl)diglycolamic acid, Ac-L-Trp-OH, Tfa-L-Phenylglycine-OH, 3-Iodobenzoic acid, 3-(4-n-Pentylbenzoyl)propionic acid, 2-Phenyl-4-quinolinecarboxylic acid, 4-Octyloxybenzoic acid, Bz-L-Met-OH, 3,4,5-Triethoxybenzoic acid, N-Lauroyl-Gly-OH, 3,5-Bis(trifluoromethyl)benzoic acid, Ac-5-Methyl-DL-Trp-OH, 2-Iodophenylacetic acid, 3-Iodo-4-methylbenzoic acid, 3-(4-n-Hexylbenzoyl)propionic acid, N-Hexanoyl-L-Phe-OH, 4-Nonyloxybenzoic acid, 4'-(Trifluoromethyl)-2-biphenylcarboxylic acid, Bz-L-Phe-OH, N-Tridecanoyl-Gly-OH, 3,5-Bis(trifluoromethyl)phenylacetic acid, 3-(4-n-Heptylbenzoyl)propionic acid, N-Hepytanoyl-L-Phe-OH, 4-Decyloxybenzoic acid, N-($\alpha,\alpha,\alpha$-trifluoro-m-tolyl) anthranilic acid, Niflumic acid, 4-(2-Hydroxyhexafluoroisopropyl)benzoic acid, N-Myristoyl-Gly-OH, 3-(4-n-Octylbenzoyl)propionic acid, N-Octanoyl-L-Phe-OH, 4-Undecyloxybenzoic acid, 3-(3,4,5-Trimethoxyphenyl)propionyl-Gly-OH, 8-Iodonaphthoic acid, N-Pentadecanoyl-Gly-OH, 4-Dodecyloxybenzoic acid, N-Palmitoyl-Gly-OH, and N-Stearoyl-Gly-OH.

34. A composition comprising a plurality of compounds of the formula:

$$T^{MS}-L-MOI$$

wherein,
  $T^{ms}$ is an organic group detectable by mass spectrometry, comprising carbon, at least one of hydrogen and fluoride, and optional atoms selected from oxygen, nitrogen, sulfur, phosphorus and iodine;
  L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid;
  MOI is a nucleic acid fragment wherein L is conjugated to the MOI at a location other than the 3' end of the MOI; and
  wherein no two compounds have either the same $T^{ms}$ or the same MOI.

35. A composition according to claim 34 wherein the plurality is greater than 2.

36. A composition according to claim 34 wherein the plurality is greater than 4.

37. A composition according to claim 34 wherein the nucleic acid fragment has a sequence complementary to a portion of a vector, wherein the fragment is capable of priming nucleotide synthesis.

38. A composition according to claim 34 wherein the $T^{ms}$ groups of members of the plurality differ by at least 2 amu.

39. A composition according to claim 34 wherein the $T^{ms}$ groups of members of the plurality differ by at least 4 amu.

40. A composition comprising water and a compound of claim 15.

41. A composition according to claim 40 further comprising buffer, having a pH of about 5 to about 9.

42. A composition according to claim 40 further comprising an enzyme and one of dATP, dGTP, dCTP, and dTTP.

43. A composition according to claim 40 further comprising an enzyme and one of ddATP, ddGTP, ddCTP, and ddTTP.

44. A composition comprising a plurality of sets of compounds, each set of compounds having the formula:

$$T^{ms}-L-MOI$$

wherein,
  $T^{ms}$ is an organic group detectable by mass spectrometry, comprising carbon, at least one of hydrogen and fluoride, and optional atoms selected from oxygen, nitrogen, sulfur, phosphorus and iodine;
  L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid;
  MOI is a nucleic acid fragment wherein L is conjugated to the MOI at a location other than the 3' end of the MOI;
  wherein within a set, all members have the same $T^{ms}$ group, and the MOI fragments have variable lengths that terminate with the same dideoxynucleotide selected from ddAMP, ddGMP, ddCMP and ddTMP; and
  wherein between sets, the $T^{ms}$ groups differ by at least 2 amu.

45. A composition according to claim 44 wherein the plurality is at least 3.

46. A composition according to claim 44 wherein the plurality is at least 5.

47. A composition comprising a first plurality of sets of compounds according to claim 44, and a second plurality of sets of compounds having the formula $$T^{ms}-L-MOI$$

wherein,
  $T^{ms}$ is an organic group detectable by mass spectrometry, comprising carbon, at least one of hydrogen and fluoride, and optional atoms selected from oxygen, nitrogen, sulfur, phosphorus and iodine;
  L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid;
  MOI is a nucleic acid fragment wherein L is conjugated to the MOI at a location other than the 3' end of the MOI; and
  wherein all members within the second plurality have an MOI sequence which terminates with the same dideoxynucleotide selected from ddAMP, ddGMP, ddCMP and ddTMP; with the proviso that the dideoxynucleotide present in the compounds of the first plurality is not the same dideoxynucleotide present in the compounds of the second plurality.

48. A kit for DNA sequencing analysis comprising a plurality of container sets, each container set comprising at least five containers, wherein a first container contains a vector, a second, third, fourth and fifth containers contain compounds of the formula:

$$T^{ms}-L-MOI$$

wherein,
  $T^{ms}$ is an organic group detectable by mass spectrometry, comprising carbon, at least one of hydrogen and fluoride, and optional atoms selected from oxygen, nitrogen, sulfur, phosphorus and iodine;
  L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid; and MOI is a nucleic acid fragment wherein L is conjugated to the MOI at a location other than the 3' end of the MOI; such that the MOI for the second, third, fourth and fifth containers is identical and complementary to a portion of the vector within the set of containers, and the $T^{ms}$ group within each container is different from the other $T^{ms}$ groups in the kit.

49. A kit according to claim 48 wherein the plurality is at least 3.

50. A kit according to claim 48 wherein the plurality is at least 5.

51. An apparatus for determining the sequence of a nucleic acid molecule in a sample, the sample including tagged nucleic acid fragments having nucleic acid fragments and tags attached to the nucleic acid fragments, comprising a separation apparatus that separates tagged nucleic acid fragments, a cleavage apparatus that receives separated tagged cleaves nucleic acid fragments and the tags from the nucleic acid fragments, each tag being correlative with a particular nucleotide of the nucleic acid fragment and detectable by electrochemical detection, and an apparatus for electrochemical detection that receives and detects electrochemical signatures of the tags.

52. The apparatus according to claim 51 further including a data processor that correlates the electrochemical signature of a tag to a particular nucleotide and to a specific sample.

53. The apparatus according to claim 51 wherein the apparatus for electrochemical detection is an apparatus for potentiostatic amperometry.

54. The apparatus according to claim 52 wherein the data processor is capable of correlating the electrochemical signatures of five or more possible tags to a particular nucleotide and to five or more specific samples.

55. The apparatus according to claim 52 wherein the data processor is capable of correlating the electrochemical signatures of sixteen or more possible tags to a particular nucleotide and to sixteen or more specific samples.

56. An apparatus for determining the sequence of a nucleic acid molecule in a sample, the sample including tagged nucleic acid fragments having nucleic acid fragments and tags attached to the nucleic acid fragments, comprising a separation apparatus that separates tagged nucleic acid fragments, a cleavage apparatus that receives separated tagged nucleic acid fragments and cleaves from the nucleic acid fragments, each tag being correlative with a particular nucleotide of the nucleic acid fragment and detectable by mass spectrometry, a mass spectrometer that receives the tags and detects a mass of a tag, and a data processor that correlates the mass of a tag to a particular nucleotide and to a specific sample.

57. The apparatus according to claim 56 wherein the data processor is capable of correlating the masses of five or more possible tags to a particular nucleotide and to five or more specific samples.

58. The apparatus according to claim 56 wherein the data processor is capable of correlating the masses of sixteen or more possible tags to a particular nucleotide and to sixteen or more specific samples.

* * * * *

UNITED STATES PATENT AND TRADEMARK OFFICE
CERTIFICATE OF CORRECTION

PATENT NO. : 6,312,893 B1  
DATED : November 6, 2001  
INVENTOR(S) : Jeffrey Van Ness et al.

It is certified that error appears in the above-identified patent and that said Letters Patent is hereby corrected as shown below:

Column 113,  
Line 36, "and $R^2$ is nucleic acid fragment" should read  
-- and $R^2$ is a nucleic acid fragment. --.

Signed and Sealed this

Nineteenth Day of August, 2003

JAMES E. ROGAN  
*Director of the United States Patent and Trademark Office*

UNITED STATES PATENT AND TRADEMARK OFFICE
CERTIFICATE OF CORRECTION

PATENT NO. : 6,312,893 B1
DATED : November 6, 2001
INVENTOR(S) : Jeffrey Van Ness et al.

It is certified that error appears in the above-identified patent and that said Letters Patent is hereby corrected as shown below:

Column 111,
Line 28, after "nucleic acid molecule," should read -- wherein the tagged fragments are selected from a set of termination fragments and a set of degradation fragments, --
Line 29, after "particular nucleotide" should read -- of the fragments --

Column 121,
Lines 15-16, "having nucleic acid fragments and tags attached to the nucleic acid fragments" should read as -- selected from tagged termination fragments and tagged degradation fragments --

Column 122,
Lines 11-12, "having nucleic acid fragments and tags attached to the nucleic acid fragments" should read as -- selected from tagged termination fragments and tagged degradation fragments --

Signed and Sealed this

Twenty-seventh Day of July, 2004

JON W. DUDAS
*Acting Director of the United States Patent and Trademark Office*

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (xi) SEQUENCE DESCRIPTION: SEQ ID NO: 1:

TGTAAAACGA CGGCCAGT                                  18

(2) INFORMATION FOR SEQ ID NO: 2:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (xi) SEQUENCE DESCRIPTION: SEQ ID NO: 2:

TGTAAAACGA CGGCCAGTA                               19

(2) INFORMATION FOR SEQ ID NO: 3:

```
        (i) SEQUENCE CHARACTERISTICS:
             (A) LENGTH: 20 base pairs
             (B) TYPE: nucleic acid
             (C) STRANDEDNESS: single
             (D) TOPOLOGY: linear (xi) SEQUENCE DESCRIPTION: SEQ ID NO: 3:

TGTAAAACGA CGGCCAGTAT                                           20

(2) INFORMATION FOR SEQ ID NO: 4:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (xi) SEQUENCE DESCRIPTION: SEQ ID NO: 4:

TGTAAAACGA CGGCCAGTAT G                                         21

(2) INFORMATION FOR SEQ ID NO: 5:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (xi) SEQUENCE DESCRIPTION: SEQ ID NO: 5:

TGTAAAACGA CGGCCAGTAT GC                                        22

(2) INFORMATION FOR SEQ ID NO: 6:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (xi) SEQUENCE DESCRIPTION: SEQ ID NO: 6:

TGTAAAACGA CGGCCAGTAT GCA                                       23

(2) INFORMATION FOR SEQ ID NO: 7:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (xi) SEQUENCE DESCRIPTION: SEQ ID NO: 7:

TGTAAAACGA CGGCCAGTAT GCAT                                      24

(2) INFORMATION FOR SEQ ID NO: 8:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (xi) SEQUENCE DESCRIPTION: SEQ ID NO: 8:

TGTAAAACGA CGGCCAGTAT GCATG                                     25

(2) INFORMATION FOR SEQ ID NO: 9:
```

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO: 9:

TGTAAAACGA CGGCCAGC                                                           18

(2) INFORMATION FOR SEQ ID NO: 10:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO: 10:

TGTAAAACGA CGGCCAGCG                                                          19

(2) INFORMATION FOR SEQ ID NO: 11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO: 11:

TGTAAAACGA CGGCCAGCGT                                                         20

(2) INFORMATION FOR SEQ ID NO: 12:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO: 12:

TGTAAAACGA CGGCCAGCGT A                                                       21

(2) INFORMATION FOR SEQ ID NO: 13:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO: 13:

TGTAAAACGA CGGCCAGCGT AC                                                      22

(2) INFORMATION FOR SEQ ID NO: 14:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO: 14:

TGTAAAACGA CGGCCAGCGT ACC                                                     23

(2) INFORMATION FOR SEQ ID NO: 15:

(i) SEQUENCE CHARACTERISTICS:

```
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO: 15:

TCGAGGTCGA CGGTATCG                                                              18

(2) INFORMATION FOR SEQ ID NO: 16:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO: 16:

GCCGCTCTAG AACTAGTG                                                              18
```